(12) United States Patent
Borchers et al.

(10) Patent No.: US 10,020,178 B2
(45) Date of Patent: Jul. 10, 2018

(54) SYSTEM AND METHOD FOR MATRIX-COATING SAMPLES FOR MASS SPECTROMETRY

(71) Applicant: UVic Industry Partnerships Inc., Victoria (CA)

(72) Inventors: Christoph Hermann Borchers, Victoria (CA); Jun Han, Victoria (CA); Xiaodong Wang, Beijing (CN)

(73) Assignee: UVic Industry Partnerships Inc., Victoria (CA)

( * ) Notice: Subject to any disclaimer, the term of this patent is extended or adjusted under 35 U.S.C. 154(b) by 0 days.

(21) Appl. No.: 15/322,037

(22) PCT Filed: Jun. 26, 2015

(86) PCT No.: PCT/CA2015/050606
§ 371 (c)(1),
(2) Date: Dec. 23, 2016

(87) PCT Pub. No.: WO2015/196303
PCT Pub. Date: Dec. 30, 2015

(65) Prior Publication Data
US 2017/0148618 A1    May 25, 2017

Related U.S. Application Data

(60) Provisional application No. 62/018,346, filed on Jun. 27, 2014.

(51) Int. Cl.
*H01J 49/00* (2006.01)
*H01J 49/04* (2006.01)
(Continued)

(52) U.S. Cl.
CPC ............ *H01J 49/0459* (2013.01); *G01N 1/28* (2013.01); *H01J 49/164* (2013.01)

(58) Field of Classification Search
CPC .. H01J 49/00; H01J 49/02; H01J 49/04; H01J 49/0409; H01J 49/0418; H01J 49/0459; H01J 49/0463
(Continued)

(56) References Cited

U.S. PATENT DOCUMENTS 5,872,010 A    2/1999 Karger et al.
5,910,656 A *  6/1999 Koster ................ H01J 49/0409
                                                  250/252.1

(Continued)

FOREIGN PATENT DOCUMENTS

WO    WO 2014/004908        1/2014

OTHER PUBLICATIONS

Bruker Daltronics, "ImagePrep: Comprehensive and Reliable Tissue Sample Preparation for MALDI Imaging," Sep. 3, 2008 (4 pages).

(Continued)

*Primary Examiner* — Jason McCormack
(74) *Attorney, Agent, or Firm* — Klarquist Sparkman, LLP

(57) ABSTRACT

Disclosed herein are embodiments of a system and method for preparing matrix-coated samples for analysis using mass spectrometry. In particular disclosed embodiments, the system and methods of using the system utilize an electric field to enhance results obtained from mass spectrometric analysis of the matrix-coated samples. The methods disclosed herein can be used to prepare biological samples that have improved characteristics facilitating the detection, localization, and/or identification of biomarkers for disease.

22 Claims, 20 Drawing Sheets

(51) Int. Cl.
*H01J 49/16* (2006.01)
*G01N 1/28* (2006.01)

(58) Field of Classification Search
USPC .................................. 250/281, 282, 288
See application file for complete search history.

(56) References Cited

U.S. PATENT DOCUMENTS

| | | |
|---|---|---|
| 6,261,430 B1 | 7/2001 | Yager et al. |
| 6,858,842 B2 | 2/2005 | Moon et al. |
| 6,956,207 B2 | 10/2005 | Corso et al. |
| 7,667,196 B2 | 2/2010 | Schurenberg et al. |
| 2003/0143493 A1 | 7/2003 | Schultz et al. |
| 2005/0152344 A1* | 7/2005 | Chiu .................. H04M 3/4938 370/352 |
| 2005/0153344 A1* | 7/2005 | Diamond ........... G01N 33/6803 435/6.11 |

OTHER PUBLICATIONS

International Search Report and Written Opinion issued for International Application No. PCT/CA2015/050606 dated Aug. 26, 2015, 11 pages.

\* cited by examiner

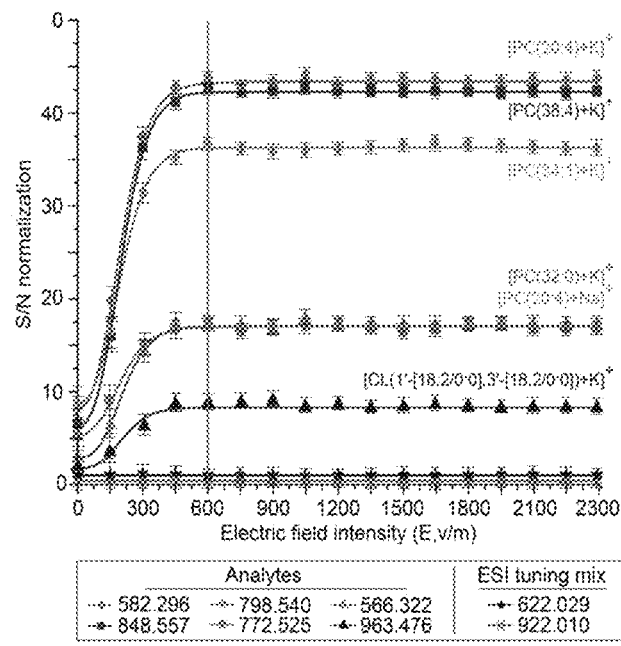
FIG. 4
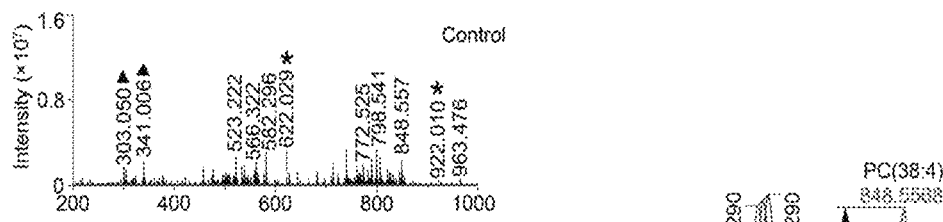
FIG. 5A
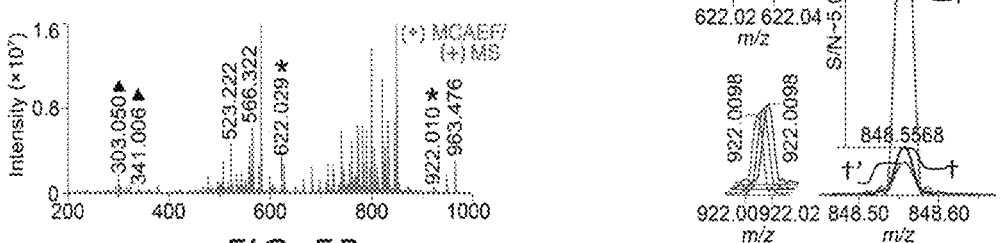
FIG. 5B
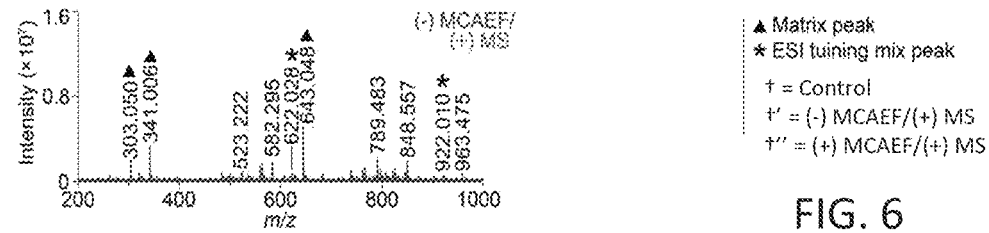
FIG. 5C
FIG. 6 m/z 826.463 m/z 826.463 m/z 919.473 m/z 919.473 m/z 778.467 m/z 778.467 m/z 865.582 m/z 865.582 m/z 848.637 m/z 975.535 m/z 772.525 m/z 741.483 m/z 893.612 m/z 701.513 m/z 718.539 m/z 8,956.73 m/z 8,956.73 m/z 12,260.31 m/z 12,260.31 m/z 18,489.51 m/z 18,489.51 m/z 13,810.68 m/z 13,810.68

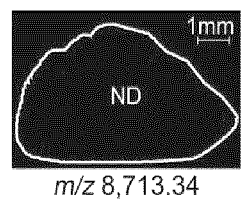 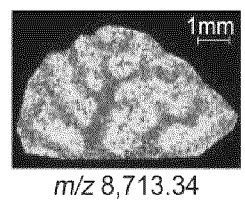
m/z 8,713.34   m/z 8,713.34
FIG. 21A   FIG. 21B
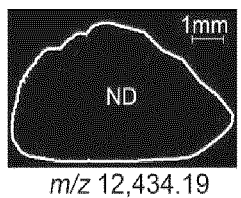 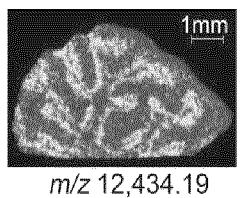 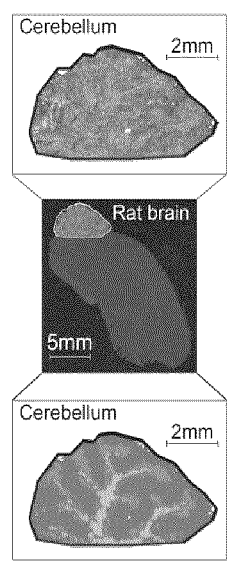
m/z 12,434.19   m/z 12,434.19
FIG. 21C   FIG. 21D
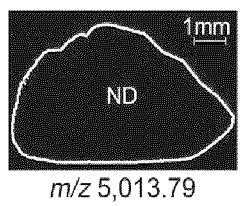 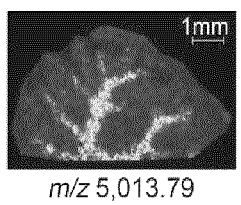
m/z 5,013.79   m/z 5,013.79
FIG. 21E   FIG. 21F
● Grey matter
● Granular layers
● White matter
0% ▬▬▬▬ 100%
FIG. 21I
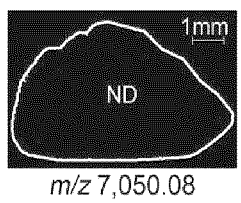 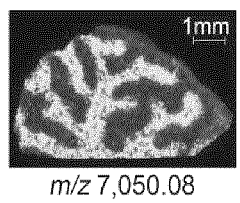
m/z 7,050.08   m/z 7,050.08
FIG. 21G   FIG. 21H

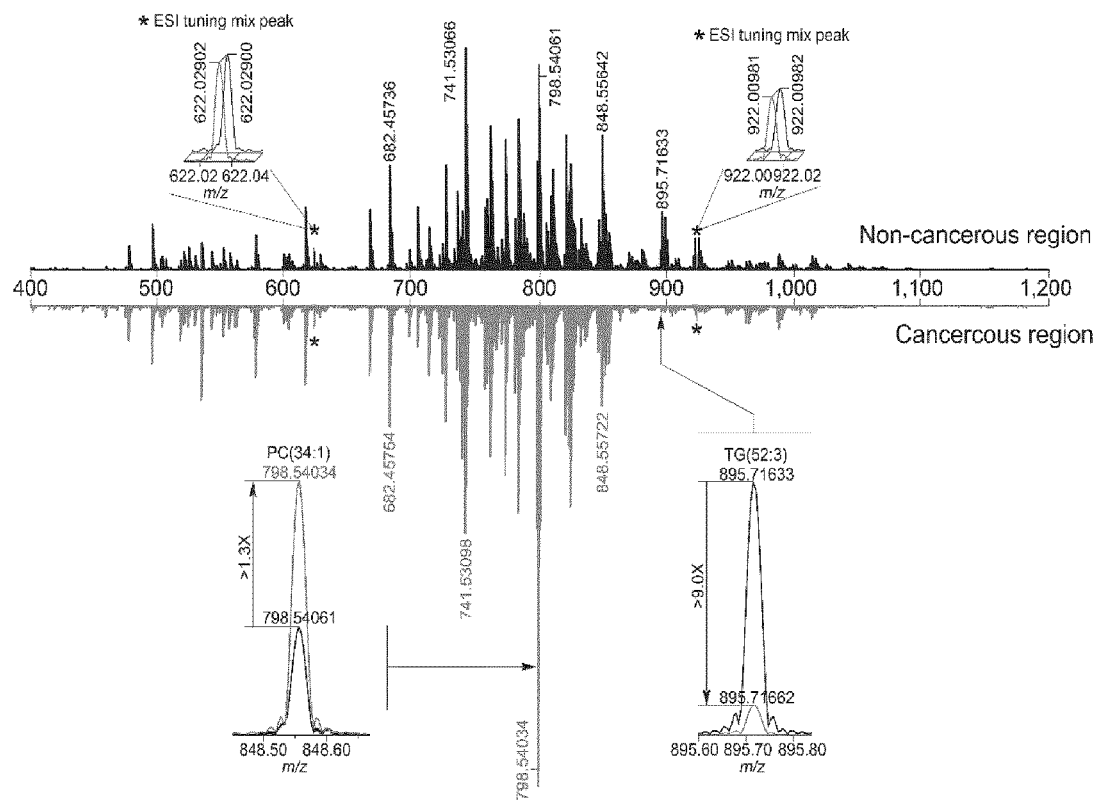
FIG. 22
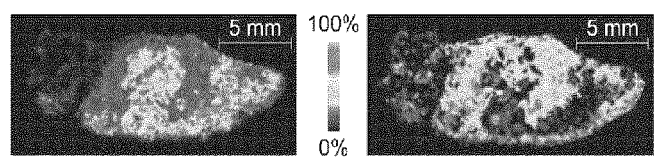
PC(34:1)
FIG. 23A
TG(52:3)
FIG. 23B
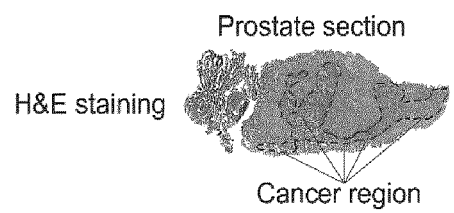
FIG. 23C

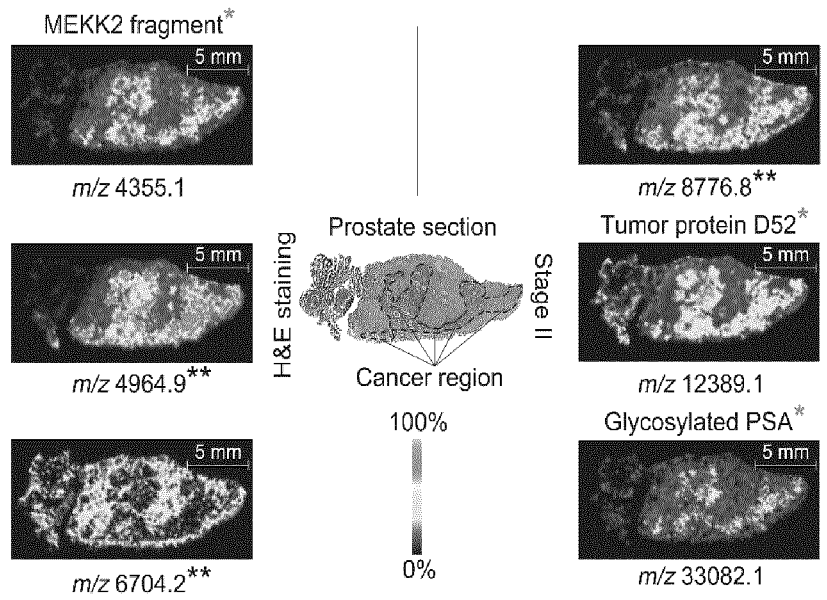
FIG. 26
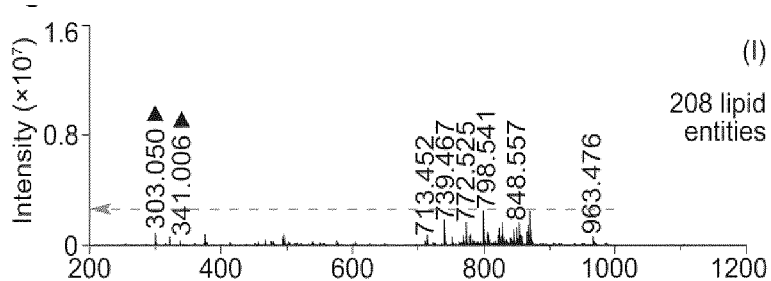
FIG. 27
FIG. 28A

SYSTEM AND METHOD FOR MATRIX-COATING SAMPLES FOR MASS SPECTROMETRY

CROSS REFERENCE TO RELATED APPLICATIONS

This is the U.S. National Stage of International Application No. PCT/CA2015/050606, filed Jun. 26, 2015, which was published in English under PCT Article 21(2), which in turn claims the benefit of and priority to the earlier filing date of U.S. Provisional Application No. 62/018,346, filed on Jun. 27, 2014, each of which is incorporated herein by reference in its entirety.

FIELD

The present disclosure concerns embodiments of a system and method for preparing matrix-coated samples for mass spectrometric analysis.

BACKGROUND

Tissue imaging by matrix-assisted laser desorption/ionization mass spectrometry (MALDI MS) is a technology that can be used to simultaneously explore and characterize the spatial distributions and relative abundances of endogenous compounds directly from the surface of a thinly-cut tissue slice. This technique can be used to produce visual images of various ionized species within tissue samples, including lipids and proteins. The locations and abundances of specific biomolecules can reflect the pathophysiology of the imaged tissue specimens; therefore, MALDI imaging has great potential for diagnostics, such as human disease biomarker discovery, particularly cancer biomarkers.

Currently, MALDI imaging has been used to detect only a small number of lipids and/or proteins in comparison to other mass spectrometric detection methods (e.g., MS/MS or LC-MS/MS). For example, only 212 lipids in rat brain, 550 lipids in porcine adrenal gland, 92 proteins in mouse lung, and 105 proteins in mouse kidney have been detected in single tissue imaging studies, whereas 119,200 lipid compounds have already been entered into the LipidBlast library using MS/MS, and 2800 proteins can be detected in human colon adenoma tissue using LC-MS/MS. Methods to improve the number of compounds detected using MALDI MS have focused on either manipulating the matrix used in MALDI MS, and/or using various sample preparation techniques, such as matrix sublimation, matrix vapor deposition/recrystallization, matrix pre-coating, solvent-free matrix dry-coating, matrix microspotting, automated inkjet matrix printing, and tissue pre-washing before matrix coating. Despite these prior efforts, however, a need in the art still exists for improved MALDI MS sample preparation methods and a system for preparing such samples.

SUMMARY

Disclosed herein are embodiments of a system, comprising a first conductive substrate associated with a biological sample, a second conductive substrate positioned parallel and opposite to the first conductive substrate, wherein the first conductive substrate and second conductive substrate are separated by a distance of 25 mm to 75 mm, a power source electrically coupled to the first conductive substrate and the second conductive substrate for establishing an electric field between the first conductive substrate and the second conductive substrate, and a matrix dispersion device capable of dispersing a matrix solution, wherein the matrix dispersion device is physically separated from the first conductive substrate and the second conductive substrate. In some embodiments, the matrix dispersion device is positioned adjacent to and between an end terminus of first conductive substrate and an end terminus of the second conductive substrate. The first conductive substrate can comprise a conductive material different from that of the second conductive substrate in some embodiments. The biological sample can be associated with the conductive material of the first conductive substrate. In some embodiments, the first conductive substrate and the second conductive substrate can be separated by a distance of 40 mm to 55 mm.

The system disclosed herein also can comprise a housing that substantially encloses at least the first conductive substrate, the second conductive substrate, and a portion of the matrix dispersion device. In some embodiments, the portion of the matrix dispersion device comprises a spray nozzle. Systems are also disclosed herein that are coupled directly or indirectly to a mass spectrometer.

Also disclosed herein are embodiments of a method for preparing mass spectrometry samples comprising positioning a first conductive substrate associated with a biological sample 25 mm to 75 mm away from a second conductive substrate, wherein the first conductive substrate and the second conductive substrate are parallel to one another, applying an electric field between the first conductive substrate and the second conductive substrate using a power source coupled to the first conductive substrate and the second conductive substrate, and spraying a matrix solution from a matrix dispersion device comprising a spray nozzle positioned perpendicular to the electric field generated between the first conductive substrate and the second conductive substrate, wherein the matrix solution is sprayed into the electric field in a direction effective to apply the matrix solution to the biological sample thereby forming a matrix layer on the biological sample.

In some embodiments, the method can further comprise allowing the droplets of the matrix solution to incubate with the biological sample in the presence of the electric field and/or drying the droplets of the matrix solution in the presence of the electric field. In some embodiments, the biological sample is sprayed 20 to 40 times. In particular embodiments, the biological sample is sprayed 30 times.

Some embodiments of the method can further comprise analyzing the biological sample and the matrix layer associated therewith for one or more compounds of interest. In some embodiments, analyzing comprises subjecting the biological sample to a mass spectrometric detection technique. Suitable mass spectrometric detection techniques include MALDI mass spectrometry. In some embodiments, the electric field is directed from the first conductive substrate to the second conductive substrate. In other embodiments, the electric field is directed from the second substrate to the first conductive substrate. Spraying the droplets into the electric field can cause an upper portion of the droplets to develop a higher electric potential than a lower portion of the droplets. In other embodiments, spraying the droplets into the electric field causes a lower portion of the droplets to develop a higher electric potential than an upper portion of the droplets. The polarized droplets can associate with the biological sample and electrically attract one or more compounds of interest within the biological sample.

In some embodiments, the matrix layer formed using the electric field comprises a higher number of compounds of interest than that of a matrix layer formed without an electric field. In some embodiments, the matrix layer formed using the electric field provides higher mass spectrometric signal-to-noise ratios for the compounds of interest than does the a matrix layer formed without an electric field. The biological sample analyzed with the disclosed method can be a prostate tissue sample, a breast tissue sample, a lung tissue sample, a skin tissue sample, a liver tissue sample, a colon tissue sample, or a combination thereof. In some embodiments, the method can be used to detect one or more lipids, proteins, nucleic acids, or combinations thereof that are present in the biological sample.

The foregoing and other objects, features, and advantages of the claimed invention will become more apparent from the following detailed description, which proceeds with reference to the accompanying figures.

BRIEF DESCRIPTION OF THE DRAWINGS

FIG. 4 is a graph of electric field intensity (E) versus signal-to-noise (S/N) normalization illustrating the effect of electric field intensity on signal-to-noise of six lipids detected by positive ion matrix-assisted laser desorption-Fourier transform ion cyclotron resonance mass spectrometry "MALDI-FTICR MS."

FIGS. 5A-5C are MALDI-FTICR mass spectra of lipids detected in control rat liver tissue sections; FIG. 5A is a MALDI-FTICR mass spectrum of a control sample; FIG. 5B is a positive ion MALDI-FTICR mass spectrum of a matrix-coated sample obtained from an embodiment of the method and system disclosed herein; FIG. 5C is a positive ion MALDI-FTICR mass spectrum of a matrix-coated sample obtained from a method embodiment wherein the electric field was reversed from that used in the sample of FIG. 5B.

FIG. 6 is an overlayed mass spectrum of "ESI tuning mix" peaks of m/z 622.029 and m/z 922.010, and PC(38:4) having an m/z 848.557, which illustrates peaks obtained from the control sample of FIG. 5A, the sample of FIG. 5B, and the sample of FIG. 5C.

FIG. 9C is a three-dimensional map of the detected ions.

FIG. 10C is a three-dimensional map of the detected ions.

FIG. 11C is a three-dimensional map of the detected ions.

FIG. 12C is a three-dimensional map of the detected ions.

FIG. 13C is a three-dimensional map of the detected ions.

FIG. 14C is a three-dimensional map of the detected ions.

FIG. 20I illustrates the different regional aspects of the tissue sample.

FIGS. 21A-21I are images comparing results obtained from control samples (FIGS. 21A, 21C, 21E, and 21G, where "ND" means the molecules were not detected in these control embodiments) and samples prepared using an embodiment of the disclosed system and method (FIGS. 21B, 21D, 21F, and 21H); FIG. 21I illustrates the different regional aspects of the tissue sample.

FIG. 22 is a mass spectrum acquired from a non-cancerous region (black) and a cancerous region (red) of a transverse human prostate tissue section prepared with and without using an embodiment of the disclosed method and system.

FIGS. 23A-23C are images of stained prostate cancer tissue sections made using an embodiment of the disclosed system and method, which provide a comparison of ion images of different compounds of interest.

FIG. 24A illustrates unique compounds of interest detected in a non-cancerous region of a sample; FIG. 24B illustrates unique compounds of interest detected in cancerous regions of a sample; and FIG. 24C illustrates compositions of the compounds of interest detected in both cell regions with different distribution patterns.

FIG. 26 is a collection of stained images of a prostate cancer tissue section comparing ion images of particular compounds of interest.

FIG. 27 is a table providing particular parameters for comparing various different embodiments of methods for coating samples.

FIGS. 28A-28D are MALDI-FTICR mass spectra obtained from the different method embodiments of coating samples provided by FIG. 27; FIG. 28A is a mass spectrum obtained from an embodiment wherein no electric field was applied during the spray, incubation, or drying period of sample preparation; FIG. 28B is a mass spectrum obtained from an embodiment wherein the electric field was applied during the spray, incubation, and drying periods of sample preparation; FIG. 28C is a mass spectrum obtained from an embodiment wherein an electric field was applied only during a spray period of sample preparation; FIG. 28D is a mass spectrum obtained from an embodiment wherein an electric field was applied only during the incubation and drying period of sample preparation.

FIG. 29A illustrates insulin mass spectra observed from the same concentration spot, indicating the stability of MALDI TOF/TOF MS for protein detection; FIG. 29B illustrates the standard curve generated from insulin spots with different concentrations; FIG. 29C shows two representative accumulated mass spectra acquired by MALDI TOF/TOF MS— with matric coating assisted by an electric field ("MCAEF") (lower) and without MCAEF (upper); and FIG. 29D shows the effect of MCAEF on the images of proteins detected on the prostate tissue sections.

DETAILED DESCRIPTION

I. Introduction and Terms

Figure 1A:
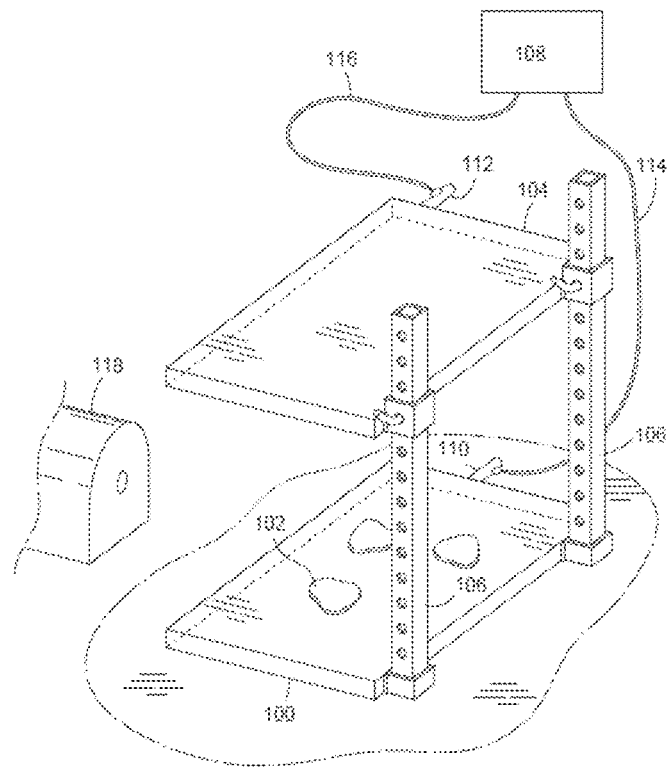
FIGS. 1A and 1B illustrate exemplary embodiments of the disclosed system.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided:

Control: A sample or procedure performed to assess test validity. In one example, a control is a quality control, such as a positive control. For example, a positive control is a procedure or sample that is similar to the actual test sample, but which is known from previous experience to give a positive result. A positive control can confirm that the basic conditions of the test produce a positive result, even if none of the actual test samples produces such a result.

In other examples, a control is a negative control. A negative control is a procedure or test sample known from previous experience to give a negative result. The negative control can demonstrate the base-line result obtained when a test does not produce a measurable positive result. In some embodiments, the value of the negative control can be treated as a "background" value to be subtracted from the test sample results.

Compound of Interest: A compound, or ion thereof, that can be detected using the method disclosed herein. In particular disclosed embodiments, the identity of the compound of interest may or may not be known prior to detection. In an independent embodiment, the compound of interest can be a biomarker, or a compound capable of acting as a biomarker.

Electrically Associate(d): This term can describe embodiments wherein a polarized droplet, as described herein, can attract, repel, and/or couple to a compound of interest present in a biological sample. The attraction, repelling, and/or coupling can occur between a portion of the polarized droplet and one or more functional groups present on the compound of interest. Coupling can include, but is not limited to, covalent coupling, electrostatic, ionic coupling, or combinations thereof.

FTICR: Fourier transform ion cyclotron resonance.

Permittivity: A measure of the resistance that is encountered when forming an electric field and can be related to electric susceptibility, which can measure how easily a dielectric polarizes in response to an electric field.

Sample: The term "sample" can refer to any liquid, semi-solid, or solid substance (or material) in or on which a compound of interest can be present. In particular disclosed embodiments, a sample can be a biological sample or a sample obtained from a biological material. A biological sample can be any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (such as a primary cell or cultured cell) or medium conditioned by any cell, tissue or organ. In some embodiments, a sample is a test sample. For example, a test sample is a cell, a tissue or cell pellet section prepared from a biological sample obtained from a subject that is at risk or has acquired a particular condition or disease.

Uniform Electric Field: An electric field created between at least two conductive substrates that is constant, or substantially constant, at every point. The magnitude of the electric field can be approximated (by ignoring edge effects) using the following equation: $E = -\Delta\phi/d$, where $\Delta\phi$ is the potential difference between two conductive substrates and d is the distance between the two conductive substrates.

II. System for Coating Samples

Disclosed herein are embodiments of a system for coating samples for analysis using mass spectrometry, such as MALDI mass spectrometry. Embodiments of the disclosed system can be used to prepare matrix-coated biological samples, such as tissue samples, that may be directly analyzed with a mass spectrometer without further manipulation. In some embodiments, the disclosed system may be used independently from a mass spectrometer, or it may be coupled directly or indirectly to a mass spectrometer.

Coated samples made using the disclosed system provide the ability to detect and identify higher numbers of biological compounds present in a particular sample than can be detected without using the disclosed system. In some embodiments, the coated samples made with embodiments of the disclosed system provide mass spectra having increased signal-to-noise ratios as compared with samples prepared using traditional sample preparation techniques. Additionally, the disclosed system can be used with methods that do not require high numbers of repetitive treatment cycles (e.g., spray, incubation, and drying cycles), as are required by current systems (such as the system disclosed by U.S. Pat. No. 7,667,196, which requires the process of nebulization, droplet deposition, and drying be repeated at least 100 times to achieve suitable results). The disclosed system embodiments also are cost effective and convenient for users as they need not require expensive components and/or set-up. The system embodiments are easily installed and can be configured for use separate from, or in conjunction with, a mass spectrometer.

Embodiments of the disclosed system can comprise at least one conductive substrate, with some embodiments comprising at least two conductive substrates. Such substrates can comprise a suitable conductive material. The conductive material can be selected from any conductive material suitable for providing an electric field. In some embodiments, the conductive material can be a metal, such as aluminum, chromium, tin, gold, silver, nickel, copper, palladium, platinum, titanium, or an alloy or combination thereof; a metal oxide, such as indium-tin oxide (ITO), ZnO, $SnO_2$, $In_2O_3$, $TiO_2$, $Fe_2O_3$, $MoSi_2$, $ReO_3$, $RuO_2$, $IrO_2$, and the like; a conductive polymer, such as a polyaniline, a polyfluorene, a polyphenylene, a polypyrene, a polyazulene, a polynaphthalene, a polypyrrole, a polycarbazole, a polyindole, a polyazepine, a polythiophene, poly(3,4-ethylenedioxythiopene), poly(p-phenylene sulfide), or combinations thereof; a carbon nanomaterial, such as carbon nanotubes; or any combination of such conductive materials. In some embodiments, the conductive material can be a single layer or a multi-layered material comprising any one or more of the conductive materials disclosed herein. In an exemplary embodiment, the conductive material is ITO.

In some embodiments, each conductive substrate independently can comprise a thin layer of the conductive material on at least one side of the conductive substrate. In such embodiments, the conductive substrate may be dipped in, adhered to, or spray-coated with the conductive material. In other disclosed embodiments, the conductive substrate independently can be made of, or substantially made of, the conductive material. In some embodiments, the conductive material of each conductive substrate may be the same or different. In an exemplary embodiment, the conductive substrate is a slide comprising a thin layer of ITO substantially coating at least one side of the slide.

In some embodiments, at least two conductive substrates are used in the system and they are positioned opposite one another in a substantially parallel orientation. The two conductive substrates can be positioned so that at least one side of a first conductive substrate comprising a conductive material faces a side of a second conductive substrate comprising a conductive material. The two conductive substrates can be separated by a suitable distance and can be held at such distance using one or more holders, such as a clamp or a receiving slot.

In some embodiments, a suitable distance is any distance that can be used that does not inhibit the formation of an electric field between the two conductive substrates. In particular disclosed embodiments, the two conductive substrates can be positioned opposite one another and separated by a distance of 25 mm to at least 100 mm, such as 25 mm to 75 mm, 30 mm to 60 mm, or 40 mm to 55 mm. In some embodiments, this distance can be measured from the surface of the two sides of the conductive substrates that face one another, from the surface of the biological sample of one conductive substrate to the surface of the conductive material of the other substrate facing the biological sample, from the surfaces of the two substrates that do not face one another, or any combination thereof. In an exemplary embodiment, two conductive substrates can be positioned opposite one another in a parallel orientation, with the side of each conductive substrate comprising the conductive material facing one another, and wherein the two conductive substrates are separated by a distance of 50 mm.

At least one conductive substrate can also comprise a biological sample. In some embodiments, at least one conductive substrate comprises a biological sample, such as a tissue sample (e.g., a fresh tissue sample, a frozen tissue sample, or a fixed tissue sample). The biological sample can be mounted onto the conductive substrate in a frozen state and then allowed to thaw on the conductive substrate. In other disclosed embodiments, the biological sample can be fixed to the conductive substrate using methods known to those of ordinary skill in the art, such as by chemically bonding the biological sample to the conductive substrate. In particular disclosed embodiments, the biological sample can be a tissue sample originating from a subject, such as a human or other mammal. The biological sample can be obtained from a subject for routine screening or from a subject who is suspected of or is suffering from a particular disorder, such as a genetic abnormality, an infection or a neoplasia. In some embodiments, the system can be used to analyze such biological samples, or it can be used to analyze "normal" samples (or control samples) that do not comprise genetic abnormalities, an infection, neoplasia, or the like. Such "normal" samples can be used as controls for comparison to biological samples that are not normal. In some embodiments, the biological samples disclosed herein can be used in a scientific study, for diagnosing a suspected malady, as prognostic indicators for treatment success or survival, for determining biomarkers of disease, or combinations thereof. In an exemplary embodiment, the biological sample is a tissue sample selected from rat brain, porcine adrenal gland, or human prostate, and it is thaw-mounted onto an ITO-containing side of a glass slide.

The system can also comprise a matrix dispersion device. In particular disclosed embodiments, the matrix dispersion device comprises a spray nozzle attached to a bottle or other container comprising a matrix solution. In some embodiments, the matrix dispersion device can comprise any spray nozzle capable of producing a dispersion of matrix droplets and spraying this dispersion into an electric field produced between two conductive substrates. For example, the spray nozzle can be selected from an electronic sprayer or spray nozzle, a pneumatically assisted thin-layer chromatography sprayer, an airbrush sprayer, or any other similar spray apparatus. In an exemplary embodiment, the matrix dispersion device can be a spray nozzle system as described in U.S. Pat. No. 7,667,196, the relevant portion of which is incorporated herein by reference.

The system may further comprise a power source and suitable components for connecting the power source to the conductive substrate. In particular disclosed embodiments, the power source can be a direct current (DC) power supply capable of applying a static voltage to the two conductive substrates so as to form a uniform electric field between the two conductive substrates. In some embodiments, the power source can be a DC power supply capable of providing an electric field having a suitable intensity, such as an intensity of +/−100 V/m to +/−2300 V/m, such as +/−200 V/m to +/−800 V/m+/−400 V/m to +/−700 V/m, or +/−400 V/m to +/−600 V/m. In an exemplary embodiment, the power supply is selected to provide an electric field having an intensity of +600 V/m or −600 V/m.

The selected power source can be connected to the conductive substrates using suitable coupling components, such as one or more metal wires connected to the conductive material (or materials) present on the two conductive substrates. Positive and negative power supply cables can be connected to the power supply. The power supply cables can be attached to the metal wires. In some embodiments, the polarity of the conductive slides can be modified according to the type of mass spectrometric detection mode ultimately used to analyze the biological sample. For example, if a positive ion mode detection method is to be used, the conductive substrate comprising the biological sample can be connected to the positive power supply cable and the oppositely facing conductive substrate can be connected to the negative power supply cable. In other embodiments using negative ion mode detection, the negative power supply cable can be attached to the conductive substrate comprising the biological sample and the positive power supply cable can be attached to the oppositely facing conductive substrate.

Embodiments of the disclosed system can further comprise a housing capable of enclosing the system components described herein. In some embodiments, the housing can substantially or completely enclose the system components. In other embodiments, the house can substantially or completely enclose certain system components, while other components need not be enclosed by the housing. In some embodiments, the housing can comprise one or more openings through which a user can place the conductive substrates into the housing and manipulate the conductive substrates into a suitable configuration as disclosed herein. In particular disclosed embodiments, the housing substantially or completely encloses at least the first and second conductive substrates, the spray nozzle of the matrix dispersion device, the power supply cables, the conductive substrate holders, or any combination thereof.

In some embodiments, the components of the system disclosed herein can be configured to comprise a first conductive substrate associated with a biological sample; a second substrate positioned parallel and opposite to the first conductive substrate, wherein the first and second conductive substrates are separated by a distance of 25 mm to 75 mm; a power source; and a matrix dispersion device capable of dispersing a matrix solution, wherein the matrix dispersion device is separated from the first and second conductive substrates. The term "separated from" as used in this context is understood to mean that the matrix dispersion device does not come into contact with the first and/or second conductive substrate, nor is it fluidly, mechanically, and/or electrically coupled to the first and/or second conductive substrate. In some embodiments, the matrix dispersion device is positioned adjacent to an electric field, such as within 0 to 400 mm, or 1 mm to 300 mm, or 1 mm to 200 mm and between an end terminus of a first conductive substrate and an end terminus of a second conductive substrate. In an independent embodiment, the conductive substrates of the disclosed system are independent of the matrix dispersion device and therefore function independent of the matrix dispersion device.

A particular embodiment of a suitable system configuration is illustrated in FIG. 1A. As illustrated in FIG. 1A, a first conductive substrate 100, which can be associated with a biological sample 102, and a second conductive substrate 104 are positioned parallel and opposite to one another using non-conductive holders 106. An external power supply 108 is connected to the first conductive substrate 100 and the second conductive substrate 104 through metal wires 110 and 112, respectively, and a positive power supply cable 114 and a negative power supply cable 116, which are attached to the metal wires 110 and 112, respectively. In the particular embodiment illustrated in FIG. 1A, the positive power supply cable 114 is electrically coupled to the first conductive substrate 100 to positively charge the first conductive substrate. A negative power supply cable 116 can be electrically coupled to the second conductive substrate 104 to negatively charge the second conductive substrate. This set-up can provide an electric field that flows from the first conductive substrate 100 to the second conductive substrate 104. A matrix dispersion device, such as sprayer 118, also can be provided through which the matrix material can be introduced into the system. Various components of certain embodiments of the system are discussed in more detail below.

Figure 2:
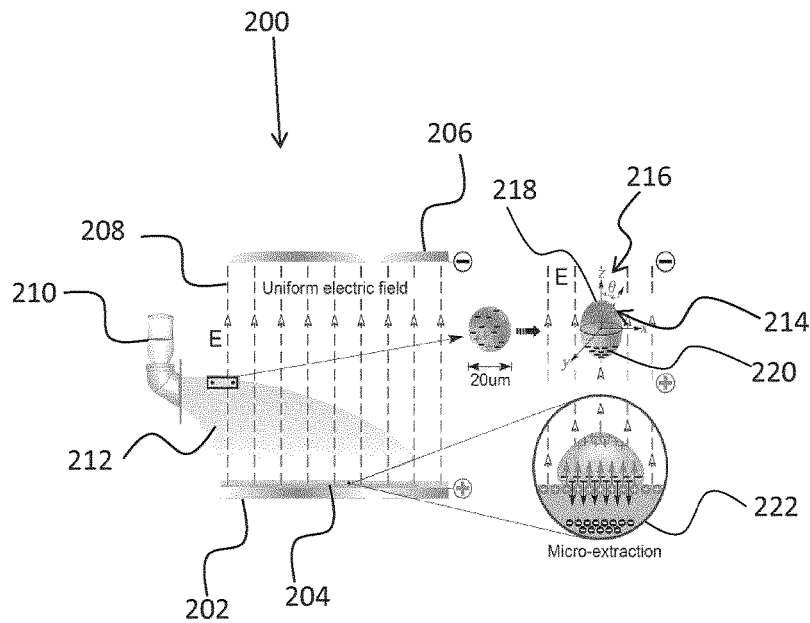
FIG. 2 is a schematic diagram of a disclosed method embodiment for coating a sample.

A schematic illustration of an embodiment of the disclosed system 200 is illustrated in FIG. 2. As illustrated in FIG. 2, a first conductive substrate 202, which can be associated with a biological sample 204, and a second conductive substrate 206 are positioned parallel and opposite to one another. An external power supply (not illustrated) is connected to the first conductive substrate 202 and the second conductive substrate 206 through power supply cables (not illustrated). In the particular embodiment illustrated in FIG. 2, the positive power supply cable is electrically coupled and positively charges the first conductive substrate 202. A negative power supply cable can be electrically coupled to the second conductive substrate 206 to negatively charge the second conductive substrate. This set-up can provide an electric field 208 formed between the first conductive substrate 202 and the second conductive substrate 206. A matrix dispersion device, such as sprayer 210, also can be provided through which the matrix material 212 can be introduced into the system.

III. Method for Preparing Samples

Disclosed herein are embodiments of a method for preparing samples for analysis using mass spectrometry, such as MALDI mass spectrometry. In some embodiments, the disclosed method provides results that are not achieved using traditional sample coating methods. The disclosed methods, for example, provide the ability to detect more species present in biological sample, such as tissue samples, and also provide mass spectra having higher signal-to-noise ratios, than can be obtained using traditional methods known in the art.

The method embodiments disclosed herein can comprise positioning a first conductive substrate at a suitable distance from a second conductive substrate. For example, the first conductive substrate and the second conductive substrate can be positioned apart from one another at a distance ranging from 25 mm to 100 mm, such as 25 mm to 75 mm, 30 mm to 60 mm, or 40 mm to 55 mm. In exemplary embodiments, the two conductive substrates are separated by a distance of 50 mm.

In particular disclosed embodiments, the first conductive substrate and the second conductive substrate can be positioned at any suitable distance disclosed above and are further positioned parallel to one another. In an independent embodiment, the two conductive substrates are positioned at a zero degree angle with respect to one another. In some embodiments, the first conductive substrate can be associated with the biological sample, and in other embodiments, the second conductive substrate can be associated with the biological sample. The two conductive substrates can be positioned in any order. For example, the first conductive substrate can be positioned first, followed by positioning of the second conductive substrate, or the second conductive substrate can be positioned first, followed by positioning of the first conductive substrate.

In some embodiments, the method can further comprise coupling the first conductive substrate and the second conductive substrate to a power source. The conductive substrates can be coupled to the power source using other system components disclosed herein, such as one or more power supply cables and/or metal wires that are coupled to the substrates. In some embodiments, a positive power supply cable can be electrically coupled to a conductive substrate associated with the biological sample and the negative power supply cable can be electrically coupled to a conductive substrate that is not associated with the biological sample. In other embodiments, the power supply cables can be reversed—that is, the negative power supply cable can be electrically coupled to a conductive substrate associated with biological sample and the positive power supply cable can be electrically coupled to a conductive substrate that is not associated with the biological sample. The manner in which the conductive substrates and the power supply cables are electrically coupled can depend on the type of mass spectrometric analysis being conducted.

Method embodiments disclosed herein can further comprise applying an electric field between the first conductive substrate and the second conductive substrate using the power supply cables coupled to the conductive substrates as disclosed above and the power source. In some embodiments, the electric field is a uniform, or substantially uniform, electric field that is produced between the two conductive substrates. The electric field can be oriented in a direction substantially perpendicular to the two conductive substrates, as illustrated in FIG. 2. According to one embodiment illustrated in FIG. 2, the electric field 208 is established between the positively charged conductive substrate 202 (such as the conductive substrate to which a positive power supply cable is coupled) and the negatively charged conductive substrate 206 (such as the conductive substrate to which a negative power supply cable is coupled). In some embodiments, the electric field boundaries can be provided by the conductive substrate boundaries. Solely by way of example, the conductive substrate can be a slide having four edges. In such embodiments, the electric field is limited to the area defined by these four edges. The conductive substrates, however, can have any size or shape and thereby define other areas occupying the electric field.

Figure 1B:
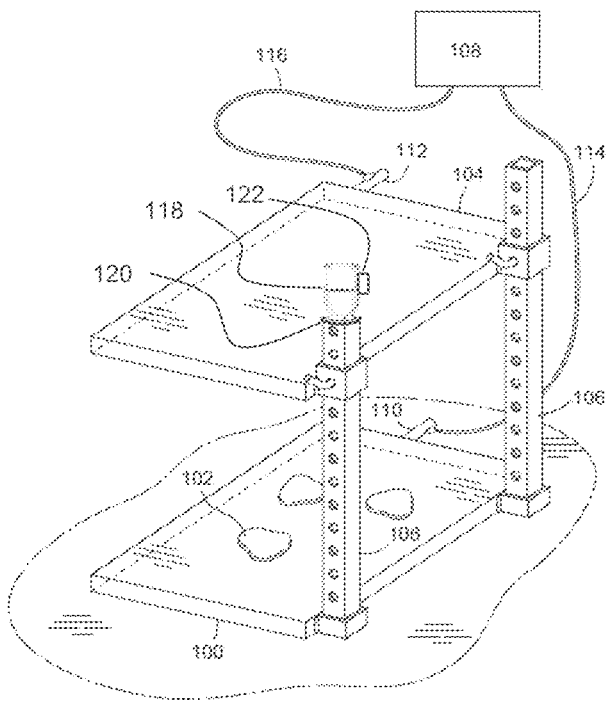

The disclosed method embodiments also can comprise spraying a matrix solution into the electric field generated between the first conductive substrate and the second conductive substrate. In some embodiments, the matrix solution can be sprayed in a direction perpendicular to that of the direction of the electric field. For example, the matrix solution can be sprayed from a matrix dispersion device that is positioned separate from, substantially parallel to, and between the first and second conductive substrates so that the matrix solution is dispersed from the matrix dispersion device into the electric field from a perpendicularly-positioned spray nozzle. An exemplary configuration is illustrated in FIGS. 1 and 2. By spraying the matrix solution into the electric field from a matrix dispersion device that comprises a spray nozzle positioned perpendicular to the electric field, matrix solution droplets can be polarized by the electric field. In an independent embodiment, the matrix solution can be sprayed in a direction parallel to the direction of the electric field and the droplets can similarly be polarized, such as by using the set-up illustrated in FIG. 1B. With reference to FIG. 1B, the conductive substrate that is not associated with the biological sample, such as substrate 104 can be modified to provide an opening 120 through which the matrix dispersion device 118 comprising a dispensing mechanism 122 can be placed thereby providing the ability to introduce the matrix solution into the electric field from a parallel direction.

In some embodiments, one or more treatment cycles can be used. Treatment cycles can comprise spraying the matrix solution, incubating the biological sample with the droplets of matrix solution, and drying the biological sample and the matrix layer associated therewith. Any number of treatment cycles may be used. In some embodiments, one treatment cycle can comprise a spraying step wherein at least one spray of the matrix material is dispersed from the matrix dispersion device. A spray cycle can last for any suitable period. For disclosed working embodiments, the spray cycle typically had a duration of 2 seconds to 4 seconds, with particular embodiments comprising one spray lasting for at least three seconds.

Some embodiments may further comprise an incubation period wherein polarized matrix droplets and the biological sample are allowed to associate with one another, thereby allowing compounds of interest present in the biological sample to electrically associate with the polarized droplets. An incubation period can last for any suitable period of time, such as 30 seconds to 90 seconds, such as 40 seconds to 80 seconds, or 50 seconds to 70 seconds, with particular embodiments using an incubation period of 60 seconds.

Additional method embodiments may further comprise a drying period wherein the biological sample and the matrix layer associated therewith are dried to facilitate subsequent analysis. The drying period can comprise passive or active drying. Passive drying is understood herein to mean drying at an ambient temperature. Active drying is understood herein to mean drying in an ambient temperature, or a temperature above ambient temperature, or a combination thereof, wherein a stream of air or inert gas can be passed over the sample or the sample can be impinged by a stream of flowing air or inert gas. In some embodiments, the drying period lasts for a period of time to provide a suitable dry sample, which in some embodiments was for 60 seconds to 120 seconds, such as 70 seconds to 110 seconds, or 80 seconds to 100 seconds, with particular embodiments lasting for 90 seconds.

In some embodiments, the number of treatment cycles disclosed above may range from 5 to 40, such as 20 to 40, or 25 to 35, or 25 to 30. In another independent embodiment, the number of spraying cycles may range from 40 to 90. In an exemplary embodiment, the number of spraying cycles is 30.

The matrix solution used in the disclosed method can be any matrix solution suitable for analysis using MALDI mass spectrometry. In particular disclosed embodiments, the matrix solution can be selected from quercetin, dithranol, 2-mercaptobenzothiazole (2-MBT), 9-aminoacridine (9-AA), sinapinic acid (SA), 1,5-diaminonaphthalene (DAN), 2,5-dihydroxybenzoic acid (DHB), 2,6-dihydroxyacetophenone (DHA), 4-para-nitroaniline (pNA), 5-nitropyridine (AAN), curcumin, α-cyano-4-hydroxy cinnamic acid (CHCA), 1,8-bis(dimethylamino)naphthalene (DMAN), N-(1-naphthyl)ethylenediamine dihydrochloride (NEDC), or a derivative or combination thereof.

In some embodiments, the electric field intensity that is used in the disclosed method can polarize the matrix droplets sprayed into the electric field generated between the first conductive substrate and the second conductive substrate, as schematically illustrated in FIG. 2. In some embodiments, the matrix droplets can have a diameter ranging from 10 μm to 30 μm, such as 15 μm to 30 μm, or 20 μm to 30 μm. Referring to FIG. 2, solely by way of example, the charge density ($\rho_A$) at a point 214 (x, y, z) on the surface of a single droplet in a uniform electric field can be calculated using Equation 1:

$$\rho_A = 3\varepsilon_0 \varepsilon_r E \cos \theta \quad (1)$$

wherein $\varepsilon_0$ is the vacuum permittivity, which can be 8.8542×10$^{-12}$ F/m; $\varepsilon_r$ is the relative permittivity; E is the electric field intensity; and θ is the angle between $R_A$ (A radius) and the electric field direction (reference number 216, as illustrated in FIG. 2). In some embodiments, $\varepsilon_r$ can be the relative permittivity of nitrogen ($N_2$), such as when the matrix dispersion is performed in a nitrogen atmosphere, and can thus be $\varepsilon_r(N_2)=1.00058$ (at 20° C.). Using this information, the electric field force of point A ($F_A$) can be calculated using Equation 2:

$$F_A = \rho_A E \Delta S_A = 3\varepsilon_0 \varepsilon_r E^2 \Delta S_A \cos \theta \quad (2)$$

wherein $\Delta S_A$ is the unit area occupied by point A. Using Equations 1 and 2, the different $F_A$ values applied to different positions of a spherical droplet can result in in-homogeneous charge distribution on the droplet surface, which can thereby cause droplet elliptical deformation. The maximum charge density appears at both ends of the polar axis (parallel to E) of a droplet (e.g., θ=0° and 180°), but with opposite net charges.

As illustrated in FIG. 2, when the direction of the applied electric field intensity ("E") moves from the positively-charged conductive substrate comprising the biological sample to the negatively-charged conductive substrate that does not comprise the biological sample, the electric potential of the upper portion of a matrix droplet 218 can be higher than that of the lower portion of the droplet 220. In embodiments where the applied electric field moves from a positively-charged conductive substrate that does not comprise the biological sample to a negatively-charged conductive substrate comprising the biological sample, the electric potential of the upper portion of a matrix droplet can be lower than that of the lower portion of the matrix droplet.

In some embodiments, after the matrix solution has been sprayed from the matrix dispersion device, the polarized droplets of matrix solution contact the surface of the biological sample associated with a conductive substrate, and thereby form a matrix layer on the surface of the biological sample. The polarized droplets that form the matrix layer can attract compounds of interest present within the biological sample that are electrically attracted to the charge of the lower portion of the droplet. This electric field-driven process can facilitate the transfer of these compounds from the biological sample into the matrix layer, referred to herein as a micro-extraction process. In some embodiments, this electric field-driven micro-extraction process can occur as soon as a polarized droplet contacts the surface of the biological sample, during the incubation period, during the drying period, or combinations thereof. A schematic illustration of an exemplary embodiment of this process is provided by FIG. 2 (illustrated in expanded view 222).

In embodiments where the matrix droplet comprises an upper portion having a higher electric potential than the lower portion of the matrix droplet, the lower portion of the droplet, which may directly contact the surface of the biological sample, can attract compounds of interest within the biological sample that are, or can be, oppositely charged. In other embodiments, the direction of the electric field can be reversed and thereby cause the lower portion of the matrix droplets to have a higher electric potential, which facilitates extraction of oppositely charged (or chargeable) compounds of interest from the biological sample into the matrix. Each embodiment can thereby result in an electric field-driven micro-extraction capable of enriching the matrix layer in positively or negatively chargeable compounds.

In some embodiments, the electric field-driven, micro-extraction process described above can occur at particular stages during which an electric field is applied. For example, in some embodiments, the electric field can be applied prior to dispersing the matrix solution, at substantially the same time as the matrix solution is dispersed, after the matrix solution is dispersed, or any combination thereof. In some embodiments, the electric field is applied before the matrix solution is dispersed and remains on for the duration of the spraying step and/or any period of time thereafter. The electric field also may be applied at substantially the same time as the matrix solution is sprayed and can remain on for the duration of the spraying step and/or any period of time thereafter. In exemplary embodiments, the electric field can be applied prior to and/or during the time period in which the matrix solution is sprayed, during the time period in which the matrix droplets are incubated with the biological sample, during the time period in which the matrix solution is dried, and any combination thereof.

The disclosed method embodiments can be used to generate higher concentrations of positively or negatively chargeable compounds of interest per unit volume of matrix relative to that obtained from embodiments wherein the disclosed system and/or method are not used. The disclosed systems and methods therefore can enhance the detection of these compounds of interest using positive or negative ion mass spectrometry analysis, such as MALDI MS. In some embodiments, the disclosed method can be used to increase the concentration of positively chargeable compounds of interest (e.g., such as amine-containing compounds or any other compound containing a functional group capable of forming a positive charge) per unit volume of matrix and therefore enhance the detection of these compounds of interest using positive ion MALDI MS. In other embodiments, the disclosed method can be used to increase the concentration of negatively chargeable compounds of interest per unit volume of matrix and therefore enhance the detection of these compounds of interest using negative ion MALDI MS.

In some embodiments, the disclosed method may further comprise analyzing the coated biological sample for one or more compounds of interest present in the biological sample. The compounds of interest can be electrically attracted to the matrix layer via the electric field-driven micro-extraction process described herein, thereby facilitating detection, identification and/or quantification of these compounds using mass spectrometry and/or other analytical techniques.

IV. Uses for Coated Samples

In particular disclosed embodiments, the coated samples prepared using the disclosed system and method can be used to detect one or more compounds of interest, such as biological molecules, exemplified by a biomarker that can indicate the existence of a disease or disorder. The compounds of interest that can be detected using the coated samples obtained from the disclosed system and/or method may be known or newly discovered. In some embodiments, the compound of interest may be a known or newly discovered biomarker that can be used to differentiate between a disease state and a non-disease state. In some embodiments, the biomarkers can be used to clearly differentiate between cancerous and non-cancerous biological samples.

In some embodiments, the compound of interest may be a protein, a lipid, a nucleic acid sequence, or combination thereof. Exemplary proteins can be antigens, such as endogenous antigens, exogenous antigens, autoantigen, a tumor antigen, or any combination thereof. In some embodiments, the protein can be any protein associated with or implicated in a disease, such as, but not limited to, prostate cancer, breast cancer, lung cancer, skin cancer, liver cancer, colon cancer, ovarian cancer, cervical cancer, brain cancer, oral cancer, colorectal cancer, esophageal cancer, pancreatic cancer, or the like. In particular disclosed embodiments, the protein can be selected from Cav-1, ERG, CRP, nm23, p53, c-erbB-2, uPA, VEGF, CEA, CA-125, CYFRA21-1, KRAS, BRCA1, BRCA2, p16, CDKN2B, p14ARF, MYOD1, CDH1, CDH13, RB1, PSA, D52, MEKK2, β-microseminoprotein, and apolipoproteins A-II, apolipoproteins C-I, S100A6, S100A8, and S100A9.

Exemplary lipids include, but are not limited to, fatty acids, glycerolipids, glycerophospholipids, sphingolipids, sterol lipids, prenol lipids, saccharolipids, and polyketides. In some embodiments, the lipid may be a phosphatidylcholine (PC), phosphatidylethanolamine (PE), phosphatidic acids (PA), phosphoglycerol (PG), sphingomyelin (SM), glycoceramide (Gly-Cer), diacylglycerol (DG), or triacylglycerol (TG).

Exemplary nucleic acid sequences can comprise at least 2 to 2000 nucleotides. In some embodiments, nucleic acid sequences that can be detected using the disclosed system and method can be selected from a nucleic acid sequence comprising a genetic aberration, such as a promoter methylation, a single nucleotide polymorphism, a copy number change, a mutation, a particular expression level, a rearrangement, or combinations thereof. In some embodiments, the nucleic acid sequence can be a sequence associated with the EGFR gene, p53, TOP2A, PTEN, ERG, the C-MYC gene, D5S271, the lipoprotein lipase (LPL) gene, RB1, N-MYC, CHOP, FUS, FKHR, ALK, Ig heavy chain, CCND1, BCL2, BCL6, MALF1, AP1, TMPRSS, ETV1, EWS, FLI1, PAX3, PAX7, AKT2, MYCL1, REL, and CSF1R.

In an exemplary embodiment, the compounds of interest can be MEKK2 (having an m/z 4355), apolipoproteins A-II (having an m/z 8705), β-microseminoprotein (having an m/z 10763), tumor protein D52 (having an m/z 12388), PSA (having an m/z 33000 to 34000), as well as species having an m/z 4964, 5002, and/or 6704.

In some embodiments, the disclosed system and method can be used to make coated samples that provide enhanced in situ detection of lipids and proteins that can be used to differentiate between cancerous and non-cancerous regions of a particular biological sample. Any type of biological sample can be analyzed using coated samples made using the disclosed method and system. In an independent embodiment, the biological sample is a human prostate cancer tissue sample.

The coated samples made using the system and method disclosed herein can be used to detect any number of compounds of interest, any number of which can be capable of acting as biomarkers for a particular disease. The coated samples made using the system and method disclosed herein can be used to detect more compounds of interest than can be detected using a control sample, such as a coated sample that is made without using the disclosed method. In some embodiments, the method and system disclosed herein can be used to make coated samples comprising 20 to 200% more compounds of interest in the matrix layer than are present in the matrix of a control sample, such as 40% to 100%, or 50% to 140%. In an exemplary embodiment, the method and system disclosed herein can be used to make coated samples comprising 53 to 134% more compounds of interest in the matrix layer than are present in the matrix of a control sample. In an independent embodiment, the control sample can be a sample that is coated with a matrix solution in the absence of an electric field. In another independent embodiment, the control sample can be a sample that is coated with a matrix solution according to any one of the method embodiments disclosed by U.S. Pat. No. 7,667,196.

Figure 3:
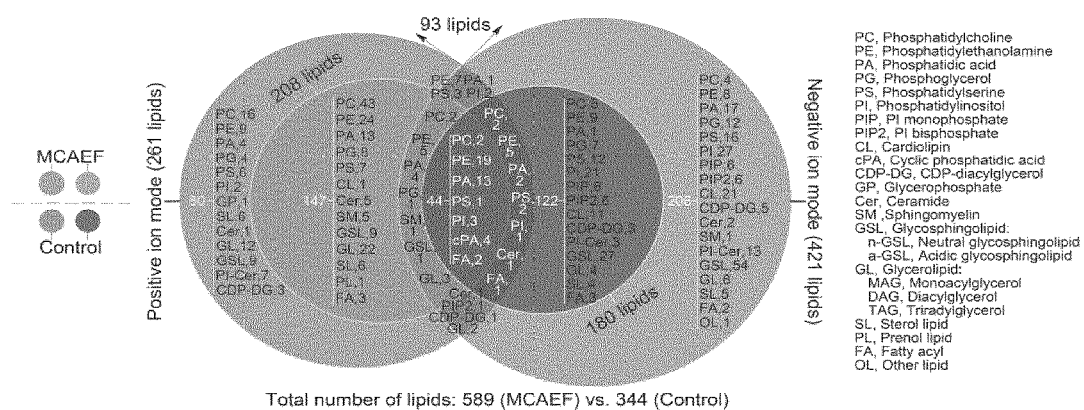
FIG. 3 is a Venn diagram showing the classification of identified compounds of interest using positive (left-most, largest circle) and negative (right-most, largest circle) ion detection.

Solely by way of example, the differences in results obtained from using a coated sample made using the disclosed method and system in comparison to a sample made using a control sample is illustrated in FIG. 3. The information provided by FIG. 3, indicates using the disclosed system and method to prepare coated samples for MALDI MS analysis can result in a significant increase in the number of compounds of interest detected using either a positive ion detection mode or a negative ion detection mode. In some embodiments, the coated samples made using the disclosed method can exhibit an increase in the number of detected compounds of interest ranging from greater than 0 to 99%, such as 1% to 90%, or 10% to 88%, or 30% to 80%. In exemplary embodiments, at least a 50% increase or an 80% increase in the number of the detected compounds of interest can be obtained. In some embodiments, the increase can range from 0 to 60%, such as 10% to 55%, or 10% to 40% when a positive ion detection mode is used. In some embodiments, 0 to 140%, such as 30% to 134%, or 30% to 100% when a negative ion detection mode is used. The disclosed method and system also can be used to make coated samples that provide the ability to detect compounds of interest that cannot be detected in control samples.

In an independent embodiment, which is intended to be exemplary and does not limit the present disclosure, biological sample imaging using positive ion MALDI MS, such as MALDI FTICR MS, of matrix-coated samples made using the disclosed method and system can be used to detect and localize from 300 to 700 compounds of interest, such as 320 to 650, or 400 to 600, any number of which may be uniquely detected in a non-diseased portion of the biological sample and/or a diseased portion of the biological sample. The number and type of compounds detected can vary depending on the type of matrix solution that is used in the method.

In an exemplary embodiment, 367 lipids can be detected, including 72 compounds uniquely detected in a non-cancerous cell region, 34 compounds uniquely detected in the cancerous cell region, and 66 compounds showing significantly different distribution patterns ($p<0.01$) between the two cell regions.

In another exemplary embodiment, 242 peptide and protein signals within the m/z 3500 to 37500 mass range can be detected, with 64 species being uniquely detected in the cancerous cell region and 27 species showing significantly different distribution patterns ($p<0.01$).

The method and system embodiments disclosed herein can be used to make samples for MALDI-MS detection and/or lipidomic and proteomic imaging of clinical tissue samples, such as clinical tissue samples of human prostate cancer, particularly stage II. Using different MALDI matrices for lipid and protein detection, a large number of peptides and proteins can be successfully detected and imaged with positive ion MS detection, with particular embodiments providing the largest groups of lipids and proteins detected in human prostate tissue in a single mass spectroscopic imaging study. Results obtained from using coated biological samples prepared by the disclosed method and system indicate significant changes in both the lipid and protein profiles in the cancer cells as compared to those in the adjacent non-cancerous cells.

V. Working Embodiments

Example 1

Materials and Reagents.

Unless otherwise noted, chemical reagents were purchased from Sigma-Aldrich (St. Louis, Mo.). The "ESI tuning mix" solution was purchased from Agilent Technologies (Santa Clara, Calif.). Rat liver, rat brain, and porcine adrenal gland specimens were purchased from Pel-Freez Biologicals (Rogers, Ark.). According to the accompanying sample information sheet, after harvesting, the tissue specimens were flash-frozen by slow immersion in liquid nitrogen to avoid shattering. The use of the animal organs involved in this study was approved by the Ethics Committee of the University of Victoria.

Tissue Sectioning.

The frozen tissue samples were sectioned to 12-µm slices in a Microm HM500 cryostat (Waldorf, Germany) at −20° C. and thaw mounted onto 25 mm×75 mm conductive ITO coated glass slides obtained from Bruker Daltonics (Bremen, Germany). The slides were then placed under a vacuum of 0.1 psi for 20 minutes before matrix coating. For protein analysis, the tissue sections were washed in Petri dish twice with 70% ethanol for 30 seconds followed by another wash with 95% ethanol for 15 seconds to remove lipids before vacuum drying and matrix coating.

Histological Staining.

Hematoxylin and eosin (H&E) staining was performed based on a previously reported procedure by R. Casadonte and R. M. Caprioli, *Nat. Protoc.*, 2011, 6, 1695-1709, the relevant portion of which is incorporated herein by reference, to obtain histological optical images.

Matrix Coating Assisted by an Electric Field.

MALDI matrix was coated inside a Bruker Daltonics ImagePrep matrix sprayer (Bremen, Germany) with an electronic sprayer. To apply a static electric field to a tissue section during matrix coating, the ITO-coated conductive slide (where the tissue section was mounted) was used as a positive or negative electrode plate. Another ITO-coated blank slide was used as the negative or positive electrode plate, and was placed parallel to and above the tissue-mounted ITO slide, 50 mm apart. The conductive sides of the two electrode plates were placed face-to-face. A voltage-adjustable power supply (Model 1672, B&K Precision Corp., Yorba Linda, Calif.) was used to apply DC voltages to the paired electrode plates through fine metal wires, which were connected to one edge of the conductive side for each of the two slides. The polarity of the tissue-coated slide was dependent on the ion detection mode of the subsequent MALDI-MS analysis. For positive ion MS detection, the tissue mounted slide was used as the positive electrode plate during matrix coating, while for negative ion MS detection the tissue mounted slide was the negative electrode plate during matrix coating.

For matrix coating, quercetin was prepared at a concentration of 2.6 mg/mL in 80:20 methanol:water, both containing 0.1% $NH_4OH$. Dithranol was dissolved in 70:30 acetonitrile (ACN):water, both containing 0.01% trifluoroacetic acid (TFA) to form a saturated matrix solution. 2-mercaptobenzothiazole (2-MBT) was prepared at a concentration of 20 mg/mL in 80:20 methanol:water, both containing 2% formic acid (FA). 9-aminoacridine (9-AA) was prepared at 20 mg/mL in 70:30 ethanol:water (with 0.2% TFA in the final mixture). Sinapinic acid (SA) was prepared at a concentration of 25 mg/mL in 80:20 ACN:water (with 0.2% TFA in the final mixture). The matrix coatings for each of the matrices were composed of a 3-second spray, a 60-second incubation, and a 90-second drying per spray cycle, and thirty cycles were applied to the tissue. The Epson Perfection 4490 Photo Scanner was used for optical images of the tissue section capturing.

MALDI-MS.

Lipids were determined using an Apex-Qe 12-Tesla hybrid quadrupole-Fourier transform ion cyclotron resonance (FTICR) mass spectrometer (Bruker Daltonics, Billerica, Mass.) equipped with an Apollo dual-mode electrospray ionization (ESI)/matrix-assisted laser desorption/ionization (MALDI) ion source. The laser source was a 355 nm solid-state Smartbeam Nd:YAG UV laser (Azura Laser AG, Berlin, Germany) operating at 200 Hz. A 1:200 diluted Agilent "ESI tuning mix" solution prepared in 60:40 isopropyl alcohol:water (with 0.1% FA in the final mixture) was used for tuning and calibration of the FTICR instrument by infusing from the ESI side of the ion source at a flow rate of 2 µL/min, so that each MALDI mass spectrum contained the reference mass peaks for internal mass calibration. Mass spectra were acquired over the mass range from 150 to 2000 Da in both the positive and negative ion modes, with broadband detection and a data acquisition size of 1,024 kilobytes per second. MALDI mass spectra were recorded by accumulating ten scans at 100 laser shots per scan in MALDI-MS profiling experiments.

For tissue imaging, a 200-µm laser raster step size (the minimum possible for the laser source) was used, and four scans (100 laser shots per scan) were summed per array position (i.e., per pixel). For protein profiling and imaging, the mass spectra were collected on an Ultraflex III MALDI time-of-flight (TOF)/TOF mass spectrometer (Bruker Daltonics, Billerica, Mass.), which were equipped with a SmartBeam laser and operated at 200 Hz in the positive and linear mode over a mass range of m/z 3000 to 40000. A laser spot diameter of 100-µm and a raster step size of 50-µm were used for protein imaging. Teaching points were generated to ensure the correct positioning of the laser for spectral acquisition by the use of FlexImaging 2.1 software (Bruker Daltonics, Billerica, Mass.). The collected mass spectra were baseline corrected and intensity normalized by total ion current. A protein standard mixture in the mass range of m/z 5000 to 25000 was used for MALDI-TOF/TOF instrument external calibration, including insulin ($[M+H]^+$, m/z 5734.52), ubiquitin I ($[M+H]^+$, m/z 8565.76), cytochrome c ($[M+H]^+$, m/z 12360.97), myoglobin ($[M+H]^+$, m/z 16953.31), trypsinogen ($[M+H]^+$, m/z 23982.00).

Data Analysis.

Lipid profiling data were viewed and processed using the Bruker DataAnalysis 4.0 software. A customized VBA script was used for batch internal mass calibration, peak de-isotoping, monoisotopic "peak picking", and peak alignment. METLIN and LIPID MAPS metabolome databases, which are incorporated herein by reference, were used for match the measured m/z values to possible metabolite entities, within an allowable mass error of ±1 ppm. Three ion forms ($[M+H]^+$, $[M+Na]^+$, and $[M+K]^+$) were allowed during database searching in the positive ion mode; the $[M-H]^-$, $[M+Na-2H]^-$, $[M+K-2H]^-$, and $[M+Cl]^-$ ion forms were allowed during database searching in the negative ion mode data processing. For protein data analysis, the Bruker FlexAnalysis 3.4 software was employed for protein spectra processing and viewing. A mass window of 0.3% and a signal to noise (S/N) ratio of 3 were selected for peak detection. The Bruker FlexImaging 2.1 software was used to reconstruct the ion maps of both detected lipids and proteins. The PDQuest 2-D Analysis 8.0.1 software (Bio-Rad, Hercules, Calif.) was used to generate 3D maps.

Lipid Extraction and LC/MS/MS.

Total lipids from the same rat brain, which have been subjected to MALDI profiling or imaging, were extracted according to a described protocol by Borchers et al. (*Anal. Chem.,* 2013, 85, 7566-7573 and *Anal. Chem.,* 2014, 86, 638-646), the relevant portion of which is incorporated herein by reference. Briefly, the rat brain tissue (ca. 20 mg) was homogenized in 200 µL of water by a Retsch MM400 mixer mill (Haan, Germany) with the aid of two 5-mm stainless steel balls for 30 seconds×2 at a vibration frequency of 30 Hz. Next, 800 µL of a mixed chloroform-methanol (1:3, v/v) solvent was added, followed by another 30-s homogenization step. Then, the tube was centrifuged at 4000×g and 4° C. for 20 minutes. The supernatants were collected and mixed with 250 µL of chloroform and 100 µL of water. After a short vortex mixing (~15 seconds) and re-centrifugation at 10600×g for 5 minutes, the lower organic phase in each tube was carefully transferred to a new tube using a 200-µL gel loading pipette tip, and then dried in a Savant SPD1010 speed-vacuum concentrator (Thermo Electron Corporation, Waltham, Mass.) and stored at −80° C. until used.

A Waters ACQUITY UPLC system coupled to a Waters Synapt HDMS quadrupole-TOF (Q-TOF) mass spectrometer (Beverly, Mass.) was used as a complementary technique for structural confirmation of most of the detected mass-matched lipid compounds. Briefly, the dried lipid extract residues were re-dissolved in 100 µL of chloroform and 8 µL aliquots were injected onto a Waters Atlantis® HILIC silica column (3 µm particle size, 4.6 mm i.d.×150 mm; Beverly, Mass.) for different lipid specie separations based on their head groups. LC/MS data were collected in both positive and negative ESI modes, with respective injections. MS/MS experiments were conducted using collision-induced dissociation (CID) applied to the trapping collision cell of the Q-TOF instrument. The optimal collision voltages were selected to obtain abundant product ions. UPLC-MS data were processed by the Waters MassLynx software (version 4.1) suite. Lipid identities were assigned by combining mass-matched metabolome database searching against the METLIN database with MS/MS spectral searching against the standard MS/MS libraries in the MET-LIN, HMDB, or LIPID MAPS databases.

Example 1A

In this embodiment, the ability of an electric field to enhance matrix deposition and on-tissue detection was determined. A Bruker ImagePrep electronic sprayer was used to disperse droplets of MALDI matrices. During the entire matrix coating process using the electronic sprayer, a uniform electric field was applied onto tissue sections that were mounted on the conductive side of ITO-coated microscopic glass slides. FIG. 1A provides a digital image of the particular system embodiment used for this particular method. In this embodiment, the tissue-mounted conductive glass slide acted as a positive or negative electrode plate, while a blank slide of the same type was placed in parallel to the tissue-mounted glass slide inside the sprayer chamber as an opposite-polarity electrode plate. The distance between the two slides was set at 50 mm. The conductive sides of the two slides were placed face-to-face. A direct current (DC) power supply was used to apply a static voltage to the two slides so as to form a uniform electric field between the two electrode plates. The polarity on each electrode plate was dependent on the subsequent MS detection mode. For positive ion detection, a DC voltage was applied to the tissue mounted slide, as indicated in the diagram of FIG. 2. For negative ion detection mode, the electrical field direction can be reversed.

In this particular embodiment, a series of 12-μm thick tissue sections prepared from a same rat liver were used and coated with quercetin (a commercially available MALDI matrix for lipidomic MALDI imaging). During the matrix coating, different DC voltages, ranging from 0 to +115 V (equivalent to electric field intensity=0 to 2300 V/m), were applied to the tissue-mounted slides. The quercetin matrix solution was used at a concentration of 2.6 mg/mL prepared in 80:20:0.1 (v/v) methanol:water:$NH_4OH$. After matrix coating using the procedure disclosed in X. Wang, J. Han, A. Chou, J. Yang, J. Pan and C. H. Borchers, *Anal. Chem.*, 2013, 85, 7566-7573, the relevant portion of which is incorporated herein by reference, these tissue sections were subjected to positive ion MALDI-FTICR MS using the same set of instrumental operation parameters. Six randomly selected lipids with different ion intensities, which were detected on the tissue sections, including five phosphatidylcholines (PCs) and one cardiolipin (CL), i.e., [PC(20:4)+Na]$^+$ (m/z 566.322), [PC(20:4)+K]$^+$ (m/z 582.296), [PC(32:0)+K]$^+$ (m/z 772.525), [PC(34:1)+K]$^+$ (m/z 798.541), [PC(38:4)+K]$^+$ (m/z 848.557), and [CL(1'-[18:2/0:0],3'-[18:2/0:0])+K]$^+$ (m/z 963.476), were selected as the representatives for calculation of the S/Ns in order to compare and optimize the applied electric field intensity. Two ions (at m/z 622.029 and 922.010), generated by infusing the Agilent "ESI tuning mix" solution from the ESI side of the ion source during the MALDI acquisitions, were used as the MALDI-process independent internal standards, and the ion at m/z 922.010 was also used for peak intensity normalization.

FIG. 4 shows that the normalized signal-to-noise ratios (S/Ns) of the 6 lipid ions were significantly increased when an electric field was applied, compared to the electric field-free (i.e., electric field intensity=0) matrix coating. In addition, the observed S/Ns were directly proportional to the applied DC voltages and reached a plateau when electric field intensity was between 600-2,300 V/m. No higher electric field intensity was tested because the maximum allowable output voltage of the DC power supply was only 120 V; however, this particular parameter is not intended to be limited to +2300 V/m, as higher values could be achieved by using a power source capable of providing more than 120 V. The mass spectra acquired in positive ion MALDI-FTICR MS from two rat liver sections at electric field intensity=0 (control) and 600 V/m, respectively, are shown in FIGS. 5A and 5B, respectively. At electric field intensity=+600 V/m, signals from the detected compounds showed an overall increase in ion intensity, as compared to the control mass spectrum. Taking the [PC(38:4)+K]$^+$ (m/z 848.557) ion as an example, a ca. 5-fold S/N increase was observed (FIG. 6).

Figure 29A:
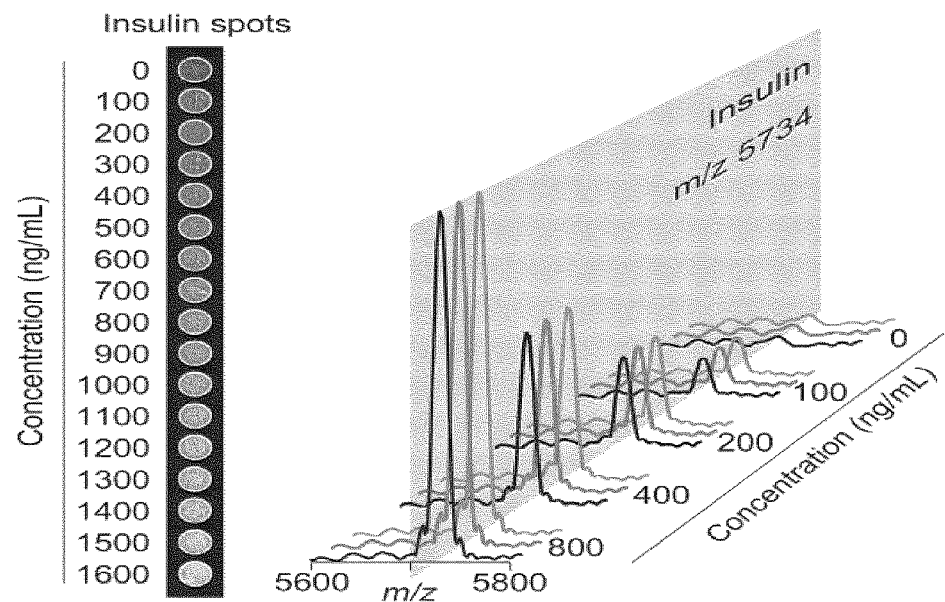
FIGS. 29A-29D illustrate graphical results obtained from analysis of representative samples disclosed herein.
Figure 29B:
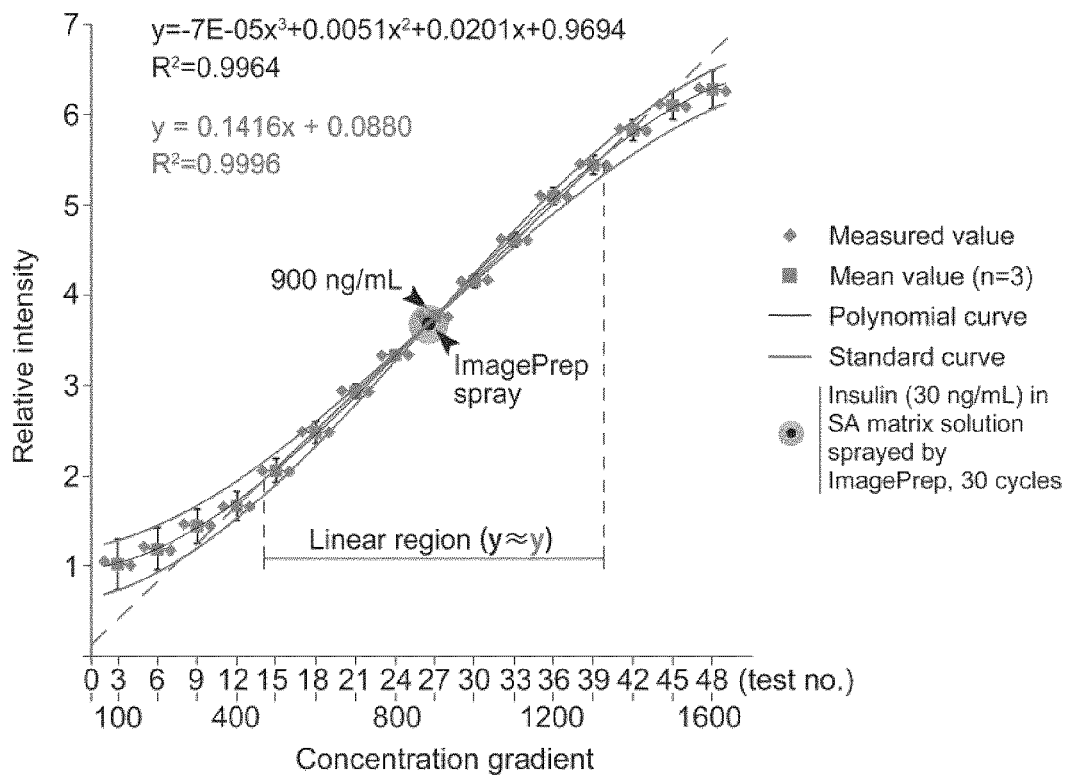
Figures 29C, 29D:
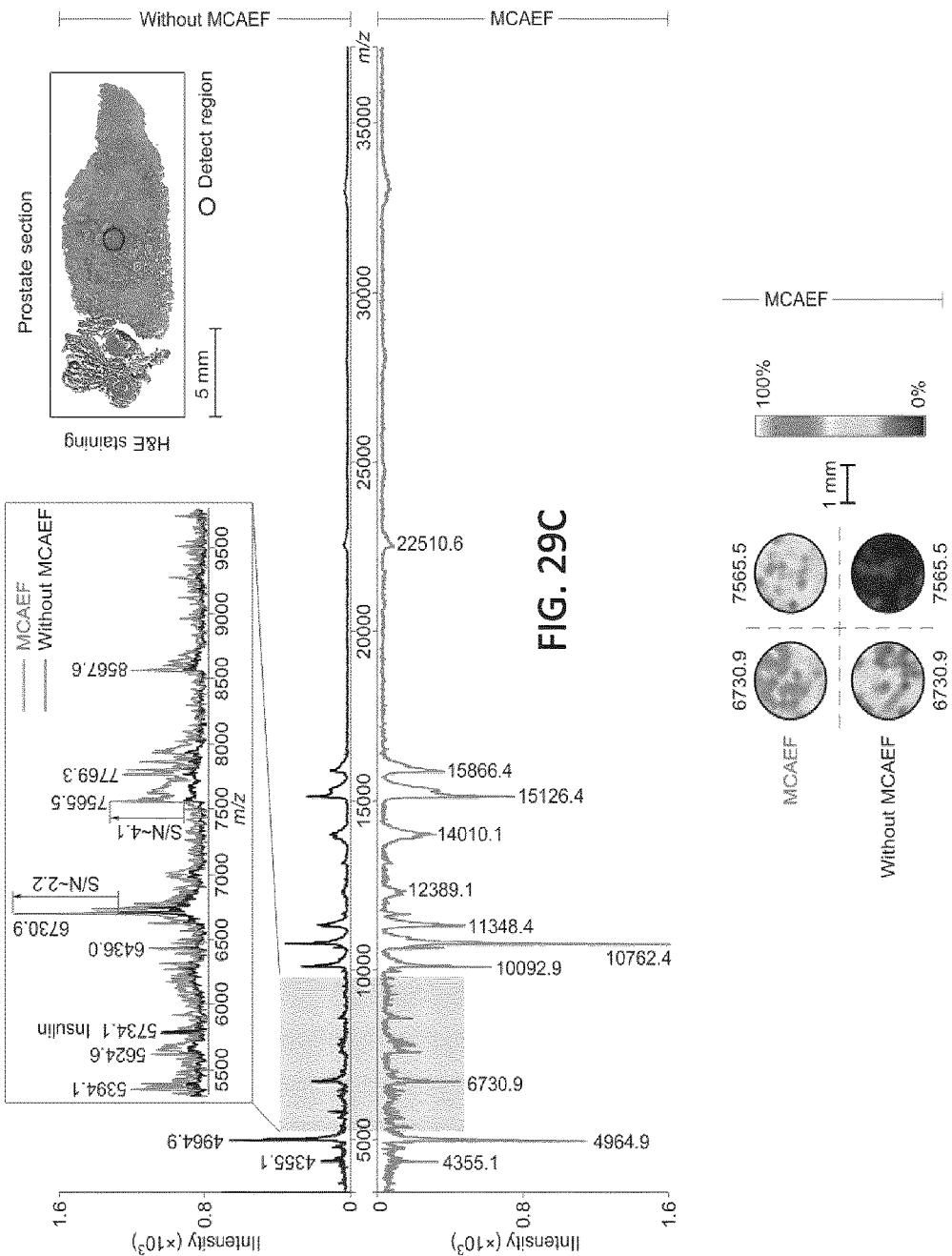

In yet another embodiment, the ability to enhance on-tissue detection was also corroborated using additional prostate tissue sections. FIG. 29C shows two representative accumulated mass spectra acquired by MALDI TOF/TOF MS—with MCAEF (lower) and without MCAEF (upper)—from a cancerous region of a human prostate tissue section. This mirror plot shows that the MCAEF provides enhanced protein detection from clinical tissue sections in the positive ion mode, and also shows that the intensities and signal-to-noise ratios (S/Ns) of the detected proteins on the mass spectra increased when MCAEF was used. The increased detection sensitivity enabled imaging of peptides and proteins across the whole mass detection range, including many higher mass weight (MW) proteins. On average, the use of MCAEF increased the S/Ns of the proteins detected in the tissue sections by a factor of 2 to 5. Taking two protein signals at m/z 6730.9 and 7565.5 as examples, MCAEF produced MALDI-TOF MS S/Ns (inset) which increased by 2.2 and 4.1 fold, respectively. FIG. 29D shows the effect of MCAEF on the images of proteins detected on the prostate tissue sections (see the inset in FIG. 29C for the H&E staining image). Protein images for m/z 6730.9 and 7565.5 from a cancerous region of a prostate tissue section were observed at higher abundance with MCAEF than without MCAEF. MCAEF not only enhances protein detection in clinical tissue by MALDI-MS, but also allowed the imaging of 9 potential biomarkers that had not previously been observed in MALDI tissue imaging.

Example 1B

In this embodiment, the direction of the electric field was reversed and different negative DC voltages were applied to the tissue mounted glass slides to induce migration of the negatively chargeable compounds of interest from the tissue surface into the thin matrix layer, which would lower the detectability of positively charged compounds of interest by positive ion MALDI-MS. As expected, poorer detection of the compounds of interest (dominantly lipids) on these tissue sections was observed in the positive ion mode, as compared to that from the electric field-free tissue section. FIG. 5C shows the mass spectrum acquired from the tissue section with an applied electric field at electric field intensity=−600 V/m. The matrix-related signals dominate this mass spectrum and much weaker lipid signals are observed than those in the mass spectrum acquired with electric field intensity=0.

Example 1C

Figure 7:
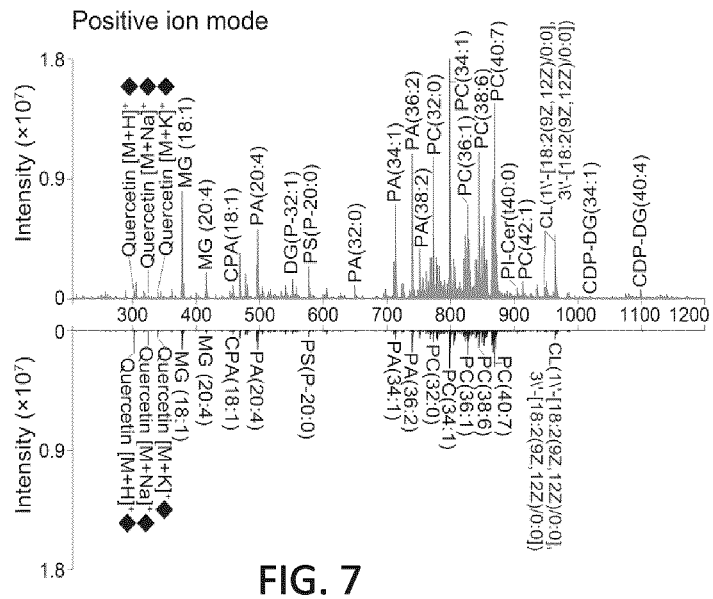
FIG. 7 is a positive ion MALDI-FTICR mass spectrum comparing compound of interest detection in rat brain for control samples (lower half) and samples coated using an embodiment of the disclosed method and system (upper half), wherein quercetin was used as the MALDI matrix.
Figure 8:
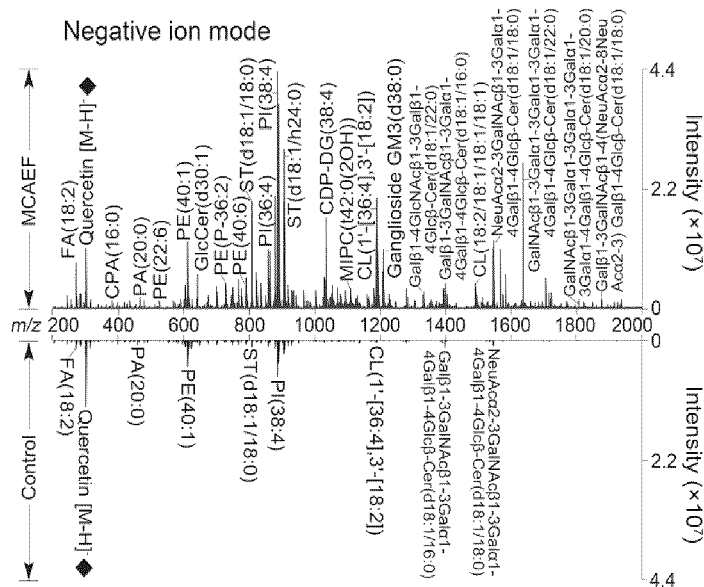
FIG. 8 is a negative ion MALDI-FTICR mass spectrum comparing compound of interest detection in rat brain for control samples (lower half) and samples coated using an embodiment of the disclosed method and system (upper half), wherein quercetin was used as the MALDI matrix.
Figures 9A, 9B:
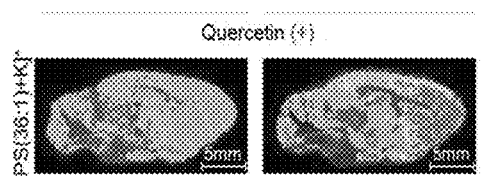
FIGS. 9A-9C are positive ion MALDI-FTICR mass spectra comparing lipid signals across sagittal tissue sections of a rat brain for control samples (FIG. 9A) and matrix-coated samples obtained using an embodiment of the disclosed method and system (FIG. 9B), wherein quercetin was used as the MALDI matrix.
Figures 10A, 10B:
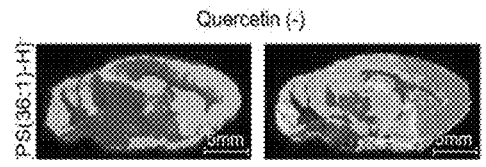
FIGS. 10A-10C are negative ion MALDI-FTICR mass spectra comparing lipid signals across sagittal tissue sections of a rat brain for control samples (FIG. 10A) and matrix-coated samples obtained using an embodiment of the disclosed method and system (FIG. 10B), wherein quercetin was used as the MALDI matrix.
Figure 9C:
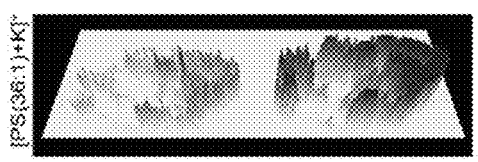
Figure 10C:
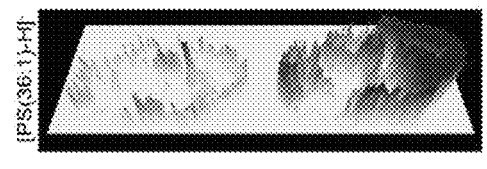
Figures 11A, 11B:
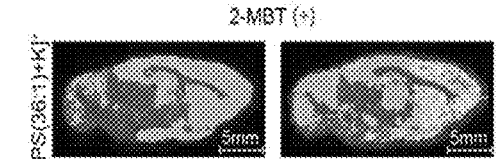
FIGS. 11A-11C are positive ion MALDI-FTICR mass spectra comparing lipid signals across sagittal tissue sections of a rat brain for control samples (FIG. 11A), and matrix-coated samples obtained using an embodiment of the disclosed method and system (FIG. 11B), wherein 2-MBT was used as the MALDI matrix.
Figures 12A, 12B:
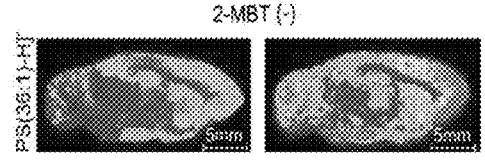
FIGS. 12A-12C are negative ion MALDI-FTICR mass spectra comparing lipid signals across sagittal tissue sections of a rat brain for control samples (FIG. 12A) and matrix-coated samples obtained using an embodiment of the disclosed method and system (FIG. 12B), wherein 2-MBT was used as the MALDI matrix.
Figure 11C:
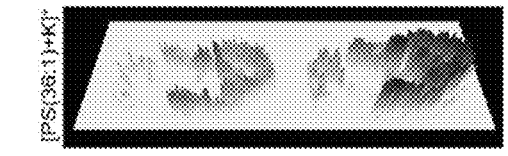
Figure 12C:
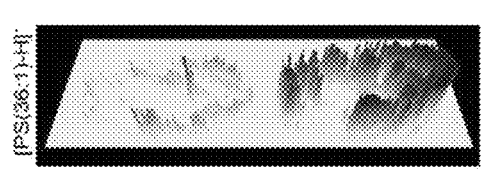
Figures 13A, 13B:
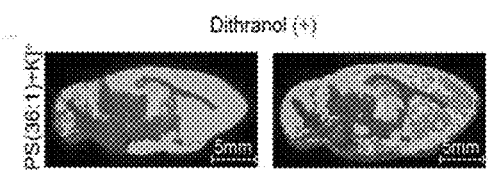
FIGS. 13A-13C are positive ion MALDI-FTICR mass spectra comparing lipid signals across sagittal tissue sections of a rat brain for control samples (FIG. 13A) and matrix-coated samples obtained using an embodiment of the disclosed method and system (FIG. 13B), wherein dithranol was used as the MALDI matrix.
Figures 14A, 14B:
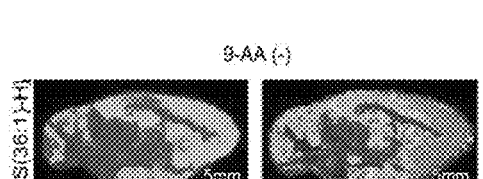
FIGS. 14A-14C are negative ion MALDI-FTICR mass spectra comparing lipid signals across sagittal tissue sections of a rat brain for control samples (FIG. 14A) and matrix-coated samples obtained using an embodiment of the disclosed method and system (FIG. 14B), wherein 9-AA was used as the MALDI matrix.
Figure 13C:
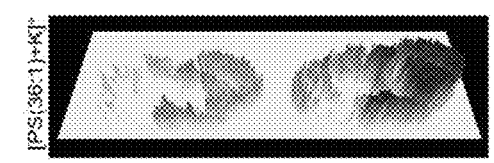
Figure 14C:
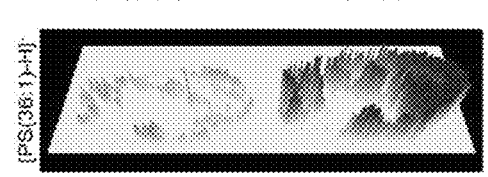
Figure 15A:
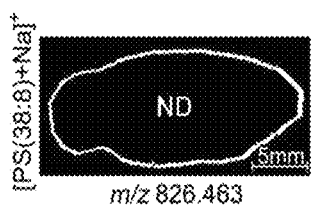
FIGS. 15A-15D are positive ion MALDI-FTICR mass spectra comparing lipid detection of two different lipids on tissue sections of a rat brain for a control sample (FIGS. 15A and 15C) and a matrix-coated sample obtained using an embodiment of the disclosed method and system (FIGS. 15B and 15D), wherein "ND" means the molecules were not detected.
Figure 15B:
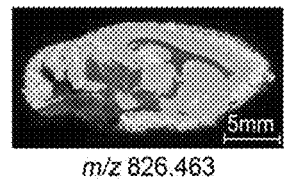
Figure 15C:
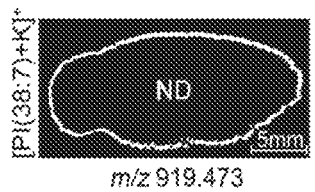
Figure 15D:
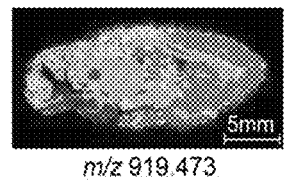
Figure 16A:
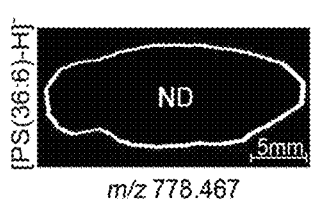
FIGS. 16A-16D are negative ion MALDI-FTICR mass spectra comparing lipid detection of two different lipids on tissue sections of a rat brain for a control sample (FIGS. 16A and 16C) and a matrix-coated sample coated obtained an embodiment of the disclosed method and system (FIGS. 16B and 16D), wherein "ND" means the molecules were not detected in the control.
Figure 16B:
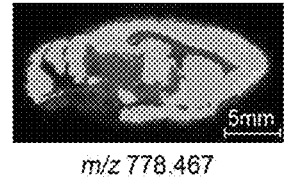
Figure 16C:
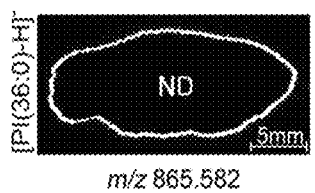
Figure 16D:
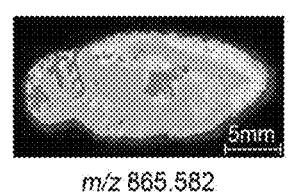
Figure 17A:
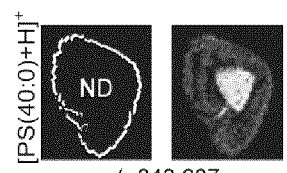
FIGS. 17A-17D are positive ion MALDI-FTICR mass spectra comparing lipid detection of four different lipids on tissue sections of a porcine adrenal gland for a control sample (left-most images of FIGS. 17A-17D) and a matrix-coated sample obtained using an embodiment of the disclosed method and system (right-most images of FIGS. 17A-17D), wherein "ND" means the molecules were not detected in the control embodiments illustrated in FIGS. 17A and 17B.
Figure 17B:
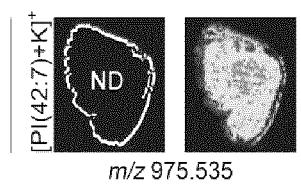
Figure 17C:
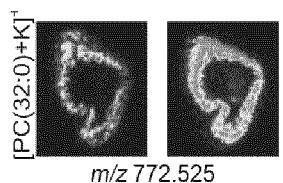
Figure 17D:
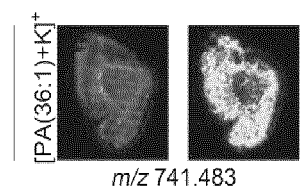
Figure 18A:
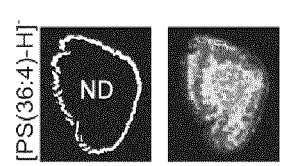
FIGS. 18A-18D are negative ion MALDI-FTICR mass spectra comparing lipid detection of four different lipids on tissue sections of a porcine adrenal gland for a control sample (left-most images of FIGS. 18A-18D) and a matrix-coated sample obtained using an embodiment of the disclosed method and system (right-most images of FIGS. 18A-18D), wherein "ND" means the molecules were not detected in the control embodiments illustrated in FIGS. 18A and 18B.
Figure 18B:
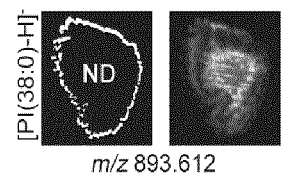
Figure 18C:
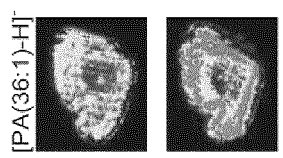
Figure 18D:
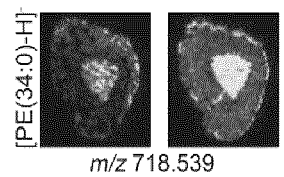

This embodiment considered whether the applied electric field could also be used for improved compound detection on other tissues and with both positive and negative ion detection by MALDI-MS. Mass spectra acquired from rat brain tissue sections in the positive and negative ion modes, with quercetin as the matrix and FTICR MS detection, with and without using disclosed embodiments, are shown in FIGS. 7 and 8, wherein FIG. 7 illustrates results obtained from negative ion mode, and FIG. 8 illustrates results using a positive ion mode. As shown, embodiments using the disclosed method and system significantly increased the lipid ion intensities not only in the positive ion mode but also in the negative ion mode. An electric field intensity of 600 V/m produced a plateau in the normalized S/Ns for rat brain lipid detection in both ion modes, above which no further increase was observed. An average of nearly 5.0- and 3.5-fold ion S/N increases were observed in the positive and negative ion detection modes, respectively, by comparing the upper (electric field intensity=600 V/m) and lower (electric field intensity=0) mass spectra of FIG. 7 and FIG. 8. Lipids detected from rat brains in the positive ion mode were mainly observed in a relatively narrow mass range of m/z 300 to 1000, while the predominant mass range in the negative ion mode for lipid detection was from m/z 200 to 1800.

A total of 589 lipid entities were successfully identified from the mass spectra displayed in the upper part of FIGS. 7 and 8. The identification was made by querying the metabolome databases based on the accurate MW determination or by using LC-MS/MS. The identities of these lipids are listed in Tables 1 and 2 provided below.

TABLE 1

Protein detection on rat brain tissue sections with and without an electric field.

| Protein ion signals (m/z) | Electric Field Applied | No Electric Field Applied |
|---|---|---|
| 3538.352 | ● | ● |
| 3574.169 | ● | ● |
| 3675.470 | ● | ● |
| 3722.314 | ● | ● |
| 3738.275 | ● | ● |
| 3751.462 | ● | ● |
| 3793.420 | ● | ● |
| 3856.084 | ● | ● |
| 3891.754 | ● | ● |
| 4380.737 | ● | ● |
| 4437.497 | ● | ● |
| 4565.023 | ● | ● |
| 4615.971 | ● | ● |
| 4742.510 | ● | ● |
| 4820.043 | ● | ○ |
| 4850.346 | ● | ● |
| 4866.411 | ● | ● |
| 4958.820 | ● | ● |
| 4977.778 | ● | ● |
| 4999.222 | ● | ● |
| 5013.794 | ● | ● |
| 5036.899 | ● | ● |
| 5130.945 | ● | ● |
| 5290.598 | ● | ● |
| 5300.176 | ● | ● |
| 5340.387 | ● | ● |
| 5400.314 | ● | ● |
| 5461.456 | ● | ● |
| 5481.327 | ● | ● |
| 5520.340 | ● | ● |
| 5545.981 | ● | ● |
| 5562.035 | ● | ● |
| 5601.981 | ● | ● |
| 5618.717 | ● | ● |
| 5631.070 | ● | ● |
| 5900.012 | ● | ● |
| 5924.120 | ● | ● |
| 5979.074 | ● | ● |
| 6061.529 | ● | ● |
| 6075.297 | ● | ● |
| 6128.078 | ● | ● |
| 6271.526 | ● | ● |
| 6334.289 | ● | ● |
| 6418.093 | ● | ● |
| 6540.643 | ● | ● |
| 6575.130 | ● | ● |
| 6588.236 | ● | ● |
| 6644.152 | ● | ● |
| 6715.758 | ● | ● |
| 6786.200 | ● | ● |
| 6908.634 | ● | ● |
| 6979.785 | ● | ● |
| 6986.383 | ● | ● |
| 6997.897 | ● | ● |
| 7018.520 | ● | ● |
| 7034.812 | ● | ● |
| 7050.082 | ● | ● |
| 7057.714 | ● | ● |
| 7075.657 | ● | ● |
| 7083.171 | ● | ● |
| 7097.338 | ● | ● |
| 7104.476 | ● | ● |
| 7136.860 | ● | ● |
| 7147.423 | ● | ● |
| 7282.681 | ● | ● |
| 7378.487 | ● | ● |
| 7531.605 | ● | ● |
| 7541.610 | ● | ● |
| 7558.504 | ● | ● |
| 7573.349 | ● | ● |
| 7595.667 | ● | ● |
| 7700.027 | ● | ● |
| 7707.629 | ● | ● |
| 7720.801 | ● | ● |
| 7736.384 | ● | ● |
| 7759.090 | ● | ● |
| 7803.068 | ● | ● |
| 7840.094 | ● | ● |
| 7856.149 | ● | ● |
| 7927.220 | ● | ● |
| 7978.141 | ● | ● |
| 8016.580 | ● | ● |
| 8034.218 | ● | ● |
| 8073.785 | ● | ● |
| 8096.365 | ● | ● |
| 8120.045 | ● | ● |
| 8259.222 | ● | ● |
| 8339.613 | ● | ● |
| 8417.663 | ● | ● |
| 8450.153 | ● | ● |
| 8492.307 | ● | ● |
| 8562.401 | ● | ● |
| 8597.974 | ● | ● |
| 8664.928 | ● | ● |
| 8685.060 | ● | ● |
| 8713.341 | ● | ● |
| 8779.136 | ● | ● |
| 8810.965 | ● | ● |
| 8910.603 | ● | ● |
| 8924.707 | ● | ● |
| 8956.732 | ● | ● |
| 8967.925 | ● | ● |
| 9119.080 | ● | ● |
| 9132.718 | ● | ● |
| 9147.621 | ● | ● |
| 9176.434 | ● | ● |
| 9197.216 | ● | ● |
| 9203.226 | ● | ● |
| 9212.509 | ● | ● |
| 9243.498 | ● | ● |

TABLE 1-continued

Protein detection on rat brain tissue sections with and without an electric field.

| Protein ion signals (m/z) | Electric Field Applied | No Electric Field Applied |
|---|---|---|
| 9300.627 | ● | ● |
| 9503.180 | ● | ● |
| 9559.853 | ● | ● |
| 9663.323 | ● | ● |
| 9935.762 | ● | ● |
| 9976.006 | ● | ● |
| 10013.503 | ● | ● |
| 10198.138 | ● | ● |
| 10253.751 | ● | ● |
| 10370.585 | ● | ● |
| 10590.128 | ● | ● |
| 10607.870 | ● | ● |
| 10652.622 | ● | ● |
| 11078.268 | ● | ● |
| 11537.309 | ● | ● |
| 11963.735 | ● | ● |
| 12062.151 | ● | ● |
| 12130.072 | ● | ● |
| 12146.023 | ● | ● |
| 12163.804 | ● | ● |
| 12260.307 | ● | ● |
| 12291.298 | ● | ● |
| 12308.046 | ● | ● |
| 12327.349 | ● | ● |
| 12351.911 | ● | ● |
| 12367.192 | ● | ● |
| 12410.538 | ● | ● |
| 12434.191 | ● | ● |
| 13421.223 | ● | ● |
| 13466.899 | ● | ● |
| 13575.922 | ● | ● |
| 13789.797 | ● | ● |
| 13810.681 | ● | ● |
| 13820.738 | ● | ● |
| 13965.553 | ● | ● |
| 14003.416 | ● | ● |
| 14045.600 | ● | ● |
| 14121.058 | ● | ● |
| 14200.535 | ● | ● |
| 14235.549 | ● | ● |
| 14281.724 | ● | ● |
| 14328.400 | ● | ● |
| 14344.060 | ● | ● |
| 14393.459 | ● | ● |
| 14405.635 | ● | ● |
| 14973.410 | ● | ● |
| 15110.357 | ● | ● |
| 15152.184 | ● | ● |
| 15176.696 | ● | ● |
| 15195.367 | ● | ● |
| 15234.664 | ● | ● |
| 15268.705 | ● | ● |
| 15357.507 | ● | ● |
| 15399.658 | ● | ● |
| 15404.119 | ● | ● |
| 15418.693 | ● | ● |
| 15432.976 | ● | ● |
| 15820.416 | ● | ● |
| 15824.612 | ● | ● |
| 15852.240 | ● | ● |
| 15856.325 | ● | ● |
| 15875.164 | ● | ● |
| 15896.496 | ● | ● |
| 15900.631 | ● | ● |
| 15954.978 | ● | ● |
| 15967.970 | ● | ● |
| 16050.173 | ● | ● |
| 16107.413 | ● | ● |
| 16152.177 | ● | ● |
| 16190.145 | ● | ● |
| 16234.994 | ● | ● |
| 16253.407 | ● | ● |
| 16263.852 | ● | ● |
| 17089.323 | ● | ● |
| 17115.000 | ● | ● |
| 17144.049 | ● | ● |
| 17164.463 | ● | ● |
| 17207.265 | ● | ● |
| 17222.162 | ● | ● |
| 17259.827 | ● | ● |
| 17274.848 | ● | ● |
| 17334.371 | ● | ● |
| 17351.926 | ● | ● |
| 17371.440 | ● | ● |
| 17390.883 | ● | ● |
| 17412.142 | ● | ● |
| 17424.799 | ● | ● |
| 17452.507 | ● | ● |
| 18061.367 | ● | ● |
| 18083.002 | ● | ● |
| 18164.265 | ● | ● |
| 18185.156 | ● | ● |
| 18207.188 | ● | ● |
| 18237.883 | ● | ● |
| 18261.518 | ● | ● |
| 18319.127 | ● | ● |
| 18342.382 | ● | ● |
| 18400.232 | ● | ● |
| 18477.136 | ● | ● |
| 18489.507 | ● | ● |
| 18521.405 | ● | ● |
| 18604.993 | ● | ● |
| 19825.509 | ● | ● |
| 21415.798 | ● | ● |
| 21491.756 | ● | ● |
| 21641.791 | ● | ● |
| 21802.218 | ● | ● |
| 21891.382 | ● | ● |
| 23365.121 | ● | ● |
| 24607.516 | ● | ● |
| 24755.332 | ● | ● |
| 25520.125 | ● | ● |
| 26154.601 | ● | ● |
| 28246.062 | ● | ● |
| 28408.456 | ● | ● |
| 28735.535 | ● | ● |
| 29216.082 | ● | ● |
| 30355.263 | ● | ● |
| 31243.892 | ● | ● |
| 32493.131 | ● | ● |
| 35507.497 | ● | ● |
| 36731.709 | ● | ● |
| Total number of proteins/peptides | 232 | 119 |

TABLE 2

Comparison of lipid detection on rat brain sections by MALDI-FTICR MS in the positive ion mode with and without an electric field and standard spray methods for quercetin coating, respectively.

| Classification | No. | Measured m/z Electric Field | Measured m/z No Electric Field | Calculated m/z | Error (ppm) Electric Field | Error (ppm) No Electric Field | Ion form | Assignment Compound | Molecular formula | Structurally specific CID ions (m/z)[a] |
|---|---|---|---|---|---|---|---|---|---|---|
| Glycerophospholipids | | | | | | | | | | |
| Phosphatidylcholines (PCs) | 1 | 478.32944 | 478.32921 | 478.32920 | 0.50 | 0.02 | [M + H]+ | PC(O-16:2) | C24H48NO6P | |
| | | 500.31143 | 500.31090 | 500.31115 | -0.56 | 0.50 | [M + Na]+ | | | |
| | | 516.28531 | 516.28499 | 516.28508 | 0.45 | -0.17 | [M + K]+ | | | |
| | 2 | 502.32660 | — | 502.32680 | -0.40 | — | [M + Na]+ | PC(O-16:1) | C24H50NO6P | |
| | | 518.30102 | 518.30067 | 518.30073 | 0.56 | -0.12 | [M + K]+ | | | |
| | 3 | 496.33958 | 496.33925 | 496.33977 | -0.38 | 0.06 | [M + H]+ | PC(16:0) | C24H50NO7P | 104, 184, 478, 496 |
| | | 534.29588 | 534.29559 | 534.29565 | 0.43 | -0.11 | [M + K]+ | | | |
| | 4 | 504.34249 | — | 504.34245 | 0.08 | — | [M + H]+ | PC(O-16:0) | C26H52NO6P | |
| | 5 | 516.30896 | 516.30887 | 516.30847 | 0.95 | 0.77 | [M + Na]+ | PC(18:4) | C26H46NO7P | |
| | 6 | 518.32450 | — | 518.32412 | 0.73 | — | [M + H]+ | PC(18:3) | C26H48NO7P | |
| | 7 | 506.36069 | 506.36056 | 506.36050 | 0.38 | 0.12 | [M + H]+ | PC(P-18:1) | C26H52NO6P | |
| | 8 | 528.34262 | 528.34236 | 528.34245 | 0.32 | -0.17 | [M + Na]+ | PC(O-18:2) | C26H52NO6P | |
| | | 544.31646 | 544.31639 | 544.31638 | 0.15 | 0.02 | [M + K]+ | | | |
| | 9 | 522.35543 | — | 522.35542 | 0.02 | — | [M + H]+ | PC(18:1) | C26H52NO7P | 104, 184, 504, 522 |
| | 10 | 560.31143 | 560.31123 | 560.31130 | 0.23 | -0.12 | [M + K]+ | | | |
| | | 524.37155 | 524.37117 | 524.37107 | 0.92 | 0.19 | [M + H]+ | PC(18:0) | C26H54NO7P | 104, 184, 506, 524 |
| | 11 | 562.32725 | 562.32677 | 562.32695 | 0.53 | -0.32 | [M + K]+ | | | |
| | | 544.33975 | 544.33970 | 544.33977 | -0.04 | -0.13 | [M + H]+ | PC(20:4) | C28H50NO7P | 104, 184, 526, 544 |
| | 12 | 582.29603 | — | 582.29565 | 0.65 | — | [M + K]+ | | | |
| | 13 | 546.35543 | — | 546.35542 | 0.02 | — | [M + H]+ | PC(20:3) | C28H52NO7P | |
| | | 548.37134 | 548.37142 | 548.37107 | 0.49 | 0.64 | [M + H]+ | PC(20:2) | C28H54NO7P | |
| | | 586.32721 | 586.32713 | 586.32695 | 0.44 | 0.31 | [M + K]+ | | | |
| | 14 | 602.32135 | 602.32227 | 602.32186 | -0.85 | 0.68 | [M + K]+ | PC(20:1) | C28H54NO8P | |
| | 15 | 604.33734 | 604.33764 | 604.33751 | -0.28 | 0.22 | [M + K]+ | PC(20:0) | C28H56NO8P | |
| | 16 | 606.29509 | 606.29527 | 606.29565 | -0.92 | -0.63 | [M + K]+ | PC(22:6) | C30H50NO7P | |
| | 17 | 608.31094 | — | 608.31130 | -0.59 | — | [M + K]+ | LysoPC(22:5) | C30H52NO7P | |
| | 18 | 610.32647 | 610.32706 | 610.32695 | -0.79 | 0.18 | [M + K]+ | PC(22:4) | C30H54NO7P | |
| | 19 | 614.35804 | 614.35835 | 614.35825 | -0.34 | 0.16 | [M + K]+ | PC(22:2) | C30H58NO7P | |
| | 20 | 616.37402 | 616.37398 | 616.37390 | 0.19 | 0.13 | [M + K]+ | PC(22:1) | C30H60NO7P | |
| | 21 | 618.38923 | 618.38967 | 618.38955 | -0.52 | 0.19 | [M + K]+ | PC(22:0) | C30H62NO7P | |
| | 22 | 644.40554 | 644.40537 | 644.40520 | 0.53 | 0.26 | [M + K]+ | LysoPC(24:1) | C32H64NO7P | |
| | 23 | 646.42107 | 646.42079 | 646.42085 | 0.34 | -0.09 | [M + K]+ | PC(24:0) | C32H66NO7P | |
| | 24 | 648.43642 | 648.43664 | 648.43650 | -0.12 | 0.22 | [M + K]+ | LysoPC(26:1) | C32H68NO7P | |
| | 25 | 650.45257 | 650.45234 | 650.45215 | 0.65 | 0.29 | [M + K]+ | LysoPC(26:0) | C32H70NO7P | |
| | 26 | 704.52283 | 704.52246 | 704.52248 | 0.50 | -0.03 | [M + H]+ | PC(30:1) | C38H74NO7P | |
| | 27 | 744.49463 | 744.49457 | 744.49401 | 0.83 | 0.75 | [M + K]+ | PC(30:0) | C38H76NO8P | |
| | 28 | 766.47843 | 766.47811 | 766.47836 | 0.09 | -0.33 | [M + K]+ | PC(32:3) | C40H74NO8P | 104, 184, 476, 732 |
| | 29 | 770.51011 | 770.50981 | 770.50966 | 0.58 | 0.19 | [M + K]+ | PC(32:1) | C40H78NO8P | |
| | 30 | 734.57001 | 734.56974 | 734.56943 | 0.79 | 0.42 | [M + H]+ | PC(32:0) | C40H80NO8P | 104, 147, 163, 184, 478, 735 |
| | | 756.55118 | 756.55161 | 756.55138 | -0.26 | 0.30 | [M + Na]+ | | | |
| | | 772.52504 | 772.52537 | 772.52531 | -0.35 | 0.08 | [M + K]+ | | | |
| | 31 | 790.47857 | 790.47818 | 790.47836 | 0.27 | -0.23 | [M + K]+ | PC(34:5) | C42H74NO8P | |

TABLE 2-continued

Comparison of lipid detection on rat brain sections by MALDI-FTICR MS in the positive ion mode with and without an electric field and standard spray methods for quercetin coating, respectively.

| Classification | No. | Measured m/z Electric Field | Measured m/z No Electric Field | Calculated m/z | Error (ppm) Electric Field | Error (ppm) No Electric Field | Ion form | Assignment Compound | Molecular formula | Structurally specific CID ions (m/z)[a] |
|---|---|---|---|---|---|---|---|---|---|---|
| | 32 | 792.49424 | 792.49398 | 792.49401 | 0.29 | −0.04 | [M + K]+ | PC(34:4) | C42H76NO8P | |
| | 33 | 794.50967 | — | 794.50966 | 0.38 | −0.01 | [M + K]+ | PC(34:3) | C42H78NO8P | |
| | 34 | 796.52530 | — | 796.52531 | 0.90 | −0.01 | [M + K]+ | PC(34:2) | C42H80NO8P | 184, 758 |
| | 35 | 760.58475 | 760.58524 | 760.58508 | −0.43 | 0.21 | [M + H]+ | PC(34:1) | C42H82NO8P | 86, 184, 577, 701, 761 |
| | | 782.56690 | 782.56776 | 782.56703 | −0.17 | 0.93 | [M + Na]+ | | | |
| | | 798.54062 | 798.54057 | 798.54096 | −0.43 | −0.49 | [M + K]+ | | | |
| | 36 | 762.60067 | — | 762.60073 | −0.08 | — | [M + H]+ | PC(34:0) | C42H84NO8P | 163, 184, 762 |
| | | 784.58279 | — | 784.58268 | 0.14 | — | [M + Na]+ | | | |
| | | 800.55681 | — | 800.55661 | 0.25 | — | [M + K]+ | | | |
| | 37 | 804.55102 | — | 804.55138 | −0.45 | — | [M + Na]+ | PC(36:4) | C44H80NO8P | 184, 783 |
| | 38 | 820.52564 | 820.52528 | 820.52531 | 0.40 | −0.04 | [M + K]+ | PC(36:3) | C44H82NO8P | 184, 785 |
| | 39 | 822.54083 | — | 822.54096 | −0.16 | — | [M + K]+ | PC(36:3) | C44H84NO6P | 184, 754 |
| | | 792.56609 | 792.56663 | 792.56678 | −0.87 | −0.19 | [M + K]+ | 1-hexadecanyl-2-(8-[3]-ladderane-octanyl)-sn-glycerophosphocholine | | |
| | 40 | 808.58219 | 808.58242 | 808.58268 | −0.61 | −0.32 | [M + Na]+ | PC(36:2) | C44H84NO8P | 184, 787 |
| | 41 | 824.55651 | 824.55618 | 824.55661 | −0.12 | −0.52 | [M + K]+ | PC(P-36:1) | C44H86NO7P | |
| | 42 | 810.57727 | — | 810.57735 | −0.10 | — | [M + H]+ | PC(36:1) | C44H86NO8P | 184, 789 |
| | | 788.61632 | — | 788.61638 | −0.08 | — | [M + H]+ | | | |
| | 43 | 826.57280 | 826.57220 | 826.57226 | 0.65 | −0.07 | [M + K]+ | PC(36:0) | C44H88NO8P | |
| | 44 | 828.58799 | 828.58806 | 828.58791 | 0.10 | 0.18 | [M + H]+ | 1-(6-[5]-ladderane-hexanoyl)-2-(8-[3]-ladderane-octanyl)-sn-glycerophosphocholine | C46H76NO7P | |
| | | 786.54364 | 786.54376 | 786.54322 | 0.53 | 0.69 | | | | |
| | 45 | 844.52562 | 844.52571 | 844.52531 | 0.37 | 0.47 | [M + K]+ | PC(38:6) | C46H80NO8P | 184, 627, 750, 809 |
| | 46 | 846.54098 | 846.54121 | 846.54096 | 0.02 | 0.30 | [M + K]+ | PC(38:5) | C46H82NO8P | 184, 627, 752, 811 |
| | 47 | 810.60115 | 810.60045 | 810.60073 | 0.52 | −0.35 | [M + H]+ | PC(38:4) | C46H84NO8P | |
| | | 832.58253 | 832.58284 | 832.58268 | −0.18 | 0.19 | [M + Na]+ | | | |
| | | 848.55675 | 848.55723 | 848.55661 | 0.16 | 0.73 | [M + K]+ | | | |
| | 48 | 850.57247 | 850.57524 | 850.57226 | 0.25 | −0.02 | [M + K]+ | PC(38:3) | C46H86NO8P | |
| | 49 | 854.60371 | 854.60387 | 854.60356 | 0.18 | 0.36 | [M + K]+ | PC(38:1) | C46H90NO8P | |
| | 50 | 840.62426 | — | 840.62430 | −0.05 | — | M + K]+ | PC(P-38:0) | C46H92NO7P | |
| | 51 | 856.61945 | 856.61947 | 856.61921 | 0.28 | 0.30 | M + K]+ | PC(38:0) | C46H92NO8P | |
| | 52 | 864.49419 | — | 864.49401 | 0.21 | — | [M + K]+ | PC(40:10) | C48H76NO8P | |
| | 53 | 866.50959 | — | 866.50966 | −0.08 | — | [M + K]+ | PC(40:9) | C48H78NO8P | |
| | 54 | 852.53071 | — | 852.53040 | 0.36 | — | [M + K]+ | 1-(8-[5]-ladderane-octanoyl)-2-(8-[3]-ladderane-octanoyl)-sn-glycerophosphocholine | C48H80NO7P | |
| | 55 | 870.54027 | 870.54121 | 870.54096 | −0.79 | 0.29 | [M + K]+ | PC(40:7) | C48H82NO8P | |
| | 56 | 856.58277 | 856.58214 | 856.58268 | 0.11 | −0.63 | [M + Na]+ | PC(40:6) | C48H84NO8P | 86, 184, 776, 834 |
| | 57 | 872.55643 | 872.55660 | 872.55661 | −0.21 | −0.01 | [M + K]+ | PC(40:5) | C48H86NO8P | |
| | 58 | 874.57191 | 874.57235 | 874.57226 | −0.40 | 0.10 | [M + K]+ | PC(40:4) | C48H88NO8P | 86, 184, 778, 836 |
| | 59 | 876.58767 | 876.58740 | 876.58791 | −0.27 | −0.58 | [M + K]+ | PC(40:3) | C48H90NO8P | 86, 184, 780, 838 |
| | | 880.61923 | — | 880.61921 | 0.02 | — | | PC(40:2) | C48H92NO8P | |

TABLE 2-continued

Comparison of lipid detection on rat brain sections by MALDI-FTICR MS in the positive ion mode with and without an electric field and standard spray methods for quercetin coating, respectively.

| Classification | No. | Measured m/z Electric Field | Measured m/z No Electric Field | Calculated m/z | Error (ppm) Electric Field | Error (ppm) No Electric Field | Ion form | Assignment Compound | Assignment Molecular formula | Structurally specific CID ions (m/z)[a] |
|---|---|---|---|---|---|---|---|---|---|---|
| | 60 | 882.63453 | 882.63526 | 882.63486 | −0.37 | 0.45 | [M + K]$^+$ | PC(40:1) | C$_{48}$H$_{94}$NO$_8$P | |
| | 61 | 906.63465 | 906.63497 | 906.63486 | −0.23 | 0.12 | [M + K]$^+$ | PC(42:3) | C$_{50}$H$_{94}$NO$_8$P | |
| | 62 | 908.65023 | — | 908.65051 | −0.31 | — | [M + K]$^+$ | PC(42:2) | C$_{50}$H$_{96}$NO$_8$P | |
| | 63 | 910.66639 | — | 910.66616 | 0.25 | — | [M + K]$^+$ | PC(42:1) | C$_{50}$H$_{98}$NO$_8$P | |
| | 64 | 936.68227 | — | 936.68181 | 0.49 | — | [M + K]$^+$ | PC(44:2) | C$_{52}$H$_{100}$NO$_8$P | |
| | 65 | 956.65043 | — | 956.65051 | −0.08 | — | [M + K]$^+$ | PC(46:6) | C$_{54}$H$_{96}$NO$_8$P | |
| Phosphatidylethanolamines (PEs) | 1 | 476.25387 | 476.25392 | 476.25378 | 0.19 | 0.29 | [M + K]$^+$ | PE(P-16:0) | C$_{21}$H$_{44}$NO$_6$P | |
| | 2 | 490.23327 | 490.23326 | 490.23305 | 0.45 | 0.43 | [M + K]$^+$ | PE(16:1) | C$_{21}$H$_{42}$NO$_7$P | |
| | 3 | 492.24870 | — | 492.24870 | 0.00 | — | [M + K]$^+$ | PE(16:0) | C$_{21}$H$_{44}$NO$_7$P | |
| | 4 | 514.23314 | 514.23336 | 514.23305 | 0.18 | 0.60 | [M + K]$^+$ | PE(18:3) | C$_{23}$H$_{42}$NO$_7$P | |
| | 5 | 516.24847 | 516.24887 | 516.24870 | −0.45 | 0.33 | [M + K]$^+$ | PE(18:2) | C$_{23}$H$_{44}$NO$_7$P | 155, 265, 308, 339, 462, 480 |
| | 6 | 518.26421 | 518.26456 | 518.26435 | −0.27 | 0.41 | [M + K]$^+$ | PE(18:1) | C$_{23}$H$_{46}$NO$_7$P | 267, 403, 462 |
| | 7 | 504.28529 | 504.28536 | 504.28508 | 0.41 | 056 | [M + K]$^+$ | PE(P-18:0) | C$_{23}$H$_{48}$NO$_6$P | 140, 153, 196, 214, 283, 419, 437, 480 |
| | 8 | 520.28006 | 520.28034 | 520.28000 | 0.12 | 0.65 | [M + K]$^+$ | PE(18:0) | C$_{23}$H$_{48}$NO$_7$P | 153, 195, 259, 303, 439, 500 |
| | 9 | 540.24891 | — | 540.24870 | 0.39 | — | [M + K]$^+$ | PE(20:4) | C$_{25}$H$_{44}$NO$_7$P | |
| | 10 | 542.26438 | — | 542.26435 | 0.06 | — | [M + K]$^+$ | PE(20:3) | C$_{25}$H$_{46}$NO$_7$P | |
| | 11 | 544.28009 | 544.27983 | 544.28000 | 0.17 | −0.31 | [M + K]$^+$ | PE(20:2) | C$_{25}$H$_{48}$NO$_7$P | |
| | 12 | 546.29566 | 546.29528 | 546.29565 | 0.02 | −0.68 | [M + K]$^+$ | PE(20:1) | C$_{25}$H$_{50}$NO$_7$P | |
| | 13 | 510.35562 | 510.35532 | 510.35542 | 0.39 | −0.20 | [M + H]$^+$ | PE(20:0) | C$_{25}$H$_{52}$NO$_7$P | |
| | | 548.31180 | | 548.31130 | 0.91 | | | | | |
| | 14 | 564.24874 | 564.24855 | 564.24870 | 0.07 | −0.27 | [M + K]$^+$ | PE(22:6) | C$_{27}$H$_{44}$NO$_7$P | |
| | 15 | 568.27959 | 568.28031 | 568.28000 | −0.72 | 0.55 | [M + K]$^+$ | PE(22:4) | C$_{27}$H$_{48}$NO$_7$P | |
| | 16 | 572.31115 | 572.31156 | 572.31130 | −0.26 | 0.45 | [M + K]$^+$ | PE(22:2) | C$_{27}$H$_{52}$NO$_7$P | |
| | 17 | 574.32675 | 574.32714 | 574.32695 | −0.35 | 0.33 | [M + K]$^+$ | PE(22:1) | C$_{27}$H$_{54}$NO$_7$P | |
| | 18 | 538.38622 | — | 538.38672 | −0.93 | — | [M + H]$^+$ | PE(22:0) | C$_{27}$H$_{56}$NO$_7$P | |
| | | 560.36859 | — | 560.36866 | −0.12 | — | [M + Na]$^+$ | | | |
| | 19 | 602.35803 | 602.35847 | 602.35825 | −0.37 | 0.37 | [M + K]$^+$ | LysoPE(24:1) | C$_{29}$H$_{58}$NO$_7$P | |
| | 20 | 644.36862 | — | 644.36881 | −0.29 | — | [M + K]$^+$ | PE(26:1) | C$_{31}$H$_{60}$NO$_7$P | |
| | 21 | 646.38438 | 646.38471 | 646.38446 | −0.12 | 0.39 | [M + K]$^+$ | PE(26:0) | C$_{31}$H$_{62}$NO$_7$P | |
| | 22 | 756.49369 | 756.49357 | 756.49401 | −0.42 | −0.58 | [M + K]$^+$ | PE(34:1) | C$_{39}$H$_{76}$NO$_7$P | |
| | 23 | 740.49921 | 740.49934 | 740.49910 | 0.15 | 0.32 | [M + K]$^+$ | PE(P-34:1) | C$_{39}$H$_{76}$NO$_8$P | |
| | 24 | 742.51414 | — | 742.51475 | −0.82 | — | [M + K]$^+$ | PE(P-34:0) | C$_{39}$H$_{78}$NO$_8$P | |
| | 25 | 750.44734 | 750.44725 | 750.44706 | 0.37 | 0.25 | [M + K]$^+$ | PE(34:4) | C$_{39}$H$_{70}$NO$_8$P | |
| | 26 | 758.51000 | 758.51025 | 758.50966 | 0.45 | 0.78 | [M + K]$^+$ | PE(34:0) | C$_{39}$H$_{78}$NO$_8$P | |
| | 27 | 764.49904 | 764.49935 | 764.49910 | −0.08 | 0.33 | [M + K]$^+$ | PE(P-36:3) | C$_{41}$H$_{76}$NO$_7$P | |
| | 28 | 780.49412 | 780.49434 | 780.49401 | 0.14 | 0.42 | [M + K]$^+$ | PE(36:3) | C$_{41}$H$_{76}$NO$_8$P | |
| | 29 | 782.50982 | — | 782.50966 | −0.20 | — | [M + K]$^+$ | PE(36:2) | C$_{41}$H$_{78}$NO$_8$P | |
| | 30 | 768.53053 | 768.53035 | 768.53040 | 0.17 | −0.07 | [M + K]$^+$ | PE(P-36:1) | C$_{41}$H$_{80}$NO$_7$P | |
| | 31 | 784.52570 | 784.52487 | 784.52531 | 0.50 | −0.56 | [M + K]$^+$ | PE(36:1) | C$_{41}$H$_{80}$NO$_8$P | |
| | 32 | 770.54624 | 770.54633 | 770.54605 | 0.25 | 0.36 | [M + K]$^+$ | PE(P-36:0) | C$_{41}$H$_{82}$NO$_7$P | |
| | 33 | 748.58529 | 748.58529 | 748.58508 | 0.28 | 0.28 | [M + H]$^+$ | PE(36:0) | C$_{41}$H$_{82}$NO$_8$P | 607, 748 |
| | 34 | 786.48354 | 786.48345 | 786.48345 | 0.11 | 0.00 | [M + K]$^+$ | PE(P-38:6) | C$_{43}$H$_{74}$NO$_7$P | |
| | 35 | 802.47840 | 802.47873 | 802.47836 | 0.05 | 0.46 | [M + K]$^+$ | PE(38:6) | C$_{43}$H$_{74}$NO$_8$P | |
| | 36 | 788.49835 | 788.49860 | 788.49910 | −0.95 | −0.63 | [M + K]$^+$ | PE(P-38:5) | C$_{43}$H$_{76}$NO$_7$P | |
| | 37 | 804.49421 | 804.49397 | 804.49401 | 0.25 | −0.05 | [M + K]$^+$ | PE(38:5) | C$_{43}$H$_{76}$NO$_8$P | |

TABLE 2-continued

Comparison of lipid detection on rat brain sections by MALDI-FTICR MS in the positive ion mode with and without an electric field and standard spray methods for quercetin coating, respectively.

| Classification | No. | Measured m/z Electric Field | Measured m/z No Electric Field | Calculated m/z | Error (ppm) Electric Field | Error (ppm) No Electric Field | Ion form | Assignment Compound | Assignment Molecular formula | Structurally specific CID ions (m/z)[a] |
|---|---|---|---|---|---|---|---|---|---|---|
| | 38 | 790.51488 | 790.51451 | 790.51475 | 0.16 | −0.30 | [M + K]$^+$ | PE(P-38:4) | $C_{43}H_{78}NO_7P$ | 341, 627, 768 or 259, 283, 303, 462, 480, 482, 500, 767 |
| | 39 | 806.50991 | 806.50956 | 806.50966 | 0.31 | −0.12 | [M + K]$^+$ | PE(38:4) | $C_{43}H_{78}NO_8P$ | |
| | 40 | 792.53052 | — | 792.53040 | 0.15 | — | [M + K]$^+$ | PE(P-38:3) | $C_{43}H_{80}NO_7P$ | |
| | 41 | 810.54083 | — | 810.54096 | −0.16 | — | [M + K]$^+$ | PE(38:2) | $C_{43}H_{82}NO_8P$ | |
| | 42 | 774.60067 | 774.60072 | 774.60073 | −0.08 | −0.01 | [M + H]$^+$ | PE(38:1) | $C_{43}H_{84}NO_8P$ | |
| | | 812.55688 | 812.55651 | 812.55661 | 0.33 | −0.12 | [M + K]$^+$ | | | |
| | 43 | 812.49979 | 812.49973 | 812.49910 | 0.85 | 0.78 | [M + K]$^+$ | PE(P-40:7) | $C_{45}H_{76}NO_7P$ | |
| | 44 | 828.49435 | — | 828.49401 | 0.41 | — | [M + K]$^+$ | PE(P-40:6) | $C_{45}H_{76}NO_8P$ | |
| | 45 | 814.51441 | 814.51423 | 814.51475 | −0.42 | −0.64 | [M + K]$^+$ | PE(P-40:6) | $C_{45}H_{78}NO_7P$ | |
| | 46 | 830.50977 | 830.50921 | 830.50966 | 0.13 | −0.54 | [M + K]$^+$ | PE(P-40:5) | $C_{45}H_{78}NO_8P$ | |
| | 47 | 816.53009 | 816.53073 | 816.53040 | −0.38 | 0.40 | [M + K]$^+$ | PE(P-40:5) | $C_{45}H_{80}NO_7P$ | |
| | 48 | 832.52507 | — | 832.52531 | −0.29 | — | [M + K]$^+$ | PE(40:5) | $C_{45}H_{80}NO_8P$ | |
| | 49 | 818.54557 | 818.54653 | 818.54605 | −0.59 | 0.59 | [M + K]$^+$ | PE(P-40:4) | $C_{45}H_{82}NO_7P$ | |
| | 50 | 834.54025 | 834.54078 | 834.54096 | −0.85 | −0.22 | [M + K]$^+$ | PE(40:4) | $C_{45}H_{82}NO_8P$ | |
| | 51 | 802.63128 | 802.63127 | 802.63203 | −0.93 | −0.95 | [M + K]$^+$ | PE(40:1) | $C_{45}H_{88}NO_8P$ | |
| | 52 | 850.47870 | — | 850.47836 | 0.40 | — | [M + K]$^+$ | PE(42:10) | $C_{47}H_{74}NO_8P$ | |
| | 53 | 852.49475 | 852.49450 | 852.49401 | 0.87 | 0.57 | [M + K]$^+$ | PE(42:9) | $C_{47}H_{76}NO_8P$ | |
| | 54 | 854.51013 | — | 854.50966 | 0.55 | — | [M + K]$^+$ | PE(42:8) | $C_{47}H_{78}NO_8P$ | |
| | 55 | 856.52505 | — | 856.52531 | −0.30 | — | [M + K]$^+$ | PE(42:7) | $C_{47}H_{80}NO_8P$ | |
| | 56 | 858.54080 | — | 858.54096 | −0.19 | — | [M + K]$^+$ | PE(42:6) | $C_{47}H_{82}NO_8P$ | |
| | 57 | 824.61619 | — | 824.61638 | −0.23 | — | [M + H]$^+$ | PE(42:4) | $C_{47}H_{86}NO_8P$ | |
| | 58 | 810.63704 | 810.63736 | 810.63712 | −0.10 | 0.30 | [M + H]$^+$ | PE(O-42:4) | $C_{47}H_{88}NO_7P$ | |
| | 59 | 864.58775 | 864.58803 | 864.58791 | −0.19 | 0.14 | [M + K]$^+$ | PE(42:3) | $C_{47}H_{88}NO_8P$ | |
| | 60 | 850.60853 | 850.60840 | 850.60865 | −0.14 | −0.29 | [M + K]$^+$ | PE(P-42:2) | $C_{47}H_{90}NO_7P$ | |
| | 61 | 845.67436 | 845.67442 | 845.67423 | 0.15 | 0.22 | [M + Na]$^+$ | PE(42:2) | $C_{47}H_{90}NO_8P$ | |
| | 62 | 852.62425 | — | 852.62430 | −0.06 | — | [M + K]$^+$ | PE(P-42:1) | $C_{47}H_{92}NO_7P$ | |
| | 63 | 868.61934 | 868.61952 | 868.61921 | 0.15 | 0.36 | [M + K]$^+$ | PE(42:1) | $C_{47}H_{92}NO_8P$ | |
| | 64 | 870.63471 | 870.63493 | 870.63486 | −0.17 | 0.08 | [M + K]$^+$ | PE(42:0) | $C_{47}H_{94}NO_8P$ | |
| | 65 | 878.50911 | — | 878.50966 | −0.63 | — | [M + K]$^+$ | PE(44:10) | $C_{49}H_{78}NO_8P$ | |
| | 66 | 880.52546 | — | 880.52531 | 0.17 | — | [M + K]$^+$ | PE(44:9) | $C_{49}H_{80}NO_8P$ | |
| | 67 | 886.57238 | 886.57251 | 886.57226 | 0.14 | 0.28 | [M + K]$^+$ | PE(44:6) | $C_{49}H_{86}NO_8P$ | |
| | 68 | 888.58780 | 888.58817 | 888.58791 | −0.12 | 0.29 | [M + K]$^+$ | PE(44:5) | $C_{49}H_{88}NO_8P$ | |
| | 69 | 896.65061 | — | 896.65051 | 0.11 | — | [M + K]$^+$ | PE(44:1) | $C_{49}H_{96}NO_8P$ | |
| Phosphatidic acids (PAs) | 1 | 475.22231 | 475.22224 | 475.22215 | 0.34 | 0.19 | [M + K]$^+$ | PA(18:1) | $C_{21}H_{41}O_7P$ | 79, 153, 171, 283, 437 |
| | 2 | 477.23744 | 477.23741 | 477.23780 | −0.75 | −0.82 | [M + K]$^+$ | PA(18:0) | $C_{21}H_{43}O_7P$ | |
| | 3 | 497.20674 | 497.20681 | 497.20650 | 0.48 | 0.62 | [M + K]$^+$ | PA(20:4) | $C_{23}H_{39}O_7P$ | 153, 171, 259, 303, 457 |
| | 4 | 499.22225 | 499.22247 | 499.22215 | 0.20 | 0.64 | [M + K]$^+$ | PA(20:3) | $C_{23}H_{41}O_7P$ | |
| | 5 | 501.23795 | 501.23790 | 501.23780 | 0.30 | 0.20 | [M + K]$^+$ | PA(20:2) | $C_{23}H_{43}O_7P$ | |
| | 6 | 487.27974 | 487.27973 | 487.27951 | 0.45 | 0.45 | [M + Na]$^+$ | PA(20:1) | $C_{23}H_{45}O_7P$ | |
| | | 503.25357 | 503.25347 | 503.25345 | 0.24 | 0.04 | [M + K]$^+$ | | | |
| | 7 | 525.23767 | 525.23791 | 525.23780 | −0.25 | 0.21 | [M + K]$^+$ | PA(22:4) | $C_{25}H_{43}O_7P$ | |
| | 8 | 531.28493 | 531.28481 | 531.28475 | 0.34 | 0.11 | [M + K]$^+$ | PA(22:1) | $C_{25}H_{49}O_7P$ | |
| | 9 | 533.30057 | 533.30061 | 533.30040 | 0.32 | 0.39 | [M + K]$^+$ | PA(22:0) | $C_{25}H_{51}O_7P$ | |
| | 10 | 679.37367 | 679.37382 | 679.37356 | 0.16 | 0.38 | [M + K]$^+$ | PA(32:4) | $C_{35}H_{61}O_8P$ | |
| | 11 | 681.38952 | 681.38945 | 681.38921 | 0.45 | 0.35 | [M + K]$^+$ | PA(32:3) | $C_{35}H_{63}O_8P$ | |

TABLE 2-continued

Comparison of lipid detection on rat brain sections by MALDI-FTICR MS in the positive ion mode with and without an electric field and standard spray methods for quercetin coating, respectively.

| Classification | No. | Measured m/z Electric Field | Measured m/z No Electric Field | Calculated m/z | Error (ppm) Electric Field | Error (ppm) No Electric Field | Ion form | Compound | Assignment Molecular formula | Structurally specific CID ions (m/z)[a] |
|---|---|---|---|---|---|---|---|---|---|---|
| | 12 | 683.40493 | 683.40504 | 683.40486 | 0.10 | 0.26 | [M + K]+ | PA(32:2) | $C_{35}H_{65}O_8P$ | |
| | 13 | 685.42113 | 685.42092 | 685.42051 | 0.90 | 0.60 | [M + K]+ | PA(32:1) | $C_{35}H_{67}O_8P$ | |
| | 14 | 687.43633 | 687.43577 | 687.43616 | 0.25 | -0.57 | [M + K]+ | PA(32:0) | $C_{35}H_{69}O_8P$ | |
| | 15 | 643.50371 | 643.50361 | 643.50370 | 0.02 | -0.14 | [M + Na]+ | PA(O-32:0) | $C_{35}H_{73}O_6P$ | |
| | 16 | 709.42087 | — | 709.42051 | 0.51 | — | [M + K]+ | PA(34:3) | $C_{37}H_{67}O_8P$ | |
| | 17 | 711.43686 | 711.43679 | 711.43616 | 0.98 | 0.89 | [M + K]+ | PA(34:2) | $C_{37}H_{69}O_8P$ | 79, 153, 255, 279, 391, 409, 671 |
| | 18 | 697.47829 | 697.4780 | 697.47788 | 0.59 | 0.17 | [M + Na]+ | PA(34:1) | $C_{37}H_{71}O_8P$ | 153, 255, 281, 391, 409, 417, 435, 673 |
| | | 713.45196 | 713.45177 | 713.45181 | 0.21 | -0.06 | [M + K]+ | PA(34:1) | $C_{37}H_{71}O_8P$ | |
| | 19 | 699.47295 | — | 699.47255 | 0.57 | — | [M + K]+ | PA(O-34:1) | $C_{37}H_{73}O_7P$ | |
| | 20 | 701.45132 | 701.45151 | 701.45166 | -0.48 | -0.21 | [M + Na]+ | PA(P-36:5) | $C_{39}H_{67}O_7P$ | |
| | 21 | 733.42038 | 733.42063 | 733.42051 | -0.18 | 0.16 | [M + K]+ | PA(36:5) | $C_{39}H_{65}O_8P$ | |
| | 22 | 735.43625 | — | 735.43616 | 0.12 | — | [M + K]+ | PA(36:4) | $C_{39}H_{67}O_8P$ | |
| | 23 | 737.45211 | 737.45231 | 737.45181 | 0.41 | 0.68 | [M + K]+ | PA(36:3) | $C_{39}H_{69}O_8P$ | 279, 281, 415, 417, 433, 435 |
| | 24 | 723.49388 | 723.49342 | 723.49353 | 0.48 | -0.15 | [M + Na]+ | PA(36:2) | $C_{39}H_{71}O_8P$ | 78, 153, 279, 283, 415, 419, 433, 437, 699 |
| | | 739.46738 | 739.46750 | 739.46746 | -0.11 | 0.05 | [M + K]+ | PA(36:2) | $C_{39}H_{71}O_8P$ | |
| | 25 | 741.48304 | — | 741.48311 | -0.09 | — | [M + K]+ | PA(36:1) | $C_{39}H_{75}O_8P$ | 79, 153, 281, 283, 417, 419, 435, 437, 701 |
| | 26 | 727.46777 | 727.46771 | 727.46731 | 0.63 | 0.55 | [M + Na]+ | PA(P-38:6) | $C_{41}H_{69}O_7P$ | |
| | 27 | 759.43543 | — | 759.43616 | -0.96 | — | [M + K]+ | PA(38:6) | $C_{41}H_{69}O_8P$ | 153, 255, 283, 391, 409, 463, 481, 719 |
| | 28 | 761.45158 | 761.45147 | 761.45181 | -0.30 | -0.45 | [M + K]+ | PA(38:5) | $C_{41}H_{71}O_8P$ | |
| | 29 | 725.51175 | 725.51189 | 725.51158 | 0.23 | 0.43 | [M + H]+ | PA(38:4) | $C_{41}H_{73}O_8P$ | 153, 259, 283, 303, 419, 437, 439, 457, 723 |
| | | 763.46801 | 763.46737 | 763.46746 | 0.72 | -0.12 | [M + K]+ | PA(38:4) | $C_{41}H_{73}O_8P$ | |
| | 30 | 749.50874 | — | 749.50918 | -0.59 | — | [M + Na]+ | PA(38:3) | $C_{41}H_{75}O_8P$ | |
| | | 765.48304 | 765.48387 | 765.48311 | -0.09 | 0.99 | [M + K]+ | PA(38:3) | $C_{41}H_{75}O_8P$ | |
| | 31 | 751.52440 | 751.52478 | 751.52483 | -0.57 | -0.07 | [M + Na]+ | PA(38:2) | $C_{41}H_{77}O_8P$ | |
| | | 767.49919 | 767.49893 | 767.49876 | 0.56 | 0.22 | [M + K]+ | PA(38:2) | $C_{41}H_{77}O_8P$ | |
| | 32 | 771.53014 | 771.53026 | 771.53006 | 0.10 | 0.26 | [M + K]+ | PA(38:0) | $C_{41}H_{81}O_8P$ | |
| | 33 | 785.45107 | 785.45156 | 785.45181 | -0.94 | -0.32 | [M + K]+ | PA(40:7) | $C_{43}H_{71}O_8P$ | |
| | 34 | 787.46788 | — | 787.46746 | 0.53 | — | [M + K]+ | PA(40:6) | $C_{43}H_{73}O_8P$ | 153, 283, 327, 419, 437, 463, 481, 747 |
| | 35 | 773.50955 | — | 773.50918 | 0.48 | — | [M + Na]+ | PA(40:5) | $C_{43}H_{75}O_8P$ | |
| | | 789.48282 | 789.48298 | 789.48311 | -0.37 | -0.16 | [M + K]+ | PA(40:5) | $C_{43}H_{75}O_8P$ | 153, 283, 329, 419, 437, 465, 483, 749 |
| | 36 | 777.54061 | 777.54072 | 777.54048 | 0.17 | 0.31 | [M + Na]+ | PA(40:3) | $C_{43}H_{79}O_8P$ | |
| | 37 | 809.45195 | — | 809.45181 | 0.17 | — | [M + K]+ | PA(42:9) | $C_{45}H_{71}O_8P$ | |
| Phosphoglycerols (PGs) | 1 | 547.24304 | 547.24337 | 547.24328 | -0.44 | 0.16 | [M + Na]+ | PG(18:2) | $C_{24}H_{45}O_9P$ | |
| | 2 | 573.25867 | 573.25907 | 573.25893 | -0.45 | 0.24 | [M + Na]+ | PG(20:3) | $C_{26}H_{47}O_9P$ | |
| | 3 | 559.30057 | 559.30086 | 559.30064 | -0.13 | 0.39 | [M + Na]+ | PG(20:2) | $C_{26}H_{49}O_9P$ | |
| | 4 | 599.27421 | 599.27468 | 599.27458 | -0.62 | 0.17 | [M + Na]+ | PG(22:4) | $C_{28}H_{49}O_9P$ | |
| | 5 | 603.30578 | 603.30597 | 603.30588 | -0.17 | 0.15 | [M + Na]+ | PG(22:2) | $C_{28}H_{53}O_9P$ | |
| | 6 | 745.47747 | — | 745.47803 | -0.75 | — | [M + K]+ | PG(P-32:0) | $C_{38}H_{75}O_9P$ | |
| | 7 | 743.48550 | — | 743.48576 | -0.35 | — | [M + H]+ | PG(34:4) | $C_{40}H_{71}O_{10}P$ | |
| | 8 | 783.45732 | 783.45743 | 783.45729 | 0.04 | 0.18 | [M + K]+ | PG(34:3) | $C_{40}H_{73}O_{10}P$ | |
| | 9 | 793.49954 | 793.49947 | 793.49901 | 0.67 | 0.58 | [M + Na]+ | PG(36:4) | $C_{42}H_{75}O_{10}P$ | |
| | 10 | 817.55534 | 817.53567 | 817.53554 | -0.24 | 0.16 | [M + K]+ | PG(36:0) | $C_{42}H_{83}O_{10}P$ | |
| | 11 | 801.56403 | — | 801.56401 | 0.02 | — | [M + H]+ | PG(38:3) | $C_{44}H_{81}O_{10}P$ | |

TABLE 2-continued

Comparison of lipid detection on rat brain sections by MALDI-FTICR MS in the positive ion mode with and without an electric field and standard spray methods for quercetin coating, respectively.

| Classification | No. | Measured m/z Electric Field | Measured m/z No Electric Field | Calculated m/z | Error (ppm) Electric Field | Error (ppm) No Electric Field | Assignment Compound | Assignment Ion form | Assignment Molecular formula | Structurally specific CID ions (m/z)[a] |
|---|---|---|---|---|---|---|---|---|---|---|
| Phosphatidylserine (PS) | 12 | 825.56146 | 825.56178 | 825.56161 | −0.18 | 0.21 | PG(38:2) | [M + Na]+ | C44H83O10P | |
| | 13 | 887.51967 | — | 887.51989 | −0.25 | — | PG(42:7) | [M + K]+ | C48H81O10P | |
| | 1 | 576.30642 | 576.30650 | 576.30621 | 0.36 | 0.50 | PS(P-20:0) | [M + K]+ | C26H52NO8P | |
| | 2 | 592.30134 | 592.30146 | 592.30113 | 0.36 | 0.56 | PS(20:0) | [M + K]+ | C26H52NO9P | |
| | 3 | 612.26968 | 612.26999 | 612.26983 | −0.25 | 0.26 | PS(22:4) | [M + K]+ | C28H48NO9P | |
| | 4 | 780.47812 | — | 780.47861 | −0.63 | — | PS(34:3) | [M + Na]+ | C40H72NO10P | |
| | 5 | 808.50976 | — | 808.50991 | −0.19 | — | PS(36:3) | [M + Na]+ | C42H76NO10P | |
| | 6 | 828.51537 | 828.51508 | 828.51514 | 0.28 | −0.07 | PS(36:1) | [M + K]+ | C42H80NO10P | |
| | 7 | 824.44713 | — | 824.44731 | −0.22 | — | PS(38:9) | [M + Na]+ | C44H68NO10P | |
| | 8 | 826.46296 | — | 826.46296 | 0.00 | — | PS(38:8) | [M + Na]+ | C44H70NO10P | |
| | 9 | 846.46807 | 846.46837 | 846.46819 | −0.14 | 0.21 | PS(38:6) | [M + K]+ | C44H74NO10P | |
| | 10 | 830.47354 | 830.47361 | 830.47328 | 0.31 | 0.40 | PS(P-38:6) | [M + K]+ | C44H74NO9P | |
| | 11 | 834.52516 | — | 834.52556 | −0.48 | — | PS(38:4) | [M + Na]+ | C44H78NO10P | |
| | 12 | 854.49493 | — | 854.49426 | 0.78 | — | PS(40:8) | [M + Na]+ | C46H74NO10P | |
| | 13 | 856.50985 | — | 856.50991 | −0.07 | — | PS(40:7) | [M + Na]+ | C46H76NO10P | |
| | 14 | 858.52587 | — | 858.52556 | 0.36 | — | PS(40:6) | [M + Na]+ | C46H78NO10P | |
| | 15 | 860.54139 | — | 860.54121 | 0.21 | — | PS(40:5) | [M + Na]+ | C46H80NO10P | |
| | 16 | 846.62150 | 846.62196 | 846.62186 | −0.43 | 0.11 | PS(40:1) | [M + Na]+ | C46H88NO10P | |
| | 17 | 830.62688 | — | 830.62695 | −0.08 | — | PS(P-40:1) | [M + Na]+ | C46H88NO9P | |
| | 18 | 848.63714 | 848.63754 | 848.63751 | −0.44 | 0.04 | PS(40:0) | [M + Na]+ | C46H90NO10P | |
| | 19 | 884.54178 | — | 884.54121 | 0.64 | — | PS(42:7) | [M + Na]+ | C48H80NO10P | |
| Phosphatidylinositols (PIs) | 1 | 919.47341 | — | 919.47334 | 0.08 | — | PI(38:7) | [M + H]+ | C47H77O13P | |
| | 2 | 925.52053 | 925.52050 | 925.52029 | 0.26 | 0.23 | PI(38:4) | [M + K]+ | C47H83O13P | 240, 259, 283, 303, 419, 437, 439, 457, 581, 599, 601, 619, 886 |
| | 3 | 945.48861 | 945.48858 | 945.48899 | −0.40 | −0.43 | PI(40:8) | [M + K]+ | C49H79O13P | |
| | 4 | 915.59576 | 915.59563 | 915.59571 | 0.05 | −0.09 | PI(40:4) | [M + H]+ | C49H87O13P | |
| | 5 | 931.53324 | — | 931.53311 | 0.14 | — | PI(42:10) | [M + H]+ | C51H79O13P | |
| | 6 | 975.53674 | — | 975.53594 | 0.82 | — | PI(42:7) | [M + H]+ | C51H85O13P | |
| | 7 | 945.58259 | — | 945.58274 | −0.16 | — | PI(P-42:6) | [M + Na]+ | C51H83O12P | |
| | 8 | 961.57721 | — | 961.57765 | −0.46 | — | PI(42:6) | [M + Na]+ | C51H87O13P | |
| Glycerophosphoinositol bis-phosphates (PIP2s) | 1 | 1035.43662 | — | 1035.43730 | −0.66 | — | PIP2(34:1) | [M + K]+ | C43H83O19P3 | |
| Glycerophosphoglycero-phosphoglycerols (cardiolipins) | 1 | 947.50279 | 947.50162 | 947.50212 | 0.71 | −0.53 | CL(1\'-[18:2(9Z,12Z)/0:0],3\'-[18:2(9Z,12Z)/0:0]) | [M + Na]+ | C45H82O15P2 | |
| | | 963.47618 | 963.47655 | 963.47605 | 0.13 | 0.52 | | [M + K]+ | | |
| Cyclic phosphatidic acids (cPAs) | 1 | 415.22193 | 415.22203 | 415.22200 | −0.17 | 0.07 | CPA(16:0) | [M + Na]+ | C19H37O6P | |
| | | 431.19611 | 431.19593 | 431.19593 | 0.42 | 0.53 | | [M + K]+ | | |
| | 2 | 455.19572 | 455.19588 | 455.19593 | −0.46 | −0.11 | CPA(18:2) | [M + Na]+ | C21H37O6P | |
| | 3 | 441.23769 | 441.23724 | 441.23765 | 0.09 | −0.93 | CPA(18:1) | [M + Na]+ | C21H39O6P | |
| | | 457.21177 | 457.21173 | 457.21158 | 0.42 | 0.33 | | [M + K]+ | | |
| | 4 | 443.25334 | 443.25320 | 443.25330 | 0.09 | −0.23 | CPA(18:0) | [M + Na]+ | C21H41O6P | |
| | | 459.22743 | 459.22741 | 459.22723 | 0.44 | 0.39 | | [M + K]+ | | |
| CDP-Glycerols | 1 | 980.53779 | — | 980.53722 | 0.58 | — | CDP-DG(34:1) | [M + H]+ | C46H83N3O15P2 | |
| | | 1018.49325 | — | 1018.49310 | 0.15 | — | | [M + K]+ | | |
| | 2 | 982.55256 | — | 982.55287 | −0.32 | — | CDP-DG(34:0) | [M + H]+ | C46H85N3O15P2 | |
| | | 1020.50867 | — | 1020.50875 | −0.08 | — | | [M + K]+ | | |

TABLE 2-continued

Comparison of lipid detection on rat brain sections by MALDI-FTICR MS in the positive ion mode with and without an electric field and standard spray methods for quercetin coating, respectively.

| Classification | No. | Measured m/z Electric Field | Measured m/z No Electric Field | Calculated m/z | Error (ppm) Electric Field | Error (ppm) No Electric Field | Ion form | Assignment Compound | Molecular formula | Structurally specific CID ions (m/z)[a] |
|---|---|---|---|---|---|---|---|---|---|---|
| | 3 | 1010.58474 | — | 1010.58417 | 0.54 | — | [M + H]+ | CDP-DG(36:0) | $C_{46}H_{89}N_3O_{15}P_2$ | |
| | 4 | 1058.58469 | — | 1058.58417 | 0.49 | — | [M + H]+ | CDP-DG(40:4) | $C_{52}H_{89}N_3O_{15}P_2$ | |
| Glycerophosphate | | 1096.54020 | — | 1096.54005 | 0.14 | — | [M + K]+ | | | |
| | 1 | 467.25531 | — | 467.25330 | 0.02 | 0.60 | [M + Na]+ | sn-3-O-(geranyl-geranyl)glycerol 1-phosphate | $C_{23}H_{41}O_6P$ | |
| | | 483.22728 | — | 483.22723 | 0.10 | — | [M + K]+ | | | |
| Sphingolipids | | | | | | | | | | |
| Ceramides (Cers) | 1 | 464.35032 | 464.35027 | 464.35005 | 0.58 | 0.47 | [M + K]+ | C-8 Ceramide | $C_{26}H_{51}NO_3$ | |
| | 2 | 602.49131 | 602.49122 | 602.49090 | 0.68 | 0.53 | [M + K]+ | Cer(d36:2) | $C_{36}H_{69}NO_3$ | |
| | 3 | 604.50685 | 604.50681 | 604.50655 | 0.50 | 0.43 | [M + K]+ | Cer(d36:1) | $C_{36}H_{71}NO_3$ | |
| | 4 | 684.47275 | — | 684.47288 | −0.19 | — | [M + K]+ | CerP(d36:1) | $C_{36}H_{72}NO_6P$ | |
| | 5 | 632.53811 | 632.53823 | 632.53785 | 0.41 | 0.60 | [M + K]+ | Cer(d38:1) | $C_{38}H_{75}NO_3$ | |
| | 6 | 686.58456 | 686.58460 | 686.58480 | −0.35 | −0.29 | [M + K]+ | Cer(d42:2) | $C_{42}H_{81}NO_3$ | |
| | 7 | 766.55160 | — | 766.55113 | 0.61 | — | [M + H]+ | CerP(d42:2) | $C_{42}H_{82}NO_6P$ | 264, 749, 767 |
| | 8 | 688.60044 | — | 688.60045 | −0.02 | — | [M + K]+ | Cer(d42:1) | $C_{42}H_{83}NO_3$ | |
| Sphingomyelins (SMs) | 1 | 703.57475 | — | 703.57485 | −0.14 | — | [M + H]+ | SM(d34:1) | $C_{39}H_{79}N_2O_6P$ | 163, 184, 682 |
| | 2 | 725.55673 | 725.55694 | 725.55680 | −0.10 | 0.19 | [M + Na]+ | SM(d36:1) | $C_{41}H_{83}N_2O_6P$ | 86, 184, 703, 731 |
| | | 753.58804 | 753.58822 | 753.58810 | −0.08 | −0.16 | [M + Na]+ | | | |
| | | 769.56224 | 769.56187 | 769.56203 | 0.27 | −0.21 | [M + K]+ | | | |
| | 3 | 797.59361 | 797.59355 | 797.59333 | 0.35 | 0.28 | [M + K]+ | SM(d38:1) | $C_{43}H_{87}N_2O_6P$ | 614, 738 |
| | 4 | 787.66858 | — | 787.66875 | −0.22 | — | [M + H]+ | SM(d40:1) | $C_{45}H_{91}N_2O_6P$ | |
| | | 825.62452 | 825.62481 | 825.62463 | −0.13 | 0.22 | [M + K]+ | | | |
| | 5 | 813.68484 | — | 813.68440 | 0.54 | — | [M + H]+ | SM(d42:2) | $C_{47}H_{93}N_2O_6P$ | 652, 776 |
| | | 851.64041 | 851.64021 | 851.64028 | 0.15 | −0.08 | [M + K]+ | | | |
| | 6 | 815.70041 | — | 815.70005 | 0.44 | — | [M + H]+ | SM(d42:1) | $C_{47}H_{95}N_2O_6P$ | 654, 778 |
| | | 837.68232 | 837.68204 | 837.68200 | 0.38 | 0.05 | [M + Na]+ | | | |
| | | 853.65645 | 853.65568 | 853.65593 | 0.61 | −0.29 | [M + K]+ | | | |
| Glycosphingolipids | 1 | 500.29841 | 500.29815 | 500.29867 | −0.52 | — | [M + K]+ | Glucosyl sphingosine | $C_{24}H_{47}NO_7$ | |
| | 2 | 828.54447 | — | 828.54436 | 0.13 | — | [M + K]+ | LacCer(d30:1) | $C_{42}H_{79}NO_{13}$ | 264, 447, 465, 627, 789, 807 |
| | 3 | 766.55942 | 766.55930 | 766.55938 | 0.05 | −0.10 | [M + K]+ | GlcCer(d36:1) | $C_{42}H_{81}NO_8$ | |
| | 4 | 856.57577 | — | 856.57566 | 0.13 | — | [M + Na]+ | LacCer(d32:1) | $C_{44}H_{83}NO_{13}$ | |
| | 5 | 852.58713 | — | 852.58652 | 0.72 | — | [M + H]+ | (3′-sulfoGalβ-Cer(d38:0(2OH)) | $C_{44}H_{85}NO_{12}S$ | |
| | 6 | 794.59095 | 794.59084 | 794.59068 | 0.34 | 0.20 | [M + K]+ | GalCer(d38:1) | $C_{44}H_{85}NO_8$ | |
| | 7 | 820.60674 | 820.60671 | 820.60633 | 0.50 | 0.46 | [M + H]+ | GlcCer(d40:2) | $C_{46}H_{87}NO_8$ | |
| | 8 | 836.60133 | — | 836.60124 | 0.11 | — | [M + K]+ | GlcCer(d16:2/24:0(2OH)) | $C_{46}H_{87}NO_9$ | |
| | 9 | 822.62190 | 822.62156 | 822.62198 | −0.10 | −0.51 | [M + K]+ | GlcCer(d40:1) | $C_{46}H_{89}NO_8$ | |
| | 10 | 928.61212 | — | 928.61220 | −0.09 | — | [M + Na]+ | LacCer(d36:1) | $C_{48}H_{91}NO_{13}$ | |
| | 11 | 832.66350 | 832.66332 | 832.66369 | −0.23 | −0.44 | [M + K]+ | GlcCer(d42:2) | $C_{48}H_{91}NO_8$ | |
| | | 848.63831 | 848.63842 | 848.63763 | 0.80 | 0.93 | [M + Na]+ | | | |
| | 12 | 892.67158 | — | 892.67197 | −0.44 | — | [M + H]+ | LacCer(d36:0) | $C_{48}H_{93}NO_{13}$ | |
| | 13 | 850.65367 | 850.65337 | 850.65328 | 0.46 | 0.11 | [M + K]+ | GlcCer(d42:1) | $C_{48}H_{93}NO_8$ | |
| | 14 | 852.66911 | — | 852.66893 | 0.21 | — | [M + K]+ | GlcCer(d42:0) | $C_{48}H_{95}NO_8$ | |
| | 15 | 876.66849 | 876.66867 | 876.66893 | −0.50 | −0.30 | [M + K]+ | GlcCer(d44:2) | $C_{50}H_{95}NO_8$ | |

TABLE 2-continued

Comparison of lipid detection on rat brain sections by MALDI-FTICR MS in the positive ion mode with and without an electric field and standard spray methods for quercetin coating, respectively.

| Classification | No. | Measured m/z Electric Field | Measured m/z No Electric Field | Calculated m/z | Error (ppm) Electric Field | Error (ppm) No Electric Field | Ion form | Assignment Compound | Molecular formula | Structurally specific CID ions (m/z)[a] |
|---|---|---|---|---|---|---|---|---|---|---|
| | 16 | 878.68466 | 878.68478 | 878.68458 | 0.09 | 0.23 | [M + K]+ | GlcCer(d44:1) | C50H97NO8 | |
| | 17 | 1010.69083 | — | 1010.69045 | 0.38 | — | [M + K]+ | Galβ1-4Glcβ-Cer(d42:2) | C54H101NO13 | |
| | 18 | 1012.70616 | — | 1012.70610 | 0.06 | — | [M + K]+ | Galβ1-4Glcβ-Cer(d42:1) | C54H103NO13 | |
| Sphingoid bases | 1 | 264.19316 | — | 264.19340 | −0.91 | — | [M + Na]+ | (4E,6E,d14:2) sphingosine | C14H27NO2 | |
| Ceramide phosphoinositols (PI-Cers) | 1 | 852.50034 | — | 852.49989 | 0.53 | — | [M + K]+ | PI-Cer(t34:0(2OH)) | C40H80NO13P | |
| | 2 | 838.61683 | — | 838.61678 | 0.06 | — | [M + H]+ | PI-Cer(d38:0) | C44H88NO11P | |
| | 3 | 864.63279 | — | 864.63243 | 0.42 | — | [M + K]+ | PI-Cer(d40:10) | C46H90NO11P | |
| | 4 | 866.64805 | — | 866.64808 | −0.03 | — | [M + H]+ | PI-Cer(d40:0) | C46H92NO11P | |
| | 5 | 904.62434 | — | 904.62494 | −0.66 | — | [M + Na]+ | PI-Cer(t40:0) | C46H92NO12P | |
| | 6 | 894.67917 | — | 894.67938 | −0.23 | — | [M + H]+ | PI-Cer(d42:0) | C48H96NO11P | |
| Neutral Lipids Glycerolipids | 7 | 1154.70941 | — | 1154.70921 | 0.17 | — | [M + K]+ | MIPC(t44:0(2OH)) | C56H110NO18P | |
| Monoacylglycerols (MAGs) | 1 | 369.24037 | 369.24012 | 369.24017 | 0.54 | −0.14 | [M + K]+ | MG (16:0) | C19H38O4 | 239, 257, 313, 331, 369 |
| | 2 | 379.28181 | 379.28191 | 379.28188 | −0.18 | 0.08 | [M + Na]+ | MG (18:1) | C21H40O4 | |
| | | 395.25575 | 395.25583 | 395.25582 | −0.18 | 0.03 | [M + K]+ | | | |
| | 3 | 397.27164 | — | 397.27147 | 0.43 | — | [M + K]+ | MG (18:0) | C21H42O4 | |
| | 4 | 417.24037 | 417.24025 | 417.24017 | 0.48 | 0.19 | [M + K]+ | MG (20:4) | C23H38O4 | |
| | 5 | 419.25581 | 419.25577 | 419.25582 | −0.02 | −0.12 | [M + K]+ | MG (20:3) | C23H40O4 | |
| | 6 | 425.26612 | — | 425.26623 | −0.26 | — | [M + Na]+ | MG (22:6) | C25H38O4 | |
| | 7 | 445.27173 | 445.27147 | 445.27147 | 0.58 | 0.58 | [M + K]+ | MG (22:4) | C25H42O4 | |
| Diacylglycerols (DAGs) | 1 | 551.50365 | 551.50347 | 551.50339 | 0.47 | 0.15 | [M + H]+ | DG(P-32:1) | C35H66O4 | |
| | | 573.48551 | — | 573.48533 | 0.31 | — | | | | |
| | | 589.45915 | — | 589.45927 | −0.20 | — | | | | |
| | 2 | 607.47032 | 607.47016 | 607.46983 | 0.81 | 0.54 | [M + K]+ | DG(32:0) | C35H68O5 | 313, 551, 569 |
| | 3 | 561.52376 | 561.52389 | 561.52412 | −0.64 | −0.41 | [M + H]+ | 1-tetradecanyl-2-(8-[3]-ladderane-octanyl)-sn-glycerol | C37H68O3 | |
| | 4 | 631.47028 | — | 631.46983 | 0.71 | — | [M + K]+ | DG(34:2) | C37H68O5 | |
| | 5 | 633.48581 | 633.48582 | 633.48548 | 0.52 | 0.54 | [M + K]+ | DG(34:1) | C37H70O5 | |
| | 6 | 619.50655 | 619.50647 | 619.50622 | 0.53 | 0.40 | [M + K]+ | DG(O-34:1) | C37H72O4 | |
| | 7 | 635.50160 | — | 635.50113 | 0.74 | — | [M + K]+ | DG(34:0) | C37H72O5 | |
| | 8 | 655.47014 | 655.46930 | 655.46983 | 0.47 | −0.81 | [M + K]+ | DG(36:4) | C38H68O5 | 229, 250, 301, 341, 597 |
| | 9 | 603.53505 | 603.53483 | 603.53469 | 0.60 | 0.23 | [M + H]+ | 1-(14-methyl-penta-decanoyl)-2-(8-[3]-ladderane-octanoyl)-sn-glycerol | C39H70O4 | |
| | | 641.49026 | 641.49016 | 641.49057 | −0.48 | −0.64 | [M + K]+ | | | |
| | 10 | 657.48501 | — | 657.48548 | −0.71 | — | [M + K]+ | DG(36:3) | C39H70O5 | |
| | 11 | 589.55554 | 589.55568 | 589.55542 | 0.20 | 0.44 | [M + H]+ | 1-hexadecanyl-2-(8-[3]-ladderane-octanyl)-sn-glycerol | C39H72O3 | |
| | | 611.53758 | — | 611.53737 | 0.34 | — | [M + Na]+ | | | |
| | 12 | 659.50127 | 659.50094 | 659.50113 | 0.21 | −0.29 | [M + K]+ | DG(36:2) | C39H72O5 | |

TABLE 2-continued

Comparison of lipid detection on rat brain sections by MALDI-FTICR MS in the positive ion mode with and without an electric field and standard spray methods for quercetin coating, respectively.

| Classification | No. | Measured m/z Electric Field | Measured m/z No Electric Field | Calculated m/z | Error (ppm) Electric Field | Error (ppm) No Electric Field | Ion form | Assignment Compound | Molecular formula | Structurally specific CID ions (m/z)[a] |
|---|---|---|---|---|---|---|---|---|---|---|
| | 13 | 661.51722 | 661.51710 | 661.51678 | 0.67 | 0.48 | [M + K]$^+$ | DG(36:1) | $C_{39}H_{72}O_5$ | |
| | 14 | 621.48715 | — | 621.48774 | −0.95 | — | [M + H]$^+$ | 1-(6-[5]-ladderane-hexanoyl)-2-(8-[3]-ladderane-octanyl)-sn-glycerol | $C_{41}H_{64}O_4$ | |
| | 15 | 679.47020 | 679.46969 | 679.46983 | 0.54 | −0.21 | [M + K]$^+$ | DG(38:6) | $C_{41}H_{68}O_5$ | |
| | 16 | 681.48559 | 681.48600 | 681.48548 | 0.16 | 0.76 | [M + K]$^+$ | DG(38:5) | $C_{41}H_{70}O_5$ | |
| | 17 | 683.50180 | 683.50113 | 683.50113 | 0.98 | 0.80 | [M + K]$^+$ | DG(38:4) | $C_{41}H_{72}O_5$ | |
| | 18 | 687.53232 | 687.53220 | 687.53243 | −0.16 | −0.33 | [M + K]$^+$ | DG(38:2) | $C_{41}H_{76}O_5$ | |
| | 19 | 689.54838 | 689.54863 | 689.54808 | 0.44 | 0.80 | [M + K]$^+$ | DG(38:1) | $C_{41}H_{78}O_5$ | |
| | 20 | 682.45663 | 682.45673 | 682.45677 | −0.21 | −0.06 | [M + Na]$^+$ | DG(40:8) | $C_{43}H_{63}D_5O_5$ | 250, 287, 301, 325, 660 |
| | 21 | 699.43846 | 699.43853 | 699.43853 | −0.10 | — | [M + K]$^+$ | DG(40:10) | $C_{43}H_{64}O_5$ | |
| | 22 | 649.51967 | 649.51920 | 649.51904 | 0.97 | 0.25 | [M + H]$^+$ | | $C_{43}H_{68}O_4$ | |
| | 23 | 635.53977 | — | 635.53977 | 0.00 | — | [M + H]$^+$ | 1-(8-[5]-ladderane-octanyl)-2-(8-[3]-ladderane-octanyl)-sn-glycerol | $C_{43}H_{70}O_3$ | |
| | 24 | 651.53511 | 651.53446 | 651.53469 | 0.64 | −0.35 | [M + H]$^+$ | 1-(8-[3]-ladderane-octanoyl)-2-(8-[3]-ladderane-octanyl)-sn-glycerol | $C_{43}H_{70}O_4$ | |
| | 25 | 707.50059 | 707.50137 | 707.50113 | −0.76 | 0.34 | [M + K]$^+$ | DG(40:6) | $C_{43}H_{72}O_5$ | |
| | 26 | 725.45413 | 725.45443 | 725.45418 | −0.07 | 0.34 | [M + K]$^+$ | DG(42:11) | $C_{45}H_{66}O_5$ | |
| Triradylglycerols (TAGs) | 1 | 869.66542 | — | 869.66537 | 0.06 | — | [M + H]$^+$ | TG(54:11) | $C_{57}H_{88}O_6$ | |
| | 2 | 873.69664 | — | 873.69667 | −0.03 | — | [M + H]$^+$ | TG(54:9) | $C_{57}H_{92}O_6$ | |
| | 3 | 995.70995 | — | 995.70991 | 0.04 | — | [M + Na]$^+$ | TG(62:15) | $C_{65}H_{96}O_6$ | |
| | 4 | 997.72583 | — | 997.72556 | −0.14 | — | [M + Na]$^+$ | TG(62:14) | $C_{65}H_{98}O_6$ | |
| | 5 | 1035.68350 | — | 1035.68385 | −0.34 | — | [M + K]$^+$ | TG(64:17) | $C_{67}H_{96}O_6$ | |
| Other Glycerolipids | 1 | 834.62108 | 834.62159 | 834.62183 | −0.90 | −0.29 | [M + Na]$^+$ | 1-(9Z,12Z-octadecadienoyl)-2-(10Z,13Z,16Z,19Z-docosatetraenoyl)-3-O-[hydroxymethyl-N,N,N-trimethyl-beta-alanine]-glycerol | $C_{50}H_{85}NO_7$ | |
| Sterol Lipids | 1 | 429.24054 | 429.24023 | 429.24017 | 0.86 | 0.14 | [M + K]$^+$ | C24 bile acids and/or its isomers | $C_{24}H_{38}O_4$ | |
| | 2 | 457.27128 | 457.27125 | 457.27147 | −0.42 | −0.48 | [M + K]$^+$ | 24-northornasterol A | $C_{26}H_{42}O_5$ | |
| | 3 | 423.30220 | — | 423.30237 | −0.40 | — | [M + K]$^+$ | Dehydrocholesterol | $C_{27}H_{44}O$ | |
| | 4 | 471.28682 | — | 471.28712 | −0.64 | — | [M + K]$^+$ | C27 bile acids and/or its isomers | $C_{27}H_{44}O_4$ | |

TABLE 2-continued

Comparison of lipid detection on rat brain sections by MALDI-FTICR MS in the positive ion mode with and without an electric field and standard spray methods for quercetin coating, respectively.

| Classification | No. | Measured m/z Electric Field | Measured m/z No Electric Field | Calculated m/z | Error (ppm) Electric Field | Error (ppm) No Electric Field | Ion form | Assignment Compound | Molecular formula | Structurally specific CID ions (m/z)[a] |
|---|---|---|---|---|---|---|---|---|---|---|
| | 5 | 409.34413 | 409.34418 | 409.34409 | 0.10 | 0.22 | [M + Na]⁺ | Cholesterol | C₂₇H₄₆O | |
| | | 425.31823 | 425.31836 | 425.31802 | 0.49 | 0.80 | [M + K]⁺ | | | |
| | 6 | 473.32356 | 473.32393 | 473.32375 | −0.40 | 0.38 | [M + Na]⁺ | C27 bile acids and/or its isomers | C₂₇H₄₆O₅ | |
| | 7 | 489.31869 | — | 489.31866 | 0.06 | — | [M + Na]⁺ | C27 bile acids and/or its isomers | C₂₇H₄₆O₆ | |
| | 8 | 485.30288 | 485.30306 | 485.30277 | 0.23 | 0.58 | [M + K]⁺ | Ergosterols and C24-methyl derivatives | C₂₈H₄₆O₄ | |
| | 9 | 431.32854 | — | 431.32844 | 0.23 | — | [M + Na]⁺ | Conicasterol B | C₂₉H₄₄O | |
| | 10 | 497.33943 | 497.33956 | 497.33915 | 0.56 | 0.82 | [M + K]⁺ | C30 isoprenoids | C₃₀H₅₀O₃ | |
| | 11 | 777.41861 | — | 777.41859 | 0.03 | — | [M + K]⁺ | Spirostanols and/or its isomers | C₄₀H₆₆O₁₂ | |
| | 12 | 827.41889 | — | 827.41898 | −0.11 | — | [M + K]⁺ | Spirostanols and/or its isomers | C₄₀H₆₈O₁₅ | |
| Prenol Lipids | 1 | 445.29235 | 445.29251 | 445.29245 | −0.22 | 0.13 | [M + Na]⁺ | 19-(3-methyl-butanoyl-oxy)-villanovane-13alpha,17-diol | C₂₅H₄₂O₅ | |
| Fatty acyls | | | | | | | | | | |
| Fatty acids (FAs) | 1 | 319.20346 | — | 319.20339 | 0.22 | — | [M + K]⁺ | FA(18:2) | C₁₈H₃₂O₂ | |
| | 2 | 321.21911 | 321.21914 | 321.21904 | 0.22 | 0.31 | [M + K]⁺ | FA(18:1) | C₁₈H₃₄O₂ | |
| | 3 | 343.20348 | 343.20408 | 343.20339 | 0.26 | −0.90 | [M + K]⁺ | FA(20:4) | C₂₀H₃₂O₂ | 59, 80, 177, 205, 259, 303 |
| | 4 | 367.20345 | 367.20339 | 367.20339 | 0.16 | 0.00 | [M + K]⁺ | FA(22:6) | C₂₂H₃₂O₂ | |
| | 5 | 393.29789 | — | 393.29753 | 0.92 | — | [M + Na]⁺ | FA(22:0) | C₂₂H₄₂O₄ | |
| | | 409.27128 | 409.27132 | 409.27147 | −0.46 | −0.37 | [M + K]⁺ | | | |
| | 6 | 465.33428 | 465.33448 | 465.33407 | 0.45 | 0.88 | [M + K]⁺ | FA(26:0) | C₂₆H₅₀O₄ | |
| Number of Lipids | | | | | | Electric Field: 261 vs. No Electric Field: 208 | | | | |
| Other compounds | 1 | 322.05478 | 322.05479 | 322.05483 | −0.16 | −0.12 | [M + K]⁺ | Guanosine | C₁₀H₁₃N₅O₅ | |
| | 2 | 327.03528 | — | 327.03526 | 0.06 | — | [M + Na]⁺ | Thymidine 3,5-cyclic monophosphate | C₁₀H₁₃N₂O₇P | |
| | 3 | 352.04158 | 352.04164 | 352.04174 | −0.45 | −0.28 | [M + Na]⁺ | Cyclic adenosine monophosphate (cAMP) | C₁₀H₁₂N₅O₆P | |
| | | 368.01550 | 368.01546 | 368.01568 | −0.49 | −0.60 | [M + K]⁺ | | | |
| | 4 | 1146.50914 | — | 1146.50865 | 0.43 | — | [M + H]⁺ | CoA(26:0) | C₄₇H₈₆N₇O₁₇P₃S | |
| | | 1168.49083 | — | 1168.49060 | 0.20 | — | [M + Na]⁺ | | | |
| Number of Lipids | | | | | | Electric Field: 4 vs. No Electric Field: 2 | | | | |

FIG. 3 shows more detailed information on the classification of these identified lipids. Of the identified lipids, 261 were detected in the positive ion mode and 421 were detected in the negative ion mode. In contrast, only 344 lipids were detected and identified from the mass spectra which were acquired from the tissue sections without using the system and method embodiments disclosed herein, shown in the lower parts of FIGS. 7 and 8. Of the 344 lipids, 208 and 180 lipid entities were identified in the positive and negative ion modes, respectively. The total number of lipids that were detected on the rat brain tissue sections showed that the disclosed method and system embodiments resulted in an approximately 70% increase in the number of the detected lipids. The disclosed system and method produced a nearly 25% increase (261/208) in the number of detected lipids in the positive ion mode and a 133% increase (421/180) in the negative ion mode. Among these detected lipids, 80 and 206 lipid entities, which respectively belonged to 13 and 18 lipid classes as summarized in FIG. 3, were only detectable in the positive and negative ion modes, respectively, when the electric field (electric field intensity=600 V/m) was applied during matrix coating. As is currently understood, the use of the method and system disclosed herein resulted in the largest number of lipids detected by MALDI-MS on rat brain tissue sections currently achieved in the art.

Example 1D

To determine whether the disclosed system and method would improve MALDI tissue imaging with the use of different MALDI matrices for the matrix coating, rat brain tissue sections were coated with four different MALDI matrices (quercetin, 2-MBT, dithranol, and 9-AA), which solutions were prepared in different solvents and having different pH values as described in above. FIGS. 9A-9C, FIGS. 11A-11C, and FIGS. 13A-13C show the paired images for the lipid [PS(36:1)+K]$^+$ (m/z 828.515) using three different MALDI matrices (i.e., quercetin, 2-MBT, and dithranol), with (FIGS. 9B, 11B, and 13B) and without (FIGS. 9A, 11A, and 13A) the use of the electric field (electric field intensity=600 V/m) during the matrix coating. FIGS. 10A-10C, FIGS. 12A-12C, and FIGS. 14A-14C showed the paired images of the same lipid [PS(36:1)-H]$^-$ (m/z 788.545) in the negative ion mode, using three different MALDI matrices (i.e., quercetin, 2-MBT, and 9-AA) and with or without the use of an electric field (electric field intensity=600 V/m) during the matrix coating. The lipid ion images obtained with the disclosed system and method show higher contrast due to the increased peak intensities, as compared to the corresponding control images, obtained without using the disclosed system and method embodiments. Considering the regions of hippocampus and hypothalamus of the rat brain as examples, both ions of PS(36:1) show distributions with finer spatial resolution using the disclosed system and method embodiments.

FIGS. 15A-15D and 16A-16D show the ionic images of four lipids, including two positive ion detected species, [PS(38:8)+Na]$^+$ (m/z 826.463) and [PI(38:7)+K]$^+$ (m/z 919.473), illustrated in FIGS. 15A-15D, and two negative ion detected species, [PS(36:6)-H]$^-$ (m/z 778.467) and [PI(36:0)-H]$^-$ (m/z 865.582), illustrated in FIGS. 16A-16D. These four lipids were not detectable on the control samples of rat brain tissue sections by MALDI-MS in embodiments where a disclosed embodiment of a method and system was not used; however, they were clearly detected in embodiments where a disclosed method and system embodiment was used. The successful detection of these lipids allowed MALDI imaging of these molecules in the tissue.

It was also determined whether the disclosed method and system could also improve MALDI imaging on tissue sections other than rat brain. Twelve-µm thick sections of porcine adrenal gland were used for imaging in both ion modes by MALDI-FTICR MS using quercetin as the matrix. Similarly, four lipids, i.e., m/z 848.637 [PS(40:0)+H]$^+$ and m/z 975.535 [PI(42:7)+K]$^+$, m/z 782.498 [PS(36:4)-H]$^-$, and m/z 893.612 [PI(38:0)-H]$^-$), which were not detectable in the control (electric field intensity=0) mass spectrum, were detected in positive and negative ion mode, respectively, using an embodiment of the disclosed method (FIGS. 17A-17D and 18A-18D, respectively). Moreover, for those weakly detected lipids in the control spectrum, including m/z 772.525 [PC(32:0)+K]$^+$ and m/z 741.483 [PA(36:1)+H]$^+$, and m/z 701.513 [PA(36:1)-H]$^-$ and m/z 718.539 [PE(34:0)-H]$^-$, the image quality of these lipids was significantly improved because of the use of a disclosed method embodiment which resulted in their finer-resolution distribution patterns in the porcine adrenal gland, as shown in FIGS. 17A-17D and 18A-18D.

These results illustrated that using disclosed system and method embodiments resulted in a remarkable enhancement of tissue imaging of lipids in the rat brain and in porcine adrenal glands in both positive and negative ion modes, and was also compatible with using different matrices. Considering the different solvents and the different pH values of the four matrix solutions, the improvements of tissue imaging with the disclosed system and method embodiments seems to be independent of the composition of the matrix solutions.

Example 1E

Figure 19:
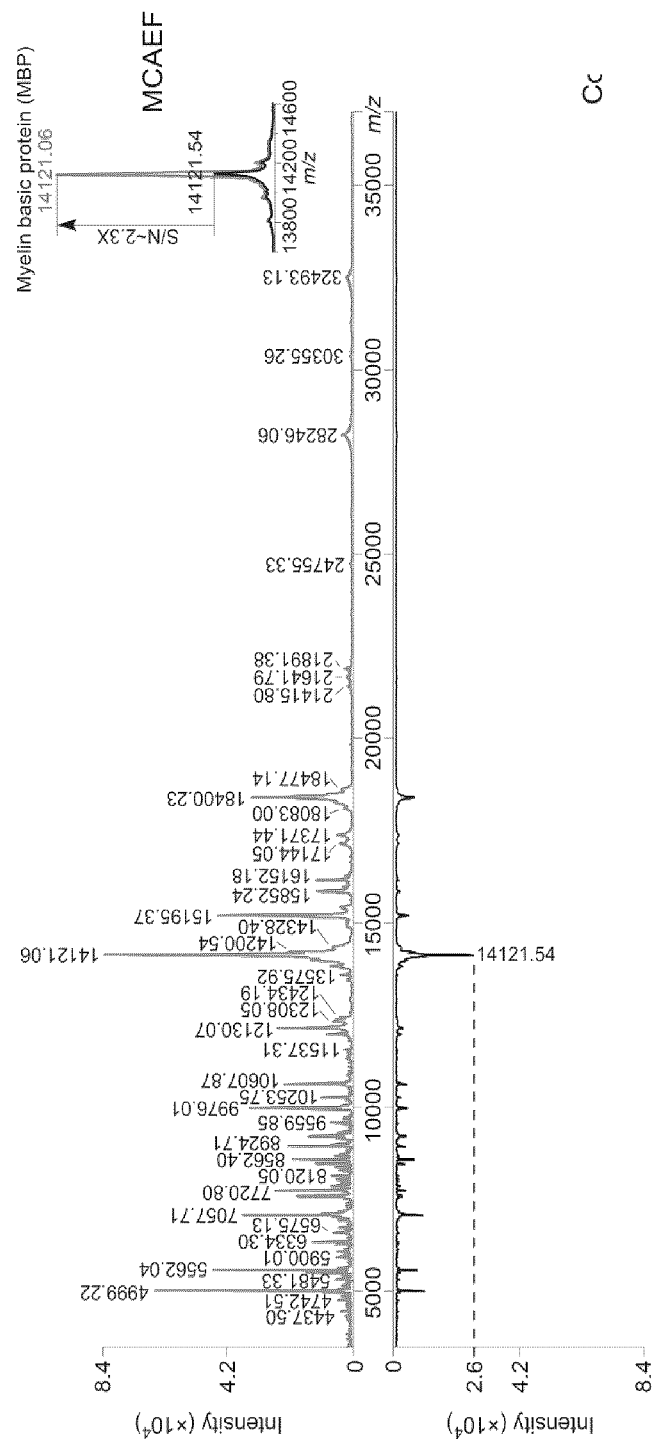
FIG. 19 is a mass spectrum comparing MALDI-TOF mass spectra acquired on a rat brain tissue section for a sample prepared using the disclosed method (red) and for a control sample (black) using sinapinic acid as the matrix.
Figure 20A:
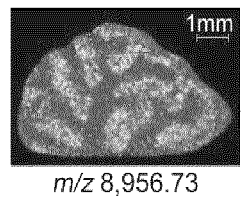
FIGS. 20A-20I are images comparing protein images obtained from control samples (FIGS. 20A, 20C, 20E, and 20G) and samples prepared using an embodiment of the disclosed system and method (FIGS. 20B, 20D, 20F, and 20H)
Figure 20B:
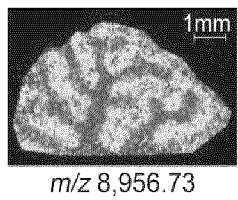
Figure 20C:
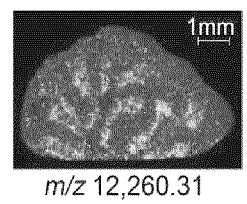
Figure 20D:
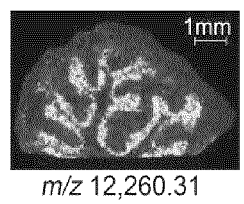
Figure 20I:
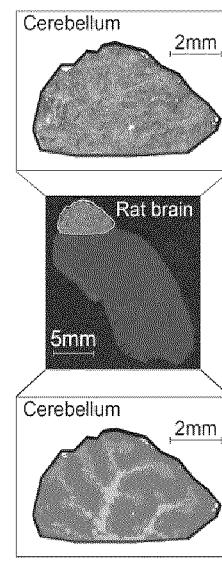
Figure 20E:
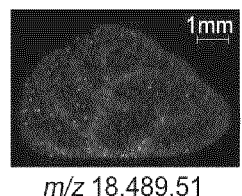
Figure 20F:
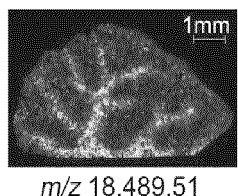
Figure 20G:
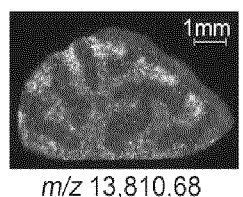
Figure 20H:
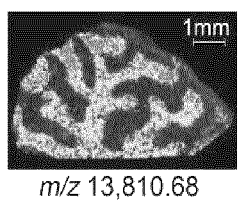

To determine if the disclosed system and method embodiments also enhanced on-tissue detection and imaging of proteins, SA was used as the matrix to coat 12-µm rat brain tissue sections, with and without an electric field, for MALDI-TOF MS imaging. FIG. 19 shows that the previously optimized electric field intensity (600 V/m) was also suitable for enhanced protein detection in the positive ion mode, and also shows that the intensities and S/Ns of the detected proteins on the mass spectra were greatly increased when an embodiment of the disclosed system and method was used. On average, using the disclosed system and method embodiments increased the S/Ns of the detected proteins on the tissue sections by a factor of 2 to 4. Considering myelin basic protein at m/z 14123.1 as an example, an embodiment of the disclosed system and method embodiments produced MALDI-TOF MS S/Ns (inset) which increased 2.3-fold. As was the case for lipids, the significantly increased detection sensitivity resulted in a larger number of proteins that were able to be detected in the rat tissue. With the disclosed system and method embodiments (electric field intensity=600 V/m), 232 protein signals were observed from the mass spectra, while only 119 protein signals were detected in the control spectrum without using the disclosed system or method. The increased detection sensitivity enabled imaging of peptides and proteins across the whole mass detection range, including many higher MW proteins. Observed protein signals are illustrated in Table 2, although the identities of most of these protein signals remain unknown. A person of ordinary skill in the art, however, could readily recognize methods for identifying these protein signals, such as by combining protein extraction, tryptic digestion, and LC-MS/MS.

FIGS. 20A-20I and FIGS. 21A-21I show the effect of the disclosed method and system on the images of proteins detected on the rat brain sections. Four proteins (at m/z 8956.73, m/z 12260.31, m/z 18489.51 and m/z 13810.68), which were detectable under both the control conditions (electric field intensity=0) and an embodiment of the disclosed method (electric field intensity=600 V/m), showed finer image resolution using an embodiment of the disclosed method and system. Spatial distributions of these proteins in the grey matter, white matter, and granular layer of the rat brain cerebellum region were more clearly observed because of the higher S/Ns. FIGS. 21A-21I shows the images of four small protein signals (m/z 8713.34, m/z 12434.19, m/z 5013.79, and m/z 7050.08). These four proteins were only detectable using an embodiment of the disclosed method and were not observable in the control embodiment. The images of these eight proteins show distinct distributions in the histological structure of the cerebellum, i.e., these protein species showed different localization in the cerebellum. Proteins represented by m/z 8956.73 and m/z 8713.34 were observed with higher abundance within the grey matter while the proteins of m/z 12260.31 and m/z 12434.19, and proteins of m/z 18489.51 and m/z 5013.79 were uniquely observed in the granular layer and the white matter of the rat brain cerebellum, respectively. Proteins of m/z 13810.68 and m/z 7050.08 were found mainly distributed in white matter and granular layers of the cerebellum, while the protein of m/z 13810.68 shows a higher abundance distribution at the end of the white matter and in the granular layers in the rat brain. This embodiment establishes that the disclosed method and system embodiments not only enhance protein detection on tissue by MALDI-MS, but also provides the opportunity to successfully image some proteins that were not previously observable in the MALDI tissue imaging experiments.

The results disclosed above demonstrate that the disclosed method and system provides increased S/Ns and higher numbers of lipids and proteins detected on tissue by MALDI-MS. The disclosed method and system showed good compatibility not only with different tissue samples but also with different MALDI matrices that were prepared in different solvents with different pH values. Without being limited to a single theory of operation, it is currently believed that the electric field-induced matrix droplet polarization and subsequent on-tissue micro-extraction of the chargeable compounds of interest into the matrix layers promotes the improved MALDI-MS detection and imaging.

Example 2

Materials and Chemicals:

A human prostate cancer specimen was obtained from BioServe Biotechnologies (Beltsville, Md., USA). The tissue specimen was obtained from a 64-year old male patient during prostate cancer surgical removal, with the patient's informed consent. According to the accompanying pathological classification information, the prostate cancer was diagnosed at stage II. This tissue specimen was stored at −80° C. upon receipt. Use of the human samples involved in this study was approved by the Ethics Committee of the University of Victoria. The "ESI tuning mix" solution was purchased from Agilent Technologies (Santa Clara, Calif., USA). The rabbit polyclonal antibody against human apoliprotein C-I (ab85870) and the biotinylated anti-rabbit immunoglobulin G (IgG, ab97051) were purchased from Abcam Inc. (Cambridge, Mass., USA). Unless otherwise noted, all other chemical reagents were purchased from Sigma-Aldrich (St. Louis, Mo., USA).

Tissue Sectioning:

The frozen prostate specimen was sectioned at −20° C. in a cryostat (Microm HM500, Waldorf, Germany). Serial tissue sections of 12-μm thickness were immediately thaw-mounted onto 25 mm×75 mm ITO-coated electrically conductive microscopic glass slides obtained from Bruker Daltonics (Bremen, Germany). Before matrix application, the tissue mounted slides were placed under a vacuum of 0.1 psi for 15 minutes in Savant SPD1010 SpeedVac Concentrator (Thermo Electron Corporation, Waltham, Mass., USA). For protein MS analysis, the tissue sections were washed in Petri dish twice with 70% ethanol for 30 seconds followed by another wash with 95% ethanol for 15 seconds to remove lipids, before vacuum drying and matrix coating. In some embodiments, the tissue sections were washed in Petri dish twice with 70% ethanol for 30 s followed by another wash with 95% ethanol for 15 s to remove lipids before matrix application. Subsequently, the tissue mounted slides were placed under a vacuum of 0.1 psi for 15 min in Savant SPD1010 SpeedVac Concentrator (Thermo Electron Corporation, Waltham, Mass., USA) for vacuum drying.

Histological Staining:

To obtain histological optical images of prostate tissue sections, hematoxylin and eosin (H&E) staining was performed according to a previously reported procedure.

Immunohistochemistry

Figure 33A:
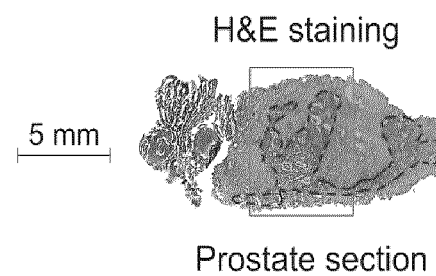
FIGS. 33A and 33B illustrate a representative tissue section used for immunohistochemical analysis (FIG. 33A) and results obtained from immunohistochemical analysis (FIG. 33B).
Figure 33B:
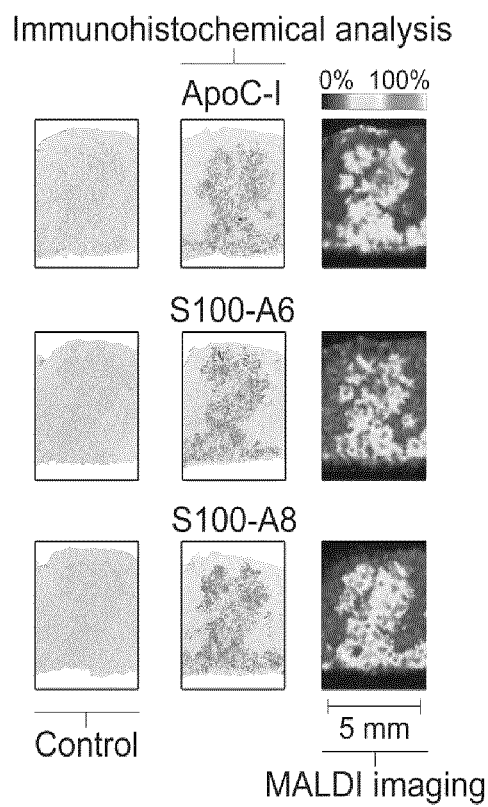

Immunostaining of the frozen tissue specimens was done using the avidin-biotin peroxidase complex method with the 'Cell and Tissue Staining" kit. Briefly, three frozen tissue sections (10 μm thick) were incubated in 0.3% hydrogen peroxide (peroxidase blocking reagent) for 15 min to block endogenous peroxide activity. The tissue sections were then exposed to the serum blocking reagent to block nonspecific binding, and endogenous avidin and biotin were blocked with the avidin-biotin blocking reagent. Two of the three tissue sections were incubated separately for 16 h at 4° C. with the two mouse monoclonal antibodies against human S100A6 and S100A8, both of which were diluted 1 to 32 with an incubation buffer composed of 1% bovine serum albumin, 1% normal donkey serum, 0.3% Triton® X-100, and 0.01% sodium azide in PBS. The tissue sections were then treated with biotinylated anti-mouse IgG for 60 min, followed by another treatment with the high sensitivity Streptavidin-HRP conjugate (HSS-HRP) reagent for 30 min, and stained with the DAB/aminoethylcarbazole chromogen solution according to the supplier's protocol. The DAB enhancer reagent (CTS010) was used to intensify the color reaction of the DAB chromogen solution. Counterstaining was done with Gill's hematoxylin (Sigma-Aldrich,). For the apolipoprotein C-I immunohistochemical analysis, the rabbit poyclonal antibody against human apoliprotein C-I and the biotinylated anti-rabbit IgG were used as the primary and secondary antibodies, respectively, using the same protocol as for human S100A6 and S100A8. Exemplary results are illustrated in FIGS. 33A and 33B.

Matrix Coating:

For lipid analysis, quercetin was dissolved in a mixed methanol:water:25% NH$_4$OH (80:20:0.4, v/v) solution at a matrix concentration of 2.6 mg/mL. SA was prepared at a concentration of 25 mg/mL in a mixed acetonitrile:water:trifluoroacetic acid (TFA) (80:20:0.2, v/v) solution, and this was used as the matrix solution for protein analysis. In some embodiments, a standard protein, insulin (m/z 5734.2) was purchased from Sigma-Aldrich (St. Louis, Mo., USA) and added at an optimized concentration of 30 ng/ml to the matrix solution for the protein analysis from the prostate tissue sections. Insulin was used as an internal standard to normalize signal intensities. Tissue sections were coated with the quercetin or SA matrix using a Bruker Daltonics ImagePrep matrix electronic sprayer (Bremen, Germany). The matrix coatings for each matrix were composed of a 3-second spray, a 60-second incubation period, and a 90-second drying per spray cycle; thirty spray cycles were applied. During the entire process of matrix deposition, a static and uniform electric field at an intensity of +600 V/m was applied to the tissue-mounted glass slides in order for enhanced positive ion MADLI-MS detection. An Epson Perfection 4490 Photo Scanner (Seiko Epson Corp., Japan) was used to capture optical images of the tissue sections.

MALDI-MS:

An Apex-Qe 12-Tesla hybrid quadrupole-Fourier transform ion cyclotron resonance (FTICR) mass spectrometer (Bruker Daltonics, Billerica, Mass., USA), equipped with an Apollo dual-mode electrospray ionization (ESI)/MALDI ion source, was used for the lipid analysis. The laser source was a 355-nm solid-state Smartbeam Nd:YAG UV laser (Azura Laser AG, Berlin, Germany) that was operated at 200 Hz. To acquire MALDI mass spectra which contained reference mass peaks for internal mass calibration, a 1:130 (v/v) diluted Agilent "ESI tuning mix" solution, prepared in isopropanol-water (60:40:0.1, v/v), was infused from the ESI side of the ion source at a flow rate of 2 µL/minute. Mass spectra were acquired over the range of m/z 150 to 1,200 Da. Each MALDI mass spectrum was recorded by accumulating ten scans at 100 laser shots per scan for MALDI-MS profiling. For imaging, the minimum possible laser raster step size of the laser source, 200 µm, was used, and five scans at 100 laser shots per scan were summed per array position.

For protein profiling and imaging, the mass spectra were acquired on an Ultraflex III MALDI time-of-fight (TOF)/TOF mass spectrometer (Bruker Daltonics, Billerica, Mass., USA), which was equipped with a SmartBeam nitrogen UV laser that was operated at 337 nm and 200 Hz, in the positive ion linear mode. The mass-detection range was m/z 3500 to 37500. A laser spot diameter of 100 µm and a raster step size of 200 µm were used for imaging data acquisition. Teaching points were generated to ensure the correct positioning of the laser for spectral acquisition by the use of the Bruker's FlexImaging 2.1 software. As in a previous study, the collected mass spectra were baseline corrected and each peak intensity was normalized by total ion current. A mixture of standard proteins including insulin ([M+H]$^+$, m/z 5734.5), ubiquitin I ([M+H]$^+$, m/z 8565.8), cytochrome c ([M+H]$^+$, m/z 12361.0), myoglobin ([M+H]$^+$, m/z 16953.3), and trypsinogen ([M+H]$^+$, m/z 23982.0), was used for external mass calibration.

Data Analysis:

Lipid profiling spectra were processed using the Bruker DataAnalysis 4.0 software. Batch internal mass calibration, peak de-isotoping, and monoisotopic "peak picking," were processed using a customized VBA script within DataAnalysis. Another custom program written with the LabView development suite was used for peak alignment with an allowable mass error of 2 ppm. To preliminarily assign the detected compounds, the metabolome databases including METLIN, LIPID MAPS, and HMDB, were used for matching the measured m/z values to possible metabolite entities, within a mass error of ±1 ppm. Three ion forms ([M+H]$^+$, [M+Na]$^+$, and [M+K]$^+$) were allowed during the database searching. The Bruker FlexAnalysis 3.4 software was employed for protein mass spectral processing and viewing. A mass window of 0.3% and a signal to noise (S/N) ratio of 3 were selected for peak detection.

The Bruker FlexImaging 2.1 software was used to reconstruct the ion maps of the detected lipids and proteins. Statistical t-tests were conducted using Microsoft Excel 2010.

Lipid Extraction and LC-MS/MS:

Total lipids were extracted from a ca. 25-mg aliquot of the human prostate tissue using a protocol previously described. Briefly, the tissue was homogenized with 200-µL water in a 2-mL Eppendorf tube with the aid of two 5-mm stainless steel balls at a vibrating frequency of 30 Hz for 30 seconds×2 on a Retsch MM400 mixer mill (Haan, Germany). Next, 800 µL of a mixed chloroform-methanol (1:3, v/v) solvent was added, followed by another 30-s homogenization step. The tube was then centrifuged at 10,600×g and 4° C. for 20 minutes in microcentrifuge. The supernatant was carefully transferred to a 1.5-mL Eppendorf tube and mixed with 250 µL of chloroform and 100 µL of water. After 15-s vortex mixing and centrifugation at 10,600×g for 5 minutes, the lower organic phase was carefully taken out using a 200-µL gel loading pipette tip and then dried in a Savant SPD1010 speed vacuum concentrator. The residue was suspended in 100 µL of 2% ACN containing 0.1% TFA, and an 8-µL aliquot was injected.

A Waters ACQUITY UPLC system coupled to a Waters Synapt HDMS quadrupole-time-of-flight (Q-TOF) mass spectrometer (Waters, Inc., Beverly, Mass., USA) was used for LC-MS/MS of lipids as a complementary technique for structural confirmation, using the same procedure as described previously. Assignment of the lipids was performed by comparing the acquired MS/MS spectra with those in the standard MS/MS libraries of the METLIN, HMDB, or LIPID MAPS database.

Protein Extraction, Digestion, and LC-MS/MS Analysis:

The protein precipitate from the lipid extraction step described above was resuspended in 300 µL of 25 mM NH$_4$HCO$_3$/25 mM dithiothreitol (pH 7.8) and incubated at 56° C. for 50 minutes. Next, the alkylation was performed by adding 300 µL of 25 mM NH$_4$HCO$_3$/100 mM idoacetamide and placing the sample in dark at room temperature for 45 minutes. After reaction, 15 µL of 25 mM NH$_4$HCO$_3$/1 M DTT was added to quench the reaction and 200 µL of 50 ng/µL sequencing-grade modified trypsin/25 mM NH$_4$HCO$_3$ solution was added. The digestion was allowed to proceed at 37° C. overnight, after which the reaction was quenched by adding 800 µL of 0.2% TFA in water. The mixed solution was loaded onto an Oasis HLB 3 cc/200 mg cartridge (Waters Inc., Milford, Mass., USA). After washes with 3×1 mL of 0.1% TFA, the peptides were eluted with 3×600 µL of 75% ACN in water containing 0.1% TFA. The pooled elutes were dried down in the same speed vacuum concentrator.

The residue was suspended in 100 µL of 2% ACN containing 0.1% TFA, and an 8-µL aliquot was loaded onto a Magic C18-AQ trapping column (100 µm I.D., 2 cm length, 5 µm, 100 Å) and separated on an in-house packed Magic C-18AQ capillary column (75 µm I.D.×15 cm, 5 µm, 100 Å, Michrom BioResources Inc, Auburn, Calif., USA) at a flow rate of 300 nl/minute using a Thermo Scientific EASY-nLC II system. The chromatographic system was coupled on-line to an LTQ Orbitrap Velos Pro mass spectrometer (Thermo Fisher Scientific, Bremen, Germany), equipped with a nano-flow electrospray ionization source operated in the positive ion mode. The mobile phase was 2% ACN in water/0.1% formic acid (solvent A) and 90% ACN in water/0.1% formic acid (solvent B) for binary gradient elution. The peptides were chromatographed on the analytical column using an elution gradient of 5% to 45% B in 45 minutes; 45% to 80% B in 2 minutes and 80% to 100% B in 2 minutes. The column was then equilibrated at 5% B for 8 minutes before the next injection. The ESI voltage was 2.3 kV and the ion transfer capillary temperature was 250° C. Other MS operation parameters included a survey scan m/z range of 400 to 2000 Da, with the data recorded in the profile mode. Survey scans were detected in the FTMS mode at 60000 FWHM (m/z 400). The automatic gain control (AGC) target was 1e6 with one microscan and a maximum inject time of 500 ms. To ensure FT detection mass accuracy, a lock mass at m/z 445.120024 (a ubiquitous siloxane contaminant) was used for real-time internal mass calibration throughout the LC-MS runs. For MS/MS, the fifteen most intense ions with charge states of +2 to +4 which had ion counts exceeding 5,000 in the survey scan were selected for collision-induced dissociation (CID) in the ion trap and the data were recorded in the centroid mode. Dynamic exclusion was applied with the following settings: repeat count, 2; repeat duration, 15 seconds; exclusion list size, 500; exclusion duration, 60 seconds and mass exclusion window, 10 ppm. The CID activation settings were as follows: isolation window, 2 Da; AGC target, 1e4; maximum ion trap inject time, 100 ms; activation time, 10 ms; activation Q, 0.250. The normalized collision energy was 35%.

The raw data files were analyzed with the Proteome Discoverer 1.4.0.228 software suite (Thermo Scientific, Bremen, Germany) to generate peak lists for proteome database searching. Protein identification was carried out with an in-house Mascot 2.2 server, searching against the Uniprot-Swissprot 20110104 (523151 sequences; 184678199 residues) and Uniprot_Trembl 130912 (41,451,118 sequences; 13208986710 residues) within the taxonomy of Homo sapiens and with the following parameters: precursor tolerance, 10 ppm; MS/MS tolerance, 0.6 Da; allowable missed cleavages during trypsin digestion, 1; fixed amino acid modification: carbamidomethylation (C); variable amino acid modification(s): deamidation (N,Q), oxidation (M), and phosphorylation (S/T/Y). The validation of the peptide assignments was based on q-Value with the Percolator settings: Max delta Cn, 0.05; Target FDR (strict), 0.01, and Target FDR (relaxed), 0.05.

Optimization of Insulin Concentration in Matrix Solution for Use as an Internal Standard for MALDI-TOF MS Analysis To normalize the signal intensities between different experiments, a standard protein (insulin) was added into the SA solution during matrix preparation to form a series of concentrations from 0 to 1600 ng/ml, with concentration intervals of 100 ng/ml. These solutions were then spotted onto a clean ITO-coated electrically conductive microscopic glass slide (FIG. 29A). After drying, the glass slide was loaded into the MALDI TOF/TOF MS for direct detection of the protein. Each spot was analyzed at least three times. As shown in FIG. 29A, similar insulin mass spectra were observed from the same concentration spot, indicating the stability of MALDI TOF/TOF MS for protein detection. FIG. 29B shows the standard curve generated from insulin spots with different concentrations. The linear concentration range for insulin was from 500 to 1300 ng/ml, and the optimum concentration of insulin was found to be 900 ng/ml. Thirty spray cycles with the ImagePrep matrix electronic sprayer was used for matrix coating at an initial concentration of insulin of 30 ng/ml. At this concentration, the relative intensity of insulin was within the linear concentration region and close to that of the 900 ng/ml insulin spot (FIG. 29B), indicating that 30 ng/ml of insulin in the SA matrix solution is the optimized concentration.

Example 2A

This embodiment concerns using the disclosed method and system to prepare biological samples of human prostate tissue sections to facilitate the detection of a large number of compounds of interest. FIG. 22 shows two accumulated mass spectra acquired by MALDI-FTICR MS from the cancerous region (upper) and the adjacent non-cancerous region (lower) of a human prostate tissue section. Both spectra show a large number of observed signals in the mass range from m/z 400 to 1200, with 367 identified lipid entities. As shown in Tables 3 to 5, most of these lipids were assigned as glycerophospholipids, sphingolipids, and neutral lipids and were in the sub-classes of phosphatidylcholine (PC), phosphatidylethanolamine (PE), phosphatidic acids (PA), phosphoglycerol (PG), sphingomyelin (SM), glycoceramide (Gly-Cer), diacylglycerol (DG), and triacylglycerol (TG). The ion maps of these lipids were reconstructed and their distribution patterns were observed. Among the 367 identified lipids, 72 and 34 compounds were uniquely detectable in the non-cancerous cell region and the cancerous cell region, respectively, as summarized in Table 3, below and Tables 4 and 5.

TABLE 3

Summary of lipids and proteins detected in the human prostate cancer (stage II) tissue

| | Unique distribution | | Non-cancerous region vs. | |
| --- | --- | --- | --- | --- |
| | Non-cancerous | Cancerous | Cancerous region (t-test) | |
| Classes | region | region | $P < 0.05$ | $P < 0.01$ |
| Lipids | 72 | 34 | 48 | 66 |
| Proteins | — | 64 | 69 | 27 |

TABLE 4

Summary of lipids detected only in the non-cancerous region of the imaged prostate tissue section.

| | | | Assignment | | Structurally |
| --- | --- | --- | --- | --- | --- |
| No. | m/z | Ion form | Compound | Molecular formula | specific CID ions (m/z)[a] |
| 1 | 482.324116 | [M + H]+ | PE(18:0) | C23H48NO7P | 140, 153, 196, 214, 283, 419, 437, 480 |
| 2 | 480.34492 | [M + H]+ | PC(O-16:1) | C24H50NO6P | |
| 3 | 573.260875 | [M + K]+ | PG(20:3) | C26H47O9P | |
| 4 | 535.334498 | [M + H]+ | PC(18:1) | C26H50NO8P | |

TABLE 4-continued

Summary of lipids detected only in the non-cancerous region of the imaged prostate tissue section.

| No. | m/z | Ion form | Compound | Molecular formula | Structurally specific CID ions (m/z)[a] |
|---|---|---|---|---|---|
| 5 | 541.349996 | [M + H]+ | PG(20:0) | C26H53O9P | |
| 6 | 510.390943 | [M + H]+ | PC(O-18:0) | C26H56NO6P | |
| 7 | 585.340781 | [M + H]+ | PI(P-18:0) | C27H53O11P | |
| 8 | 552.342446 | [M + Na]+ | 2-(8-[3]-ladderane-octanyl)-sn-glycero-3-phosphocholine | C28H52NO6P | |
| 9 | 605.321528 | [M + K]+ | PG(22:1) | C28H55O9P | |
| 10 | 566.380702 | [M + H]+ | PC(20:0) | C28H56NO8P | |
| 11 | 546.44928 | [M + Na]+ | Cer(d32:2) | C32H61NO4 | |
| 12 | 593.400982 | [M + K]+ | TG(30:0) | C33H62O6 | |
| 13 | 534.488071 | [M + H]+ | Cer(d34:3) | C34H63NO3 | |
| 14 | 538.519371 | [M + H]+ | Cer(d34:1) | C34H67NO3 | |
| 15 | 554.514353 | [M + H]+ | Cer(34:1) | C34H67NO4 | |
| 16 | 658.445073 | [M + H]+ | PE(30:3) | C35H64NO8P | |
| 17 | 647.464632 | [M + H]+ | PA(32:1) | C35H67O8P | |
| 18 | 623.410847 | [M + K]+ | DG(34:6) | C37H60O5 | |
| 19 | 793.423897 | [M + K]+ | PI(28:0) | C37H71O13P | |
| 20 | 581.550337 | [M + H]+ | DG(O-34:1) | C37H72O4 | |
| 21 | 639.555817 | [M + H]+ | TG(36:0) | C39H74O6 | |
| 22 | 659.450318 | [M + K]+ | 1-(6-[5]-ladderane-hexanoyl)-2-(8-[3]-ladderane-octanyl)-sn-glycerol | C41H64O4 | |
| 23 | 637.556702 | [M + H]+ | 1-(8-[3]-ladderane-octanyl)-2-(8-[3]-ladderane-octanyl)-sn-glycerol | C43H72O3 | |
| 24 | 1077.447313 | [M + H]+ | PIP3(34:1) | C43H84O22P4 | |
| 25 | 737.579229 | [M + Na]+ | TG(42:4) | C45H78O6 | |
| 26 | 959.598538 | [M + K]+ | PI(40:1) | C49H93O13P | |
| 27 | 866.674677 | [M + H]+ | PC(42:4) | C50H92NO8P | |
| 28 | 884.721341 | [M + H]+ | PE(46:2) | C51H98NO8P | |
| 29 | 1044.695504 | [M + H]+ | MIPC(d40:0(2OH)) | C52H102NO17P | |
| 30 | 1060.692005 | [M + H]+ | MIPC(t40:0(2OH)) | C52H102NO18P | |
| 31 | 892.678982 | [M + H]+ | PC(44:5) | C52H94NO8P | |
| 32 | 855.740554 | [M + Na]+ | TG(50:1) | C53H100O6 | |
| 33 | 857.756862 | [M + Na]+ | TG(50:0) | C53H102O6 | |
| 34 | 867.686781 | [M + K]+ | TG(50:3) | C53H96O6 | |
| 35 | 868.689902 | [M + K]+ | TG(50:0)(d5) | C53H97D5O6 | |
| 36 | 853.722748 | [M + Na]+ | TG(50:2) | C53H98O6 | |
| 37 | 1087.686544 | [M + Na]+ | Ganglioside GA2 (34:1) | C54H100N2O18 | |
| 38 | 944.707876 | [M + Na]+ | PC(46:4) | C54H100NO8P | |
| 39 | 998.747813 | [M + Na]+ | LacCer(d42:0) | C54H105NO13 | |
| 40 | 1094.678338 | [M + K]+ | MIPC(d42:0) | C54H106NO16P | |
| 41 | 1072.727123 | [M + H]+ | MIPC(d42:0(2OH)) | C54H106NO17P | |
| 42 | 1088.717745 [M + H]+ 1110.706325 [M + Na]+ 1126.686791 [M + K]+ | | MIPC(t42:0(2OH)) | C54H106NO18P | |
| 43 | 928.772882 | [M + H]+ | PC(46:1) | C54H106NO8P | |
| 44 | 952.783645 | [M + Na]+ | PC(46:0) | C54H108NO8P | |
| 45 | 1069.721083 [M + Na]+ 1085.694929 [M + K]+ | | NeuAcalpha2-3Galbeta-Cer(d38:1) | C55H102N2O16 | |
| 46 | 901.760548 | [M + K]+ | TG(52:0) | C55H106O6 | |
| 47 | 875.710367 [M + Na]+ 891.684853 [M + K]+ | | TG(52:5) | C55H96O6 | |
| 48 | 1000.76516 [M + H]+ 1022.747109 [M + Na]+ | | Galbeta1-4Glcbeta-Cer(d44:2) | C56H105NO13 | |
| 49 | 1002.781249 [M + H]+ 1024.763192 [M + Na]+ | | Galbeta1-4Glcbeta-Cer(d44:1) | C56H107NO13 | |
| 50 | 1026.779859 | [M + Na]+ | LacCer(d44:0) | C56H109NO13 | |
| 51 | 1099.774557 | [M + H]+ | GlcNα1-6Ins-1-P-Cer(t44:0) | C56H111N2O16P | |
| 52 | 1075.767317 | [M + H]+ | NeuAcalpha2-3Galbeta-Cer(d40:1) | C57H106N2O16 | |
| 53 | 901.722261 | [M + Na]+ | TG(54:6) | C57H98O6 | |
| 54 | 1050.77085 | [M + Na]+ | PS-NAc(52:1) | C58H110NO11P | |
| 55 | 943.714624 | [M + K]+ | TG(56:7) | C59H100O6 | |
| 56 | 929.755446 [M + Na]+ 945.733126 [M + K]+ | | TG(56:6) | C59H102O6 | |

TABLE 4-continued

Summary of lipids detected only in the non-cancerous region of the imaged prostate tissue section.

| No. | m/z | Ion form | Compound | Molecular formula | Structurally specific CID ions (m/z)[a] |
|---|---|---|---|---|---|
| 57 | 931.773508 | [M + Na]+ | TG(56:5) | C59H104O6 | |
|  | 947.746977 | [M + K]+ | | | |
| 58 | 933.78912 | [M + Na]+ | TG(56:4) | C59H106O6 | |
|  | 949.764101 | [M + K]+ | | | |
| 59 | 935.805674 | [M + Na]+ | TG(56:3) | C59H108O6 | |
|  | 951.778881 | [M + K]+ | | | |
| 60 | 953.793082 | [M + K]+ | TG(56:2) | C59H110O6 | |
| 61 | 942.85186 | [M + Na]+ | TG(56:0) | C59H114O6 | |
| 62 | 999.741312 | [M + Na]+ | TG(62:13) | C65H100O6 | |
| 63 | 1001.749518 | [M + Na]+ | TG(62:12) | C65H102O6 | |
| 64 | 1023.738105 | [M + Na]+ | TG(64:15) | C67H100O6 | |
| 65 | 1025.750662 | [M + Na]+ | TG(64:14) | C67H102O6 | |
| 66 | 1027.766642 | [M + Na]+ | TG(64:13) | C67H104O6 | |
| 67 | 1021.7207 | [M + Na]+ | TG(64:16) | C67H98O6 | |
| 68 | 1049.75059 | [M + Na]+ | TG(66:16) | C69H102O6 | |
|  | 1065.726359 | [M + K]+ | | | |
| 69 | 1051.767325 | [M + Na]+ | TG(66:15) | C69H104O6 | |
| 70 | 1053.784349 | [M + Na]+ | TG(66:14) | C69H106O6 | |
| 71 | 1055.803964 | [M + Na]+ | TG(66:13) | C69H108O6 | |
| 72 | 1045.721354 | [M + Na]+ | TG(66:18) | C69H98O6 | |
|  | 1061.69462 | [M + K]+ | | | |

Note:
[a] Structurally specific CID ions of extracted lipids were detected by LC-MS/MS using CID. Bold fragment ions were detected in the positive ion mode, and un-bolded fragment ions were detected in the negative ion mode. The "*" indicated "$p < 0.05$" and "**" indicated "$p < 0.01$".

TABLE 5

Summary table of lipids detected only in the cancerous regions of the prostate tissue.

| No. | m/z | Ion form | Compound | Molecular formula | Structurally specific CID ions (m/z)[a] |
|---|---|---|---|---|---|
| 1 | 476.253415 | [M + K]+ | | C21H44NO6P | |
| 2 | 476.274855 | [M + Na]+ | PE(16:0) | C21H44NO7P | 153, 196, 214, 255, 378, 409, 452 |
| 3 | 506.264199 | [M + K]+ | PC(14:0) | C22H46NO7P | |
| 4 | 499.222132 | [M + K]+ | PA(20:3) | C23H41O7P | |
| 5 | 514.230689 | [M + K]+ | PE(18:3) | C23H42NO7P | |
| 6 | 502.241492 | [M + H]+ | PC(16:4) | C24H40NO8P | |
|  | 524.251683 | [M + Na]+ | | | |
| 7 | 556.207227 | [M + K]+ | PS(18:4) | C24H40NO9P | |
| 8 | 527.253295 | [M + Na]+ | PG(18:4) | C24H41O9P | |
| 9 | 525.237458 | [M + K]+ | PA(22:4) | C25H43O7P | |
| 10 | 508.340075 | [M + H]+ | PE(20:1) | C25H50NO7P | |
|  | 546.296909 | [M + K]+ | | | |
| 11 | 574.290842 | [M + K]+ | PC(18:1) | C26H50NO8P | 104, 184, 504, 522 |
| 12 | 580.279503 | [M + K]+ | PC(20:5) | C28H48NO7P | |
| 13 | 583.299389 | [M + Na]+ | PG(22:4) | C28H49O9P | |
| 14 | 589.344418 | [M + Na]+ | PG(22:1) | C28H55O9P | |
| 15 | 606.296313 | [M + K]+ | PC(22:6) | C30H50NO7P | |
| 16 | 662.511917 | [M + H]+ | PC(P-28:0) | C36H72NO7P | |
| 17 | 794.436892 | [M + K]+ | PS(34:4) | C40H70NO10P | |
| 18 | 841.426387 | [M + K]+ | PI(32:4) | C41H71O13P | |
| 19 | 816.433041 | [M + K]+ | PS(36:7) | C42H68NO10P | |
| 20 | 820.452542 | [M + K]+ | PS(36:5) | C42H72NO10P | |
| 21 | 672.626969 | [M + Na]+ | Cer(d42:1) | C42H83NO3 | |
| 22 | 869.457687 | [M + K]+ | PI(34:4) | C43H75O13P | |
| 23 | 840.421242 | [M + K]+ | PS(38:9) | C44H68NO10P | |
| 24 | 895.473337 | [M + K]+ | PI(36:5) | C45H77O13P | |
| 25 | 897.491508 | [M + K]+ | PI(36:4) | C45H79O13P | |
| 26 | 787.561212 | [M + Na]+ | PA(P-42:4) | C45H81O7P | |
| 27 | 898.499492 | [M + K]+ | PS(42:8) | C48H78NO10P | |
| 28 | 880.676821 | [M + Na]+ | PE(44:1) | C49H96NO8P | |
| 29 | 879.673671 | [M + K]+ | SM(d44:2) | C49H97N2O6P | |
| 30 | 882.692866 | [M + Na]+ | PE(44:0) | C49H98NO8P | |

TABLE 5-continued

Summary table of lipids detected only in the cancerous regions of the prostate tissue.

| | | Assignment | | Structurally |
| No. | m/z | Ion form | Molecular formula | specific CID ions (m/z)[a] |
| --- | --- | --- | --- | --- |
| 31 | 881.690603 | [M + K]+ | SM(d44:1) | C49H99N2O6P |
| 32 | 893.52674 | [M + Na]+ | PG(44:10) | C50H79O10P |
| 33 | 1010.69032 | [M + K]+ | Galbeta1-4Glcbeta-Cer(d42:2) | C54H101NO13 |
| 34 | 1118.698912 | [M + K]+ | Galalpha1-4Galbeta1-4Glcbeta-Cer(d38:1) | C56H105NO18 |

Note:
[a] Structurally specific CID ions of extracted lipids were detected by LC-MS/MS using CID. Bold fragment ions were detected in the positive ion mode, and un-bolded fragment ions were detected in the negative ion mode. The "*" indicated "$p < 0.05$" and "**" indicated "$p < 0.01$".

The remaining 261 lipid entities were detected in both cell regions. Based on t-tests, ca. 43.7% (114) of these 261 lipid entities showed differential distributions between the cancerous and the non-cancerous cell regions ($p<0.05$), and 66 lipids showed significantly different distribution patterns ($p<0.01$). The identities of these lipids are listed in Table 6. Taking PC(34:1) (m/z 798.540) and TG(52:3) (m/z 895.716), as examples, up-regulation of PC(34:1) and down-regulation of TG(52:3) was found in the cancerous region, as indicated in the two insets of FIG. 22. The ion density maps for PC(34:1) and TG(52:3) are shown in FIGS. 23A and 23B. From these two ion maps, the cancerous and non-cancerous cell regions of the prostate tissue section can be distinguished much more easily than from to the optical H&E staining image.

TABLE 6

Summary of lipids differentially expressed between the non-cancerous and cancerous regions of the imaged prostate tissue

| | | | Assignment | | Non-cancerous areas | | Cancerous areas | | | | Structurally specific CID ions |
| No. | m/z | Ion form | Compound | Molecular formula | aveg | stdev | aveg | stdev | Exp. | p-value | (m/z)[a] |
| --- | --- | --- | --- | --- | --- | --- | --- | --- | --- | --- | --- |
| 1 | 497.2067 | [M + K]+ | PA(20:4) | C23H39O7P | 1.69 | 0.07 | | 0.03 | ↑ | 0.0373605* | 153, 171, 259, 303, 457 |
| 2 | 483.2482 | [M + Na]+ | PA(20:3) | C23H41O7P | 0.04 | 0.00 | 0.12 | 0.00 | ↑↑ | 0.0000025** | |
| 3 | 478.3293 | [M + H]+ | PC(O-16:2) | C24H48NO6P | 3.41 | 0.15 | 5.30 | 0.84 | ↑ | 0.0180573* | |
| 4 | 535.2992 | [M + Na]+ | PG(18:0) | C24H49O9P | 1.02 | 0.02 | 3.53 | 0.09 | ↑↑ | 0.0000013** | |
| 5 | 502.3293 | [M + Na]+ | PC(O-16:1) | C24H50NO6P | 0.91 | 0.02 | 1.70 | 0.21 | ↑ | 0.0292535* | |
| 6 | 496.3398 | [M + H]+ | PC(16:0) | C24H50NO7P | 6.41 | 0.27 | 8.43 | 0.38 | ↑ | 0.0169219* | |
| | 534.2957 | [M + K]+ | | | 3.82 | 0.10 | 13.32 | 0.50 | ↑↑ | 0.0000053** | 104, 184, 478, 496 |
| 7 | 504.3449 | [M + Na]+ | PC(O-16:0) | C24H52NO6P | 1.69 | 0.14 | 3.23 | 0.15 | ↑ | 0.0214074* | |
| 8 | 518.3218 | [M + H]+ | PC(18:3) | C26H48NO7P | 2.28 | 0.06 | 5.27 | 0.31 | ↑↑ | 0.0000787** | |
| 9 | 522.3556 | [M + H]+ | PC(18:1) | C26H52NO7P | 1.82 | 0.14 | 2.41 | 0.08 | ↑ | 0.0304636* | 104, 184, 504, 522 |
| 10 | 576.3069 | [M + K]+ | PS(P-20:0) | C26H52NO8P | 1.20 | 0.09 | 1.94 | 0.19 | ↑ | 0.0367984* | |
| 11 | 562.3273 | [M + K]+ | PC(18:0) | C26H54NO7P | 1.41 | 0.01 | 3.55 | 0.13 | ↑↑ | 0.0000079** | 104, 184, 506, 524 |
| 12 | 552.307 | [M + Na]+ | PE(22:4) | C27H48NO7P | 1.23 | 0.09 | 2.17 | 0.48 | ↑ | 0.0284172* | |
| 13 | 618.3844 | [M + K]+ | PC(22:0) | C30H62NO7P | 0.79 | 0.08 | 0.98 | 0.05 | ↑ | 0.0213214* | |
| 14 | 558.4649 | [M + Na]+ | Cer(d34:2) | C34H65NO3 | 0.70 | 0.01 | 1.01 | 0.03 | ↑↑ | 0.0000459** | |
| 15 | 576.4986 | [M + Na]+ | Cer(d34:1(2OH)) | C34H67NO4 | 5.04 | 0.10 | 10.07 | 0.26 | ↑↑ | 0.0000059** | |
| 16 | 551.5036 | [M + H]+ | DG(P-32:1) | C35H66O4 | 3.24 | 0.19 | 4.34 | 0.11 | ↑↑ | 0.0009822** | |
| 17 | 578.5227 | [M + H]+ | Cer(d36:3(2OH)) | C36H67NO4 | 2.07 | 0.03 | 4.17 | 0.06 | ↑↑ | 0.0000006** | |
| 18 | 602.493 | [M + K]+ | Cer(d36:2) | C36H69NO3 | 0.81 | 0.08 | 1.08 | 0.11 | ↑ | 0.0244472* | |
| 19 | 604.5085 | [M + K]+ | Cer(d36:1) | C36H71NO3 | 1.03 | 0.11 | 1.47 | 0.05 | ↑ | 0.0370339* | |
| 20 | 777.4244 | [M + K]+ | PI(P-28:0) | C37H71O12P | 0.20 | 0.02 | 0.68 | 0.03 | ↑↑ | 0.0000280** | |
| 21 | 736.4422 | [M + K]+ | PC(30:4) | C38H68NO8P | 0.43 | 0.04 | 1.03 | 0.03 | ↑↑ | 0.0000281** | |
| 22 | 738.4558 | [M + K]+ | PC(30:3) | C38H70NO8P | 2.20 | 0.26 | 4.55 | 0.16 | ↑↑ | 0.0001972** | |
| 23 | 704.5226 | [M + H]+ | PC(30:1) | C38H74NO8P | 7.31 | 0.27 | 2.56 | 0.07 | ↓↓ | 0.0000076** | |
| 24 | 706.5384 | [M + H]+ | PC(30:0) | C38H76NO8P | 1.92 | 0.40 | 1.07 | 0.06 | ↓ | 0.0217115* | |
| | 744.4943 | [M + K]+ | | | 2.15 | 0.10 | 3.13 | 0.39 | ↑ | 0.0141731* | |
| 25 | 701.4535 | [M + Na]+ | PA(P-36:5) | C39H67O7P | 0.14 | 0.01 | 0.25 | 0.02 | ↑ | 0.0177334* | |
| 26 | 735.4367 | [M + K]+ | PA(36:4) | C39H69O8P | 0.82 | 0.07 | 2.48 | 0.17 | ↑↑ | 0.0000890** | |
| 27 | 603.5352 | [M + H]+ | 1-(14-methyl-pentadecanoyl)-2-(8-[3]-ladderane-octanyl)-sn-glycerol | C39H70O4 | 2.37 | 0.25 | 3.51 | 0.26 | ↑ | 0.0536454* | |

TABLE 6-continued

Summary of lipids differentially expressed between the non-cancerous and cancerous regions of the imaged prostate tissue

| | | | Assignment | | Non-cancerous areas | | Cancerous areas | | | | Structurally specific CID ions |
|---|---|---|---|---|---|---|---|---|---|---|---|
| No. | m/z | Ion form | Compound | Molecular formula | aveg | stdev | aveg | stdev | Exp. | p-value | (m/z)[a] |
| 28 | 721.478 | [M + Na]+ | PA(36:3) | C39H71O8P | 1.38 | 0.06 | 2.37 | 0.31 | ↑ | 0.0559352* | |
| | 737.4523 | [M + K]+ | | | 5.40 | 0.54 | 10.25 | 0.57 | ↑↑ | 0.0004408** | 279, 281, 415, 417, 433, 435 |
| 29 | 723.4944 | [M + Na]+ | PA(36:2) | C39H73O8P | 5.40 | 0.44 | 10.54 | 0.75 | ↑↑ | 0.0005108** | 78, 153, 279, 283, |
| | 739.4679 | [M + K]+ | | | 7.62 | 0.67 | 37.64 | 0.58 | ↑↑ | 0.0000005** | 415, 419, 433, 437, 699 |
| 30 | 741.4881 | [M + K]+ | PA(36:1) | C39H75O8P | 1.17 | 0.06 | 1.93 | 0.07 | ↑↑ | 0.0001399** | 79, 153, 281, 283, 417, 419, 435, 437, 701 |
| 31 | 740.4992 | [M + K]+ | PE(P-34:1) | C39H76NO7P | 5.00 | 0.44 | 9.94 | 0.52 | ↑↑ | 0.0002266** | |
| 32 | 740.5184 | [M + Na]+ | PE(34:1) | C39H76NO8P | 0.84 | 0.03 | 1.00 | 0.04 | ↑ | 0.0614841* | |
| 33 | 739.5143 | [M + K]+ | SM(d34:2) | C39H77N2O6P | 1.55 | 0.02 | 1.43 | 0.06 | ↓ | 0.0236850* | |
| 34 | 703.5751 | [M + H]+ | SM(d34:1) | C39H79N2O6P | 11.99 | 0.55 | 6.18 | 0.31 | ↓↓ | 0.0000888** | 163, 184, 682 |
| 35 | 724.4973 | [M + H]+ | PC(32:5) | C40H70NO8P | 1.93 | 0.25 | 5.88 | 0.34 | ↑↑ | 0.0000852** | |
| 36 | 764.4722 | [M + K]+ | PC(32:4) | C40H72NO8P | 1.67 | 0.28 | 3.02 | 0.58 | ↑ | 0.0222108* | |
| 37 | 766.4882 | [M + K]+ | PC(32:3) | C40H74NO8P | 1.94 | 0.31 | 3.20 | 0.26 | ↑ | 0.0556853* | |
| 38 | 801.5377 | [M + Na]+ | PS(34:1) | C40H76NO10P | 0.92 | 0.01 | 2.38 | 0.04 | ↑↑ | 0.0000004** | |
| 39 | 768.5018 | [M + K]+ | PC(32:2) | C40H76NO8P | 0.52 | 0.13 | 1.22 | 0.02 | ↑↑ | 0.0025441** | |
| 40 | 738.5282 | [M + K]+ | GlcCer(d18:1/16:0) | C40H77NO8 | 0.57 | 0.11 | 1.80 | 0.25 | ↑↑ | 0.0150283* | |
| 41 | 771.5145 | [M + Na]+ | PG(36:1) | C40H77O10P | 1.77 | 0.09 | 2.81 | 0.38 | ↑ | 0.0941550* | |
| 42 | 732.554 | [M + H]+ | PC(32:1) | C40H78NO8P | 4.21 | 0.58 | 2.14 | 0.24 | ↓↓ | 0.0047170** | |
| | 754.5361 | [M + Na]+ | | | 2.01 | 0.40 | 2.88 | 0.32 | ↑ | 0.0422628* | |
| 43 | 773.5328 | [M + Na]+ | PG(34:0) | C40H79O10P | 1.65 | 0.17 | 3.06 | 0.57 | ↑ | 0.0143597* | |
| 44 | 735.5733 | [M + H]+ | PG(P-34:0) | C40H79O9P | 5.57 | 0.54 | 3.70 | 0.33 | ↓ | 0.0685495* | |
| 45 | 756.5231 | [M + Na]+ | PC(P-32:0) | C40H80NO7P | 0.79 | 0.07 | 1.03 | 0.07 | ↑ | 0.0132178* | |
| 46 | 734.5701 | [M + H]+ | PC(14:0/18:0) | C40H80NO8P | 11.72 | 0.46 | 8.39 | 1.27 | ↓ | 0.0129218* | |
| 47 | 756.5518 | [M + Na]+ | PC(32:0) | C40H80NO8P | 9.73 | 0.77 | 11.86 | 0.44 | ↑ | 0.0140246* | 104, 147, 163, 184, 478, 735 |
| 48 | 739.4411 | [M + Na]+ | PA(38:8) | C41H65O8P | 0.77 | 0.01 | 3.55 | 0.05 | ↑↑ | 0.0000001** | |
| 49 | 727.4669 | [M + Na]+ | PA(P-38:6) | C41H69O7P | 1.04 | 0.12 | 1.29 | 0.07 | ↑ | 0.0369815* | |
| 50 | 763.4684 | [M + K]+ | PA(38:4) | C41H73O8P | 2.61 | 0.37 | 5.33 | 0.46 | ↑↑ | 0.0013753** | 153, 259, 283, 303, 419, 437, 439, 457, 723 |
| 51 | 765.4844 | [M + K]+ | PA(38:3) | C41H75O8P | 4.06 | 0.61 | 6.09 | 0.33 | ↑ | 0.0701323* | |
| 52 | 782.5209 | [M + K]+ | PE(36:2) | C41H78NO8P | 1.13 | 0.06 | 1.78 | 0.15 | ↑ | 0.0208801* | |
| 53 | 746.5702 | [M + H]+ | PE(36:1) | C41H80NO8P | 0.66 | 0.01 | 0.91 | 0.04 | ↑↑ | 0.0005446** | |
| | 768.5519 | [M + Na]+ | | | 0.87 | 0.05 | 1.39 | 0.04 | ↑ | 0.0144679* | |
| | 784.5246 | [M + K]+ | | | 1.07 | 0.12 | 4.37 | 0.35 | ↑↑ | 0.0001004** | |
| 54 | 733.5574 | [M + H]+ | PA(38:0) | C41H81O8P | 1.68 | 0.26 | 0.92 | 0.07 | ↓↓ | 0.0078440** | |
| 55 | 772.4953 | [M + Na]+ | PC(34:6) | C42H72NO8P | 0.97 | 0.09 | 1.46 | 0.03 | ↑↑ | 0.0008789** | |
| 56 | 790.4876 | [M + K]+ | PC(34:5) | C42H74NO8P | 2.34 | 0.25 | 1.71 | 0.01 | ↓ | 0.0114721* | |
| 57 | 795.515 | [M + Na]+ | PG(36:3) | C42H77O10P | 1.01 | 0.04 | 1.89 | 0.17 | ↑ | 0.0103858* | |
| 58 | 778.5361 | [M + Na]+ | PC(34:3) | C42H78NO8P | 0.89 | 0.03 | 0.83 | 0.03 | ↓ | 0.0488693* | |
| | 794.5097 | [M + K]+ | | | 1.47 | 0.22 | 2.90 | 0.53 | ↑ | 0.0125980* | |
| 59 | 797.5286 | [M + Na]+ | PG(36:2) | C42H79O10P | 7.66 | 0.63 | 15.11 | 0.26 | ↑↑ | 0.0000450** | |
| 60 | 796.5251 | [M + K]+ | PC(34:2) | C42H80NO8P | 15.63 | 2.77 | 35.39 | 4.98 | ↑↑ | 0.0038725** | 184, 758 |
| 61 | 799.5448 | [M + Na]+ | PG(36:1) | C42H81O10P | 13.33 | 0.12 | 31.70 | 0.38 | ↑↑ | 0.0000001** | |
| 62 | 750.5763 | [M + Na]+ | CerP(d42:2) | C42H82NO6P | 1.10 | 0.05 | 1.66 | 0.29 | ↑ | 0.0312908* | |
| 63 | 782.5681 | [M + Na]+ | PC(34:1) | C42H82NO8P | 21.47 | 3.14 | 29.37 | 0.40 | ↑ | 0.0124254* | 86, 184, 577, 701, 761 |
| | 798.5406 | [M + K]+ | | | 28.03 | 2.03 | 69.00 | 0.01 | ↑↑ | 0.0000040** | 86, 184, 577, 701, 761 |
| 64 | 797.5601 | [M + K]+ | PE-Cer(d40:2(2OH)) | C42H83N2O7P | 0.65 | 0.12 | 1.35 | 0.01 | ↑↑ | 0.0004876** | |
| 65 | 800.5516 | [M + K]+ | PC(34:0) | C42H84NO8P | 3.32 | 0.03 | 8.57 | 0.13 | ↑↑ | 0.0000003** | 163, 184, 762 |
| 66 | 783.6025 | [M + Na]+ | PE-Cer(d40:1(2OH)) | C42H85N2O7P | 0.84 | 0.01 | 0.96 | 0.06 | ↑ | 0.0396891* | |
| | 799.5763 | [M + K]+ | | | 1.00 | 0.08 | 2.47 | 0.08 | ↑↑ | 0.0000257** | |
| 67 | 775.5263 | [M + Na]+ | PA(40:4) | C43H77O8P | 1.01 | 0.06 | 1.17 | 0.00 | ↑ | 0.0111192* | |
| 68 | 806.5098 | [M + K]+ | PE(38:4) | C43H78NO8P | 1.12 | 0.02 | 3.93 | 0.15 | ↑↑ | 0.0000052** | 341, 627, 768 or 259, 283, 303, 462, 480, 482, 500, 767 |
| 69 | 793.5706 | [M + K]+ | SM(d38:3) | C43H83N2O6P | 1.22 | 0.13 | 1.50 | 0.01 | ↑ | 0.0193614* | |
| 70 | 796.5565 | [M + K]+ | PE(P-38:1) | C43H84NO7P | 1.16 | 0.05 | 3.10 | 0.07 | ↑↑ | 0.0000025** | |
| 71 | 774.6006 | [M + H]+ | PE(38:1) | C43H84NO8P | 1.75 | 0.16 | 2.43 | 0.05 | ↑ | 0.0217709* | |
| | 812.5625 | [M + K]+ | | | 0.64 | 0.05 | 1.76 | 0.06 | ↑↑ | 0.0000149** | |
| 72 | 825.5929 | [M + H]+ | PI(O-34:0) | C43H85O12P | 0.40 | 0.08 | 1.49 | 0.03 | ↑↑ | 0.0002871** | |
| 73 | 783.5721 | [M + K]+ | PA(P-40:0) | C43H85O7P | 10.66 | 1.14 | 13.54 | 0.40 | ↑ | 0.0147330* | |
| 74 | 782.5981 | [M + Na]+ | PE(P-38:0) | C43H86NO7P | 1.69 | 0.17 | 2.52 | 0.41 | ↑ | 0.0293319* | |
| | 798.572 | [M + K]+ | | | 2.14 | 0.15 | 5.16 | 0.14 | ↑↑ | 0.0000131** | |
| 75 | 798.5916 | [M + Na]+ | PE(38:0) | C43H86NO8P | 1.45 | 0.00 | 2.93 | 0.04 | ↑↑ | 0.0000005** | |

TABLE 6-continued

Summary of lipids differentially expressed between the non-cancerous and cancerous regions of the imaged prostate tissue

| No. | m/z | Ion form | Compound | Molecular formula | Non-cancerous aveg | Non-cancerous stdev | Cancerous aveg | Cancerous stdev | Exp. | p-value | Structurally specific CID ions (m/z)[a] |
|---|---|---|---|---|---|---|---|---|---|---|---|
| 76 | 781.619 | [M + Na]+ | SM(d38:1) | C43H87N2O6P | 0.84 | 0.05 | 1.94 | 0.22 | ↑↑ | 0.0011030** | |
| | 797.5914 | [M + K]+ | | | 2.10 | 0.13 | 4.55 | 0.22 | ↑↑ | 0.0000778 | 614, 738** |
| 77 | 796.4936 | [M + Na]+ | PC(36:8) | C44H72NO8P | 1.09 | 0.21 | 2.41 | 0.43 | ↑↑ | 0.0084568** | |
| 78 | 798.5095 | [M + Na]+ | PC(36:7) | C44H74NO8P | 2.43 | 0.08 | 5.71 | 0.35 | ↑↑ | 0.0000907** | |
| | 784.5854 | [M + H]+ | | | 7.61 | 0.73 | 5.86 | 0.37 | ↓ | 0.0212876* | |
| 79 | 806.5682 | [M + Na]+ | PC(36:3) | C44H82NO8P | 5.74 | 0.18 | 9.05 | 0.66 | ↑↑ | 0.0011418** | |
| | 822.541 | [M + K]+ | | | 10.52 | 2.72 | 19.17 | 1.14 | ↑↑ | 0.0070860 | 184, 785** |
| 80 | 825.5602 | [M + Na]+ | PG(38:2) | C44H83O10P | 6.74 | 1.93 | 12.86 | 0.53 | ↑↑ | 0.0060825** | |
| 81 | 824.5571 | [M + K]+ | PC(36:2) | C44H84NO8P | 10.16 | 0.33 | 28.35 | 0.35 | ↑↑ | 0.0000003 | 184, 787** |
| 82 | 827.5769 | [M + Na]+ | PG(38:1) | C44H85O10P | 3.32 | 0.10 | 5.21 | 0.30 | ↑↑ | 0.0004988** | |
| 83 | 826.5727 | [M + K]+ | PC(36:1) | C44H86NO8P | 6.79 | 0.51 | 9.83 | 0.24 | ↑↑ | 0.0007221 | 184, 789** |
| 84 | 812.6148 | [M + Na]+ | PC(36:0) | C44H88NO8P | 3.98 | 0.54 | 2.50 | 0.06 | ↓ | 0.0937006* | |
| | 828.5784 | [M + K]+ | | | 1.01 | 0.05 | 1.59 | 0.01 | ↑↑ | 0.0000509** | |
| 85 | 799.5136 | [M + K]+ | PA(P-42:6) | C45H77O7P | 1.17 | 0.08 | 2.73 | 0.08 | ↑↑ | 0.0000217** | |
| 86 | 947.5022 | [M + Na]+ | CL(1\'-[18:2(9Z,12Z)/0:0],3\'-[18:2(9Z,12Z)/0:0]) | C45H82O15P2 | 1.17 | 0.08 | 1.39 | 0.02 | ↑ | 0.0961547* | |
| | 963.4727 | [M + K]+ | | | 0.47 | 0.04 | 0.87 | 0.07 | ↑ | 0.0119495* | |
| 87 | 822.5743 | [M + K]+ | PE(P-40:2) | C45H86NO7P | 0.88 | 0.01 | 1.57 | 0.02 | ↑↑ | 0.0000010** | |
| 88 | 808.6165 | [M + Na]+ | PE(P-40:1) | C45H88NO7P | 0.70 | 0.02 | 0.93 | 0.07 | ↑ | 0.0572715* | |
| 89 | 826.6287 | [M + Na]+ | PE(40:0) | C45H90NO8P | 2.44 | 0.11 | 4.15 | 0.20 | ↑↑ | 0.0002050** | |
| 90 | 825.6236 | [M + K]+ | SM(d40:1) | C45H91N2O6P | 4.82 | 0.21 | 8.49 | 0.41 | ↑↑ | 0.0001673** | |
| 91 | 827.6325 | [M + K]+ | SM(d40:0) | C45H93N2O6P | 0.72 | 0.02 | 1.30 | 0.10 | ↑ | 0.0674861* | |
| 92 | 824.5246 | [M + Na]+ | PC(38:8) | C46H76NO8P | 0.96 | 0.05 | 2.52 | 0.04 | ↑↑ | 0.0000026** | |
| 93 | 844.5251 | [M + K]+ | PC(38:6) | C46H80NO8P | 2.39 | 0.02 | 2.61 | 0.06 | ↑ | 0.0312404* | |
| 94 | 846.5407 | [M + K]+ | PC(38:5) | C46H82NO8P | 7.28 | 0.06 | 6.57 | 0.13 | ↓↓ | 0.0009244 | 184, 627, 750, 809** |
| 95 | 849.5598 | [M + Na]+ | PG(40:4) | C46H83O10P | 10.08 | 0.39 | 7.12 | 0.29 | ↓↓ | 0.0004640** | |
| 96 | 848.5564 | [M + K]+ | PC(38:4) | C46H84NO8P | 19.66 | 0.76 | 14.28 | 0.13 | ↓↓ | 0.0002719 | 184, 627, 752, 811** |
| 97 | 852.5896 | [M + K]+ | PC(38:2) | C46H88NO8P | 0.98 | 0.07 | 1.53 | 0.01 | ↑ | 0.0151157* | |
| 98 | 823.514 | [M + Na]+ | PA(44:8) | C47H77O8P | 0.39 | 0.01 | 1.00 | 0.00 | ↑↑ | 0.0000004** | |
| 99 | 848.5921 | [M + K]+ | PE(O-42:4) | C47H88NO7P | 1.50 | 0.06 | 1.06 | 0.03 | | 0.0481175* | |
| 100 | 789.6198 | [M + K]+ | TG(44:0) | C47H90O6 | 2.10 | 0.45 | 1.36 | 0.03 | ↓ | 0.0480358* | |
| 101 | 833.5879 | [M + Na]+ | SM(d42:3) | C47H91N2O6P | 4.56 | 0.67 | 3.11 | 0.11 | ↓ | 0.0207636* | |
| 102 | 839.6373 | [M + Na]+ | PA(44:0) | C47H93O8P | 1.47 | 0.01 | 1.64 | 0.08 | ↑ | 0.0182998* | |
| 103 | 854.6599 | [M + Na]+ | PE(42:0) | C47H94NO8P | 2.86 | 0.18 | 4.41 | 0.18 | ↑↑ | 0.0004268** | |
| 104 | 837.6821 | [M + Na]+ | SM(d42:1) | C47H95N2O6P | 2.39 | 0.22 | 3.84 | 0.60 | ↑ | 0.0171714* | |
| | 853.6558 | [M + K]+ | | C47H95N2O6P | 5.28 | 0.40 | 8.80 | 0.45 | ↑↑ | 0.0005381 | 654, 778** |
| 105 | 855.66 | [M + K]+ | SM(d42:0) | C47H97N2O6P | 0.97 | 0.03 | 1.49 | 0.05 | ↑ | 0.0105460* | |
| 106 | 848.521 | [M + Na]+ | PC(40:10) | C48H76NO8P | 1.52 | 0.07 | 1.15 | 0.03 | ↓ | 0.0117340* | |
| 107 | 824.5921 | [M + Na]+ | 1-(8-[3]-ladderane-octanyl)-2-(8-[3]-ladderane-octanyl)-sn-glycerophosphocholine | C48H84NO6P | 1.23 | 0.08 | 2.19 | 0.09 | ↑↑ | 0.0001696** | |
| 108 | 874.5731 | [M + K]+ | PC(40:5) | C48H86NO8P | 1.38 | 0.09 | 1.15 | 0.05 | ↓ | 0.0181475* | 86, 184, 778, 836 |
| 109 | 928.612 | [M + K]+ | LacCer(d36:1) | C48H91NO13 | 0.88 | 0.03 | 1.85 | 0.21 | ↑↑ | 0.0013744** | |
| 110 | 810.6605 | [M + H]+ | 1-(2E,6E-phytadienyl)-2-(2E,6E-phytadienyl)-sn-glycero-3-phosphocholine | C48H92NO6P | 0.87 | 0.02 | 1.66 | 0.10 | ↑↑ | 0.0001507** | |
| 111 | 775.6042 | [M + Na]+ | DG(46:6) | C49H84O5 | 0.83 | 0.07 | 1.18 | 0.06 | ↑ | 0.0324074* | |
| 112 | 961.5772 | [M + Na]+ | PI(42:6) | C51H87O13P | 1.15 | 0.25 | 2.85 | 0.35 | ↑ | 0.0224463* | |
| 113 | 895.7163 | [M + K]+ | TG(52:3) | C55H100O6 | 8.71 | 0.45 | 0.82 | 0.07 | ↓↓ | 0.0000075** | |
| 114 | 897.7324 | [M + K]+ | TG(52:2) | C55H102O6 | 8.84 | 0.35 | 0.74 | 0.04 | ↓↓ | 0.0000010** | |

Note:
[a] Structurally specific CID ions of extracted lipids were detected by LC-MS/MS using CID. BOLD fragment ions were detected in the positive ion mode, and un-bolded fragment ions were detected in the negative ion mode.
The "*" indicated "$p < 0.05$" and "**" indicated "$p < 0.01$".

Figure 24A:
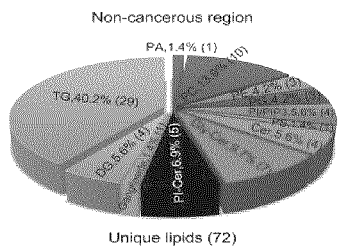
FIGS. 24A-24C are pie charts illustrating compositional analysis of compounds of interest detected on samples prepared using embodiments of the disclosed system and method.
Figure 24B:
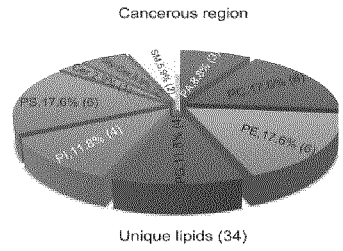
Figure 24C:
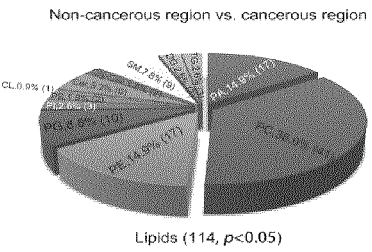

FIGS. 24A-24C shows the class compositions of the 220 lipids that showed different distributions between the cancerous and the non-cancerous cell regions. These included the 72 lipids uniquely detected in the non-cancerous region, the 34 lipids uniquely detected in the cancerous region, and 114 lipids that were differentially distributed between the cancerous and non-cancerous regions with p<0.05 for the t-tests. As shown in FIG. 24A, the 72 uniquely detected lipids in the non-cancerous region consisted of 29 TGs (40.2%), 10 PCs (13.9%), 7 Gly-Cers (9.7%), 5 ceramide phosphoinositols (PI-Cers) (6.9%), 4 DGs (5.6%), 4 Cers (5.6%), 4 PI/PI trisphosphates (PI/PIP3s) (5.6%), 3 PEs (4.2%), 3 PGs (4.2%), 1 PA (1.4%), 1 phosphatidylserine (PS) (1.4%), and 1 ganglioside (1.4%). The 34 uniquely detected lipids in the cancerous region (FIG. 24B) included 6 PCs (17.6%), 6 PEs (17.6%), 6 PSs (17.6%), 4 PGs (11.8%), 4 PIs (11.8%), 3 PAs (8.8%), 2 SMs (5.9%), 2 Gly-Cers (5.9%), and 1 Cer (2.9%). Comparison of the lipids detected in these two regions indicated that there were 33 acylglycerides (4 DGs and 29 TGs) only detectable in the non-cancerous cell region while being completely undetectable in the cancerous cell region. Without being limited to a single theory of operation, it is currently believed that, unlike other malignant cancer cells that preferentially rely on increased glucose consumption through glycolysis to provide energy for rapid cell proliferation, prostate cancer is characterized by low glycolysis because of very weakly expressed GLUT1 mRNA and protein in human prostate carcinoma tissue. Instead, prostate cancer cells predominantly use fatty acid β-oxidation as the alternative metabolic pathway to provide the energy for cell proliferation and growth. This requires an abundant supply of free fatty acids that can result from hydrolysis of glycerides, which may induce the depletion of these DGs and TGs in the cancerous cell region and may explain the low levels detected.

Glycerophospholipid and sphingolipid are the major lipid components of cell membranes. As shown in FIGS. 24A-24C, among the 220 detected lipids that displayed differential distributions between the cancerous and the non-cancerous cell regions, ca. 82% were phospholipids and sphingolipids. The significant changes in the distribution patterns of these molecules between the cancerous and non-cancerous cell regions indicated changes in the lipid composition of the prostate cancer cell membranes. These results demonstrate that the total amounts of phospholipid and sphingolipid were increased in the membranes of cancerous cells compared to noncancerous cells.

Example 2B

Figure 25:
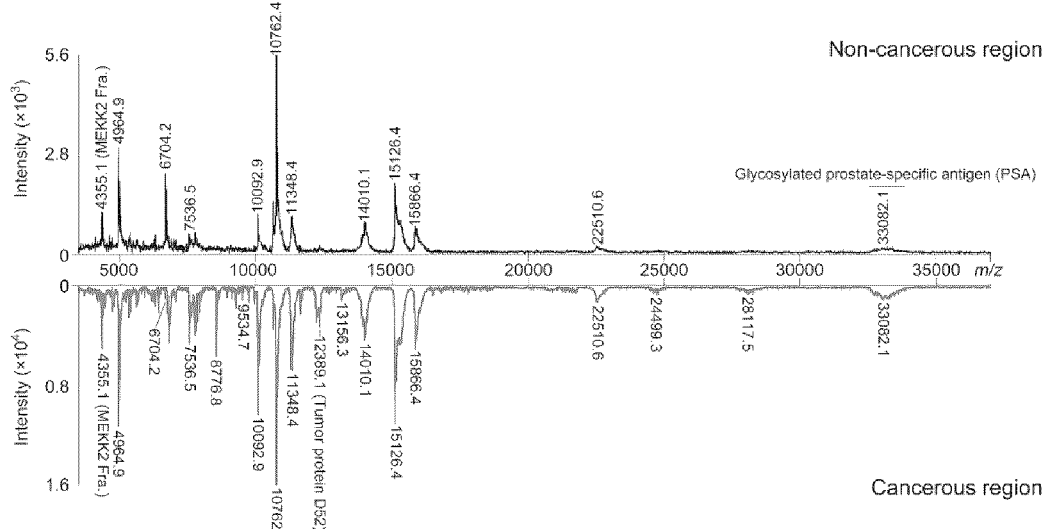
FIG. 25 is a MALDI-TOF spectrum of compounds of interest detected on a transverse prostate cancer tissue section.
Figure 28B:
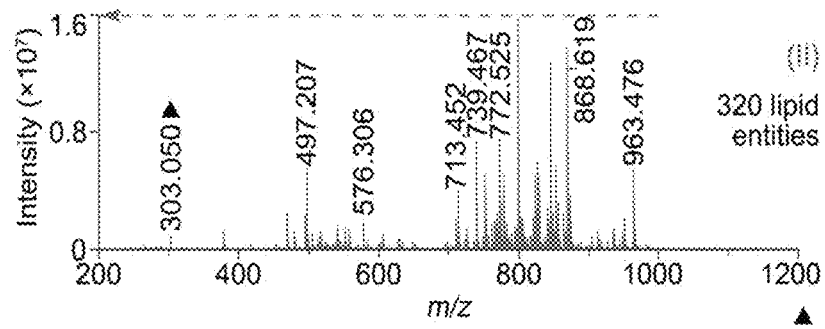
Figure 28C:
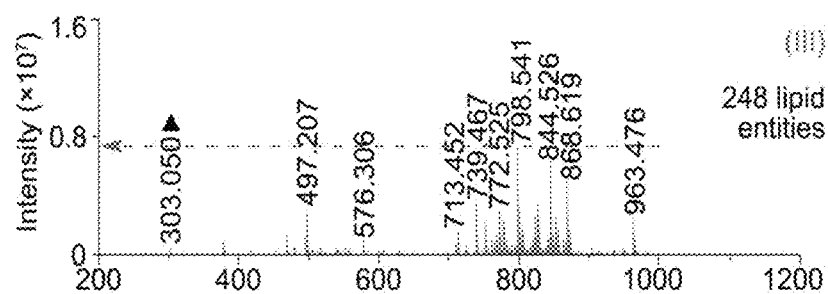
Figure 28D:
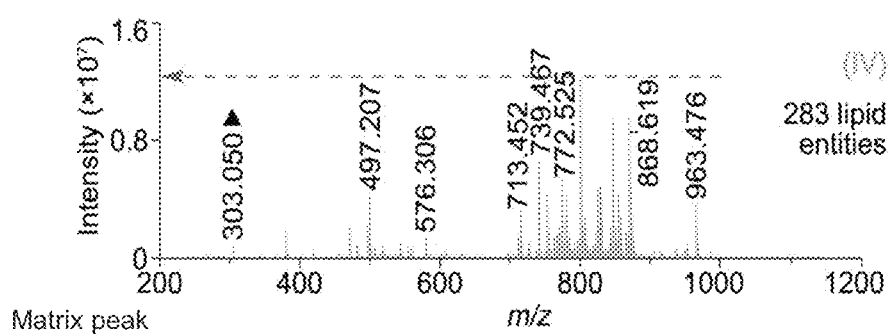
Figure 30:
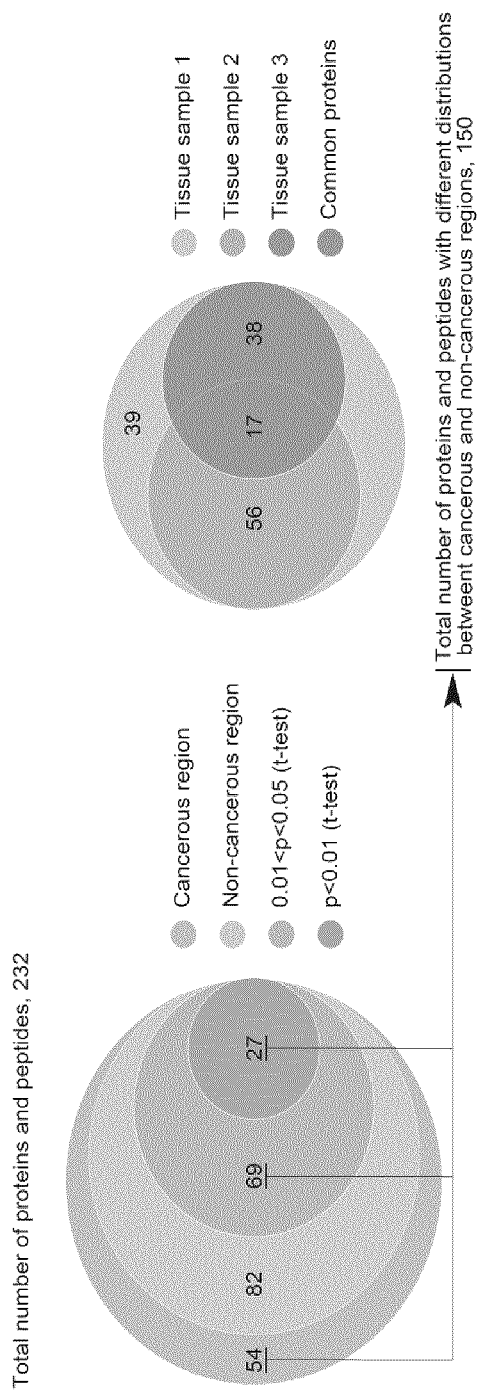
FIG. 30 is an illustration of the total number of proteins and peptides detected (detected lipids are not provided in FIG. 30).

FIG. 25 shows two mass spectra of the proteins detected by MALDI-TOF/MS from the cancerous region (lower) and the adjacent non-cancerous region (upper) of the prostate tissue. A larger number of peptide and protein signals within the mass range of 3500 to 13000 Da were observed in the cancerous cell region than in the non-cancerous cell region. A total of 242 peptide and protein signals were detected at a S/N of ≥3 in the prostate tissue and the m/z values of these signals are listed in Table 7 (and illustrated in FIG. 30). Due to the lack of sufficient sensitivity of MALDI-MS/MS for on-tissue protein identification, capillary liquid chromatography-tandem mass spectrometry (LC-MS/MS) was used to provide the identities of the detected peptides and proteins. By proteome database searching using a Mascot server, 274 proteins were identified. The matched peptides and the identified proteins are also listed in Table 7. Among these identified proteins, 73 matched the MALDI-MS measured molecular weights of the 242 observed signals, though protein assignments based solely on molecular weight matching cannot be completely confident. Among these proteins, >95% proteins were found to be secreted proteins or membrane proteins which are located in the extracellular region of cell.

Figure 31:
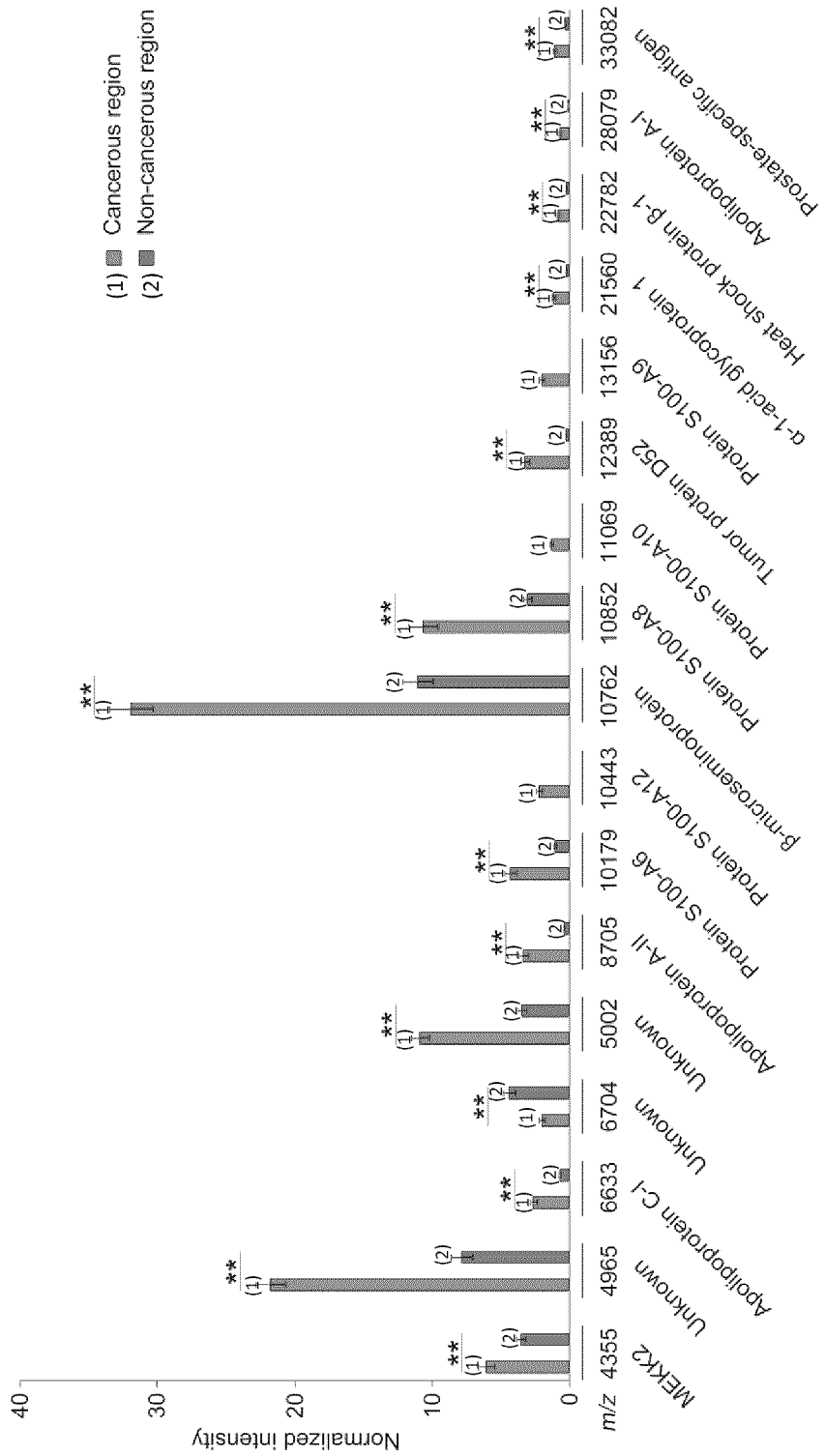
FIG. 31 shows a comparison of normalized ion intensities of the 17 peptides and proteins differentially expressed in the cancerous and non-cancerous regions in particular embodiments disclosed herein.

Among the 242 detected peptide and protein signals, 64 were uniquely detected in the cancerous region and the other 178 were detected in both regions. For these 178 species, t-tests indicated that 96 showed differential distributions with p<0.05 and 27 showed significantly different distribution patterns, with p<0.01. In some embodiments, of the 178 species detected in both tissue regions, 69 showed significantly different distribution patters at the p<0.05 level; 27 of these showed significantly different distribution patterns at p<0.01. 17 of these (including PSA, tumor protein D52, and a fragment of mitogen-activated protein kinase/extracellular signal-regulated kinase kinase kinase 2) could be detected in both tissue regions in all three prostate tissue samples. As shown in Table 7, among the 27 peptides and proteins with significantly different distributions between the two regions of the tissue, 26 were found to be up-regulated and 1 was found to be down-regulated in the cancerous region, according to their reconstructed ion maps. In some embodiments, a total of 150 detected peptide and proteins showed different distribution patterns between the cancerous and non-cancerous regions of the prostate tissue section. Of these peptides and proteins, 17 species were observed in all three prostate tissue samples, as all three prostate tissues, as compared to only 5 proteins detected in previous MSI studies, indicating that more than 3 times potential biomarkers were found using the disclosed device and method. Based on the current study, FIG. 31 shows a comparison of normalized ion intensities of the 17 peptides and proteins differentially expressed in the cancerous and non-cancerous regions, i.e., m/z 4355.1 (MEKK2 fragment), m/z 4964.9, m/z 6633.1 (apolipoprotein C-I), m/z 6704.2, m/z 5002.2, m/z 8705.2 (apolipoprotein A-II), m/z 10179.1 (protein S100-A6), m/z 10442.6 (protein S100-A12), m/z 10762.4 (β-microseminoprotein), m/z 10851.7 (protein S100-A8), m/z 11069.2 (protein S100-A10), m/z 12389.1 (tumor protein D52), m/z 13156.2 (protein S100-A9), m/z 21560.2 (α-1-acid glycoprotein 1), m/z 22782.3 (heat shock protein β-1), m/z 28079.3 (apolipoprotein A-I), and m/z 33082.1 (PSA). All of the peptides and proteins were detected with higher intensities from the cancerous cell region than from non-cancerous cell region, except for the ion at m/z 6704.2.

Some of the peptides and proteins that were uniquely detected in the cancerous cell region or showed differential distributions between the two regions of the tissue regions have been determined to be potential biomarkers for prostate cancer using LC-MS/MS or MALDI-MSI. These biomarkers include MEKK2 (m/z 4355), apolipoproteins A-II (m/z 8705), β-microseminoprotein (m/z 10763), tumor protein D52 (m/z 12388), PSA (m/z 33000 to 34000), together with a few unknown species, for example, those at m/z 4964, 5002, and 6704. Among these potential biomarkers, only 4 proteins or protein fragments, including m/z 4355.1 (MEKK2 fragment), m/z 4964, 5002, and 6704, were detected by MALDI-MSI, which is far from meeting requirements of MSI for biomarker discovery. FIG. 26 shows the ion maps for six detected proteins, i.e., m/z 4355.1 (MEKK2 fragment), m/z 4964.9, m/z 6704.2, m/z 8776.8, m/z 12389.1 (tumor protein D52), and m/z 33175.3 (PSA). As can be observed from these images, these proteins showed significantly different distributions between the normal region and the cancerous region of the prostate tissue section. The peptide at m/z 4964.9 had a higher abundance in the cancerous region while the peptide at m/z 6704.2 had a higher abundance in the non-cancerous region. The ion of m/z 4355 (a MEKK2 fragment) has been shown to be a marker for discriminating prostate cancer from uninvolved tissue, due to its overexpression in cancer cells. Based on the ion map of m/z 4355 in FIG. 26, this MEKK2 fragment was mainly distributed in the cancerous region. In addition to these two ions, a small protein was detected at m/z 8776.8 as well as the identified tumor protein D52 and PSA, which were found to be more abundant in the cancerous cell region.

In some embodiments, five of the peptides and proteins that were uniquely detected in the cancerous cell region or which showed differential distributions between the two regions of the tissue regions have been previously reported as potential biomarkers for prostate cancer by LC-MS/MS or MALDI-MSI. These previously reported biomarkers included MEKK2 (m/z 4355), apolipoproteins A-II (m/z 8705), β-microseminoprotein (m/z 10762), tumor protein D52 (m/z 12389), PSA (m/z 33000 to 34000), together with a few unknown species, for example, those at m/z 4964, 5002, and 6704. Of the previously reported potential biomarkers, only 4 proteins or protein fragments, including m/z 4355.1 (MEKK2 fragment), m/z 4964, 5002, and 6704, had previously been detected by MALDI-MSI.

Figure 32:
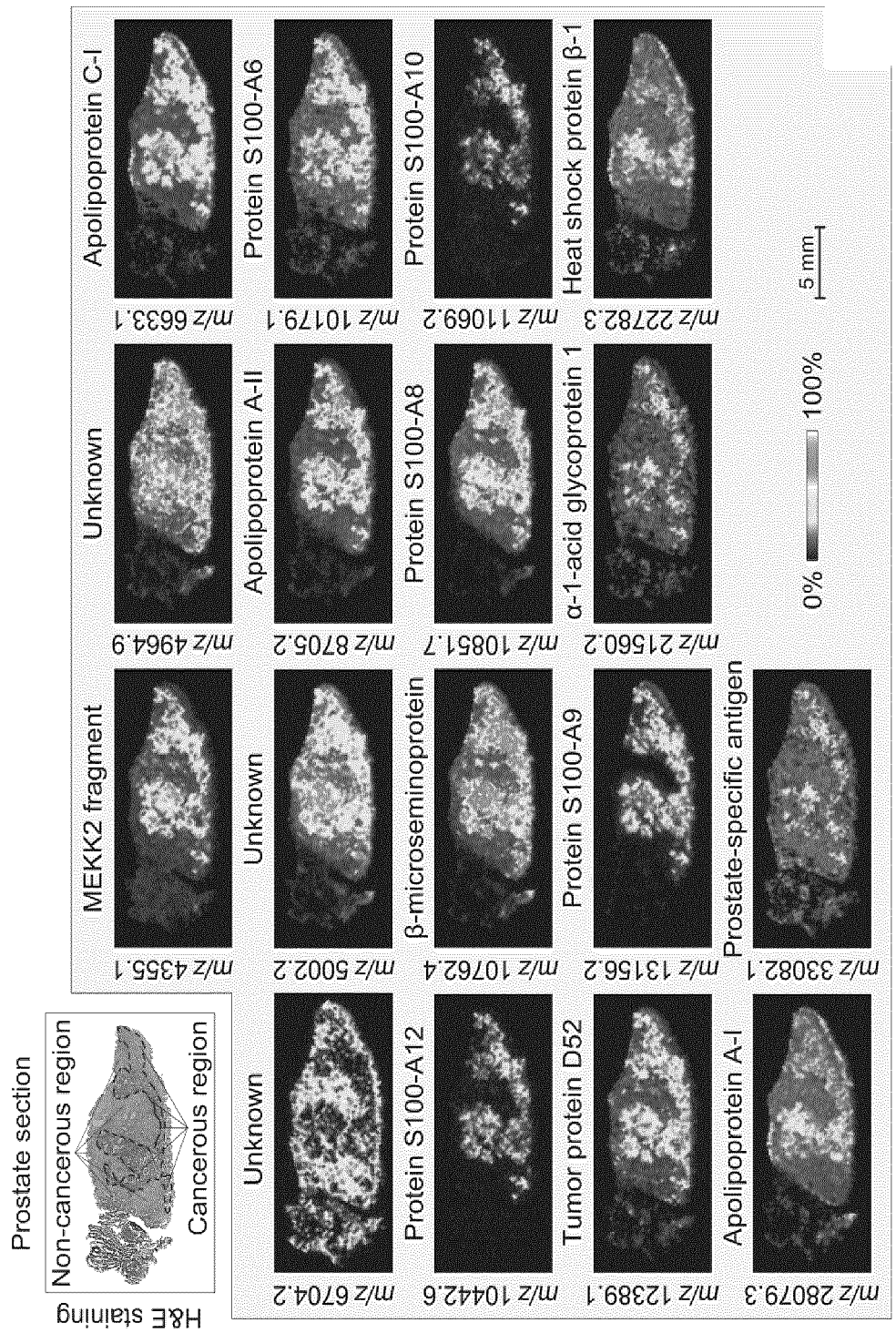
FIG. 32 provides ion maps of 17 peptides and proteins detected on prostate tissue section in particular disclosed embodiments.

The ion maps of these 17 peptides and proteins detected on prostate tissue section are shown in FIG. 32. As can be observed from these images, these proteins showed visually different distributions between the non-cancerous region and the cancerous region of the prostate tissue section. The peptide at m/z 4964.9 had a higher abundance in the cancerous region while the peptide at m/z 6704.2 had a higher abundance in the non-cancerous region. This observation was consistent with a previous study, although the identities of these two species remain unknown. In a previous study, the ion at m/z 4355 (a MEKK2 fragment) was shown to be a marker for discriminating prostate cancer from uninvolved tissue, due to its overexpression in cancer cells. Based on the ion map of m/z 4355.1 in FIG. 32, this MEKK2 fragment was mainly distributed in the cancerous region in our study as well, which is also consistent with the previous MSI study.

All of the other differentially expressed proteins were determined to be more abundant in the cancerous cell region (FIG. 32). Among these 17 species, 5 identified proteins were assigned to the family of S100 proteins, and 3 of them (i.e., protein S100-A9, protein S100-A10, protein S100-A12), were uniquely detected in the cancerous region. Although several members of the S100 protein family have been proven to be useful as biomarkers for tumors and epidermal differentiation, such as schwannomas, neurofibromas, and melanomas, this is the first time that the correlation between S100 proteins and prostate cancer has been shown. S100 proteins have been implicated in a variety of intra-/extra-cellular functions, including protein phosphorylation, $Ca^{2+}$ homeostasis, cell growth and differentiation, inflammatory response, and the like. Differential expression of protein S100-A6, S100-A8, S100-A9, S100-A10, and S100-A12 between the cancerous and non-cancerous regions of a prostate tissue section reflects the different cell states in these cell regions, showing the potential for the use of these proteins as biomarkers for prostate cancer. In lipid transport, many apolipoproteins have been reported to be important structural components of lipoprotein particles, cofactors for enzymes, and ligands for cell-surface receptors, especially the apolipoprotein subclasses of C and A. In this embodiment, 3 apolipoproteins—including apolipoprotein C-I, A-I and A-II—were also found with higher abundance in cancerous region than non-cancerous region of prostate tissue, suggesting a difference in lipid metabolisms between the cancerous and non-cancerous regions of the prostate tissue.

TABLE 7

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc | Exp | t-test |
|---|---|---|---|---|---|---|---|---|---|---|---|---|
| 1 | | | 4312.0 | | | | | | | ✓ | | |
| 2 | Q9Y2U5 | 4335.4 | 4355.1 | 42.3 | 72.22 | Mitogen-activated protein kinase/extra-cellular signal-regulated kinase kinase 2 (MEKK2) (Fragment) (specific for prostate cancer) | Extracellular region, cytoplasm, nucleus | DVRVKFEHRGE K SSSPKKQNDVRV KFEHRG KAKSSSPKKQN DVRVKFEHRGE KRIL | | ✓ | ↑ | ** |
| 3 | | | 4390.6 | | | | | | ✓ | | | |
| 4 | | | 4441.0 | | | | | | ✓ | | | |
| 5 | | | 4738.4 | | | | | | ✓ | | | |
| 6 | | | 4786.2 | | | | | | ✓ | | | |
| 7 | P62328 | 4921.5 + Ox (M) | 4936.6 | 337.87 | 77.27 | Thymosin beta-4 | Extracellular region, cytoplasm, cytoskeleton | SDKPDMAEIEK + Oxidation (M) SDKPDMAEIEKF DK KTETQEKNPLPS K NPLPSKETIEQEK TETQEKNPLPSK | ✓ | ✓ | ↑ | ** |
| 8 | | | 4964.9 | | | | | | ✓ | ✓ | ↑ | ** |
| 9 | | | 5002.2 | | | | | | ✓ | ✓ | ↑ | ** |
| 10 | | | 5055.0 | | | | | | ✓ | ✓ | ↑ | * |
| 11 | | | 5105.3 | | | | | | | ✓ | | |

TABLE 7-continued

Protein detection in human prostate tissue sections by MALDI-TOF/MS using sinapinic acid as the matrix.

| No. | Access. | Theor. MW [a] | Expt. MW | Score | PMF coverage (%) | Description | Subcellular location | Unique peptides [b] | Non-canc. | Canc. | Exp | t-test |
|---|---|---|---|---|---|---|---|---|---|---|---|---|
| 12 | | | 5176.3 | | | | | | | ✓ | | |
| 13 | | | 5237.7 | | | | | | ✓ | | ↑ | |
| 14 | | | 5394.1 | | | | | | | | | |
| 15 | | | 5400.8 | | | | | | | ✓ | | |
| 16 | | | 5624.6 | | | | | | ✓ | | | |
| 17 | | | 5666.4 | | | | | | | ✓ | ↑ | |
| 18 | | | 5683.8 | | | | | | | ✓ | | |
| 19 | | | 6318.4 | | | | | | ✓ | ✓ | ↑ | * |
| 20 | | | 6436.0 | | | | | | ✓ | ✓ | | |
| 21 | P02654 | 6630.6 | 6633.1 | 41.23 | 13.25 | Apolipoprotein C-I | Secreted | LKEFGNTLEDK EFGNTLEDK | ✓ | ✓ | ↑ | ** |
| 22 | | | 6704.2 | | | | | | ✓ | ✓ | ↓ | ** |
| 23 | | | 6730.9 | | | | | | ✓ | ✓ | ↑ | * |
| 24 | P48539 | 6791.4 | 6790.4 | 332.62 | 43.55 | Purkinje cell protein 4 | Cytoplasm | KVQEEFDIDMD APETER + Oxidation (M) VQEEFDIDMDAP ETER + Oxidation (M) AAVAIQSQFR | ✓ | ✓ | ↑ | |
| 25 | | | 7565.5 | | | | | | ✓ | ✓ | ↑ | ** |
| 26 | | | 7615.6 | | | | | | ✓ | ✓ | ↑ | |
| 27 | | | 7668.0 | | | | | | ✓ | ✓ | ↑ | |
| 28 | | | 7735.2 | | | | | | ✓ | ✓ | ↑ | |
| 29 | | | 7769.3 | | | | | | ✓ | ✓ | ↑ | * |

TABLE 7-continued

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc. | Exp | t-test |
|---|---|---|---|---|---|---|---|---|---|---|---|---|
| 30 | P56385 | 7802.1 | 7807.4 | 68.32 | 10.14 | ATP synthase subunit e, mitochondrial | Cell membrane, mitochondrion | YNYLKPR | ✓ | ✓ | ↑ | * |
| 31 | | | 7868.1 | | | | | | ✓ | ✓ | ↑ | * |
| 32 | | | 7873.3 | | | | | | ✓ | ✓ | ↑ | |
| 33 | | | 7934.7 | | | | | | ✓ | ✓ | ↑ | |
| 34 | | | 7963.6 | | | | | | ✓ | ✓ | ↑ | |
| 35 | | | 8567.6 | | | | | | ✓ | ✓ | ↑ | |
| 36 | | | 8602.1 | | | | | | | ✓ | | |
| 37 | | | 8606.5 | | | | | | | ✓ | | |
| 38 | | | 8776.8 | | | | | | | ✓ | | |
| 39 | P02652 | 8707.9 | 8705.2 | 129.76 | 31 | Apolipoprotein A-II | Secreted | EPCVESLVSQYF QTVTDYGK | ✓ | ✓ | ↑ | ** |
| 40 | B1ALW1 | 9451.9 | 9450.8 | 109.48 | 25.88 | Thioredoxin | Secreted, cytoplasm, extracellular region | TAFQEALDAAG DK VGEFSGANK | | ✓ | | |
| 41 | | 9531.6 | 9534.7 | 52.6 | 10.68 | Matrix Gla protein | Secreted | NANTFISPQQR | | ✓ | | |
| 42 | | | 9957.0 | | | | | | | ✓ | | |
| 43 | H0YFX9 | 9975.6 | 9974.7 | 86.09 | 28.26 | Histone H2A (Fragment) | Extracellular region, cytoplasm, nucleus | VTIAQGGVLPNI QAVLLPK HLQLAIR | ✓ | ✓ | ↑ | * |
| 44 | | | 9993.4 | | | | | | ✓ | ✓ | ↑ | * |
| 45 | O75531 | 10058.6 + Ox(M) 10080.3 | 10073.0 10080.5 | 126.67 | 13.48 | Barrier-to-autointegration factor | Extracellular region, cytoplasm | AYVVLGQFLVL K LENEKDLEEAE EYKEAR | ✓ | ✓ | ↑ | * |

TABLE 7-continued

Protein detection in human prostate tissue sections by MALDI-TOF/MS using sinapinic acid as the matrix.

| No. | Access. | Mass wt (MW, Da) Theor. MW [a] | Expt. MW | PMF Score | PMF coverage (%) | Description | Subcellular location | Unique peptides [b] | Non-canc. | Canc. | Exp | t-test |
|---|---|---|---|---|---|---|---|---|---|---|---|---|
| 46 | E5RIW3 | 10080.3 + Ox (M) | 10092.9 | 184.86 | 50 | Tubulin-specific chaperone A | Cell membrane, cytoplasm, cytoskeleton | DLEEAEEYKEAR RLEAAYLDLQR MRAEDGENYDI KK + Oxidation (M) AEDGENYDIKK AEDGENYDIK | | | | |
| 47 | | | 10112.9 | | | | | | ✓ | ✓ | ↑ | * |
| 48 | P06703 | 10179.7 | 10179.1 | 196.71 | 56.67 | Protein S100-A6 | Cytoplasm, cell membrane, peripheral membrane protein | ACPLDQAIGLLV AIFHK LQDAEIAR DQEVNFQEYVT FLGALALIYNEA LKG | ✓ | ✓ | ↑ | ** |
| 49 | | | 10223.9 | | | | | | ✓ | ✓ | ↑ | * |
| 50 | | | 10254.3 | | | | | | ✓ | ✓ | ↑ | * |
| 51 | P02775 | 10265.8 | 10266.0 | 42.22 | 18.75 | Platelet basic protein | Secreted, extracellular region/space | GTHCNQVEVIAT LK KICLDPDAPR | | ✓ | | |
| 52 | | | 10268.2 | | | | | | | ✓ | | |
| 53 | | | 10281.1 | | | | | | | ✓ | | |
| 54 | | | 10283.1 | | | | | | | ✓ | | |
| 55 | | | 10346.5 | | | | | | ✓ | ✓ | ↑ | * |
| 56 | P63167 | 10366.5 | 10366.3 | 129.5 | 24.72 | Dynein light chain 1 | Plasma membrane, cytoplasm, cytoskeleton | NFGSYVTHETK YNPTWHCIVGR | | ✓ | | |
| 57 | Protein S100-A12 (P80511) | 10443.9 | 10442.6 | 167.32 | 31.52 | Protein S100-A12 | Secreted, cytoplasm, cytoskeleton, cell membrane, peripheral membrane protein | TKLEEHLEGIVNI FHQYSVR LEEHLEGIVNIFH QYSVR TKLEEHLEGIVNI FHQYSVRK KGHFDTLSK GHFDTLSK | | ✓ | | |

TABLE 7-continued

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc. | Exp | t-test |
|---|---|---|---|---|---|---|---|---|---|---|---|---|
| 58 | | | 10649.0 | | | | | | | √ | ↑ | * |
| 59 | | | 10709.0 | | | | | | √ | √ | ↑ | * |
| 60 | P08118 | 10763.2 | 10762.4 | 99.18 | 48.25 | Beta-microseminoprotein (specific for prostate cancer) | Secreted, extracellular space | HPINSEWQTDNC ETCTCYETEISCC TLVSTPVGYDK KTCSVSEWII | √ | √ | ↑ | ** |
| 61 | | | 10782.5 | | | | | | √ | √ | ↑ | * |
| 62 | | | 10837.6 | | | | | | √ | √ | ↑ | * |
| 63 | P05109 | 10834.5 + Ox (M) | 10851.7 | 320.47 | 76.34 | Protein S100-A8 | Secreted, cytoplasm, cytoskeleton, cell membrane, peripheral membrane protein | ELDINTDGAVNF QEFLILVIK LLETECPQYIR ALNSIIDVYHK KLLETECPQYIR GADVWFK MLTELEKALNSII DVYHKYSLIK + Oxidation (M) MLTELEK GNFHAVYR | √ | √ | ↑ | ** |
| 64 | | | 10875.0 | | | | | | √ | √ | ↑ | * |
| 65 | | | 10922.6 | | | | | | √ | √ | ↑ | * |
| 66 | | | 10970.1 | | | | | | √ | √ | ↑ | * |
| 67 | | | 11023.6 | | | | | | √ | √ | ↑ | * |
| 68 | P60903 | 11071.9 | 11069.2 | 45.29 | 17.53 | Protein S100-A10 | Extrinsic to plasma membrane | EFPGFLENQKDP LAVDK | | √ | ↑ | * |
| 69 | | | 11268.0 | | | | | | √ | √ | ↑ | ** |
| 70 | P0CG05 | 11293.6 | 11293.8 | 298.45 | 74.53 | Ig lambda-2 chain C region | Extracellular region, plasma membrane | YAASSYLSLTPE QWK AGVETTTPSK ATLVCLISDFYP GAVTVAWK | √ | √ | ↑ | * |

TABLE 7-continued

Protein detection in human prostate tissue sections by MALDI-TOF/MS using sinapinic acid as the matrix.

| No. | Access. | Theor. MW [a] | Expt. MW | Score | PMF coverage (%) | Description | Subcellular location | Unique peptides [b] | Non-canc. | Canc. | Exp | t-test |
|---|---|---|---|---|---|---|---|---|---|---|---|---|
| 71 | | | 11348.4 | | | | | SYSCQVTHEGST VEK AAPSVTLFPPSSE ELQANK | ✓ | | | |
| 72 | P62805 | 11367.3 | 11368.1 | 223.5 | 50.49 | Histone H4 | Extracellular region, nucleus, chromosome | ISGLIYEETR TVTAMDVVYAL K VFLENVIR DNIQGITKPAIR DAVTYTEHAK | ✓ | ✓ | ↑ | ** |
| 73 | | | 11417.1 | | | | | | ✓ | ✓ | ↑ | * |
| 74 | | | 11468.7 | | | | | | ✓ | ✓ | ↑ | * |
| 75 | | | 11516.6 | | | | | | ✓ | ✓ | ↑ | * |
| 76 | P01834 | 11608.9 | 11608.2 | 528.75 | 80.19 | Ig kappa chain C region | Extracellular region, plasma membrane | VDNALQSGNSQ ESVTEQDSK TVAAPSVFIFPPS DEQLK DSTYSLSSTLTLS K VYACEVTHQGL SSPVTK SGTASVVCLLNN FYPR | ✓ | ✓ | ↑ | * |
| 77 | | | 11643.5 | | | | | | ✓ | ✓ | ↑ | * |
| 78 | | | 11691.5 | | | | | | ✓ | ✓ | ↑ | * |
| 79 | | | 11695.0 | | | | | | | ✓ | | |
| 80 | P61769 | 11731.2 | 11730.1 | 170.34 | 26.89 | Beta-2-microglobulin | Secreted, extracellular region/space, plasma membrane | SNFLNCYVSGFH PSDIEVDLLK VEHSDLSFSK | | ✓ | | |
| 81 | | | 12166.7 | | | | | | ✓ | ✓ | ↑ | |
| 82 | | | 12205.5 | | | | | | ✓ | ✓ | ↑ | |

TABLE 7-continued

Protein detection in human prostate tissue sections by MALDI-TOF/MS using sinapinic acid as the matrix.

| No. | Access. | Mass wt (MW, Da) Theor. MW a) | Mass wt (MW, Da) Expt. MW | Score | PMF coverage (%) | Description | Subcellular location | Unique peptides b) | Non-canc. | Canc. | Exp | t-test |
|---|---|---|---|---|---|---|---|---|---|---|---|---|
| 83 | | | 12254.4 | | | | | | | ✓ | | |
| 84 | | | 12306.7 | | | | | | | ✓ | | |
| 85 | | | 12312.6 | | | | | | | ✓ | | |
| 86 | P14174 | 12345.1 | 12345.3 12350.5 | 99.33 | 17.39 | Macrophage migration inhibitory factor | Secreted, cell surface | LLCGLLAER PMFIVNTNVPR + Oxidation (M) | ✓ | ✓ | ↑ | ** |
| 87 | E5RFR7 | 12388.9 | 12389.1 | 27.95 | 13.51 | Tumor protein D52 (specific for prostate and ovarian cancer) | Cytoplasm, cytoplasmic membrane | VEEEIQTLSQVL AAK | ✓ | ✓ | ↑ | ** |
| 88 | | | 12405.8 | | | | | | | ✓ | | |
| 89 | Q99988 | 12514.5 | 12516.6 | 211.94 | 10.39 | Growth/differentiation factor 15 | Secreted, extracellular region/space | TDTGVSLQTYD DLLAK ASLEDLGWADW VLSPR | | ✓ | | |
| 90 | G3V2V8 | 13078.2 | 13078.8 | 85.68 | 13.11 | Epididymal secretory protein E1 | Secreted, extracellular region | EVNVSPCFTQPC QLSK | | ✓ | | |
| 91 | | | 13148.7 | | | | | | | ✓ | | |
| 92 | | | 13153.9 | | | | | | | ✓ | | |
| 93 | P06702 | 13110.8 + Ox (M) | 13156.2 | 631.39 | 81.58 | Protein S100-A9 | Secreted, cytoplasm, cytoskeleton, cell membrane, peripheral membrane protein | QLSFEEFIMLMA R VIEHIMEDLDTN ADK + Oxidation (M) QLSFEEFIMLMA R + Oxidation (M) VIEHIMEDLDTN ADK NIETIINTFHQYS VK | | ✓ | | |

TABLE 7-continued

Protein detection in human prostate tissue sections by MALDI-TOF/MS using sinapinic acid as the matrix.

| No. | Access. | Mass wt (MW, Da) Theor. MW [a] | Expt. MW | PMF Score | coverage (%) | Description | Subcellular location | Unique peptides [b] | Non-canc. | Canc. | Exp | t-test |
|---|---|---|---|---|---|---|---|---|---|---|---|---|
| | | | | | | | | LGHPDTLNQGEFK | | | | |
| | | | | | | | | MHEGDEGPGHH | | | | |
| | | | | | | | | HKPGLGEGTP | | | | |
| | | | | | | | | KDLQNFLK | | | | |
| | | | | | | | | LTWASHEK | | | | |
| | | | | | | | | MHEGDEGPGHH | | | | |
| | | | | | | | | HKPGLGEGTP + Oxidation (M) | | | | |
| | | | | | | | | DLQNFLK | | | | |
| 94 | | | 13195.5 | | | | | | | √ | | |
| 95 | | | 13755.9 | | | | | | | √ | | |
| 96 | P02766 | 13761.4 | 13761.6 | 641.82 | 68.71 | Transthyretin | Secreted, cytoplasm, extracellular region/space | KAADDTWEPPA SGK | √ | √ | ↑ | |
| | | | | | | | | TSESGELHGLTT | | | | |
| | | | | | | | | EEEFVEGIYK | | | | |
| | | | | | | | | GSPAINVAHVFR | | | | |
| | | | | | | | | YTIAALLSPYSY | | | | |
| | | | | | | | | STTAVVTNPKE | | | | |
| | | | | | | | | YTIAALLSPYSY | | | | |
| | | | | | | | | STTAVVTNPK | | | | |
| | | | | | | | | ALGISPFHEHAE | | | | |
| | | | | | | | | VVFTANDSGPR | | | | |
| | | | | | | | | TSESGELHGLTT | | | | |
| | | | | | | | | EEEFVEGIYKVEI | | | | |
| | | | | | | | | DTK | | | | |
| 97 | | | 13775.3 | | | | | | √ | √ | ↑ | * |
| 98 | | | 13785.0 | | | | | | √ | √ | ↑ | |
| 99 | | | 13799.0 | | | | | | √ | √ | ↑ | |
| 100 | | | 13805.3 | | | | | | √ | √ | ↑ | * |
| 101 | | | 13811.2 | | | | | | √ | √ | ↑ | * |
| 102 | | | 13817.3 | | | | | | √ | √ | ↑ | |
| 103 | | | 13826.0 | | | | | | √ | √ | ↑ | |

TABLE 7-continued

Protein detection in human prostate tissue sections by MALDI-TOF/MS using sinapinic acid as the matrix.

| No. | Access. | Mass wt (MW, Da) Theor. MW a) | Mass wt (MW, Da) Expt. MW | PMF Score | PMF coverage (%) | Description | Subcellular location | Unique peptides b) | Non-canc. | Canc. | Exp | t-test |
|---|---|---|---|---|---|---|---|---|---|---|---|---|
| 104 | | | 13836.1 | | | | | | | ✓ | ↑ | * |
| 105 | | | 13849.2 | | | | | | ✓ | ✓ | ↑ | * |
| 106 | Q99879 | 13858.1 | 13857.3 | 114.55 | 41.27 | Histone H2B type 1-M | Extracellular region, nucleus, chromosome | AMGIMNSFVNDI FER LLLPGELAK EIQTAVR QVHPDTGISSK | ✓ | ✓ | ↑ | * |
| 107 | | | 13865.0 | | | | | | | ✓ | ↑ | * |
| 108 | | | 13867.6 | | | | | | ✓ | ✓ | ↑ | |
| 109 | | | 13873.0 | | | | | | ✓ | ✓ | ↑ | |
| 110 | | | 13878.9 | | | | | | ✓ | ✓ | ↑ | * |
| 111 | | | 13892.3 | | | | | | ✓ | ✓ | ↑ | |
| 112 | | | 13902.9 | | | | | | ✓ | ✓ | ↑ | * |
| 113 | H7BYH4 | 13909.4 | 13911.0 | 486.14 | 51.11 | Superoxide dismutase [Cu-Zn] | Extracellular region, cytoplasm | DGVADVSIEDSV ISLSGDHCIIGR HVGDLGNVTAD KDGVADVSIEDS VISLSGDHCIIGR HVGDLGNVTAD K | ✓ | ✓ | ↑ | ** |
| 114 | P14555 | 13921.9 | 13922.3 | 231.16 | 29.86 | Phospholipase A2, membrane associated | Membrane, peripheral membrane protein, extracellular space | GLTRGLHGFHV HEFGDNTAGCTS AGPHFNPLSR EAALSYGFYGC HCGVGGR AAATCFAR CCVTHDCCYK YQYYSNK | ✓ | ✓ | ↑ | |
| 115 | | | 13933.1 | | | | | | ✓ | ✓ | ↑ | * |
| 116 | | | 13947.3 | | | | | | ✓ | ✓ | ↑ | |
| 117 | | | 13952.8 | | | | | | ✓ | ✓ | ↑ | |

TABLE 7-continued

Protein detection in human prostate tissue sections by MALDI-TOF/MS using sinapinic acid as the matrix.

| No. | Access. | Mass wt (MW, Da) Theor. MW [a] | Expt. MW | PMF Score | coverage (%) | Description | Subcellular location | Unique peptides [b] | Non-canc. | Canc. | Exp | t-test |
|---|---|---|---|---|---|---|---|---|---|---|---|---|
| 118 | | | 13960.3 | | | | | | ✓ | ✓ | ↑ | * |
| 119 | | | 13968.5 | | | | | | ✓ | ✓ | ↑ | |
| 120 | | | 13978.4 | | | | | | ✓ | ✓ | ↑ | |
| 121 | | | 13987.1 | | | | | | ✓ | ✓ | ↑ | |
| 122 | | | 14003.3 | | | | | | ✓ | ✓ | ↑ | |
| 123 | | | 14013.1 | | | | | | ✓ | ✓ | ↑ | * |
| 124 | | | 14018.7 | | | | | | ✓ | ✓ | ↑ | |
| 125 | | | 14036.0 | | | | | | ✓ | ✓ | ↑ | * |
| 126 | | | 14049.6 | | | | | | ✓ | ✓ | ↑ | |
| 127 | | | 14054.1 | | | | | | ✓ | ✓ | ↑ | * |
| 128 | | | 14066.8 | | | | | | ✓ | ✓ | ↑ | |
| 129 | | | 14078.8 | | | | | | ✓ | ✓ | ↑ | |
| 130 | | | 14084.9 | | | | | | ✓ | ✓ | ↑ | |
| 131 | | | 14090.0 | | | | | | ✓ | ✓ | ↑ | |
| 132 | | | 14097.1 | | | | | | ✓ | ✓ | ↑ | * |
| 133 | | | 14107.8 | | | | | | ✓ | ✓ | ↑ | |
| 134 | | | 14114.4 | | | | | | ✓ | ✓ | ↑ | |
| 135 | | | 14121.4 | | | | | | ✓ | ✓ | ↑ | |
| 136 | | | 14136.8 | | | | | | ✓ | ✓ | ↑ | |
| 137 | P03950 | 14142.9 | 14140.5 | 44.71 | 17.01 | Angiogenin | Secreted, extracellular space, nucleolus | YTHFLTQHYDA KPQGR SSFQVTTCK | ✓ | ✓ | ↑ | * |
| 138 | | | 14150.1 | | | | | | | ✓ | ↑ | |
| 139 | | | 14158.5 | | | | | | ✓ | ✓ | ↑ | |

TABLE 7-continued

Protein detection in human prostate tissue sections by MALDI-TOF/MS using sinapinic acid as the matrix.

| No. | Access. | Theor. MW [a] | Expt. MW | Score | PMF coverage (%) | Description | Subcellular location | Unique peptides [b] | Non-canc. | Canc. | Exp | t-test |
|---|---|---|---|---|---|---|---|---|---|---|---|---|
| 140 | | | 14162.7 | | | | | | √ | √ | ↑ | |
| 141 | | | 14173.8 | | | | | | √ | √ | ↑ | |
| 142 | | | 14192.9 | | | | | | √ | √ | ↑ | * |
| 143 | | | 14197.9 | | | | | | √ | √ | ↑ | * |
| 144 | | | 14209.3 | | | | | | √ | √ | ↑ | |
| 145 | | | 14228.4 | | | | | | √ | √ | ↑ | |
| 146 | | | 14240.5 | | | | | | √ | √ | ↑ | |
| 147 | | | 14251.4 | | | | | | √ | √ | ↑ | |
| 148 | | | 14290.6 | | | | | | √ | √ | | |
| 149 | P09382 | 14584.5 | 14585.7 | 257.5 | 39.26 | Galectin-1 | Secreted, extracellular space, cell surface | FNAHGDANTIVC NSK ACGLVASNLNL KPGECLR TPGAVNACHLS | | √ | | |
| 150 | P61626 | 14700.7 | 14701.7 | 109.12 | 33.78 | Lysozyme C | Secreted, extracellular space | CSALLQDNIADA VACAK WESGYNTR LGMDGYR YWCNDGK TFVNITPAEVGV LVGK DSLLQDGEFSM DLR DSLLQDGEFSM | | √ | | |
| 151 | P07737 | 15054.2 | 15053.5 | 380.5 | 50 | Profilin-1 | Plasma membrane | DLR + Oxidation (M) DSPSVWAAVPG K TLVLLMGK CYFMASHLR + Oxidation (M) EGVHGGLINK | √ | √ | ↑ | |

TABLE 7-continued

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc. | Exp | t-test |
|---|---|---|---|---|---|---|---|---|---|---|---|---|
| 152 | | 15082.1 | | | | | | | √ | √ | ↑ | * |
| 153 | P69905 | 15126.4 | 15126.4 | 2727.2 | 96.48 | Hemoglobin subunit alpha | Extracellular region | KVADALTNAVA HVDDMPNALSA LSDLHAHK VADALTNAVAH VDDMPNALSAL SDLHAHK VADALTNAVAH VDDMPNALSAL SDLHAHK + Oxidation (M) KVADALTNAVA HVDDMPNALSA LSDLHAHK + Oxidation (M) TYPPHFDLSHGS AQVK LLSHCLLVTLAA HLPAEFTPAVHA SLDKFLASVSTV LTSK VGAHAGEYGAE ALER FLASVSTVLTSK LLSHCLLVTLAA HLPAEFTPAVHA SLDK MFLPPTTKTYF PHFDLSHGSAQV K MFLSFPTTK LLSHCLLVTLAA HLPAEFTPAVHA SLDKFLASVSTV LTSKYR VDPVNFKLLSHC LLVTLAAHLPAE FTPAVHASLDK LRVDPVNFKLLS HCLLVTLAAHLP AEFTPAVHASLD K | √ | √ | ↑ | * |

TABLE 7-continued

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc. | Exp | t-test |
|---|---|---|---|---|---|---|---|---|---|---|---|---|
| 154 | | | 15180.3 | | | | | VGAHAGEYGAE ALERMFLSFPTT K | | | | |
| 155 | | | 15238.0 | | | | | MFLSFPTTK + Oxidation (M) | | | | |
| 156 | | | 15295.3 | | | | | VGAHAGEYGAE ALERMFLSFPTT | | | | |
| 157 | | | 15339.3 | | | | | KTYPPHFDLSHG | ✓ | ✓ | ↑ | * |
| 158 | | | 15391.8 | | | | | SAQVK | ✓ | ✓ | ↑ | * |
| 159 | | | 15439.6 | | | | | TNVKAAWGK | ✓ | ✓ | ↑ | |
| 160 | | | 15494.6 | | | | | LRVDPVNFK | ✓ | ✓ | ↑ | |
| 161 | | | 15510.4 | | | | | | ✓ | ✓ | ↑ | |
| 162 | | 15561.1 | | | | | | | | | | |
| 163 | | | 15813.7 | | | | | | ✓ | ✓ | ↑ | * |
| 164 | P68871 | 15867.2 | 15866.4 | 2764.3 | 95.24 | Hemoglobin subunit beta | Extracellular region | SAVTALWGKVN VDEVGGEALGR FFESFGDLSTPD AVMGNPK VLGAFSDGLAH LDNLK LLGNVLVCVLA HHFGK GTFATLSELHCD K | | ✓ | ↑ | |

TABLE 7-continued

Protein detection in human prostate tissue sections by MALDI-TOF/MS using sinapinic acid as the matrix.

| No. | Access. | Mass wt (MW, Da) Theor. MW [a] | Expt. MW | PMF Score | coverage (%) | Description | Subcellular location | Unique peptides [b] | Non-canc. | Canc. | Exp | t-test |
|---|---|---|---|---|---|---|---|---|---|---|---|---|
| | | | | | | | | GTFATLSELHCD | | | | |
| | | | | | | | | KLHVDPENFR | | | | |
| | | | | | | | | VVAGVANALAH | | | | |
| | | | | | | | | KYH | | | | |
| | | | | | | | | LLGNVLVCVLA | | | | |
| | | | | | | | | HHFGKEFTPPVQ | | | | |
| | | | | | | | | AAYQK | | | | |
| | | | | | | | | VHLTPEEKSAVT | | | | |
| | | | | | | | | ALWGKVNVDEV | | | | |
| | | | | | | | | GGEALGR | | | | |
| | | | | | | | | VNVDEVGGEAL | | | | |
| | | | | | | | | GR | | | | |
| | | | | | | | | KVLGAFSDGLA | | | | |
| | | | | | | | | HLDNLK | | | | |
| | | | | | | | | SAVTALWGK | | | | |
| | | | | | | | | LLVVYPWTQR | | | | |
| | | | | | | | | VVAGVANALAH | | | | |
| | | | | | | | | K | | | | |
| | | | | | | | | EFTPPVQAAYQK | | | | |
| | | | | | | | | EFTPPVQAAYQK | | | | |
| | | | | | | | | VVAGVANALAH | | | | |
| | | | | | | | | K | | | | |
| | | | | | | | | FFESFGDLSTPD | | | | |
| | | | | | | | | AVMGNPK + | | | | |
| | | | | | | | | Oxidation (M) | | | | |
| | | | | | | | | VLGAFSDGLAH | | | | |
| | | | | | | | | LDNLKGTFATLS | | | | |
| | | | | | | | | ELHCDK | | | | |
| | | | | | | | | SAVTALWGKVN | | | | |
| | | | | | | | | VDEVGGEALGR | | | | |
| | | | | | | | | LLVVYPWTQR | | | | |
| | | | | | | | | VHLTPEEK | | | | |
| | | | | | | | | LHVDPENFRLLG | | | | |
| | | | | | | | | NVLVCVLAHHF | | | | |
| | | | | | | | | GKEFTPPVQAAY | | | | |
| | | | | | | | | QK | | | | |
| 165 | | | 15881.4 | | | | | LHVDPENFR | √ | √ | ↑ | * |
| 166 | | | 15892.6 | | | | | EFTPPVQAAYQK | √ | √ | ↑ | |
| | | | | | | | | VVAGVANALAH | | | | |
| | | | | | | | | KYH | | | | |

TABLE 7-continued

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc. | Exp | t-test |
|---|---|---|---|---|---|---|---|---|---|---|---|---|
| 167 | | | 15903.8 | | | | | | √ | √ | ↑ | |
| 168 | | | 15913.9 | | | | | | √ | √ | | |
| 169 | P02042 | 15924.3 | 15924.6 | 1435.2 | 86.39 | Hemoglobin subunit delta | Extracellular region | VLGAFSDGLAH LDNLK VNVDAVGGEAL GR LLGNVLVCVLA R GTFSQLSELHCD K FFESFGDLSSPD AVMGNPK + Oxidation (M) EFTPQMAAYQ K EFTPQMAAYQ K + Oxidation (M) KVLGAFSDGLA HLDNLK LLVVYPWTQR VVAGVANALAH K GTFSQLSELHCD KLHVDPENFR VHLTPEEK LHVDPENFR | √ | √ | ↑ | |
| 170 | | | 15962.0 | | | | | | √ | √ | ↑ | |
| 171 | | | 16000.3 | | | | | | √ | √ | ↑ | |
| 172 | | | 16043.8 | | | | | | √ | √ | ↑ | |
| 173 | | | 16096.4 | | | | | | √ | √ | ↑ | |
| 174 | | | 16143.6 | | | | | | √ | √ | ↑ | |
| 175 | | | 16192.8 | | | | | | √ | √ | ↑ | |
| 176 | | | 16245.4 | | | | | | | √ | ↑ | |

TABLE 7-continued

Protein detection in human prostate tissue sections by MALDI-TOF/MS using sinapinic acid as the matrix.

| No. | Access. | Mass wt (MW, Da) Theor. MW a) | Mass wt (MW, Da) Expt. MW | PMF Score | PMF coverage (%) | Description | Subcellular location | Unique peptides b) | Non-canc. | Canc. | Exp | t-test |
|---|---|---|---|---|---|---|---|---|---|---|---|---|
| 177 | | 16515.5 | | | | | | | | √ | | |
| 178 | P62158 | 16706.4 | 16705.7 | 853.5 | 73.8 | Calmodulin | Extracellular region, cytoplasm, cytoskeleton | VFDKDGNGYISA AELR<br>EADIDGDGQVN<br>YEEFVQMMTAK<br>MKDTDSEEEIR<br>DGNGYISAAELR<br>EAFSLFDKDGDG TITTK<br>MKDTDSEEEIRE AFR<br>HVMTNLGEKLT<br>DEEVDEMIR<br>EAFSLFDK<br>DTDSEEEIREAF R<br>DTDSEEEIR<br>EILVGDVGQTVD<br>DPYATFVK<br>NILEEGKEILVG<br>DVGQTVDDPYA<br>TFVK | √ | √ | ↑ | * |
| 179 | E9PP50 | 17864.7 | 17863.4 | 577.97 | 58.13 | Cofilin-1 (Fragment) | Plasma membrane | ASGVAVSDGVIK<br>HELQANCYEEV<br>KDR<br>YALYDATYETK<br>KEDLVFIFWAPE<br>SAPLK<br>AVLFCLSEDKK<br>VLGDVIEVHGK | | √ | | |
| 180 | E9PR44 | 20030.7 | 20030.4 | 66.34 | 24.14 | Alpha-crystallin B chain (Fragment) | Cell surface, plasma membrane | MDIAIHHPWIR + Oxidation (M)<br>QDEHGFISR<br>EEKPAVTAAPK<br>TVYFAEEVQCE<br>GNSFHK<br>GYGYGQGAGTL<br>STDKGESLGIK<br>NLDSTTVAVHG<br>EEIYCK<br>GYGYGQGAGTL<br>STDK | | √ | | |

TABLE 7-continued

Protein detection in human prostate tissue sections by MALDI-TOF/MS using sinapinic acid as the matrix.

| No. | Access. | Mass wt (MW, Da) Theor. MW a) | Mass wt (MW, Da) Expt. MW | PMF Score | PMF coverage (%) | Description | Subcellular location | Unique peptides b) | Non-canc. | Canc. | Exp | t-test |
|---|---|---|---|---|---|---|---|---|---|---|---|---|
| 181 | P21291 | 20567.4 | 20567.6 | 951.66 | 64.77 | Cysteine and glycine-rich protein 1 | Cell surface, plasma membrane | GLESTTLADKDG EIYCK GFGFGQGAGAL VHSE CSQAVYAAEK KNLDSTTVAVH GEEIYCK GLESTTLADK HEEAPGHRPTTN PNASK SCFLCMVCK GNDISSGTVLSD YVGSGPPK WSGPLSLQEVDE QPQHPLHVTYA GAAVDELGK | √ | √ | ↑ | ** |
| 182 | P30086 | 20925.6 | 20925.4 | 617.71 | 73.26 | Phosphatidy-lethanolamine-binding protein 1 | Cell surface, plasma membrane | LYTLVLTDPDAP SR NRPTSISWDGLD SGK APVAGTCYQAE WDDYVPK CDEPILSNR YVWLVYEQDRP LK LYEQLSGK MGAPESGLAEY LFDK MGAPESGLAEY LFDK + Oxidation (M) LATDKNDPHLC | √ | √ | ↑ | * |
| 183 | P02794 | 21094.5 | 21094.6 | 296.14 | 54.1 | Ferritin heavy chain | Extracellular region, cytosol | DFIETHYLNEQV K QNYHQDSEAAI NR YFLHQSHEER ELGDHVTNLR IFLQDIK TTASTSQVR EQLGEFYEALDC LR | | √ | | |

TABLE 7-continued

Protein detection in human prostate tissue sections by MALDI-TOF/MS using sinapinic acid as the matrix.

| No. | Access. | Mass wt (MW, Da) Theor. MW a) | Mass wt (MW, Da) Expt. MW | PMF Score | PMF coverage (%) | Description | Subcellular location | Unique peptides b) | Non-canc. | Canc. | Exp | t-test |
|---|---|---|---|---|---|---|---|---|---|---|---|---|
| 184 | P02763 | 21560.1 | 21560.2 | 558.18 | 40.8 | Alpha-1-acid glycoprotein 1 | Secreted, extracellular space | NWGLSVYADKP ETTK YVGGQEHFAHL LILR TYMLAFDVNDE KNWGLSVYADK PETTK TYMLAFDVNDE K SDVVYTDWK | √ | √ | ↑ | ** |
| 185 | | | 22510.6 | | | | | | √ | √ | ↑ | |
| 186 | P80723 | 22562.2 | 22563.0 | 927.6 | 78.9 | Brain acid soluble protein 1 | Cell membrane, lipid-anchor | APEQEQAAPGPA AGGEAPK AEGAATEEEGTP K EKPDQDAEGKA EEK SDGAPASDSKPG SSEAAPSSK ESEPQAAAEPAE AK AQGPAASAEEPK PVEAPAANSDQT VTVK AEPPKAPEQEQA APGPAAGGEAP K AQGPAASAEEPK PVEAPAANSDQT VTVKE ETPAATEAPSST PK KTEAPAAPAAQ ETK AARAAAPAES AAPAAGEEPSKE EGEPK GYNVNDEK EQLGEFYEALDC LCIPR | √ | √ | ↑ | ** |

TABLE 7-continued

Protein detection in human prostate tissue sections by MALDI-TOF/MS using sinapinic acid as the matrix.

| No. | Access. | Mass wt (MW, Da) Theor. MW a) | Expt. MW | Score | PMF coverage (%) | Description | Subcellular location | Unique peptides b) | Non-canc. | Canc. | Exp | t-test |
|---|---|---|---|---|---|---|---|---|---|---|---|---|
| 187 | P19652 | 21651.2 | 21651.9 | 324.68 | 35.32 | Alpha-1-acid glycoprotein 2 | Secreted, extracellular space | TLMFGSYLDDE KNWGLSFYADK PETTK EHVAHLLFLR | √ | √ | ↑ | ** |
| 188 | P32119 | 21760.7 | 21761.3 | 107.47 | 18.69 | Peroxiredoxin-2 | Cell surface, cytoplasm | EGGLGPLNIPLL ADVTR QITVNDLPVGR LSEDYGVLK TLMALGSLAVT K TDMFQTVDLFE GK AAEDYGVIK KYDEELEER EFTESQLQEGK LGFQVWLK QMEQVAQFLK LVEWIIVQCGPD VGRPDR LVNSLYPDGSKP VK | √ | √ | ↑ | * |
| 189 | Q01995 | 22479.7 | 22479.2 | 1003.6 | 81.09 | Transgelin | Cell surface, cytoplasm | HVIGLQMGSNR + Oxidation (M) HVIGLQMGSNR VPENPPSMVFK QMEQVAQFLK + Oxidation (M) YDEELEER GASQAGMTGYG RPR + Oxidation (M) GDPNWFMK GPSYGMSR GASQAGMTGYG RPR VPENPPSMVFK + Oxidation (M) APEQEQAAPGPA AGGEAPK AEGAATEEEGTP K EKPDQDAEGKA EEK | √ | √ | ↑ | * |

TABLE 7-continued

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc | Exp | t-test |
|---|---|---|---|---|---|---|---|---|---|---|---|---|
| 190 | P80723 | 22562.2 | 22563.1 | 927.57 | 78.85 | Brain acid soluble protein 1 | Cell membrane, lipid-anchor | SDGAPASDSKPG SSEAAPSSK ESEPQAAAEPAE AK AQGPAASAEEPK PVEAPAANSDQT VTVK AEPPKAPEQEQA APGPAAGGEAP K AQGPAASAEEPK PVEAPAANSDQT VTVKE ETPAATEAPSST PK KTEAPAAPAAQ ETK AAEAAAPAES AAPAAGEEPSKE EGEPK GYNVNDEK VPLQQNFQDNQ FQGK WYVVGLAGNAI | ✓ | ✓ | ↑ | |
| 191 | P80188 | 22588.1 | 22587.9 | 234.5 | 33.33 | Neutrophil gelatinase-associated lipocalin | Secreted, extracellular region/space, cytoplasm | LR TFVPGCQPGEFT LGNIK SLGLPENHIVFP VPIDQCIDG | ✓ | ✓ | ↑ | ** |
| 192 | | | 22636.8 | | | | | | ✓ | ✓ | ↑ | * |
| 193 | | | 22684.7 | | | | | | ✓ | ✓ | ↑ | |
| 194 | | | 22735.2 | | | | | | ✓ | ✓ | ↑ | |
| 195 | P04792 | 22782.5 | 22782.3 | 587.97 | 85.85 | Heat shock protein beta-1 | Cell surface, plasma membrane | LFDQAFGLPR LATQSNEITIPVT FESR DGVVEITGK AQLGGPEAAK KYTLPPGVDPTQ VSSLSPEGTLT VEAPMPK | ✓ | ✓ | ↑ | ** |

TABLE 7-continued

Protein detection in human prostate tissue sections by MALDI-TOF/MS using sinapinic acid as the matrix.

| No. | Access. | Mass wt (MW, Da) Theor. MW [a] | Expt. MW | PMF Score | coverage (%) | Description | Subcellular location | Unique peptides [b] | Non-canc. | Canc. | Exp | t-test |
|---|---|---|---|---|---|---|---|---|---|---|---|---|
| 196 | | | 22819.7 | | | | | QLSSGVSEIR QDEHGYISR LPEEWSQWLGG SSWPGYVRPLPP AAIESPAVAAPA YSR KYTLPPGVDPTQ VSSSLSPEGTLT VEAPMPK + Oxidation (M) VSLDVNHFAPDE LTVK HEERQDEHGYIS R VPFSLLR GPSWDPFR | | | | |
| 197 | | | 22847.8 | | | | | | √ | √ | ↑ | |
| 198 | A8K8G0 | 22963.7 | 22963.8 | 95.32 | 21.15 | Hepatoma-derived growth factor | Extracellular space | GPPQEEEBEDE EEEATKEDAEAP GIR YQVFFGTHETA FLGPK NSCPPTSELLGTS DR | √ | √ | ↑ | |
| 199 | P22352 | 23463.7 | 23463.4 | 270.06 | 28.32 | Glutathione peroxidase 3 | Secreted, extracellular space | QEPGENSEILPTL K YVRPGGGFVPNF QLFEK AGLAASLAGPHS IVGR | √ | √ | ↑ | * |
| 200 | P08294 | 24132.8 | 24132.5 | 233.66 | 46.25 | Extracellular superoxide dismutase [Cu-Zn] | Secreted, extracellular space, cytoplasm | LACCVVGVCGP GLWER AVVHAGEDDL GR AIHVHQFGDLSQ GCESTGPHYNPL AVPHPQHPGDF GNFAVR RDDDGALHAAC | | √ | | |

TABLE 7-continued

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc. | Exp | t-test |
|---|---|---|---|---|---|---|---|---|---|---|---|---|
| 201 | A8MTM1 | 24498.8 | 24499.2 | 138.29 | 19.82 | Carbonyl reductase [NADPH] 1 | Cytoplasm | QVQPSATLDAA QPR GQAAVQQLQAE GLSPR EYGGLDVLVNN AGIAFK DINAYNCEEPTE K | | ✓ | | |
| 202 | P30041 | 24901.8 | 24901.6 | 195.12 | 25 | Peroxiredoxin-6 | Cytoplasmic membrane-bounded vesicle, cytoplasm, | ELAILLGMLDPA EKDEK LPPPIIDDR FHDFLGDSWGIL FSHPR | ✓ | ✓ | ↑ | * |
| 203 | P17931 | 26021.1 | 26022.3 | 69.75 | 5.6 | Galectin-3 | Secreted, cytoplasm, nucleus, plasma membrane | VAVNDAHLLQY NHR | | ✓ | | |
| 204 | P08311 | 26757.7 | 26757.4 | 52.48 | 22.35 | Cathepsin G | Cell surface, plasma membrane | VSSFLPWIR GDSGGPLLCNN VAHGIVSYGK AQEGLRPGTLCT VAGWGR NVNPVALPR | | ✓ | | |
| 205 | P07858 | 27815.1 | 27814.7 | 195.01 | 5.31 | Cathepsin B | Secreted, extracellular space | NGPVEGAFSVYS DFLLYK | | ✓ | | |
| 206 | | | 28020.5 | | | | | | ✓ | ✓ | ↑ | |
| 207 | | | 28063.6 | | | | | | ✓ | ✓ | ↑ | |
| 208 | P02647 | 28078.6 | 28079.3 | 868.44 | 56.55 | Apolipoprotein A-1 | Secreted, plasma membrane | LLDNWDSVTSTF SK DYVSQFEGSALG K EQLGPVTQEFW DNLEK VKDLATVYVDV LK VSFLSALEEYTK LREQLGPVTQEF WDNLEK | ✓ | ✓ | ↑ | ** |

TABLE 7-continued

Protein detection in human prostate tissue sections by MALDI-TOF/MS using sinapinic acid as the matrix.

| No. | Access. | Mass wt (MW, Da) Theor. MW a) | Mass wt (MW, Da) Expt. MW | PMF Score | PMF coverage (%) | Description | Subcellular location | Unique peptides b) | Non-canc. | Canc. | Exp | t-test |
|---|---|---|---|---|---|---|---|---|---|---|---|---|
| 209 | | | 28117.5 | | | | | ATEHLSTLSEK QGLLPVLESFK AKPALEDLR THLAPYSDELR LSPLGEEMR ETEGLRQEMSK WQEEMELYR VQPYIDDFQK | | √ | | |
| 210 | | | 28162.0 | | | | | | √ | √ | ↑ | * |
| 211 | | | 28202.3 | | | | | | √ | √ | ↑ | |
| 212 | | | 28283.0 | | | | | | √ | √ | ↑ | |
| 213 | P00918 | 29114.9 | 29114.5 | 139.61 | 14.23 | Carbonic anhydrase 2 | Cell membrane, cytoplasm, extracellular space | AVQQPDGLAVL GIFLK QSPVDIDTHTAK GGPLDGTYR DSCQGDSGGPL VCK VPIMENHICDAK VTYYLDWIHHY VPK | √ | √ | ↑ | ** |
| 214 | Q15661-2 | 29533.1 | 29532.2 | 280.56 | 30.08 | Isoform 2 of Tryptase alpha/beta-1 | Secreted, extracellular space | DDMLCAGNTR YHLGAYTGDDV R WPWQVSLR SKWPWQVSLR LPPPFPLK EELQANGSAPA ADKEEPAAAGS GAASPSAAEK | | √ | | |
| 215 | P29966 | 31423.5 | 31424.1 | 328.34 | 38.55 | Myristoylated alanine-rich C-kinase substrate | Plasma membrane, cytoplasm, cytoskeleton | GEAAAERPGEA AVASSPSK EAGEGGEAEAP AAEGGK GEPAAAAPEA GASPVEK | √ | √ | ↑ | * |

TABLE 7-continued

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc | Exp | t-test |
|---|---|---|---|---|---|---|---|---|---|---|---|---|
| 216 | E7EUT4 | 31547.9 | 31548.5 | 815.66 | 56.31 | Glyceraldehyde-3-phosphate dehydrogenase | Plasma membrane, cytoplasm, nucleus | EAPAEGEAAEPG SPTAAEGEAASA ASSTSSPK WGDAGAEYVVE STGVFTTMEK IISNASCTTNCLA PLAK LVINGNPITIFQE R VPTANVSVVDL TCR LISWYDNEFGYS NR VIHDNFGIVEGL MTTVHAITATQ K GILGYTEHQVVS SDFNSDTHSSTF DAGAGIALNDH FVK GALQNIIPASTG AAK LDFTGNLIEDIED GTFSK RLDFTGNLIEDIE DGTFSK LSLLEELSLAEN QLLK | | ✓ | | |
| 217 | P20774 | 31734.4 | 31731.3 | 477.28 | 40.94 | Mimecan | Secreted, extracellular space, extracellular matrix | LEGNPIVLGK VIHLQFNNIASIT DDTFCK DFADIPNLR LNNLTFLYLDHN ALESVPLNLPES LR LTLFNAK DRIEEIR HPNSFICLK HVEDVPAFQAL GSLNDLQFFR YSLTYIYTGLSK YYYDGKDYIEF NK | ✓ | ✓ | ↑ | * |

TABLE 7-continued

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc. | Exp | t-test |
|---|---|---|---|---|---|---|---|---|---|---|---|---|
| 218 | P25311 | 32144.9 | 32145.9 | 537.95 | 45.97 | Zinc-alpha-2-glycoprotein | Secreted, extracellular space, plasma membrane | AYLEEECPATLR AGEVQEPELR QKWEAEPVYVQ R QDPPSVVVTSHQ APGEK WEAEPVYVQR EIPAWVPFDPAA QITK QVEGMEDWKQ DSQLQK AYLEEECPATLR K YYYDGK IDVHWTR | | √ | | |
| 219 | P01009-3 | 32343.5 | 32345.1 | 428.82 | 42.06 | Alpha-1-antitrypsin | Secreted, extracellular space | TLNQPDSQLQLT TGNGLFLSEGLK VFSNGADLSGVT EEAPLK SASLHLPK SVLGQLGITK DTVFALVNYIFF K LSITGTYDLK TDTSHHDQDHP TFNK ELDRDTVFALV NYIPFK LQHLENELTHDII TK LYHSEAFTVNFG DTEEAKK FLEDVKK QINDYVEK | √ | √ | ↑ | ** |
| 230 | | | 32671.4 | | | | | | √ | √ | ↑ | |
| 231 | | | 32714.7 | | | | | | √ | √ | ↑ | |
| 232 | | | 32766.8 | | | | | | √ | √ | ↑ | |
| 233 | | | 32836.7 | | | | | | √ | √ | ↑ | |

TABLE 7-continued

Protein detection in human prostate tissue sections by MALDI-TOF/MS using sinapinic acid as the matrix.

| No. | Access. | Mass wt (MW, Da) Theor. MW [a] | Expt. MW | PMF Score | PMF coverage (%) | Description | Subcellular location | Unique peptides [b] | Non-canc. | Canc. | Exp | t-test |
|---|---|---|---|---|---|---|---|---|---|---|---|---|
| 234 | P07951-2 | 32989.8 | 32988.4 | 1772.3 | 76.41 | Isoform 2 of Tropomyosin beta chain | Cell surface, plasma membrane, cytoplasm, cytoskeleton | CKQLEEEQQAL QK QLEEQQALQK LKGTEDEVEKYS ESVK LKGTEDEVEK GTEDEVEKYSES VK QLEEQQALQK K EAQEKLEQAEK | ✓ | ✓ | ↑ | * |
| 235 | P07288 | 33000-34000 (glycoprotein) | 32991.7 | 434.51 | 64.37 | Prostate-specific antigen | Secreted, extracellular region | STCSGDSGGPLV CNGVLQGITSW GSEPCALPERPS LYTK LSEPAELTDAVK KLQCVDLHVISN DVCAQVHPQK LQCVDLHVISND VCAQVHPQK FLRPGDDSSHDL MLLR HSQPWQVLVAS R HSLFHPEDTGQV FQVSHSFPHPLY DMSLLK + Oxidation (M) IVGGWECEK FMLCAGR + Oxidation (M) FMLCAGR | ✓ | ✓ | ↑ | ** |
| | | | 33004.6 | | | | | | | | | |
| | | | 33015.9 | | | | | | | | | |
| | | | 33020.9 | | | | | | | | | |
| | | | 33034.7 | | | | | | | | | |
| | | | 33082.1 | | | | | | | | | |
| | | | 33137.7 | | | | | | | | | |
| | | | 33184.5 | | | | | | | | | |
| | | | 33252.7 | | | | | | | | | |
| | | | 33307.1 | | | | | | | | | |
| | | | 33354.0 | | | | | | | | | |
| | | | 33407.0 | | | | | | | | | |
| 236 | | | 33450.1 | | | | | | ✓ | ✓ | ↑ | * |
| 237 | | | 33506.5 | | | | | | ✓ | ✓ | ↑ | |
| 238 | | | 33560.3 | | | | | | ✓ | ✓ | ↑ | |
| 239 | | | 33637.6 | | | | | | ✓ | ✓ | ↑ | * |

TABLE 7-continued

Protein detection in human prostate tissue sections by MALDI-TOF/MS using sinapinic acid as the matrix.

| No. | Access. | Mass wt (MW, Da) Theor. MW [a] | Mass wt (MW, Da) Expt. MW | PMF Score | PMF coverage (%) | Description | Subcellular location | Unique peptides [b] | Non-canc. | Canc. | Exp | t-test |
|---|---|---|---|---|---|---|---|---|---|---|---|---|
| 240 | A6NLG9 | 34875.5 | 34874.1 | 113.11 | 10.1 | Biglycan | Secreted, extracellular space, cell surface | IQAIELEDLLR EISPDTTLLDLQ NNDISELR TDASDVKPC ATFGCHDGYSL | √ | √ | ↑ | |
| 241 | P02749 | 36254.6 | 36255.9 | 129.27 | 18.84 | Beta-2-glycoprotein 1 | Secreted, cell surface | DGPEEIECTK FICPLTGLWPINT LK TFYEPGEEITYSC KPGYVSR | √ | √ | ↑ | ** |
| 242 | P51884 | 36660.9 | 36663.0 | 379.5 | 26.63 | Lumican | Secreted, extracellular space, extracellular matrix | SLEDLQLTHNK SLEYIDLSFNQI AR NIPTVNENLENY YLEVNQLEK FNALQYLR LPSGLPVSLLTL YLDNNK NNQIDHIDEK | √ | | ↑ | * |

Note:
[a], The theoretical MW values were all calculated using the ExPASy Compute pI/MW tool (http://kr.expasy.org/tools/pi_tool/html.). [b], Unique peptides of detectable protein on prostate cancer tissue section were analyzed by a Waters ACQUITY UPLC system coupled to a LTQ Orbitrap Velos-Pro mass spectrometer.

Example 2C

In this particular embodiment, some tumor-susceptible proteins that have previously been detected as potential biomarkers for other cancers, including apolipoprotein C-I for breast and stomach cancers, S100 A6 for pancreatic cancer, and S100 A8 and A9 for colorectal and gastric cancers, were also detected in prostate cancer tissue for the first time, as currently understood based on the state of the art. The proteins that were found to be either up-regulated or down-regulated in the cancerous region are summarized in Table 7. To verify the MALDI imaging observations, immuno-histological staining was performed for apolipoprotein C-I, S100A6, and S100A8. As shown in FIGS. 33A and 33B these three proteins were expressed at significantly higher levels in the cancerous region than in the non-cancerous region, which was consistent with the results from the MALDI imaging. This consistency highlights the great potential of MALDI imaging for the discovery of new cancer biomarkers. Taken together, these embodiments illustrated the ability of the disclosed method and system embodiments to make coated samples capable of providing the largest group of the potential protein biomarkers for prostate cancer that have been detected in a single MALDI-MSI study.

Example 3

In this embodiment, it was established that the disclosed method and system produced higher signal-to-noise ratios and detected more compounds of interest than one or more control samples. Matrix coating in this particular method was carried using a Bruker ImagePrep electronic sprayer. Thirty spray cycles were performed to coat a thinly-cut tissue section with the matrix. Each spray cycle comprised a 3-s spray step, a 60-s incubation step, and a 90-s drying step. A control embodiment and three method embodiments, as disclosed herein, were conducted, each of which is described in FIG. 27 as I to IV. These embodiments were conducted with four consecutive 12-µm rat brain tissue sections sliced from the same rat brain. After the matrix coating with quercetin, on-tissue detection was performed by MALDI-FTICR MS using the identical set of MS operating and data acquisition parameters. FIGS. 28A-28D shows the four mass spectra, corresponding to the four experiments (I to IV, respectively) that were acquired from the hippocampus region of the four tissue sections. Table 8, below, lists the detected and identified lipid entities and the observed S/N±standard derivation for each of the identified lipid entities from the mass spectra. In summary, 320, 248, and 283 lipid entities were detected from the spectra II to IV, respectively, as compared to only 208 lipid entities detected from the spectrum I, corresponding to the control embodiment. As can be seen from Table 8, the S/Ns of the detected lipids in the spectra II to IV were clearly higher than those in the spectrum I. Without being limited to a particular theory of operation, it is currently believed that applying the electric field during periods other than just the spray cycle can improve results.

TABLE 8

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

| Class | No. | Electric field (Measured m/z) Matrix coating | | | | Calc m/z | Electric field (Average S/N, n = 3) Matrix coating | |
|---|---|---|---|---|---|---|---|---|
| | | I | II | III | IV | | I | II |
| Glycerophospholipids | 1 | 478.32921 | 478.32944 | 478.32928 | 478.32951 | 478.32920 | 139.9 ± 18.6 | 383.6 ± 13.5 |
| Phosphatidylcholines | | 500.31090 | 500.31143 | 500.31066 | 500.31203 | 500.31115 | 3.7 ± 2.1 | 11.2 ± 2.4 |
| (PCs) | | 516.28499 | 516.28531 | 516.28541 | 516.28563 | 516.28508 | 22.4 ± 3.7 | 49.4 ± 4.4 |
| | 2 | — | 502.32660 | — | — | 502.32680 | — | 13.9 ± 3.5 |
| | | — | 518.30102 | — | 518.30122 | 518.30073 | — | 15.2 ± 4.8 |
| | 3 | — | 496.33958 | — | 496.33830 | 496.33977 | — | 13.2 ± 4.6 |
| | | 534.29559 | 534.29588 | 534.29588 | 534.29580 | 534.29565 | 25.4 ± 5.9 | 57.6 ± 4.8 |
| | 4 | — | 504.34249 | 504.34267 | 504.34272 | 504.34245 | — | 12.2 ± 5.6 |
| | 5 | 516.30887 | 516.30896 | 516.30845 | 516.30886 | 516.30847 | 12.4 ± 5.5 | 49.4 ± 6.1 |
| | 6 | — | 518.32450 | — | 518.32407 | 518.32412 | — | 15.2 ± 5.8 |
| | 7 | 506.36056 | 506.36069 | 506.36043 | 506.36065 | 506.36050 | 77.2 ± 11.0 | 132.9 ± 8.1 |
| | 8 | — | 528.34262 | — | 528.34269 | 528.34245 | — | 21.4 ± 5.1 |
| | | 544.31639 | 544.31646 | 544.31718 | 544.31689 | 544.31638 | 5.7 ± 3.7 | 21.7 ± 6.4 |
| | | — | 522.35543 | 522.53496 | 522.53563 | 522.35542 | — | 12.1 ± 3.1 |
| | | 560.31123 | 560.31143 | 560.31151 | 560.31156 | 560.31130 | 9.5 ± 5.7 | 24.7 ± 3.9 |
| | 10 | 524.37117 | 524.37155 | 524.37130 | 524.37093 | 524.37107 | 8.3 ± 7.1 | 34.4 ± 6.4 |
| | | 562.32677 | 562.32725 | 562.32757 | 562.32771 | 562.32695 | 8.6 ± 4.7 | 23.1 ± 3.7 |
| | 11 | 544.33970 | 544.33975 | 544.33927 | 544.33968 | 544.33977 | 6.3 ± 3.2 | 15.0 ± 5.6 |
| | | — | 582.29603 | — | — | 582.29565 | — | 5.5 ± 3.3 |
| | 12 | — | 546.35543 | — | — | 546.35542 | — | 5.1 ± 2.6 |
| | 13 | 548.37142 | 548.37134 | 548.37140 | 548.37095 | 548.37107 | 6.9 ± 4.6 | 11.7 ± 3.9 |
| | | 586.32713 | 586.32721 | 586.32703 | 586.32704 | 586.32695 | 9.2 ± 3.9 | 19.1 ± 5.3 |
| | 14 | 602.32227 | 602.32135 | 602.32157 | 602.32169 | 602.32186 | 5.1 ± 3.6 | 14.1 ± 6.1 |
| | 15 | 604.33764 | 604.33734 | 604.33725 | 604.33788 | 604.33751 | 7.3 ± 5.4 | 20.7 ± 7.6 |
| | 16 | 606.29527 | 606.29509 | 606.29593 | 606.29558 | 606.29565 | 24.3 ± 8.2 | 53.8 ± 7.1 |
| | 17 | — | 608.31094 | — | 608.31167 | 608.31130 | — | 10.3 ± 4.8 |
| | 18 | 610.32706 | 610.32647 | 610.32657 | 610.32668 | 610.32695 | 9.0 ± 5.2 | 18.9 ± 6.1 |
| | 19 | 614.35835 | 614.35804 | 614.35851 | 614.35816 | 614.35825 | 7.0 ± 3.5 | 15.3 ± 4.9 |
| | 20 | 616.37398 | 616.37402 | 616.37386 | 616.37396 | 616.37390 | 7.4 ± 3.1 | 16.3 ± 5.8 |
| | 21 | 618.38967 | 618.38923 | 618.38966 | 618.38985 | 618.38955 | 5.5 ± 3.4 | 17.8 ± 5.8 |
| | 22 | 644.40537 | 644.40554 | 644.40528 | 644.40540 | 644.40520 | 5.8 ± 3.6 | 13.7 ± 4.6 |
| | 23 | 646.42079 | 646.42107 | 646.42048 | 646.42042 | 646.42085 | 6.1 ± 4.2 | 13.7 ± 4.3 |
| | 24 | 648.43664 | 648.43642 | 648.43663 | 648.43635 | 648.43650 | 5.6 ± 3.0 | 18.4 ± 4.9 |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

|  |  |  |  |  |  |  |  |  |
|---|---|---|---|---|---|---|---|---|
|  | 25 | 650.45234 | 650.45257 | 650.45177 | 650.45262 | 650.45215 | 5.0 ± 2.6 | 14.9 ± 3.4 |
|  | 26 | 704.52246 | 704.52283 | 704.52289 | 704.52249 | 704.52248 | 19.1 ± 5.3 | 47.2 ± 8.4 |
|  | 27 | 744.49457 | 744.49463 | 744.49418 | 744.49469 | 744.49401 | 6.6 ± 4.3 | 27.4 ± 6.8 |
|  | 28 | 766.47811 | 766.47843 | 766.47816 | 766.47839 | 766.47836 | 9.1 ± 5.8 | 20.5 ± 6.7 |
|  | 29 | 770.50981 | 770.51011 | 770.51028 | 770.51021 | 770.50966 | 10.2 ± 6.4 | 27.6 ± 7.2 |
|  |  | 734.56954 | 734.57001 | 734.56907 | 734.56950 | 734.56943 | 5.0 ± 3.7 | 14.9 ± 4.2 |
|  | 30 | 756.55161 | 756.55118 | 756.55135 | 756.55167 | 756.55138 | 20.2 ± 6.1 | 50.2 ± 5.4 |
|  |  | 772.52537 | 772.52504 | 772.52518 | 775.52511 | 772.52531 | 181.4 ± 12.1 | 415.2 ± 15.7 |
|  | 31 | 790.47818 | 790.47857 | 790.47825 | 790.47820 | 790.47836 | 6.4 ± 3.2 | 23.5 ± 5.5 |
|  | 32 | 792.49398 | 792.49424 | 792.49442 | 792.49458 | 792.49401 | 6.3 ± 3.4 | 14.8 ± 5.5 |
|  | 33 | — | 794.50967 | — | 794.50971 | 794.50966 | — | 14.2 ± 4.1 |
|  | 34 | — | 796.52530 | 796.52567 | 796.52576 | 796.52531 | — | 16.1 ± 5.1 |
|  | 35 | 760.58524 | 760.58475 | 760.58506 | 760.58503 | 760.58508 | 5.3 ± 3.7 | 15.7 ± 4.6 |
|  |  | 782.56776 | 782.56690 | 782.56710 | 782.56734 | 782.56703 | 27.4 ± 5.4 | 77.9 ± 8.1 |
|  |  | 798.54057 | 798.54062 | 798.54052 | 798.54069 | 798.54096 | 188.8 ± 16.3 | 683.8 ± 18.0 |
|  | 36 | — | 762.60067 | — | 762.60111 | 762.60073 | — | 29.6 ± 5.6 |
|  |  | — | 784.58279 | 784.58291 | 784.58283 | 784.58268 | — | 9.3 ± 3.8 |
|  |  | — | 800.55681 | 800.55630 | 800.55657 | 800.55661 | — | 84.3 ± 10.6 |
|  | 37 | — | 804.55102 | — | 804.55126 | 804.55138 | — | 20.2 ± 5.1 |
|  |  | 820.52528 | 820.52564 | 820.52513 | 820.52528 | 820.52531 | 37.3 ± 6.4 | 159.0 ± 13.5 |
|  | 38 | — | 822.54083 | — | 822.54072 | 822.54096 | — | 27.7 ± 5.8 |
|  | 39 | 792.56663 | 792.56609 | 792.56656 | 792.56654 | 792.56678 | 5.1 ± 3.3 | 14.8 ± 5.9 |
|  | 40 | 808.58242 | 808.58219 | 808.58282 | 808.58298 | 808.58268 | 6.3 ± 3.7 | 15.3 ± 4.8 |
|  |  | 824.55618 | 824.55651 | 824.55661 | 824.55654 | 824.55661 | 36.0 ± 5.7 | 86.8 ± 8.3 |
|  | 41 | — | 810.57727 | 810.57742 | 810.57762 | 810.57735 | — | 15.1 ± 5.0 |
|  | 42 | — | 788.61632 | 788.61684 | 788.61601 | 788.61638 | — | 9.6 ± 4.1 |
|  |  | 826.57220 | 826.57280 | 826.57285 | 826.57299 | 826.57226 | 97.1 ± 12.5 | 361.4 ± 20.1 |
|  | 43 | 828.58806 | 828.58799 | 828.58769 | 828.58747 | 828.58791 | 16.3 ± 6.4 | 53.8 ± 7.2 |
|  | 44 | 786.54376 | 786.54364 | 786.54326 | 786.54396 | 786.54322 | 6.5 ± 3.7 | 16.9 ± 5.6 |
|  | 45 | 844.52571 | 844.52562 | 844.52517 | 844.52539 | 844.52531 | 17.7 ± 7.2 | 74.3 ± 11.2 |
|  | 46 | 846.54121 | 846.54098 | 846.54049 | 846.54129 | 846.54096 | 14.2 ± 6.5 | 54.7 ± 8.3 |
|  |  | 810.60045 | 810.60115 | 810.59994 | 810.60041 | 810.60073 | 9.1 ± 5.1 | 28.3 ± 6.8 |
|  | 47 | 832.58284 | 832.58253 | 832.58254 | 832.58241 | 832.58268 | 11.4 ± 5.5 | 20.4 ± 6.3 |
|  |  | 848.55723 | 848.55675 | 848.55674 | 848.55693 | 848.55661 | 165.5 ± 15.2 | 885.3 ± 25.5 |
|  | 48 | 850.57224 | 850.57247 | 850.57276 | 850.57215 | 850.57226 | 10.3 ± 3.6 | 27.4 ± 6.4 |
|  | 49 | 854.60387 | 854.60371 | 854.60345 | 854.60317 | 854.60356 | 6.2 ± 3.4 | 23.4 ± 5.7 |
|  | 50 | — | 840.62426 | 840.62452 | 840.62411 | 840.62430 | — | 15.7 ± 5.4 |
|  | 51 | 856.61947 | 856.61945 | 856.61958 | 856.61948 | 856.61921 | 11.8 ± 4.2 | 39.1 ± 7.0 |
|  | 52 | — | 864.49419 | — | — | 864.49401 | — | 12.0 ± 4.0 |
|  | 53 | — | 866.50959 | — | 866.50955 | 866.50966 | — | 12.5 4.3 |
|  | 54 | — | 852.53071 | — | — | 852.53040 | — | 15.2 ± 5.0 |
|  | 55 | 870.54121 | 870.54027 | 870.54113 | 870.54091 | 870.54096 | 6.4 ± 3.1 | 33.2 ± 6.5 |
|  | 56 | 856.58214 | 856.58277 | 856.58257 | 586.58275 | 856.58268 | 6.6 ± 3.7 | 19.9 ± 5.0 |
|  |  | 872.55660 | 872.55643 | 872.55644 | 872.55652 | 872.55661 | 23.5 ± 5.2 | 120.2 ± 13.6 |
|  | 57 | 874.57235 | 874.57191 | 874.57248 | 874.57213 | 874.57226 | 17.9 ± 5.3 | 52.1 ± 8.8 |
|  | 58 | 876.58740 | 876.58767 | 876.58757 | 876.58750 | 876.58791 | 26.0 ± 5.5 | 60.9 ± 13.4 |
|  | 59 | — | 880.61923 | — | 880.61956 | 880.61921 | — | 10.6 ± 4.3 |
|  | 60 | 882.63526 | 882.63453 | 882.63598 | 882.63597 | 882.63486 | 7.2 ± 3.8 | 20.3 ± 5.3 |
|  | 61 | 906.63497 | 906.63465 | 906.63490 | 906.63489 | 906.63486 | 6.2 ± 3.3 | 24.6 ± 5.6 |
|  | 62 | — | 908.65023 | 908.65095 | 908.65022 | 908.65051 | — | 14.5 ± 4.4 |
|  | 63 | 910.66627 | 910.66639 | 910.66605 | 910.66601 | 910.66616 | 6.7 ± 3.4 | 22.2 ± 5.5 |
|  | 64 | — | 936.68227 | — | — | 936.68181 | — | 8.2 ± 5.3 |
|  | 65 | — | 956.65043 | — | — | 956.65051 | — | 6.7 ± 3.3 |
| Phosphatidylethanolamines (PEs) | 1 | 476.25392 | 476.25387 | 476.25338 | 476.25372 | 476.25378 | 5.0 ± 2.1 | 23.6 ± 5.6 |
|  | 2 | 490.23326 | 490.23327 | 490.23309 | 490.23304 | 490.23305 | 5.1 ± 2.2 | 10.2 ± 4.2 |
|  | 3 | — | 492.24870 | — | 492.24864 | 492.24870 | — | 8.7 ± 4.0 |
|  | 4 | 514.23336 | 514.23314 | 514.23292 | 514.23296 | 514.23305 | 5.2 ± 2.3 | 14.4 ± 4.5 |
|  | 5 | 516.24887 | 516.24847 | 516.24846 | 516.24850 | 516.24870 | 5.5 ± 2.4 | 11.6 ± 4.4 |
|  | 6 | 518.26456 | 518.26421 | 518.26449 | 518.26420 | 518.26435 | 5.3 ± 2.3 | 8.4 ± 4.2 |
|  | 7 | 504.28536 | 504.28529 | 504.28511 | 504.28509 | 504.28508 | 8.5 ± 4.3 | 25.2 ± 5.7 |
|  | 8 | 520.28034 | 520.28006 | 520.28042 | 520.2803 | 520.28000 | 5.3 ± 2.2 | 15.4 ± 4.5 |
|  | 9 | — | 540.24891 | — | 540.24865 | 540.24870 | — | 23.6 ± 5.3 |
|  | 10 | — | 542.26438 | 542.26443 | 542.26435 | 542.26435 | — | 33.4 ± 7.2 |
|  | 11 | 544.27983 | 544.28009 | 544.28046 | 544.28016 | 544.28000 | 5.0 ± 2.1 | 8.5 ± 4.3 |
|  | 12 | 546.29528 | 546.29566 | 546.29545 | 546.29560 | 546.29565 | 6.5 ± 3.4 | 26.2 ± 5.4 |
|  | 13 | 510.35532 | 510.35562 | 510.35540 | 510.35541 | 510.35542 | 5.0 ± 2.2 | 10.5 ± 4.3 |
|  |  | — | 548.31180 | 548.31144 | 548.31163 | 548.31130 | — | 9.5 ± 4.1 |
|  | 14 | 564.24855 | 564.24874 | 564.24876 | 564.24878 | 564.24870 | 6.8 ± 3.4 | 11.4 ± 4.3 |
|  | 15 | 568.28031 | 568.27959 | 568.28016 | 568.28013 | 568.28000 | 5.6 ± 2.6 | 14.4 ± 4.2 |
|  | 16 | 572.31156 | 572.31115 | 572.31110 | 572.31131 | 572.31130 | 7.3 ± 3.9 | 17.5 ± 5.1 |
|  | 17 | 574.32714 | 574.32675 | 574.32685 | 574.32687 | 574.32695 | 6.3 ± 3.4 | 21.9 ± 5.3 |
|  | 18 | — | 538.38622 | — | — | 538.38672 | — | 9.9 ± 4.4 |
|  |  | — | 560.36859 | 560.36855 | 560.36857 | 560.36866 | — | 24.7 ± 5.5 |
|  | 19 | 602.35847 | 602.35803 | 602.35824 | 602.38532 | 602.35825 | 6.7 ± 3.3 | 31.2 ± 5.9 |
|  | 20 | — | 644.36862 | 644.36895 | 644.36883 | 644.36881 | — | 9.6 ± 4.3 |
|  | 21 | 646.38471 | 646.38438 | 646.38473 | 646.38470 | 646.38446 | 8.2 ± 4.4 | 26.4 ± 5.4 |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

|  |  |  |  |  |  |  |  |  |
|---|---|---|---|---|---|---|---|---|
|  | 22 | 756.49357 | 756.49369 | 756.49403 | 756.49403 | 756.49401 | 5.4 ± 2.3 | 10.2 ± 4.6 |
|  | 23 | 740.49934 | 740.49921 | 740.49931 | 740.49889 | 740.49910 | 76.0 ± 10.1 | 233.7 ± 16.5 |
|  | 24 | — | 742.51414 | 742.51473 | 742.51482 | 742.51475 | 11.0 ± 4.6 | 24.3 ± 6.5 |
|  | 25 | 750.44725 | 750.44734 | 750.44706 | 750.44698 | 750.44706 | 8.9 ± 5.0 | 36.2 ± 6.9 |
|  | 26 | 758.51025 | 758.51000 | 758.50997 | 758.50987 | 758.50966 | 6.1 ± 3.1 | 17.1 ± 5.3 |
|  | 27 | 764.49935 | 764.49904 | 764.49920 | 764.49929 | 764.49910 | 12.4 ± 4.8 | 21.6 ± 5.6 |
|  | 28 | 780.49434 | 780.49412 | 780.49438 | 780.49414 | 780.49401 | 6.9 ± 3.4 | 13.8 ± 5.7 |
|  | 29 | — | 782.50982 | — | 782.50983 | 782.50966 | — | 9.6 ± 4.5 |
|  | 30 | 768.53035 | 768.53053 | 768.53064 | 768.53057 | 768.53040 | 5.4 ± 2.5 | 15.3 ± 5.0 |
|  | 31 | 784.52487 | 784.52570 | 784.52509 | 784.52544 | 784.52531 | 6.3 ± 2.8 | 14.1 ± 4.6 |
|  | 32 | 770.54633 | 770.54624 | 770.54604 | 770.54620 | 770.54605 | 9.6 ± 4.4 | 62.3 ± 8.4 |
|  | 33 | 748.58529 | 748.58529 | 748.58494 | 748.58528 | 748.58508 | 14.1 ± 4.6 | 31.0 ± 6.5 |
|  | 34 | 786.48345 | 786.48354 | 786.48341 | 786.48361 | 786.48345 | 10.5 ± 4.5 | 24.9 ± 5.4 |
|  | 35 | 802.47873 | 802.47840 | 802.47816 | 802.47839 | 802.47836 | 5.0 ± 2.3 | 8.7 ± 4.3 |
|  | 36 | 788.49860 | 788.49835 | 788.49898 | 788.49917 | 788.49910 | 9.7 ± 4.6 | 21.6 ± 5.2 |
|  | 37 | 804.49397 | 804.49421 | 804.49407 | 804.49406 | 804.49401 | 8.4 ± 4.2 | 14.6 ± 4.7 |
|  | 38 | 790.51451 | 790.51488 | 790.51460 | 790.51479 | 790.51475 | 10.2 ± 4.3 | 23.5 ± 5.6 |
|  | 39 | 806.50956 | 806.50991 | 806.50965 | 806.50983 | 806.50966 | 8.6 ± 4.3 | 48.3 ± 7.7 |
|  | 40 | — | 792.53052 | — | — | 792.53040 | — | 6.3 ± 3.2 |
|  | 41 | — | 810.54083 | — | — | 810.54096 | — | 5.1 ± 2.6 |
|  | 42 | 774.60072 | 774.60067 | 774.60074 | 774.60072 | 774.60073 | 23.1 ± 5.5 | 60.0 ± 8.3 |
|  |  | 812.55688 | 812.55673 | 812.55651 | 812.55661 | 812.55651 | 6.9 ± 3.5 | 17.3 ± 5.3 |
|  | 43 | 812.49973 | 812.49979 | 812.49940 | 812.49967 | 812.49910 | 15.9 ± 4.8 | 33.2 ± 6.7 |
|  | 44 | — | 828.49435 | 828.49409 | 828.49425 | 828.49401 | — | 23.2 ± 5.6 |
|  | 45 | 814.51423 | 814.51441 | 814.51507 | 814.51515 | 814.51475 | 7.4 ± 3.5 | 14.2 ± 5.0 |
|  | 46 | 830.50921 | 830.50977 | 830.50983 | 830.50988 | 830.50966 | 5.4 ± 2.3 | 15.3 ± 4.8 |
|  | 47 | 816.53073 | 816.53009 | 816.52979 | 816.53026 | 816.53040 | 6.8 ± 3.5 | 17.1 ± 5.2 |
|  | 48 | — | 832.52507 | — | — | 832.52531 | — | 5.6 ± 2.4 |
|  | 49 | 818.54653 | 818.54557 | 818.54617 | 818.54630 | 818.54605 | 6.7 ± 3.5 | 17.8 ± 5.3 |
|  | 50 | 834.54078 | 834.54025 | 834.54090 | 834.54079 | 834.54096 | 7.8 ± 3.6 | 21.6 ± 5.5 |
|  | 51 | 802.63127 | 802.63128 | 802.63221 | 802.63239 | 802.63203 | 11.7 ± 4.5 | 23.8 ± 5.6 |
|  | 52 | — | 850.47870 | — | 850.47867 | 850.47836 | — | 7.5 ± 3.5 |
|  | 53 | 852.49450 | 852.49475 | 852.49415 | 852.49418 | 852.49401 | 18.5 ± 5.0 | 96.6 ± 14.1 |
|  | 54 | — | 854.51013 | 854.51001 | 854.51033 | 854.50966 | — | 36.4 ± 6.8 |
|  | 55 | — | 856.52505 | — | 856.25252 | 856.52531 | — | 9.1 ± 4.5 |
|  | 56 | — | 858.54080 | — | — | 858.54096 | — | 5.3 ± 2.2 |
|  | 57 | — | 824.61619 | 824.61635 | 824.61643 | 824.61638 | — | 10.5 ± 4.2 |
|  | 58 | 810.63736 | 810.63704 | 810.63724 | 817.63736 | 810.63712 | 6.8 ± 3.6 | 20.3 ± 5.2 |
|  | 59 | 864.58803 | 864.58775 | 864.58764 | 864.58787 | 864.58791 | 8.8 ± 3.6 | 18.5 ± 5.1 |
|  | 60 | 850.60840 | 850.60853 | 850.60862 | 850.60878 | 850.60865 | 5.2 ± 2.1 | 12.7 ± 4.5 |
|  | 61 | 845.67442 | 845.67436 | 845.67460 | 845.67429 | 845.67423 | 5.0 ± 2.1 | 11.2 ± 4.3 |
|  | 62 | — | 852.62425 | — | 852.62424 | 852.62430 | — | 14.1 ± 5.0 |
|  | 63 | 868.61952 | 868.61934 | 868.61941 | 868.61936 | 868.61921 | 6.2 ± 3.1 | 13.4 ± 4.8 |
|  | 64 | 870.63493 | 870.63471 | 870.63470 | 870.63484 | 870.63486 | 5.9 ± 2.8 | 13.3 ± 4.7 |
|  | 65 | — | 878.50911 | 878.50958 | 878.50963 | 878.50966 | — | 8.9 ± 3.7 |
|  | 66 | — | 880.52546 | — | — | 880.52531 | — | 5.3 ± 2.2 |
|  | 67 | 886.57251 | 886.57238 | 886.57246 | 886.57210 | 886.57226 | 5.0 ± 2.0 | 17.8 ± 5.3 |
|  | 68 | 888.58817 | 888.58780 | 888.58787 | 888.58776 | 888.58791 | 5.0 ± 2.0 | 15.0 ± 4.8 |
|  | 69 | — | 896.65061 | — | 896.65088 | 896.65051 | — | 7.4 ± 3.4 |
| Phosphatidic | 1 | 475.22224 | 475.22231 | 475.22218 | 475.22237 | 475.22215 | 5.0 ± 2.1 | 12.3 ± 4.3 |
| acids | 2 | 477.23741 | 477.23744 | 477.23784 | 477.23792 | 477.23780 | 5.1 ± 2.2 | 7.6 ± 3.4 |
| (PAs) | 3 | 497.20681 | 497.20674 | 497.20651 | 497.20632 | 497.20650 | 15.7 ± 5.1 | 30.7 ± 6.3 |
|  | 4 | 499.22247 | 499.22225 | 499.22209 | 499.22218 | 499.22215 | 5.0 ± 2.2 | 21.2 ± 5.3 |
|  | 5 | 501.23790 | 501.23795 | 501.23770 | 501.23734 | 501.23780 | 5.1 ± 2.3 | 18.2 ± 6.0 |
|  | 6 | 487.27973 | 487.27974 | 487.27967 | 487.27951 | 487.27951 | 11.4 ± 4.5 | 20.8 ± 5.2 |
|  |  | 503.25347 | 503.25357 | 503.25374 | 503.25332 | 503.25345 | 5.2 ± 2.1 | 17.7 ± 5.7 |
|  | 7 | 525.23791 | 525.23767 | 525.23770 | 525.23756 | 525.23780 | 7.8 ± 3.5 | 22.4 ± 5.6 |
|  | 8 | 531.28481 | 531.28493 | 531.28467 | 531.28463 | 531.28475 | 8.0 ± 3.4 | 15.2 ± 4.9 |
|  | 9 | 533.30061 | 533.30057 | 533.30024 | 533.30043 | 533.30040 | 5.2 ± 2.3 | 19.7 ± 4.3 |
|  | 10 | 679.37382 | 679.37367 | 679.37359 | 679.37374 | 679.37356 | 5.3 ± 3.4 | 20.4 ± 4.2 |
|  | 11 | 681.38945 | 681.38952 | 681.38910 | 681.38956 | 681.38921 | 5.0 ± 2.5 | 16.6 ± 3.4 |
|  | 12 | 683.40504 | 683.40493 | 683.40481 | 683.40497 | 683.40486 | 5.2 ± 2.4 | 9.5 ± 3.1 |
|  | 13 | 685.42092 | 685.42113 | 685.42053 | 685.42041 | 685.42051 | 5.2 ± 2.4 | 16.4 ± 4.2 |
|  | 14 | 687.43577 | 687.43633 | 687.43626 | 687.43626 | 687.43616 | 5.3 ± 2.5 | 14.1 ± 3.3 |
|  | 15 | 643.50361 | 643.50371 | 643.50333 | 643.50384 | 643.50370 | 5.2 ± 2.4 | 13.9 ± 3.6 |
|  | 16 | — | 709.42087 | 709.42030 | 709.42052 | 709.42051 | 5.3 ± 2.3 | 23.4 ± 5.2 |
|  | 17 | 711.43679 | 711.43686 | 711.43644 | 711.43664 | 711.43616 | 6.1 ± 2.6 | 28.0 ± 5.3 |
|  | 18 | 697.4780 | 697.47829 | 697.47786 | 697.47787 | 697.47788 | 16.8 ± 3.6 | 56.3 ± 7.8 |
|  |  | 713.45177 | 713.45196 | 713.45179 | 713.45180 | 713.45181 | 93.9 ± 8.9 | 463.8 ± 18.7 |
|  | 19 | — | 699.47295 | — | 699.47276 | 699.47255 | — | 6.5 ± 3.1 |
|  | 20 | 701.45151 | 701.45132 | 701.45185 | 701.45154 | 701.45166 | 5.3 ± 2.5 | 16.5 ± 4.7 |
|  | 21 | 733.42063 | 733.42038 | 733.42047 | 733.42047 | 733.42051 | 5.2 ± 2.1 | 14.8 ± 4.2 |
|  | 22 | — | 735.43625 | 735.43623 | 735.43638 | 735.43616 | — | 8.0 ± 3.6 |
|  | 23 | 737.45231 | 737.45211 | 737.45122 | 737.45139 | 737.45181 | 6.1 ± 2.8 | 23.2 ± 4.7 |
|  | 24 | 723.49342 | 723.49388 | 723.49373 | 723.49385 | 723.49353 | 14.8 ± 4.4 | 65.0 ± 7.8 |
|  |  | 739.46750 | 739.46738 | 739.46722 | 739.46742 | 739.46746 | 108.8 ± 9.5 | 542.8 ± 20.1 |
|  | 25 | — | 741.48304 | 741.48326 | 741.48345 | 741.48311 | — | 9.3 ± 4.1 |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

|  |  |  |  |  |  |  |  |  |
|---|---|---|---|---|---|---|---|---|
|  | 26 | 727.46771 | 727.46777 | 727.46756 | 727.46785 | 727.46731 | 7.8 ± 3.5 | 11.4 ± 4.3 |
|  | 27 | — | 759.43543 | — | 759.43629 | 759.43616 | — | 7.1 ± 3.2 |
|  | 28 | 761.45147 | 761.45158 | 761.45174 | 761.45189 | 761.45181 | 24.2 ± 6.1 | 91.0 ± 8.7 |
|  | 29 | 725.51189 | 725.51175 | 725.51177 | 725.51147 | 725.51158 | 6.7 ± 3.6 | 25.4 ± 5.2 |
|  |  | 763.46737 | 763.46801 | 763.46702 | 763.46733 | 763.46746 | 9.4 ± 3.8 | 38.5 ± 5.8 |
|  | 30 | — | 749.50874 | — | — | 749.50918 | — | 6.1 ± 2.5 |
|  |  | 765.48387 | 765.48304 | 765.48338 | 765.48346 | 765.48311 | 10.6 ± 4.5 | 29.1 ± 8.2 |
|  | 31 | 751.52478 | 751.52440 | 751.52497 | 751.52476 | 751.52483 | 5.5 ± 2.4 | 15.2 ± 4.1 |
|  |  | 767.49893 | 767.49919 | 767.49898 | 767.49897 | 767.49876 | 33.4 ± 5.7 | 138.7 ± 10.2 |
|  | 32 | 771.53026 | 771.53014 | 771.53009 | 771.53006 | 771.53006 | 5.1 ± 2.4 | 10.3 ± 5.3 |
|  | 33 | 785.45156 | 785.45107 | 785.45189 | 785.45182 | 785.45181 | 14.0 ± 4.1 | 33.9 ± 5.8 |
|  | 34 | — | 787.46788 | 787.46738 | 787.46753 | 787.46746 | — | 22.4 ± 5.2 |
|  | 35 | — | 773.50955 | — | 773.50926 | 773.50918 | — | 8.6 ± 3.8 |
|  |  | 789.48298 | 789.48282 | 789.48328 | 789.48335 | 789.48311 | 12.4 ± 3.6 | 56.6 ± 7.9 |
|  | 36 | 777.54072 | 777.54061 | 777.54067 | 777.54036 | 777.54048 | 5.7 ± 3.0 | 16.6 ± 5.3 |
|  | 37 | — | 809.45195 | — | 809.45167 | 809.45181 | — | 7.9 ± 4.5 |
| Phosphoglycerols | 1 | 547.24337 | 547.24304 | 547.24339 | 547.24346 | 547.24328 | 5.1 ± 2.0 | 11.7 ± 5.0 |
| (PGs) | 2 | 573.25907 | 573.25897 | 573.25893 | 573.25897 | 573.25893 | 5.0 ± 2.0 | 9.9 ± 4.6 |
|  | 3 | 559.30086 | 559.30057 | 559.30077 | 559.30066 | 559.30064 | 14.0 ± 5.3 | 71.9 ± 9.9 |
|  | 4 | 599.27468 | 599.27421 | 599.27451 | 599.27468 | 599.27458 | 7.1 ± 3.4 | 14.2 ± 5.6 |
|  | 5 | 603.30597 | 603.30578 | 603.30555 | 603.30566 | 603.30588 | 14.0 ± 5.7 | 31.2 ± 7.0 |
|  | 6 | — | 745.47747 | 745.47808 | 745.47811 | 745.47803 | — | 11.2 ± 4.8 |
|  | 7 | — | 743.48550 | — | 743.48589 | 743.48576 | — | 7.6 ± 3.5 |
|  | 8 | 783.45743 | 783.45732 | 783.45738 | 783.45734 | 783.45729 | 13.1 ± 5.0 | 36.9 ± 7.7 |
|  | 9 | 793.49947 | 793.49954 | 793.49909 | 793.49914 | 793.49901 | 12.1 ± 4.8 | 29.8 ± 7.2 |
|  | 10 | 817.53567 | 817.53534 | 817.53538 | 817.53570 | 817.53554 | 6.8 ± 3.2 | 19.5 ± 6.5 |
|  | 11 | — | 801.56403 | 801.56403 | 801.56415 | 801.56401 | — | 31.0 ± 7.5 |
|  | 12 | 825.56178 | 825.56146 | 825.56130 | 825.65160 | 825.56161 | 10.8 ± 4.3 | 40.0 ± 11.2 |
|  | 13 | — | 887.51967 | — | — | 887.51989 | — | 5.1 ± 2.6 |
| Phosphatidylserine | 1 | 576.30650 | 576.30642 | 576.30634 | 576.30643 | 576.30621 | 6.3 ± 3.1 | 17.7 ± 5.1 |
| (PS) | 2 | 592.30146 | 592.30134 | 592.30114 | 592.30117 | 592.30113 | 5.3 ± 2.6 | 15.3 ± 5.4 |
|  | 3 | 612.26999 | 612.26968 | 612.26980 | 612.26991 | 612.26983 | 7.9 ± 3.6 | 33.5 ± 9.6 |
|  | 4 | — | 780.47812 | 780.47845 | 780.47888 | 780.47861 | — | 14.8 ± 4.6 |
|  | 5 | — | 808.50976 | 808.50943 | 808.50986 | 808.50991 | — | 12.0 ± 4.8 |
|  | 6 | 828.51508 | 828.51537 | 828.515 | 828.515 | 828.51514 | 38.0 ± 7.9 | 107.8 ± 9.4 |
|  | 7 | — | 824.44713 | — | 824.44735 | 824.44731 | — | 10.5 ± 5.0 |
|  | 8 | — | 826.46296 | 826.46253 | 826.46242 | 826.46296 | — | 19.8 ± 6.1 |
|  | 9 | 846.46837 | 846.46807 | 846.46819 | 846.46814 | 846.46819 | 35.7 ± 7.5 | 165.6 ± 15.0 |
|  | 10 | 830.47361 | 830.47354 | 830.47338 | 830.47321 | 830.47328 | 9.6 ± 4.1 | 49.2 ± 11.9 |
|  | 11 | — | 834.52516 | — | 834.52561 | 834.52556 | — | 8.9 ± 4.6 |
|  | 12 | — | 854.49493 | — | 854.49424 | 854.49426 | — | 7.3 ± 3.3 |
|  | 13 | — | 856.50985 | — | — | 856.50991 | — | 5.3 ± 2.5 |
|  | 14 | — | 858.52587 | 858.52585 | 858.52577 | 858.52556 | — | 18.0 ± 5.9 |
|  | 15 | — | 860.54139 | — | 860.54120 | 860.54121 | — | 8.9 ± 4.5 |
|  | 16 | 846.62196 | 846.62150 | 846.621 | 846.621 | 846.62186 | 34.2 ± 7.1 | 54.7 ± 12.4 |
|  | 17 | — | 830.62688 | — | — | 830.62695 | — | 6.2 ± 3.1 |
|  | 18 | 848.63754 | 848.63714 | 848.63742 | 848.63764 | 848.63751 | 9.6 ± 4.3 | 49.4 ± 15.3 |
|  | 19 | — | 884.54178 | 884.54134 | 884.54120 | 884.54121 | — | 9.6 ± 4.6 |
| Phosphatidylinositols | 1 | — | 919.47341 | — | 919.47332 | 919.47334 | — | 8.9 ± 3.9 |
| (PIs) | 2 | 925.52050 | 925.52053 | 925.52027 | 925.52038 | 925.52029 | 6.3 ± 3.0 | 26.7 ± 6.1 |
|  | 3 | 945.48835 | 945.48861 | 945.48894 | 945.48875 | 945.48899 | 5.1 ± 2.0 | 24.6 ± 5.7 |
|  | 4 | 915.59563 | 915.59576 | 915.59560 | 915.59565 | 915.59571 | 6.7 ± 3.2 | 24.8 ± 5.8 |
|  | 5 | — | 931.53324 | 931.53339 | 931.53319 | 931.53311 | — | 16.8 ± 5.1 |
|  | 6 | — | 975.53674 | — | 975.53592 | 975.53594 | — | 9.6 ± 4.2 |
|  | 7 | — | 945.58259 | — | — | 945.58274 | — | 5.1 ± 2.0 |
|  | 8 | — | 961.57721 | — | — | 961.57765 | — | 6.6 ± 3.3 |
| Glycerophosphoinositol bisphosphates (PIP2s) | 1 | — | 1035.43662 | 1035.43735 | 1035.43725 | 1035.43730 | — | 18.7 ± 6.3 |
| Glycerophosphoglycero- | 1 | 947.50162 | 947.50279 | 947.50243 | 947.50255 | 947.50212 | 72.1 ± 9.8 | 146.3 ± 14.9 |
| phosphoglycerols (cardiolipins) |  | 963.47655 | 963.47618 | 963.47637 | 963.47607 | 963.47605 | 335.6 ± 16.4 | 1486.4 ± 38.8 |
| Cyclic | 1 | 415.22203 | 415.22193 | 415.22224 | 415.22208 | 415.22200 | 7.2 ± 3.3 | 15.3 ± 5.6 |
| phosphatidic |  | 431.19616 | 431.19611 | 431.19573 | 431.19589 | 431.19593 | 5.6 ± 2.3 | 18.9 ± 6.5 |
| acids | 2 | 455.19588 | 455.19572 | 455.19594 | 455.19563 | 455.19593 | 8.6 ± 5.5 | 36.0 ± 8.4 |
| (cPAs) | 3 | 441.23724 | 441.23769 | 441.23761 | 441.23778 | 441.23765 | 5.0 ± 2.1 | 9.8 ± 4.8 |
|  |  | 457.21173 | 457.21177 | 457.21152 | 457.21179 | 457.2158 | 7.8 ± 3.5 | 31.5 ± 8.0 |
|  | 4 | 443.25320 | 443.25334 | 443.25360 | 443.25344 | 443.25330 | 5.3 ± 2.3 | 11.2 ± 5.0 |
|  |  | 459.22741 | 459.22743 | 459.22761 | 459.22738 | 459.22723 | 14.1 ± 5.3 | 31.3 ± 8.0 |
| CDP- | 1 | — | 980.53779 | — | 980.53711 | 980.53722 | — | 7.8 ± 3.5 |
| Glycerols |  | — | 1018.49325 | — | 1018.49318 | 1018.49310 | — | 10.3 ± 5.9 |
|  | 2 | — | 982.55256 | 982.55295 | 982.55284 | 982.55287 | — | 12.0 ± 5.0 |
|  |  | — | 1020.50867 | — | — | 1020.50875 | — | 5.0 ± 2.0 |
|  | 3 | — | 1010.58474 | — | 1010.58419 | 1010.58417 | — | 7.8 ± 3.5 |
|  | 4 | — | 1058.58469 | — | — | 1058.58417 | — | 5.4 ± 2.5 |
|  |  | — | 1096.54020 | 1096.54005 | 1096.54030 | 1096.54005 | — | 10.9 ± 4.7 |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

| | | | | | | | | |
|---|---|---|---|---|---|---|---|---|
| Glycerophosphate | 1 | — | 467.25331 | — | 467.25328 | 467.25330 | — | 6.3 ± 3.0 |
| | | — | 483.22728 | 483.22732 | 483.22731 | 483.22723 | — | 29.2 ± 7.9 |
| Sphingolipids | 1 | 464.35027 | 464.35032 | 464.35002 | 464.35017 | 464.35005 | 5.1 ± 2.2 | 8.7 ± 4.1 |
| Ceramides | 2 | 602.49122 | 602.49131 | 602.49080 | 602.49086 | 602.49090 | 6.7 ± 3.1 | 21.2 ± 6.2 |
| (Cers) | 3 | 604.50681 | 604.50685 | 604.50625 | 604.50674 | 604.50655 | 5.3 ± 2.0 | 10.7 ± 4.3 |
| | 4 | — | 684.47275 | — | 684.47268 | 684.47288 | — | 9.5 ± 4.2 |
| | 5 | 632.53823 | 632.53811 | 632.53764 | 632.53784 | 632.53785 | 7.5 ± 3.6 | 27.3 ± 7.5 |
| | 6 | 686.58460 | 686.58456 | 686.58453 | 686.58482 | 686.58480 | 7.4 ± 3.5 | 16.4 ± 5.4 |
| | 7 | — | 766.55160 | 766.55116 | 766.55102 | 766.55113 | — | 13.0 ± 5.2 |
| | 8 | — | 688.60044 | — | 688.60040 | 688.60045 | — | 7.3 ± 3.1 |
| Sphingomyelins | 1 | — | 703.57475 | 703.57490 | 703.57487 | 703.57485 | — | 8.7 ± 4.2 |
| (SMs) | | 725.55694 | 725.55673 | 725.55684 | 725.55677 | 725.55680 | 6.2 ± 2.7 | 24.5 ± 6.2 |
| | 2 | 753.58822 | 753.58804 | 753.58830 | 753.58840 | 753.58810 | 12.3 ± 4.1 | 22.9 ± 5.7 |
| | | 769.56187 | 769.56224 | 769.56217 | 769.56203 | 769.56217 | 86.2 ± 9.9 | 138.3 ± 13.6 |
| | 3 | 797.59355 | 797.59361 | 797.59388 | 797.59353 | 797.59333 | 5.5 ± 2.4 | 9.1 ± 5.1 |
| | 4 | — | 787.66858 | — | — | 787.66875 | — | 7.3 ± 4.2 |
| | | 825.62481 | 825.62452 | 825.62483 | 825.62443 | 825.62463 | 20.8 ± 5.3 | 40.0 ± 7.5 |
| | 5 | — | 813.68484 | — | 813.68451 | 813.68440 | — | 12.2 ± 5.0 |
| | | 851.64021 | 851.64041 | 851.64026 | 851.64033 | 851.64028 | 7.6 ± 3.6 | 12.2 ± 4.1 |
| | 6 | — | 815.70041 | 815.70019 | 815.70013 | 815.70005 | — | 8.0 ± 3.4 |
| | | 837.68204 | 837.68232 | 837.68213 | 837.68204 | 837.68200 | 12.2 ± 4.3 | 28.4 ± 5.1 |
| | | 853.65568 | 853.65645 | 853.65584 | 853.65590 | 853.65593 | 6.4 ± 3.3 | 13.7 ± 5.2 |
| Glycosphingolipids | 1 | 500.29815 | 500.29867 | 500.29862 | 500.29856 | 500.29841 | 21.2 ± 5.2 | 53.7 ± 7.4 |
| | 2 | — | 828.54447 | 828.54430 | 828.54435 | 828.54436 | — | 16.2 ± 5.2 |
| | 3 | 766.55930 | 766.55942 | 766.55929 | 766.55958 | 766.55938 | 6.7 ± 3.4 | 14.3 ± 4.5 |
| | 4 | — | 856.57577 | — | — | 856.57566 | — | 7.5 ± 3.9 |
| | 5 | — | 852.58713 | — | 852.58738 | 852.58652 | — | 10.1 ± 5.5 |
| | 6 | 794.59084 | 794.59095 | 794.59072 | 794.59081 | 794.59068 | 8.5 ± 4.5 | 14.2 ± 6.3 |
| | 7 | 820.60671 | 820.60674 | 820.60645 | 820.60653 | 820.60633 | 70.3 ± 11.2 | 159.0 ± 16.3 |
| | 8 | — | 836.60133 | — | — | 836.60124 | — | 5.2 ± 2.5 |
| | 9 | 822.62156 | 822.62190 | 822.62172 | 822.62174 | 822.62198 | 10.6 ± 6.1 | 17.7 ± 8.3 |
| | 10 | — | 928.61212 | 928.62127 | 928.62116 | 928.61220 | — | 18.6 ± 9.4 |
| | 11 | 832.66332 | 832.66350 | 832.66377 | 832.66385 | 832.66369 | 5.9 ± 2.8 | 14.0 ± 6.2 |
| | | 848.63842 | 848.63831 | 848.63782 | 848.63774 | 848.63763 | 9.5 ± 5.9 | 49.8 ± 13.5 |
| | 12 | — | 892.67158 | 892.67173 | 892.67185 | 892.67197 | — | 8.2 ± 5.3 |
| | 13 | 850.65337 | 850.65367 | 850.65323 | 850.65338 | 850.65328 | 5.2 ± 2.1 | 19.2 ± 6.7 |
| | 14 | — | 852.66911 | — | — | 852.66893 | — | 7.3 ± 4.3 |
| | 15 | 876.66867 | 876.66849 | 876.66873 | 876.66889 | 876.66893 | 26.0 ± 13.1 | 60.9 ± 16.1 |
| | 16 | 878.68478 | 878.68466 | 878.68449 | 878.68463 | 878.68458 | 5.4 ± 2.4 | 15.5 ± 5.8 |
| | 17 | — | 1010.69083 | — | — | 1010.69045 | — | 6.5 ± 2.8 |
| | 18 | — | 1012.70616 | — | — | 1012.70610 | — | 5.6 ± 2.3 |
| Sphingoid bases | 1 | — | 264.19316 | — | — | 264.19340 | — | 6.5 ± 3.1 |
| Ceramide | 1 | — | 852.50034 | 852.49982 | 852.49998 | 852.49989 | — | 13.2 ± 4.3 |
| phosphoinositols | 2 | 838.61641 | 838.61683 | 838.61671 | 838.61680 | 838.61678 | 14.0 ± 5.1 | 52.6 ± 9.1 |
| (PI- | 3 | 864.63248 | 864.63279 | 864.63277 | 864.63219 | 864.63243 | 63.1 ± 13.2 | 186.1 ± 20.1 |
| Cers) | 4 | 866.64825 | 866.64805 | 866.64823 | 866.64808 | 866.64808 | 77.1 ± 14.3 | 256.8 ± 23.4 |
| | 5 | — | 904.62434 | — | 904.62497 | 904.62494 | — | 8.9 ± 4.4 |
| | 6 | 894.679 | 894.67917 | 894.67952 | 894.67927 | 894.67938 | 5.6 ± 2.4 | 11.6 ± 4.2 |
| | 7 | — | 1154.70941 | — | 1154.70940 | 1154.70921 | — | 8.4 ± 4.2 |
| Neutral | 1 | 369.24012 | 369.24037 | 369.24014 | — | 369.24017 | 5.4 ± 2.3 | 10.3 ± 5.1 |
| Lipids | 2 | — | 379.28181 | — | — | 379.28188 | — | 5.1 ± 2.0 |
| Glycerolipids | | — | 395.25575 | — | — | 395.25582 | — | 5.4 ± 2.3 |
| Monoacylglycerols | 3 | — | 397.27164 | — | — | 397.27147 | — | 5.5 ± 2.0 |
| (MAGs) | 4 | — | 417.24037 | — | — | 417.24017 | — | 5.7 ± 2.5 |
| | 5 | 419.25577 | 419.25581 | 419.25546 | 419.25564 | 419.25582 | 5.4 ± 2.2 | 17.3 ± 5.8 |
| | 6 | — | 425.26612 | — | — | 425.26623 | — | 5.2 ± 2.3 |
| | 7 | 445.27173 | 445.27173 | 445.27126 | 445.27130 | 445.27147 | 5.3 ± 2.0 | 8.0 ± 3.2 |
| Diacylglycerols | 1 | 551.50347 | 551.50365 | 551.50360 | 551.50349 | 551.50339 | 60.8 ± 13.1 | 287.8 ± 16.8 |
| (DAGs) | | — | 573.48551 | 573.48547 | 573.48539 | 573.48533 | — | 9.9 ± 4.0 |
| | | — | 589.45915 | — | 589.45918 | 589.45927 | — | 7.9 ± 3.2 |
| | 2 | 607.47016 | 607.47032 | 607.46982 | 607.46976 | 607.46983 | 6.7 ± 2.7 | 16.6 ± 5.3 |
| | 3 | 561.52389 | 561.52376 | 561.52370 | 561.52410 | 561.52412 | 5.3 ± 2.4 | 7.6 ± 3.1 |
| | 4 | — | 631.47028 | — | — | 631.46983 | — | 5.2 ± 2.0 |
| | 5 | 633.48582 | 633.48581 | 633.48549 | 633.48538 | 633.48548 | 6.4 ± 3.1 | 11.5 ± 5.2 |
| | 6 | 619.50647 | 619.50655 | 619.50631 | 619.50645 | 619.50622 | 5.2 ± 2.2 | 7.9 ± 3.2 |
| | 7 | — | 635.50160 | — | 635.50131 | 635.50113 | — | 7.6 ± 3.1 |
| | 8 | 655.46930 | 655.47014 | 655.46992 | 655.46986 | 655.46983 | 6.8 ± 3.2 | 16.0 ± 5.1 |
| | 9 | 603.53483 | 603.53505 | 603.53425 | 603.53452 | 603.53469 | 27.2 ± 8.2 | 54.1 ± 13.2 |
| | 10 | — | 657.48501 | — | — | 657.48548 | — | 5.3 ± 2.4 |
| | 11 | 589.55568 | 589.55554 | 589.55533 | 589.55549 | 589.55542 | 5.1 ± 2.0 | 7.9 ± 3.3 |
| | | — | 611.53758 | 611.53720 | 611.53737 | 611.53737 | — | 7.4 ± 3.1 |
| | 12 | 659.50094 | 659.50127 | 659.501 | 659.501 | 659.50113 | 5.4 ± 2.3 | 10.5 ± 4.2 |
| | 13 | 661.51710 | 661.51722 | 661.51665 | 661.51648 | 661.51678 | 5.7 ± 2.4 | 9.4 ± 3.7 |
| | 14 | — | 621.48715 | 621.48768 | 621.48770 | 621.48774 | — | 7.9 ± 3.2 |
| | 15 | — | 679.47020 | — | — | 679.46983 | — | 6.4 ± 2.5 |
| | 16 | — | 681.48559 | — | — | 681.48548 | — | 6.0 ± 2.4 |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

| Class | No. | | | | | | | |
|---|---|---|---|---|---|---|---|---|
| | 17 | 683.50168 | 683.50180 | 683.50112 | 683.50122 | 683.50113 | 5.0 ± 2.0 | 8.4 ± 3.6 |
| | 18 | 687.53220 | 687.53232 | 687.53233 | 687.53229 | 687.53243 | 6.0 ± 2.6 | 10.3 ± 4.2 |
| | 19 | 689.54863 | 689.54838 | 689.54804 | 689.54821 | 689.54808 | 5.2 ± 2.0 | 8.1 ± 3.5 |
| | 20 | 682.45673 | 682.45663 | 682.45666 | 682.45674 | 682.45677 | 11.5 ± 4.4 | 24.6 ± 6.5 |
| | 21 | — | 699.43846 | 699.43845 | 699.43846 | 699.43853 | — | 9.0 ± 3.6 |
| | 22 | 649.51920 | 649.51967 | 649.51932 | 649.51942 | 649.51904 | 6.7 ± 2.8 | 15.7 ± 5.2 |
| | 23 | — | 635.53977 | — | 635.53957 | 635.53977 | — | 7.3 ± 3.0 |
| | 24 | 651.53446 | 651.53511 | 651.53481 | 651.53509 | 651.53469 | 15.6 ± 5.3 | 52.2 ± 9.0 |
| | 25 | 707.50137 | 707.50059 | 707.50159 | 707.50138 | 707.50113 | 5.3 ± 2.2 | 9.3 ± 4.3 |
| | 26 | 725.45443 | 725.45413 | 725.45407 | 725.45419 | 725.45418 | 7.6 ± 3.1 | 15.4 ± 5.3 |
| Triradylglycerols (TAGs) | 1 | — | 869.66542 | 869.66546 | 869.66533 | 869.66537 | — | 11.2 ± 4.4 |
| | 2 | — | 873.69664 | — | — | 873.69667 | — | 6.7 ± 3.2 |
| | 3 | — | 995.70995 | — | — | 995.70991 | — | 5.8 ± 2.5 |
| | 4 | — | 997.72583 | — | 997.72531 | 997.72556 | — | 7.8 ± 3.2 |
| | 5 | — | 1035.68350 | — | 1035.68378 | 1035.68385 | — | 11.0 ± 4.5 |
| Other Glycerolipids | 1 | 834.62159 | 834.62108 | 834.62174 | 834.62165 | 834.62183 | 15.3 ± 5.3 | 46.4 ± 12.3 |
| Sterol Lipids | 1 | 429.24023 | 429.24054 | 429.24022 | 429.24017 | 429.24017 | 6.1 ± 2.9 | 13.6 ± 4.3 |
| | 2 | 457.27125 | 457.27128 | 457.27159 | 457.27135 | 457.27147 | 8.5 ± 4.4 | 31.5 ± 7.6 |
| | 3 | — | 423.30220 | — | — | 423.30237 | — | 5.7 ± 2.6 |
| | 4 | — | 471.28682 | — | — | 471.28712 | — | 6.4 ± 3.1 |
| | 5 | 409.34418 | 409.34413 | 409.34404 | 409.34418 | 409.34409 | 6.2 ± 3.0 | 15.2 ± 5.6 |
| | | 425.31836 | 425.31823 | 425.31805 | 425.31808 | 425.31802 | 6.0 ± 2.8 | 13.5 ± 5.3 |
| | 6 | 473.32393 | 473.32356 | 473.32378 | 473.32357 | 473.32375 | 5.7 ± 2.5 | 14.7 ± 5.8 |
| | 7 | — | 489.31869 | — | — | 489.31866 | — | 6.0 ± 2.8 |
| | 8 | 485.30306 | 485.30288 | 485.30275 | 485.30296 | 485.30277 | 5.5 ± 2.4 | 12.5 ± 5.0 |
| | 9 | — | 431.32854 | — | 431.32866 | 431.32844 | — | 6.4 ± 3.1 |
| | 10 | 497.33956 | 497.33943 | 497.33920 | 497.33919 | 497.33915 | 6.4 ± 3.0 | 10.6 ± 4.7 |
| | 11 | — | 777.41861 | — | — | 777.41859 | — | 5.4 ± 2.3 |
| | 12 | 827.41889 | 827.41886 | 827.41890 | 827.41898 | — | — | 11.9 ± 4.8 |
| Prenol Lipids | 1 | 445.29251 | 445.29235 | 445.29231 | 445.29241 | 445.29245 | 5.0 ± 2.0 | 7.2 ± 4.4 |
| Fatty acyls Fatty acids (FAs) | 1 | — | 319.20346 | — | — | 319.20339 | — | 5.0 ± 2.3 |
| | 2 | 321.21914 | 321.21911 | 321.21903 | 321.21924 | 321.21904 | 5.4 ± 2.2 | 15.0 ± 6.0 |
| | 3 | 343.20408 | 343.20348 | 343.20335 | 343.20339 | 343.20339 | 6.0 ± 2.7 | 20.2 ± 6.0 |
| | 4 | 367.20339 | 367.20345 | 367.20332 | 367.20339 | 367.20339 | 5.4 ± 2.3 | 10.1 ± 5.2 |
| | 5 | — | 393.29789 | 393.29743 | 393.29776 | 393.29753 | — | 21.6 ± 6.5 |
| | | 409.27132 | 409.27128 | 409.27160 | 409.27133 | 409.27147 | 7.2 ± 3.3 | 23.9 ± 6.3 |
| | 6 | 465.33448 | 465.33428 | 465.33406 | 465.33421 | 465.33407 | 13.2 ± 5.3 | 23.2 ± 6.2 |
| Other compounds | 1 | 322.05479 | 322.05478 | 322.05479 | 322.05464 | 322.05483 | 12.3 ± 5.1 | 28.3 ± 6.6 |
| | 2 | — | 327.03528 | — | — | 327.03526 | — | 6.0 ± 2.6 |
| | 3 | 352.04164 | 352.04158 | 352.04170 | 352.04169 | 352.04174 | 5.2 ± 2.3 | 12.0 ± 6.0 |
| | | 368.01546 | 368.01550 | 368.01581 | 368.01559 | 368.01568 | 5.8 ± 2.5 | 20.1 ± 7.1 |
| | 4 | — | 1146.50914 | — | 1146.50857 | 1146.50865 | — | 8.4 ± 5.4 |
| | | — | 1168.49083 | — | 1168.49027 | 1168.49060 | — | 6.5 ± 2.9 |

| | | Electric field (Average S/N, n = 3) | | Assignment | | |
|---|---|---|---|---|---|---|
| | | Matrix coating | | Ion | | Molecular |
| Class | No. | III | IV | form | Compnd | formula |
| Glycerophospholipids Phosphatidylcholines (PCs) | 1 | 204.0 ± 15.1 | 271.2 ± 16.9 | [M + H]⁺ | PC(O-16:2) | $C_{24}H_{48}NO_6P$ |
| | | 5.5 ± 2.0 | 6.4 ± 3.6 | [M + Na]⁺ | | |
| | | 24.5 ± 5.2 | 37.9 ± 4.3 | [M + K]⁺ | | |
| | 2 | — | — | [M + Na]⁺ | PC(O-16:1) | $C_{24}H_{50}NO_6P$ |
| | | — | 11.4 ± 7.1 | [M + K]⁺ | | |
| | 3 | — | 8.7 ± 5.3 | [M + H]⁺ | PC(16:0) | $C_{24}H_{50}NO_7P$ |
| | | 30.1 ± 8.3 | 41.6 ± 7.5 | [M + K]⁺ | | |
| | 4 | 8.5 ± 6.1 | 10.4 ± 5.9 | [M + Na]⁺ | PC(O-16:0) | $C_{24}H_{52}NO_6P$ |
| | 5 | 24.5 ± 8.1 | 37.9 ± 6.9 | [M + H]⁺ | PC(18:4) | $C_{26}H_{46}NO_7P$ |
| | 6 | — | 12.8 ± 7.8 | [M + H]⁺ | PC(18:3) | $C_{26}H_{48}NO_7P$ |
| | 7 | 91.8 ± 7.9 | 106.9 ± 9.3 | [M + H]⁺ | PC(P-18:1) | $C_{26}H_{52}NO_6P$ |
| | 8 | — | 14.7 ± 3.7 | [M + Na]⁺ | PC(O-18:2) | $C_{26}H_{52}NO_6P$ |
| | | 12.8 ± 4.6 | 18.5 ± 5.8 | [M + K]⁺ | | |
| | | 3.7 ± 2.2 | 10.7 ± 5.2 | [M + H]⁺ | PC(18:1) | $C_{26}H_{52}NO_7P$ |
| | | 11.9 ± 6.4 | 18.8 ± 5.8 | [M + K]⁺ | | |
| | 10 | 18.4 ± 6.3 | 27.7 ± 5.5 | [M + H]⁺ | PC(18:0) | $C_{26}H_{54}NO_7P$ |
| | | 15.8 ± 5.9 | 18.1 ± 4.5 | [M + K]⁺ | | |
| | 11 | 7.7 ± 2.7 | 8.3 ± 3.2 | [M + H]⁺ | PC(20:4) | $C_{28}H_{50}NO_7P$ |
| | | — | — | [M + K]⁺ | | |
| | 12 | — | — | [M + H]⁺ | PC(20:3) | $C_{28}H_{52}NO_7P$ |
| | 13 | 7.3 ± 5.1 | 8.2 ± 4.7 | [M + H]⁺ | PC(20:2) | $C_{28}H_{54}NO_7P$ |
| | | 10.3 ± 4.6 | 14.5 ± 3.8 | [M + K]⁺ | | |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

| | | | | | |
|---|---|---|---|---|---|
| 14 | 5.4 ± 3.1 | 9.3 ± 4.6 | [M + K]$^+$ | PC(20:1) | $C_{28}H_{54}NO_8P$ |
| 15 | 9.5 ± 6.3 | 16.1 5.6 | | PC(20:0) | $C_{28}H_{56}NO_8P$ |
| 16 | 30.0 ± 7.9 | 36.7 ± 8.4 | [M + K]$^+$ | PC(22:6) | $C_{30}H_{50}NO_7P$ |
| 17 | — | 7.4 ± 5.4 | [M + K]$^+$ | LysoPC (22:5) | $C_{30}H_{52}NO_7P$ |
| 18 | 13.2 ± 6.7 | 17.2 5.8 | [M + K]$^+$ | PC(22:4) | $C_{30}H_{54}NO_7P$ |
| 19 | 9.1 ± 3.8 | 10.8 ± 5.1 | [M + K]$^+$ | PC(22:2) | $C_{30}H_{58}NO_7P$ |
| 20 | 8.3 ± 3.3 | 13.6 ± 6.4 | [M + K]$^+$ | PC(22:1) | $C_{30}H_{60}NO_7P$ |
| 21 | 9.2 ± 4.1 | 13.6 ± 5.3 | [M + K]$^+$ | PC(22:0) | $C_{30}H_{62}NO_7P$ |
| 22 | 8.1 ± 3.8 | 10.1 ± 3.3 | [M + K]$^+$ | LysoPC (24:1) | $C_{32}H_{64}NO_7P$ |
| 23 | 8.9 ± 3.4 | 11.1 ± 4.6 | [M + K]$^+$ | PC(24:0) | $C_{32}H_{66}NO_7P$ |
| 24 | 10.7 ± 3.7 | 16.6 ± 5.1 | [M + K]$^+$ | LysoPC (26:1) | $C_{32}H_{68}NO_7P$ |
| 25 | 8.9 ± 3.7 | 11.4 ± 4.8 | [M + K]$^+$ | LysoPC (26:0) | $C_{32}H_{70}NO_7P$ |
| 26 | 25.6 ± 6.8 | 33.5 ± 7.6 | [M + H]$^+$ | PC(30:1) | $C_{38}H_{74}NO_8P$ |
| 27 | 16.7 ± 3.8 | 20.3 ± 5.9 | [M + K]$^+$ | PC(30:0) | $C_{38}H_{76}NO_8P$ |
| 28 | 15.9 ± 5.4 | 19.9 ± 6.1 | [M + K]$^+$ | PC(32:3) | $C_{40}H_{74}NO_8P$ |
| 29 | 20.4 ± 6.6 8.3 ± 4.6 | 24.3 ± 7.0 12.3 ± 6.1 | [M + K]$^+$ [M + H]$^+$ | PC(32:1) | $C_{40}H_{78}NO_8P$ |
| 30 | 39.5 ± 6.7 282.7 ± 13.7 | 42.7 ± 5.9 325.5 ± 16.4 | [M + Na]$^+$ [M + K]$^+$ | PC(32:0) | $C_{40}H_{80}NO_8P$ |
| 31 | 12.3 ± 4.5 | 22.4 ± 5.6 | [M + K]$^+$ | PC(34:5) | $C_{42}H_{74}NO_8P$ |
| 32 | 9.4 ± 5.1 | 13.2 ± 4.4 | [M + K]$^+$ | PC(34:4) | $C_{42}H_{76}NO_8P$ |
| 33 | — | 12.7 ± 5.0 | [M + K]$^+$ | PC(34:3) | $C_{42}H_{78}NO_8P$ |
| 34 | 9.4 ± 5.9 | 13.4 ± 6.3 | [M + K]$^+$ | PC(34:2) | $C_{42}H_{80}NO_8P$ |
| 35 | 8.7 ± 4.1 39.6 ± 6.3 350.2 ± 13.4 | 15.4 ± 5.3 73.2 ± 7.2 595.8 ± 16.3 | [M + H]$^+$ [M + Na]$^+$ [M + K]$^+$ | PC(34:1) | $C_{42}H_{82}NO_8P$ |
| 36 | — 6.2 ± 2.8 63.4 ± 8.4 | 23.7 ± 6.4 8.6 ± 4.1 70.6 ± 9.5 | [M + H]$^+$ [M + Na]$^+$ [M + K]$^+$ | PC(34:0) | $C_{42}H_{84}NO_8P$ |
| 37 | — 86.3 ± 9.6 | 18.9 ± 6.4 126.3 ± 12.8 | [M + Na]$^+$ [M + K]$^+$ | PC(36:4) | $C_{44}H_{80}NO_8P$ |
| 38 | — | 15.7 ± 6.1 | [M + K]$^+$ | PC(36:3) | $C_{44}H_{82}NO_8P$ |
| 39 | 8.4 ± 4.2 | 13.0 ± 4.6 | [M + K]$^+$ | 1-hexadecanyl-2-(8-[3]-ladderane-octanyl)-sn-glycerophosphocholine | $C_{44}H_{84}NO_6P$ |
| 40 | 8.6 ± 5.3 57.8 ± 6.6 | 13.7 ± 6.6 82.1 ± 5.9 | [M + Na]$^+$ [M + K]$^+$ | PC(36:2) | $C_{44}H_{84}NO_8P$ |
| 41 | 7.8 ± 4.7 | 12.9 ± 5.5 | [M + K]$^+$ | PC(P-36:1) | $C_{44}H_{86}NO_7P$ |
| 42 | 5.6 ± 3.4 177.5 ± 15.2 | 8.4 ± 4.6 274.8 ± 18.6 | [M + H]$^+$ [M + K]$^+$ | PC(36:1) | $C_{44}H_{86}NO_8P$ |
| 43 | 33.8 ± 6.8 | 41.0 ± 6.5 | [M + K]$^+$ | PC(36:0) | $C_{44}H_{88}NO_8P$ |
| 44 | 9.7 ± 4.3 | 13.4 ± 5.8 | [M + H]$^+$ | 1-(6-[5]-ladderane-hexanoyl)-2-(8-[3]-ladderane-octanyl)-sn-glycerophosphocholine | $C_{46}H_{76}NO_7P$ |
| 45 | 40.9 ± 8.6 | 58.2 ± 8.1 | [M + K]$^+$ | PC(38:6) | $C_{46}H_{80}NO_8P$ |
| 46 | 31.5 ± 7.1 16.8 ± 4.4 | 45.5 ± 7.7 26.2 ± 5.3 | [M + K]$^+$ [M + H]$^+$ | PC(38:5) | $C_{46}H_{82}NO_8P$ |
| 47 | 17.4 ± 6.0 516.1 ± 19.4 | 18.5 ± 6.1 714.3 ± 23.7 | [M + Na]$^+$ [M + K]$^+$ | PC(38:4) | $C_{46}H_{84}NO_8P$ |
| 48 | 18.5 ± 4.2 | 23.6 ± 5.8 | [M + K]$^+$ | PC(38:3) | $C_{46}H_{86}NO_8P$ |
| 49 | 15.7 ± 5.5 | 20.1 ± 5.6 | [M + K]$^+$ | PC(38:1) | $C_{46}H_{90}NO_8P$ |
| 50 | 7.5 ± 4.4 | 10.3 ± 6.0 | M + K]$^+$ | PC(P-38:0) | $C_{46}H_{92}NO_7P$ |
| 51 | 31.2 ± 6.4 | 35.5 ± 6.6 | M + K]$^+$ | PC(38:0) | $C_{46}H_{92}NO_8P$ |
| 52 | — | — | [M + K]$^+$ | PC(40:10) | $C_{48}H_{76}NO_8P$ |
| 53 | — | 10.3 ± 4.0 | [M + K]$^+$ | PC(40:9) | $C_{48}H_{78}NO_8P$ |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

| | | | | | | |
|---|---|---|---|---|---|---|
| | 54 | — | — | [M + K]$^+$ | 1-(8-[5]-ladderane-octanoyl)-2-(8-[3]-ladderane-octanyl)-sn-glycerophosphocholine | $C_{48}H_{80}NO_7P$ |
| | 55 | 25.3 ± 4.7 | 30.5 ± 6.1 | [M + K]$^+$ | PC(40:7) | $C_{48}H_{82}NO_8P$ |
| | 56 | 12.1 ± 4.4 | 15.7 ± 5.1 | [M + Na]$^+$ | PC(40:6) | $C_{48}H_{84}NO_8P$ |
| | | 89.3 ± 10.6 | 118.0 ± 14.1 | [M + K]$^+$ | | |
| | 57 | 32.6 ± 7.1 | 40.3 ± 7.6 | [M + K]$^+$ | PC(40:5) | $C_{48}H_{86}NO_8P$ |
| | 58 | 42.6 ± 7.6 | 55.8 ± 8.3 | [M + K]$^+$ | PC(40:4) | $C_{48}H_{88}NO_8P$ |
| | 59 | — | 8.3 ± 4.0 | [M + K]$^+$ | PC(40:2) | $C_{48}H_{92}NO_8P$ |
| | 60 | 16.8 ± 5.1 | 18.9 ± 5.0 | [M + K]$^+$ | PC(40:1) | $C_{48}H_{94}NO_8P$ |
| | 61 | 18.9 ± 4.9 | 21.3 ± 5.3 | [M + K]$^+$ | PC(42:3) | $C_{50}H_{94}NO_8P$ |
| | 62 | 10.2 ± 4.2 | 12.9 ± 4.3 | [M + K]$^+$ | PC(42:2) | $C_{50}H_{96}NO_8P$ |
| | 63 | 18.9 ± 5.1 | 20.3 ± 5.3 | [M + K]$^+$ | PC(42:1) | $C_{50}H_{98}NO_8P$ |
| | 64 | — | — | [M + K]$^+$ | PC(44:2) | $C_{52}H_{100}NO_8P$ |
| | 65 | — | — | [M + K]$^+$ | PC(46:6) | $C_{54}H_{96}NO_8P$ |
| Phosphatidylethanolamines (PEs) | 1 | 14.1 ± 4.4 | 19.3 ± 5.1 | [M + K]$^+$ | PE(P-16:0) | $C_{21}H_{44}NO_6P$ |
| | 2 | 7.9 ± 4.0 | 8.8 ± 4.1 | [M + K]$^+$ | PE(16:1) | $C_{21}H_{42}NO_7P$ |
| | 3 | — | 8.3 ± 4.1 | [M + K]$^+$ | PE(16:0) | $C_{21}H_{44}NO_7P$ |
| | 4 | 9.6 ± 4.2 | 13.4 ± 4.4 | [M + K]$^+$ | PE(18:3) | $C_{23}H_{42}NO_7P$ |
| | 5 | 7.1 ± 3.7 | 8.0 ± 4.0 | [M + K]$^+$ | PE(18:2) | $C_{23}H_{44}NO_7P$ |
| | 6 | 6.7 ± 3.6 | 8.1 ± 4.0 | [M + K]$^+$ | PE(18:1) | $C_{23}H_{46}NO_7P$ |
| | 7 | 15.6 ± 4.6 | 23.3 ± 5.3 | [M + K]$^+$ | PE(P-18:0) | $C_{23}H_{48}NO_6P$ |
| | 8 | 9.6 ± 4.2 | 13.6 ± 4.4 | [M + K]$^+$ | PE(18:0) | $C_{23}H_{48}NO_7P$ |
| | 9 | — | 17.2 ± 4.8 | [M + K]$^+$ | PE(20:4) | $C_{25}H_{44}NO_7P$ |
| | 10 | 20.8 ± 5.2 | 28.8 ± 5.5 | [M + K]$^+$ | PE(20:3) | $C_{25}H_{46}NO_7P$ |
| | 11 | 7.2 ± 3.8 | 7.8 ± 4.0 | [M + K]$^+$ | PE(20:2) | $C_{25}H_{48}NO_7P$ |
| | 12 | 15.4 ± 4.5 | 19.7 ± 5.2 | [M + K]$^+$ | PE(20:1) | $C_{25}H_{50}NO_7P$ |
| | 13 | 7.4 ± 3.9 | 8.1 ± 4.1 | [M + H]$^+$ | PE(20:0) | $C_{25}H_{52}NO_7P$ |
| | | 5.1 ± 2.3 | 6.8 ± 3.3 | [M + K]$^+$ | | |
| | 14 | 9.3 ± 4.1 | 10.0 ± 4.3 | [M + K]$^+$ | PE(22:6) | $C_{27}H_{44}NO_7P$ |
| | 15 | 8.8 ± 4.0 | 11.2 ± 4.3 | [M + K]$^+$ | PE(22:4) | $C_{27}H_{48}NO_7P$ |
| | 16 | 10.4 ± 4.4 | 15.3 ± 4.6 | [M + K]$^+$ | PE(22:2) | $C_{27}H_{52}NO_7P$ |
| | 17 | 15.1 ± 4.5 | 19.3 ± 4.8 | [M + K]$^+$ | PE(22:1) | $C_{27}H_{54}NO_7P$ |
| | 18 | — | — | [M + H]$^+$ | PE(22:0) | $C_{27}H_{56}NO_7P$ |
| | | 11.9 ± 4.5 | 18.8 ± 5.0 | [M + Na]$^+$ | | |
| | 19 | 14.0 ± 4.3 | 25.8 ± 5.6 | [M + K]$^+$ | LysoPE (24:1) | $C_{29}H_{58}NO_7P$ |
| | 20 | 6.6 ± 3.5 | 9.2 ± 4.2 | [M + K]$^+$ | PE(26:1) | $C_{31}H_{60}NO_8P$ |
| | 21 | 15.1 ± 5.0 | 23.6 ± 6.3 | [M + K]$^+$ | PE(26:0) | $C_{31}H_{62}NO_8P$ |
| | 22 | 7.5 ± 3.5 | 8.9 ± 4.3 | [M + K]$^+$ | PE(34:1) | $C_{39}H_{76}NO_8P$ |
| | 23 | 186.6 ± 13.9 | 222.8 ± 15.7 | [M + K]$^+$ | PE(P-34:1) | $C_{39}H_{76}NO_7P$ |
| | 24 | 16.2 ± 5.3 | 20.5 ± 5.7 | [M + K]$^+$ | PE(P-34:0) | $C_{39}H_{78}NO_7P$ |
| | 25 | 25.3 ± 5.6 | 33.0 ± 6.4 | [M + K]$^+$ | PE(34:4) | $C_{39}H_{70}NO_8P$ |
| | 26 | 9.1 ± 4.0 | 16.2 ± 5.1 | [M + K]$^+$ | PE(34:0) | $C_{39}H_{78}NO_8P$ |
| | 27 | 16.3 ± 5.1 | 19.0 ± 5.3 | [M + K]$^+$ | PE(P-36:3) | $C_{41}H_{76}NO_7P$ |
| | 28 | 8.5 ± 4.2 | 11.7 ± 5.3 | [M + K]$^+$ | PE(36:3) | $C_{41}H_{76}NO_8P$ |
| | 29 | — | 9.3 ± 4.3 | [M + K]$^+$ | PE(36:2) | $C_{41}H_{78}NO_8P$ |
| | 30 | 8.7 ± 4.3 | 13.7 ± 4.8 | [M + K]$^+$ | PE(P-36:1) | $C_{41}H_{80}NO_7P$ |
| | 31 | 9.7 ± 4.5 | 12.8 ± 5.1 | [M + K]$^+$ | PE(36:1) | $C_{41}H_{80}NO_8P$ |
| | 32 | 39.9 ± 7.1 | 47.8 ± 7.6 | [M + K]$^+$ | PE(P-36:0) | $C_{41}H_{82}NO_7P$ |
| | 33 | 20.7 ± 5.2 | 23.0 ± 5.5 | [M + H]$^+$ | PE(36:0) | $C_{41}H_{82}NO_8P$ |
| | 34 | 14.7 ± 4.8 | 22.4 ± 5.3 | [M + K]$^+$ | PE(P-38:6) | $C_{43}H_{74}NO_7P$ |
| | 35 | 6.1 ± 3.1 | 7.6 ± 4.1 | [M + K]$^+$ | PE(38:6) | $C_{43}H_{74}NO_8P$ |
| | 36 | 15.4 ± 5.0 | 19.6 ± 5.3 | [M + K]$^+$ | PE(P-38:5) | $C_{43}H_{76}NO_7P$ |
| | 37 | 10.2 ± 4.2 | 13.7 ± 4.8 | [M + K]$^+$ | PE(38:5) | $C_{43}H_{76}NO_8P$ |
| | 38 | 16.3 ± 5.1 | 21.4 ± 5.3 | [M + K]$^+$ | PE(P-38:4) | $C_{43}H_{78}NO_7P$ |
| | 39 | 34.6 ± 6.7 | 43.9 ± 7.2 | [M + K]$^+$ | PE(38:4) | $C_{43}H_{78}NO_8P$ |
| | 40 | — | — | [M + K]$^+$ | PE(P-38:3) | $C_{43}H_{80}NO_7P$ |
| | 41 | — | — | [M + K]$^+$ | PE(38:2) | $C_{43}H_{82}NO_8P$ |
| | 42 | 45.3 ± 7.3 | 50.5 ± 7.8 | [M + H]$^+$ | PE(38:1) | $C_{43}H_{84}NO_8P$ |
| | | 12.7 ± 4.6 | 15.9 ± 5.0 | [M + K]$^+$ | | |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

|  |  |  |  |  |  |  |
|---|---|---|---|---|---|---|
|  | 43 | 28.6 ± 5.6 | 30.1 ± 6.5 | $[M + K]^+$ | PE(P-40:7) | $C_{45}H_{76}NO_7P$ |
|  | 44 | 16.7 ± 5.2 | 20.6 ± 5.4 | $[M + K]^+$ | PE(40:7) | $C_{45}H_{76}NO_8P$ |
|  | 45 | 11.2 ± 4.3 | 13.7 ± 4.7 | $[M + K]^+$ | PE(P-40:6) | $C_{45}H_{78}NO_7P$ |
|  | 46 | 8.4 ± 4.2 | 13.1 ± 4.6 | $[M + K]^+$ | PE(40:6) | $C_{45}H_{78}NO_8P$ |
|  | 47 | 9.2 ± 4.5 | 16.2 ± 5.1 | $[M + K]^+$ | PE(P-40:5) | $C_{45}H_{80}NO_7P$ |
|  | 48 | — | — | $[M + K]^+$ | PE(40:5) | $C_{45}H_{80}NO_8P$ |
|  | 49 | 10.8 ± 4.1 | 15.3 ± 4.7 | $[M + K]^+$ | PE(P-40:4) | $C_{45}H_{82}NO_7P$ |
|  | 50 | 16.8 ± 4.9 | 20.5 ± 5.3 | $[M + K]^+$ | PE(40:4) | $C_{45}H_{82}NO_8P$ |
|  | 51 | 16.9 ± 4.8 | 22.4 ± 5.4 | $[M + H]^+$ | PE(40:1) | $C_{45}H_{88}NO_8P$ |
|  | 52 | — | 6.4 ± 3.0 | $[M + K]^+$ | PE(42:10) | $C_{47}H_{74}NO_8P$ |
|  | 53 | 62.7 ± 8.5 | 78.1 ± 12.4 | $[M + K]^+$ | PE(42:9) | $C_{47}H_{76}NO_8P$ |
|  | 54 | 26.5 ± 5.7 | 30.8 ± 6.1 | $[M + K]^+$ | PE(42:8) | $C_{47}H_{78}NO_8P$ |
|  | 55 | — | 6.7 ± 3.6 | $[M + K]^+$ | PE(42:7) | $C_{47}H_{80}NO_8P$ |
|  | 56 | — | — | $[M + K]^+$ | PE(42:6) | $C_{47}H_{82}NO_8P$ |
|  | 57 | 7.4 ± 3.5 | 8.8 ± 3.8 | $[M + H]^+$ | PE(42:4) | $C_{47}H_{86}NO_8P$ |
|  | 58 | 13.5 ± 4.7 | 18.7 ± 5.0 | $[M + H]^+$ | PE(O-42:4) | $C_{47}H_{88}NO_7P$ |
|  | 59 | 11.3 ± 4.4 | 16.5 ± 4.8 | $[M + K]^+$ | PE(42:3) | $C_{47}H_{88}NO_8P$ |
|  | 60 | 7.5 ± 3.5 | 11.8 ± 4.6 | $[M + K]^+$ | PE(P-42:2) | $C_{47}H_{90}NO_7P$ |
|  | 61 | 7.7 ± 3.6 | 10.8 ± 4.1 | $[M + Na]^+$ | PE(42:2) | $C_{47}H_{90}NO_8P$ |
|  | 62 | — | 11.9 ± 4.6 | $[M + K]^+$ | PE(P-42:1) | $C_{47}H_{92}NO_7P$ |
|  | 63 | 8.5 ± 3.5 | 11.7 ± 4.5 | $[M + K]^+$ | PE(42:1) | $C_{47}H_{92}NO_8P$ |
|  | 64 | 9.8 ± 4.0 | 12.1 ± 4.7 | $[M + K]^+$ | PE(42:0) | $C_{47}H_{94}NO_8P$ |
|  | 65 | 6.3 ± 3.3 | 7.5 ± 3.6 | $[M + K]^+$ | PE(44:10) | $C_{49}H_{78}NO_8P$ |
|  | 66 | — | — | $[M + K]^+$ | PE(44:9) | $C_{49}H_{80}NO_8P$ |
|  | 67 | 12.3 ± 4.3 | 15.1 ± 4.9 | $[M + K]^+$ | PE(44:6) | $C_{49}H_{86}NO_8P$ |
|  | 68 | 10.4 ± 4.1 | 14.5 ± 5.2 | $[M + K]^+$ | PE(44:5) | $C_{49}H_{88}NO_8P$ |
|  | 69 | — | 5.1 ± 2.2 | $[M + K]^+$ | PE(44:1) | $C_{49}H_{96}NO_8P$ |
| Phosphatidic acids (PAs) | 1 | 7.4 ± 3.3 | 11.5 ± 4.4 | $[M + K]^+$ | PA(18:1) | $C_{21}H_{41}O_7P$ |
|  | 2 | 6.4 ± 3.1 | 7.1 ± 3.3 | $[M + K]^+$ | PA(18:0) | $C_{21}H_{43}O_7P$ |
|  | 3 | 22.4 ± 5.6 | 24.6 ± 5.8 | $[M + K]^+$ | PA(20:4) | $C_{23}H_{39}O_7P$ |
|  | 4 | 10.2 ± 4.2 | 16.1 ± 5.0 | $[M + K]^+$ | PA(20:3) | $C_{23}H_{41}O_7P$ |
|  | 5 | 13.0 ± 4.9 | 15.0 ± 5.2 | $[M + K]^+$ | PA(20:2) | $C_{23}H_{43}O_7P$ |
|  | 6 | 14.7 ± 4.7 | 16.0 ± 5.0 | $[M + Na]^+$ | PA(20:1) | $C_{23}H_{45}O_7P$ |
|  |  | 12.3 ± 4.3 | 14.6 ± 4.7 | $[M + K]^+$ |  |  |
|  | 7 | 12.6 ± 4.4 | 20.3 ± 5.1 | $[M + K]^+$ | PA(22:4) | $C_{25}H_{43}O_7P$ |
|  | 8 | 11.4 ± 4.7 | 14.6 ± 4.8 | $[M + K]^+$ | PA(22:1) | $C_{25}H_{49}O_7P$ |
|  | 9 | 13.2 ± 3.3 | 17.9 ± 4.2 | $[M + K]^+$ | PA(22:0) | $C_{25}H_{51}O_7P$ |
|  | 10 | 16.3 ± 3.5 | 18.7 ± 4.1 | $[M + K]^+$ | PA(32:4) | $C_{35}H_{61}O_8P$ |
|  | 11 | 10.7 ± 3.2 | 15.1 ± 3.3 | $[M + K]^+$ | PA(32:3) | $C_{35}H_{63}O_8P$ |
|  | 12 | 7.8 ± 2.9 | 9.0 ± 3.0 | $[M + K]^+$ | PA(32:2) | $C_{35}H_{65}O_8P$ |
|  | 13 | 10.4 ± 3.5 | 14.7 ± 4.3 | $[M + K]^+$ | PA(32:1) | $C_{35}H_{67}O_8P$ |
|  | 14 | 9.9 ± 3.1 | 13.5 ± 3.2 | $[M + K]^+$ | PA(32:0) | $C_{35}H_{69}O_8P$ |
|  | 15 | 8.4 ± 2.6 | 12.8 ± 3.2 | $[M + Na]^+$ | PA(O-32:0) | $C_{35}H_{73}O_6P$ |
|  | 16 | 18.8 ± 4.6 | 22.1 ± 5.0 | $[M + K]^+$ | PA(34:3) | $C_{37}H_{67}O_8P$ |
|  | 17 | 20.5 ± 5.1 | 26.2 ± 5.3 | $[M + K]^+$ | PA(34:2) | $C_{37}H_{69}O_8P$ |
|  | 18 | 41.7 ± 7.3 | 47.4 ± 7.5 | $[M + Na]^+$ | PA(34:1) | $C_{37}H_{71}O_8P$ |
|  |  | 301.2 ± 14.4 | 384.3 ± 16.2 | $[M + K]^+$ |  |  |
|  | 19 | — | 5.1 ± 2.3 | $[M + K]^+$ | PA(O-34:1) | $C_{37}H_{73}O_7P$ |
|  | 20 | 12.4 ± 3.6 | 14.9 ± 4.5 | $[M + Na]^+$ | PA(P-36:5) | $C_{39}H_{67}O_7P$ |
|  | 21 | 8.5 ± 3.6 | 13.2 ± 4.0 | $[M + K]^+$ | PA(36:5) | $C_{39}H_{67}O_8P$ |
|  | 22 | 5.3 ± 2.4 | 7.6 ± 2.9 | $[M + K]^+$ | PA(36:4) | $C_{39}H_{69}O_8P$ |
|  | 23 | 18.4 ± 4.3 | 22.0 ± 4.5 | $[M + K]^+$ | PA(36:3) | $C_{39}H_{71}O_8P$ |
|  | 24 | 57.1 ± 6.3 | 62.7 ± 7.0 | $[M + Na]^+$ | PA(36:2) | $C_{39}H_{73}O_8P$ |
|  |  | 443.8 ± 17.3 | 522.8 ± 19.8 | $[M + K]^+$ |  |  |
|  | 25 | 7.4 ± 3.3 | 8.5 ± 3.4 | $[M + K]^+$ | PA(36:1) | $C_{39}H_{75}O_8P$ |
|  | 26 | 10.1 ± 4.1 | 11.0 ± 4.2 | $[M + Na]^+$ | PA(P-38:6) | $C_{41}H_{69}O_7P$ |
|  | 27 | — | 6.5 ± 2.8 | $[M + K]^+$ | PA(38:6) | $C_{41}H_{69}O_8P$ |
|  | 28 | 84.2 ± 8.1 | 86.2 ± 8.3 | $[M + K]^+$ | PA(38:5) | $C_{41}H_{71}O_8P$ |
|  | 29 | 23.9 ± 5.0 | 24.5 ± 5.1 | $[M + H]^+$ | PA(38:4) | $C_{41}H_{73}O_8P$ |
|  |  | 32.0 ± 5.6 | 33.8 ± 5.7 | $[M + K]^+$ |  |  |
|  | 30 | — | — | $[M + Na]^+$ | PA(38:3) | $C_{41}H_{75}O_8P$ |
|  |  | 26.5 ± 7.3 | 27.4 ± 7.5 | $[M + K]^+$ |  |  |
|  | 31 | 13.0 ± 4.0 | 14.7 ± 4.2 | $[M + Na]^+$ | PA(38:2) | $C_{41}H_{77}O_8P$ |
|  |  | 122.8 ± 9.7 | 127.8 ± 10.0 | $[M + K]^+$ |  |  |
|  | 32 | 8.4 ± 4.7 | 9.1 ± 5.0 | $[M + K]^+$ | PA(38:0) | $C_{41}H_{81}O_8P$ |
|  | 33 | 26.6 ± 4.9 | 33.5 ± 5.8 | $[M + K]^+$ | PA(40:7) | $C_{43}H_{71}O_8P$ |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

| | | | | | | |
|---|---|---|---|---|---|---|
| | | 34 | 17.5 ± 4.6 | 20.7 ± 5.0 | $[M + K]^+$ | PA(40:6) | $C_{43}H_{73}O_8P$ |
| | | 35 | — | 7.5 ± 3.4 | $[M + Na]^+$ | PA(40:5) | $C_{43}H_{75}O_8P$ |
| | | | 46.7 ± 7.1 | 51.3 ± 7.3 | $[M + K]^+$ | | |
| | | 36 | 12.4 ± 4.7 | 14.9 ± 5.1 | $[M + Na]^+$ | PA(40:3) | $C_{43}H_{79}O_8P$ |
| | | 37 | — | 6.4 ± 4.1 | $[M + K]^+$ | PA(42:9) | $C_{45}H_{71}O_8P$ |
| Phosphoglycerols (PGs) | 1 | 8.2 ± 4.5 | 8.9 ± 4.7 | $[M + K]^+$ | PG(18:2) | $C_{24}H_{45}O_9P$ |
| | 2 | 6.5 ± 3.3 | 8.7 ± 4.1 | $[M + K]^+$ | PG(20:3) | $C_{26}H_{47}O_9P$ |
| | 3 | 36.6 ± 7.2 | 53.3 ± 8.6 | $[M + Na]^+$ | PG(20:2) | $C_{26}H_{49}O_9P$ |
| | 4 | 8.8 ± 3.9 | 13.5 ± 5.3 | $[M + K]^+$ | PG(22:4) | $C_{28}H_{49}O_9P$ |
| | 5 | 23.7 ± 5.7 | 27.8 ± 6.8 | $[M + K]^+$ | PG(22:2) | $C_{28}H_{53}O_9P$ |
| | 6 | 8.7 ± 3.7 | 10.3 ± 4.8 | $[M + K]^+$ | PG(P-32:0) | $C_{38}H_{75}O_9P$ |
| | 7 | | 5.1 ± 2.1 | $[M + H]^+$ | PG(34:4) | $C_{40}H_{71}O_{10}P$ |
| | 8 | 31.4 ± 7.2 | 34.7 ± 7.5 | $[M + K]^+$ | PG(34:3) | $C_{40}H_{73}O_{10}P$ |
| | 9 | 19.5 ± 6.6 | 28.0 ± 7.1 | $[M + Na]^+$ | PG(36:4) | $C_{42}H_{75}O_{10}P$ |
| | 10 | 14.3 ± 6.1 | 17.5 ± 6.3 | $[M + K]^+$ | PG(36:0) | $C_{42}H_{83}O_{10}P$ |
| | 11 | 21.5 ± 5.8 | 25.8 ± 6.4 | $[M + H]^+$ | PG(38:3) | $C_{44}H_{81}O_{10}P$ |
| | 12 | 31.9 ± 7.7 | 39.5 ± 10.4 | $[M + Na]^+$ | PG(38:2) | $C_{44}H_{83}O_{10}P$ |
| | 13 | — | — | $[M + K]^+$ | PG(42:7) | $C_{48}H_{81}O_{10}P$ |
| Phosphatidylserine (PS) | 1 | 12.4 ± 4.4 | 15.8 ± 5.4 | $[M + K]^+$ | PS(P-20:0) | $C_{26}H_{52}NO_8P$ |
| | 2 | 10.7 ± 5.1 | 13.6 ± 4.2 | $[M + K]^+$ | PS(20:0) | $C_{26}H_{52}NO_9P$ |
| | 3 | 27.3 ± 6.4 | 32.3 ± 7.8 | $[M + K]^+$ | PS(22:4) | $C_{28}H_{48}NO_9P$ |
| | 4 | 10.3 ± 5.0 | 13.8 ± 4.8 | $[M + Na]^+$ | PS(34:3) | $C_{40}H_{72}NO_{10}P$ |
| | 5 | 5.3 ± 2.3 | 10.5 ± 4.6 | $[M + Na]^+$ | PS(36:3) | $C_{42}H_{76}NO_{10}P$ |
| | 6 | 89.6 ± 8.6 | 92.6 ± 8.7 | $[M + K]^+$ | PS(36:1) | $C_{42}H_{80}NO_{10}P$ |
| | 7 | — | 9.0 ± 4.1 | $[M + Na]^+$ | PS(38:9) | $C_{44}H_{68}NO_{10}P$ |
| | 8 | 14.0 ± 5.3 | 17.3 ± 5.7 | $[M + Na]^+$ | PS(38:8) | $C_{44}H_{70}NO_{10}P$ |
| | 9 | 134.5 ± 13.4 | 145.4 ± 14.7 | $[M + K]^+$ | PS(38:6) | $C_{44}H_{74}NO_{10}P$ |
| | 10 | 38.6 ± 10.2 | 47.9 ± 11.6 | $[M + K]^+$ | PS(P-38:6) | $C_{44}H_{74}NO_9P$ |
| | 11 | — | 6.7 ± 3.4 | $[M + Na]^+$ | PS(38:4) | $C_{44}H_{78}NO_{10}P$ |
| | 12 | — | 5.1 ± 2.4 | $[M + Na]^+$ | PS(40:8) | $C_{46}H_{74}NO_{10}P$ |
| | 13 | — | — | $[M + Na]^+$ | PS(40:7) | $C_{46}H_{76}NO_{10}P$ |
| | 14 | 12.5 ± 4.9 | 16.9 ± 5.6 | $[M + Na]^+$ | PS(40:6) | $C_{46}H_{78}NO_{10}P$ |
| | 15 | — | 6.4 ± 3.4 | $[M + Na]^+$ | PS(40:5) | $C_{46}H_{80}NO_{10}P$ |
| | 16 | 41.5 ± 10.5 | 45.5 ± 11.6 | $[M + H]^+$ | PS(40:1) | $C_{46}H_{88}NO_{10}P$ |
| | 17 | — | — | $[M + H]^+$ | PS(P-40:1) | $C_{46}H_{88}NO_9P$ |
| | 18 | 39.8 ± 14.7 | 47.2 ± 15.0 | $[M + H]^+$ | PS(40:0) | $C_{46}H_{90}NO_{10}P$ |
| | 19 | 6.4 ± 3.1 | 7.8 ± 3.7 | $[M + Na]^+$ | PS(42:7) | $C_{48}H_{80}NO_{10}P$ |
| Phosphatidylinositols (PIs) | 1 | — | 6.5 ± 3.1 | $[M + K]^+$ | PI(38:7) | $C_{47}H_{77}O_{13}P$ |
| | 2 | 14.5 ± 5.3 | 19.3 ± 6.1 | $[M + K]^+$ | PI(38:4) | $C_{47}H_{83}O_{13}P$ |
| | 3 | 11.7 ± 4.6 | 15.3 ± 5.0 | $[M + K]^+$ | PI(40:8) | $C_{49}H_{79}O_{13}P$ |
| | 4 | 13.7 ± 4.7 | 20.4 ± 5.2 | $[M + H]^+$ | PI(40:4) | $C_{49}H_{87}O_{13}P$ |
| | 5 | 9.1 ± 4.1 | 11.5 ± 4.7 | $[M + H]^+$ | PI(42:10) | $C_{51}H_{79}O_{13}P$ |
| | 6 | — | 7.0 ± 3.5 | $[M + K]^+$ | PI(42:7) | $C_{51}H_{85}O_{13}P$ |
| | 7 | — | — | $[M + Na]^+$ | PI(P-42:6) | $C_{51}H_{87}O_{12}P$ |
| | 8 | — | — | $[M + Na]^+$ | PI(42:6) | $C_{51}H_{87}O_{13}P$ |
| Glycerophosphoinositol bisphosphates (PIP2s) | 1 | 9.3 ± 4.2 | 11.6 ± 5.2 | $[M + K]^+$ | PIP2(34:1) | $C_{43}H_{83}O_{19}P_3$ |
| Glycerophosphoglycero-phosphoglycerols (cardiolipins) | 1 | 96.5 ± 10.1 | 104.1 ± 10.5 | $[M + Na]^+$ | CL(1\'-[18:2(9Z,12Z)/0:0], 3\'-[18:2(9Z,12Z)/0:0]) | $C_{45}H_{82}O_{15}P_2$ |
| | | 772.1 ± 26.7 | 866.1 ± 28.2 | $[M + K]^+$ | | |
| Cyclic phosphatidic acids (cPAs) | 1 | 9.4 ± 4.8 | 13.7 ± 5.2 | $[M + Na]^+$ | CPA(16:0) | $C_{19}H_{37}O_6P$ |
| | | 7.7 ± 3.4 | 14.6 ± 5.8 | $[M + K]^+$ | | |
| | 2 | 21.9 ± 6.8 | 31.7 ± 8.1 | $[M + K]^+$ | CPA(18:2) | $C_{21}H_{37}O_6P$ |
| | 3 | 6.2 ± 3.5 | 8.5 ± 4.6 | $[M + Na]^+$ | CPA(18:1) | $C_{21}H_{39}O_6P$ |
| | | 19.4 ± 6.6 | 29.2 ± 7.8 | $[M + K]^+$ | | |
| | 4 | 7.0 ± 3.2 | 8.8 ± 4.7 | $[M + Na]^+$ | CPA(18:0) | $C_{21}H_{41}O_6P$ |
| | | 23.3 ± 6.7 | 29.0 ± 7.7 | $[M + K]^+$ | | |
| CDP-Glycerols | 1 | — | 6.4 ± 3.1 | $[M + H]^+$ | CDP-DG(34:1) | $C_{46}H_{83}N_3O_{15}P_2$ |
| | | — | 8.4 ± 5.4 | $[M + K]^+$ | | |
| | 2 | 5.6 ± 2.3 | 7.6 ± 3.4 | $[M + H]^+$ | CDP-DG(34:0) | $C_{46}H_{85}N_3O_{15}P_2$ |
| | | — | — | $[M + K]^+$ | | |
| | 3 | — | 6.0 ± 2.8 | $[M + H]^+$ | CDP-DG(36:0) | $C_{46}H_{89}N_3O_{15}P_2$ |
| | 4 | — | — | $[M + H]^+$ | CDP-DG(40:4) | $C_{52}H_{89}N_3O_{15}P_2$ |
| | | 7.9 ± 3.6 | 9.1 ± 4.3 | $[M + K]^+$ | | |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

| Category | # | Col A | Col B | Adduct | Lipid | Formula |
|---|---|---|---|---|---|---|
| Glycerophosphate | 1 | — | 5.0 ± 2.2 | [M + Na]+ | sn-3-O-(geranylgeranyl)glycerol 1-phosphate | $C_{23}H_{41}O_6P$ |
| | | 15.9 ± 6.5 | 28.2 ± 7.6 | [M + K]+ | | |
| Sphingolipids Ceramides (Cers) | 1 | 5.6 ± 2.3 | 6.0 ± 2.8 | [M + K]+ | C-8 Ceramide | $C_{26}H_{51}NO_3$ |
| | 2 | 14.0 ± 5.4 | 17.8 ± 5.7 | [M + K]+ | Cer(d36:2) | $C_{36}H_{69}NO_3$ |
| | 3 | 7.9 ± 3.3 | 9.1 ± 4.0 | [M + K]+ | Cer(d36:1) | $C_{36}H_{71}NO_3$ |
| | 4 | — | 6.7 ± 3.0 | [M + K]+ | CerP(d36:1) | $C_{36}H_{72}NO_6P$ |
| | 5 | 18.1 ± 5.8 | 21.1 ± 6.3 | [M + K]+ | Cer(d38:1) | $C_{38}H_{75}NO_3$ |
| | 6 | 8.4 ± 4.0 | 13.5 ± 5.1 | [M + K]+ | Cer(d42:2) | $C_{42}H_{81}NO_3$ |
| | 7 | 8.4 ± 4.1 | 11.6 ± 4.6 | [M + K]+ | CerP(d42:2) | $C_{42}H_{82}NO_6P$ |
| | 8 | — | 5.0 ± 2.2 | [M + K]+ | Cer(d42:1) | $C_{42}H_{83}NO_3$ |
| Sphingomyelins (SMs) | 1 | 5.0 ± 2.0 | 7.3 ± 3.4 | [M + H]+ | SM(d34:1) | $C_{39}H_{79}N_2O_6P$ |
| | | 15.4 ± 4.2 | 23.9 ± 5.9 | [M + Na]+ | | |
| | 2 | 16.7 ± 4.5 | 18.3 ± 4.8 | [M + Na]+ | SM(d36:1) | $C_{41}H_{83}N_2O_6P$ |
| | | 88.3 ± 10.1 | 103.8 ± 12.3 | [M + K]+ | | |
| | 3 | 6.2 ± 3.8 | 7.6 ± 4.3 | [M + K]+ | SM(d38:1) | $C_{43}H_{87}N_2O_6P$ |
| | 4 | — | — | [M + H]+ | SM(d40:1) | $C_{45}H_{91}N_2O_6P$ |
| | | 37.9 ± 7.1 | 39.5 ± 7.3 | [M + K]+ | | |
| | 5 | — | 7.8 ± 3.9 | [M + H]+ | SM(d42:2) | $C_{47}H_{93}N_2O_6P$ |
| | | 9.9 ± 3.8 | 11.2 ± 4.0 | [M + K]+ | | |
| | 6 | 5.8 ± 3.4 | 7.2 ± 3.0 | [M + H]+ | SM(d42:1) | $C_{47}H_{95}N_2O_6P$ |
| | | 22.6 ± 4.8 | 25.4 ± 4.9 | [M + Na]+ | | |
| | | 8.4 ± 4.6 | 11.1 ± 5.1 | [M + K]+ | | |
| Glycosphingolipids | 1 | 32.7 ± 6.7 | 46.1 ± 7.0 | [M + K]+ | Glucosyl sphingosine | $C_{24}H_{47}NO_7$ |
| | 2 | 11.9 ± 4.1 | 14.8 ± 4.8 | [M + Na]+ | LacCer(d30:1) | $C_{42}H_{79}NO_{13}$ |
| | 3 | 9.3 ± 4.0 | 13.2 ± 4.2 | [M + K]+ | GlcCer(d36:1) | $C_{42}H_{81}NO_8$ |
| | 4 | — | — | [M + Na]+ | LacCer(d32:1) | $C_{44}H_{83}NO_{13}$ |
| | 5 | — | 8.8 ± 4.3 | [M + H]+ | (3'-sulfo)Galβ-Cer(d38:0(2OH)) | $C_{44}H_{85}NO_{12}S$ |
| | 6 | 10.5 ± 5.6 | 12.7 ± 5.9 | [M + K]+ | GalCer(d38:1) | $C_{44}H_{85}NO_8$ |
| | 7 | 106.8 ± 13.5 | 126.3 ± 14.2 | [M + K]+ | GlcCer(d40:2) | $C_{46}H_{87}NO_8$ |
| | 8 | — | — | [M + K]+ | GlcCer(d16:2/24:0(2OH)) | $C_{46}H_{87}NO_9$ |
| | 9 | 12.6 ± 6.3 | 15.7 ± 7.2 | [M + K]+ | GlcCer(d40:1) | $C_{46}H_{89}NO_8$ |
| | 10 | 13.8 ± 6.5 | 16.6 ± 8.7 | [M + K]+ | LacCer(d36:1) | $C_{48}H_{91}NO_{13}$ |
| | 11 | 9.5 ± 5.0 | 13.5 ± 6.1 | [M + Na]+ | GlcCer(d42:2) | $C_{48}H_{91}NO_8$ |
| | | 32.2 ± 12.1 | 46.4 ± 13.0 | [M + K]+ | | |
| | 12 | 6.3 ± 3.4 | 7.5 ± 4.1 | [M + H]+ | LacCer(d36:0) | $C_{48}H_{93}NO_{13}$ |
| | 13 | 12.7 ± 5.4 | 16.2 ± 6.1 | [M + K]+ | GlcCer(d42:1) | $C_{48}H_{93}NO_8$ |
| | 14 | — | — | [M + K]+ | GlcCer(d42:0) | $C_{48}H_{95}NO_8$ |
| | 15 | 42.6 ± 14.5 | 54.8 ± 15.7 | [M + K]+ | GlcCer(d44:2) | $C_{50}H_{95}NO_8$ |
| | 16 | 10.8 ± 4.8 | 13.5 ± 5.1 | [M + K]+ | GlcCer(d44:1) | $C_{50}H_{97}NO_8$ |
| | 17 | — | — | [M + K]+ | Galβ1-4Glcβ-Cer(d42:2) | $C_{54}H_{101}NO_{13}$ |
| | 18 | — | — | [M + K]+ | Galβ1-4Glcβ-Cer(d42:1) | $C_{54}H_{103}NO_{13}$ |
| Sphingoid bases | 1 | — | — | [M + Na]+ | (4E,6E,d14:2) sphingosine | $C_{14}H_{27}NO_2$ |
| Ceramide phosphoinositols (PI-Cers) | 1 | 7.8 ± 3.7 | 10.1 ± 4.1 | [M + K]+ | PI-Cer(t34:0(2OH)) | $C_{40}H_{80}NO_{13}P$ |
| | 2 | 34.7 ± 8.4 | 49.4 ± 8.8 | [M + H]+ | PI-Cer(d38:0) | $C_{44}H_{88}NO_{11}P$ |
| | 3 | 130.8 ± 13.4 | 160.5 ± 17.8 | [M + H]+ | PI-Cer(d40:10) | $C_{46}H_{90}NO_{11}P$ |
| | 4 | 196.4 ± 21.5 | 200.5 ± 22.0 | [M + H]+ | PI-Cer(d40:0) | $C_{46}H_{92}NO_{11}P$ |
| | 5 | — | 5.0 ± 2.3 | [M + Na]+ | PI-Cer(t40:0) | $C_{46}H_{92}NO_{12}P$ |
| | 6 | 7.1 ± 3.4 | 9.9 ± 4.0 | [M + H]+ | PI-Cer(d42:0) | $C_{48}H_{96}NO_{11}P$ |
| | 7 | — | 6.5 ± 3.1 | [M + K]+ | MIPC(t44:0(2OH)) | $C_{56}H_{110}NO_{18}P$ |
| Neutral Lipids Glycerolipids Monoacylglycerols (MAGs) | 1 | 8.5 ± 3.4 | 9.7 ± 4.5 | [M + K]+ | MG (16:0) | $C_{16}H_{38}O_4$ |
| | 2 | — | — | [M + Na]+ | MG (18:1) | $C_{21}H_{40}O_4$ |
| | 3 | — | — | [M + K]+ | MG (18:0) | $C_{21}H_{42}O_4$ |
| | 4 | — | — | [M + K]+ | MG (20:4) | $C_{23}H_{38}O_4$ |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

|  |  |  |  |  |  |  |
|---|---|---|---|---|---|---|
|  | 5 | 9.6 ± 4.4 | 12.0 ± 5.2 | [M + K]$^+$ | MG (20:3) | $C_{23}H_{40}O_4$ |
|  | 6 | — | — | [M + Na]$^+$ | MG (22:6) | $C_{25}H_{38}O_4$ |
|  | 7 | 6.3 ± 2.8 | 7.4 ± 3.0 | [M + K]$^+$ | MG (22:4) | $C_{25}H_{42}O_4$ |
| Diacylglycerols (DAGs) | 1 | 141.0 ± 14.0<br>6.5 ± 2.9<br>— | 203.1 ± 15.7<br>8.8 ± 3.7<br>6.5 ± 2.9 | [M + H]$^+$ | DG(P-32:1) | $C_{35}H_{66}O_4$ |
|  | 2 | 8.2 ± 3.3 | 13.6 ± 4.8 | [M + K]$^+$ | DG(32:0) | $C_{35}H_{68}O_5$ |
|  | 3 | 5.8 ± 2.6 | 6.8 ± 3.0 | [M + H]$^+$ | 1-tetradecanyl-2-(8-[3]-ladderane-octanyl)-sn-glycerol | $C_{37}H_{68}O_3$ |
|  | 4 | — | — | [M + K]$^+$ | DG(34:2) | $C_{37}H_{68}O_5$ |
|  | 5 | 7.3 ± 4.5 | 9.4 ± 4.9 | [M + K]$^+$ | DG(34:1) | $C_{37}H_{70}O_5$ |
|  | 6 | 5.9 ± 2.6 | 6.8 ± 3.3 | [M + K]$^+$ | DG(O-34:1) | $C_{37}H_{72}O_4$ |
|  | 7 | — | 5.1 ± 2.3 | [M + K]$^+$ | DG(34:0) | $C_{37}H_{72}O_5$ |
|  | 8 | 8.5 ± 3.4 | 12.6 ± 4.6 | [M + K]$^+$ | DG(36:4) | $C_{39}H_{68}O_5$ |
|  | 9 | 30.2 ± 10.5 | 44.8 ± 12.1 | [M + H]$^+$ | 1-(14-methyl-pentadecanoyl)-2-(8-[3]-ladderane-octanyl)-sn-glycerol | $C_{39}H_{70}O_4$ |
|  | 10 | — | — | [M + K]$^+$ | DG(36:3) | $C_{39}H_{70}O_5$ |
|  | 11 | 6.5 ± 3.1<br>5.2 ± 2.1 | 7.0 ± 3.2<br>6.4 ± 2.7 | [M + H]$^+$<br>[M + Na]$^+$ | 1-hexadecanyl-2-(8-[3]-ladderane-octanyl)-sn-glycerol | $C_{39}H_{72}O_3$ |
|  | 12 | 8.4 ± 3.5 | 9.8 ± 3.7 | [M + K]$^+$ | DG(36:2) | $C_{39}H_{72}O_5$ |
|  | 13 | 7.3 ± 3.1 | 8.1 ± 3.5 | [M + K]$^+$ | DG(36:1) | $C_{39}H_{72}O_5$ |
|  | 14 | 5.3 ± 2.2 | 7.0 ± 2.7 | [M + H]$^+$ | 1-(6-[5]-ladderane-hexanoyl)-2-(8-[3]-ladderane-octanyl)-sn-glycerol | $C_{41}H_{64}O_4$ |
|  | 15 | — | — | [M + K]$^+$ | DG(38:6) | $C_{41}H_{68}O_5$ |
|  | 16 | — | — | [M + K]$^+$ | DG(38:5) | $C_{41}H_{70}O_5$ |
|  | 17 | 6.1 ± 2.4 | 7.8 ± 3.2 | [M + K]$^+$ | DG(38:4) | $C_{41}H_{72}O_5$ |
|  | 18 | 7.4 ± 3.1 | 9.6 ± 4.0 | [M + K]$^+$ | DG(38:2) | $C_{41}H_{76}O_5$ |
|  | 19 | 7.3 ± 3.0 | 7.6 ± 3.2 | [M + K]$^+$ | DG(38:1) | $C_{41}H_{78}O_5$ |
|  | 20 | 18.7 ± 6.1 | 22.6 ± 6.3 | [M + Na]$^+$ | DG(40:8) | $C_{43}H_{63}D_5O_5$ |
|  | 21 | 7.8 ± 3.2 | 8.5 ± 3.4 | [M + K]$^+$ | DG(40:10) | $C_{43}H_{64}O_5$ |
|  | 22 | 9.9 ± 4.5 | 13.4 ± 4.7 | [M + H]$^+$ | 1-(8-[5]-ladderane-octanoyl)-2-(8-[3]-ladderane-octanyl)-sn-glycerol | $C_{43}H_{68}O_4$ |
|  | 23 | — | 6.2 ± 2.6 | [M + H]$^+$ | 1-(8-[5]-ladderane-octanyl)-2-(8-[3]-ladderane-octanyl)-sn-glycerol | $C_{43}H_{70}O_3$ |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

| | | | | | | |
|---|---|---|---|---|---|---|
| | | 24 | 26.4 ± 6.8 | 38.6 ± 8.7 | [M + H]$^+$ | 1-(8-[3]-ladderane-octanoyl-2-(8-[3]-ladderane-octanyl)-sn-glycerol | $C_{43}H_{70}O_4$ |
| | | 25 | 6.4 ± 2.8 | 8.0 ± 3.4 | [M + K]$^+$ | DG(40:6) | $C_{43}H_{72}O_5$ |
| | | 26 | 10.8 ± 4.2 | 13.1 ± 4.4 | [M + K]$^+$ | DG(42:11) | $C_{45}H_{66}O_5$ |
| Triradylglycerols (TAGs) | 1 | 7.6 ± 3.1 | 8.8 ± 3.7 | [M + H]$^+$ | TG(54:11) | $C_{57}H_{88}O_6$ |
| | 2 | — | — | [M + H]$^+$ | TG(54:9) | $C_{57}H_{92}O_6$ |
| | 3 | — | — | [M + Na]$^+$ | TG(62:15) | $C_{65}H_{96}O_6$ |
| | 4 | — | 5.3 ± 2.2 | [M + Na]$^+$ | TG(62:14) | $C_{65}H_{98}O_6$ |
| | 5 | — | 6.1 ± 3.0 | [M + K]$^+$ | TG(64:17) | $C_{67}H_{96}O_6$ |
| Other Glycerolipids | 1 | 27.6 ± 8.4 | 37.2 ± 10.2 | [M + Na]$^+$ | 1-(9Z,1Z-octadecadienoyl)-2-(10Z,13Z,16Z,19Z-docosatetraenoyl)-3-O-[hydroxymethyl-N,N,N-trimethyl-beta-alanine]-glycerol | $C_{50}H_{85}NO_7$ |
| Sterol Lipids | 1 | 7.7 ± 3.5 | 10.5 ± 4.1 | [M + K]$^+$ | C24 bile acids and/or its isomers | $C_{24}H_{38}O_4$ |
| | 2 | 16.4 ± 5.4 | 29.2 ± 7.0 | [M + K]$^+$ | 24-northornasterol A | $C_{26}H_{42}O_4$ |
| | 3 | — | — | [M + K]$^+$ | Dedydrocholesterol | $C_{27}H_{44}O$ |
| | 4 | — | — | [M + K]$^+$ | C27 bile acids and/or its isomers | $C_{27}H_{44}O_4$ |
| | 5 | 7.4 ± 3.4 | 13.3 ± 4.2 | [M + Na]$^+$ | Cholesterol | $C_{27}H_{46}O$ |
| | | 7.8 ± 3.5 | 9.7 ± 4.5 | [M + K]$^+$ | | |
| | 6 | 6.4 ± 3.0 | 8.6 ± 4.4 | [M + Na]$^+$ | C27 bile acids and/or its isomers | $C_{27}H_{46}O_5$ |
| | 7 | — | — | [M + Na]$^+$ | C27 bile acids and/or its isomers | $C_{27}H_{46}O_6$ |
| | 8 | 7.8 ± 3.5 | 10.3 ± 4.8 | [M + K]$^+$ | Ergosterols and C24-methyl derivatives | $C_{28}H_{46}O_4$ |
| | 9 | — | 5.6 ± 2.5 | [M + Na]$^+$ | Conicasterol B | $C_{29}H_{44}O$ |
| | 10 | 7.3 ± 3.4 | 9.8 ± 4.6 | [M + K]$^+$ | C30 isoprenoids | $C_{30}H_{50}O_3$ |
| | 11 | — | — | [M + K]$^+$ | Spirostanols and/or its isomers | $C_{40}H_{66}O_{12}$ |
| | 12 | 7.9 ± 3.5 | 9.5 ± 4.6 | [M + K]$^+$ | Spirostanols and/or its isomers | $C_{40}H_{68}O_{15}$ |
| Prenol Lipids | 1 | 5.3 ± 2.3 | 5.7 ± 2.5 | [M + Na]$^+$ | 19-(3-methyl-butanoyloxy)-villanovane-13alpha,17-diol | $C_{25}H_{42}O_5$ |

TABLE 8-continued

Comparison of lipid detection by MALDI-FTICR MS from the hippocampus region of four rat brain tissue sections with and without electric field applied during the three different steps of each matrix spray cycle. See FIG. 27A for information concerning I, II, III, and IV.

| | | | | | | |
|---|---|---|---|---|---|---|
| Fatty acyls | 1 | — | — | $[M + K]^+$ | FA(18:2) | $C_{18}H_{32}O_2$ |
| Fatty acids | 2 | 8.7 ± 4.2 | 10.9 ± 5.3 | $[M + K]^+$ | FA(18:1) | $C_{18}H_{34}O_2$ |
| (FAs) | 3 | 11.4 ± 4.7 | 19.1 ± 5.6 | $[M + K]^+$ | FA(20:4) | $C_{20}H_{32}O_2$ |
| | 4 | 8.5 ± 5.3 | 9.7 ± 5.1 | $[M + K]^+$ | FA(22:6) | $C_{22}H_{32}O_2$ |
| | 5 | 8.8 ± 5.6 | 18.0 ± 5.8 | $[M + Na]^+$ | FA(22:0) | $C_{22}H_{42}O_4$ |
| | | 11.4 ± 5.7 | 15.9 ± 6.0 | $[M + K]^+$ | | |
| | 6 | 18.8 ± 5.6 | 21.1 ± 6.2 | $[M + K]^+$ | FA(26:0) | $C_{26}H_{50}O_4$ |
| Other | 1 | 19.3 ± 5.7 | 27.7 ± 6.4 | $[M + K]^+$ | Guanosine | $C_{10}H_{13}N_5O_5$ |
| compounds | 2 | — | — | $[M + Na]^+$ | Thymidine 3,5-cyclic monophosphate | $C_{10}H_{13}N_2O_7P$ |
| | 3 | 8.5 ± 5.5 | 10.8 ± 5.4 | $[M + Na]^+$ | Cyclic adenosine monophosphate (cAMP) | $C_{10}H_{12}N_5O_6P$ |
| | | 11.9 ± 5.8 | 17.4 ± 6.5 | $[M + K]^+$ | | |
| | 4 | — | 6.3 ± 2.8 | $[M + H]^+$ | CoA(26:0) | $C_{47}H_{86}N_7O_{17}P_3S$ |
| | | — | 5.3 ± 2.4 | $[M + Na]^+$ | | |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A system, comprising:
a first conductive substrate;
a second conductive substrate positioned parallel and opposite to the first conductive substrate, wherein the first conductive substrate and second conductive substrate are separated by a distance of 25 mm to 75 mm;
a power source electrically coupled to the first conductive substrate and the second conductive substrate for establishing an electric field between the first conductive substrate and the second conductive substrate; and
a matrix dispersion device capable of dispersing a matrix solution, wherein the matrix dispersion device is physically separated from the first conductive substrate and the second conductive substrate and wherein the matrix dispersion device is configured to disperse droplets of the matrix solution for polarization by the electric field for application of polarized matrix solution droplets to a biological sample.

2. The system of claim 1, wherein the matrix dispersion device is positioned adjacent to and between an end terminus of the first conductive substrate and an end terminus of the second conductive substrate.

3. The system of claim 1, wherein the first conductive substrate comprises a conductive material different from that of the second conductive substrate.

4. The system of claim 1, wherein the biological sample is associated with a conductive material of the first conductive substrate.

5. The system of claim 1, wherein the first conductive substrate and the second conductive substrate are separated by a distance of 40 mm to 55 mm.

6. The system of claim 1, further comprising a housing that substantially encloses at least the first conductive substrate, the second conductive substrate, and a portion of the matrix dispersion device which comprises a spray nozzle.

7. A system for preparing a sample for MALDI-MS analysis, comprising:
a first conductive substrate comprising a conductive material and associated with a tissue sample;
a second conductive substrate comprising a conductive material positioned parallel and opposite to the first conductive substrate, wherein the first conductive substrate and second conductive substrate are separated by a distance of 40 mm to 55 mm;
a power source coupled to the first conductive substrate and the second conductive substrate for establishing an electric field between the first conductive substrate and the second conductive substrate;
a matrix dispersion device capable of dispersing a matrix solution, wherein the matrix dispersion device is physically separated from, and is positioned adjacent to and between, the first conductive substrate and the second conductive substrate; and
a housing substantially enclosing the first conductive substrate, the second conductive substrate, and a spray nozzle of the matrix dispersion device.

8. A system according to claim 1, further comprising a mass spectrometer capable of analyzing a matrix-coated biological sample.

9. A method, comprising:
positioning a first conductive substrate associated with a biological sample 25 mm to 75 mm away from a second conductive substrate, wherein the first conductive substrate and the second conductive substrate are parallel to one another;
applying an electric field between the first conductive substrate and the second conductive substrate using a power source coupled to the first conductive substrate and the second conductive substrate; and
spraying a matrix solution from a matrix dispersion device comprising a spray nozzle positioned perpendicular to the electric field generated between the first conductive substrate and the second conductive substrate, wherein the matrix solution is sprayed into the electric field in a direction effective to polarize and apply the matrix solution to the biological sample thereby forming a matrix layer on the biological sample.

10. The method of claim 9, further comprising allowing droplets of the matrix solution to incubate with the biological sample in the presence of the electric field.

11. The method of claim 9, further comprising drying droplets of the matrix solution in the presence of the electric field.

12. The method of claim 9, wherein the biological sample is sprayed 20 to 40 times.

13. The method of claim 9, further comprising analyzing the biological sample and the matrix layer associated therewith for one or more compounds of interest by subjecting the biological sample to a mass spectrometric detection technique.

14. The method of claim 13, wherein the mass spectrometric detection technique is MALDI mass spectrometry.

15. The method of claim 9, wherein the electric field is directed from the first conductive substrate to the second conductive substrate or wherein the electric field is directed from the second conductive substrate to the first conductive substrate.

16. The method of claim 9, wherein spraying the droplets into the electric field causes an upper portion of the droplets to develop a higher electric potential than a lower portion of the droplets.

17. The method of claim 9, wherein spraying the matrix solution into the electric field causes a lower portion of droplets of the matrix solution to develop a higher electric potential than an upper portion of droplets of the matrix solution and wherein polarized droplets associate with the biological sample and electrically attract one or more compounds of interest within the biological sample.

18. The method of claim 9, wherein the matrix layer formed using the electric field contains at least 50% more compounds of interest than a matrix layer formed without an electric field and/or wherein the matrix layer formed using the electric field provides higher signal-to-noise ratios than a matrix layer formed without an electric field.

19. The method of claim 9, wherein the biological sample is a prostate tissue sample, a breast tissue sample, a lung tissue sample, a skin tissue sample, a liver tissue sample, a colon tissue sample, or a combination thereof and the method is used to detect one or more lipids, proteins, nucleic acids, or combinations thereof that are present in the biological sample.

20. The method of claim 9, wherein the method is used to detect apolipoprotein C-I, S100 A6, or S100 A8.

21. The system of claim 1, wherein the matrix dispersion device is configured to disperse droplets of the matrix solution into the electric field.

22. A method of using the device of claim 1, comprising:

associating a biological sample with the first conductive substrate;

positioning the first conductive substrate 25 mm to 75 mm away from the second conductive substrate;

applying an electric field between the first conductive substrate and the second conductive substrate using a power source coupled to the first conductive substrate and the second conductive substrate; and spraying the matrix solution from the matrix dispersion device such that matrix solution droplets enter the electric field, are polarized, and form a matrix layer on the biological sample.

* * * * *